United States Patent
Sina et al.

(10) Patent No.: US 12,404,540 B2
(45) Date of Patent: Sep. 2, 2025

(54) EPIGENETIC BIOMARKER AND USES THEREFOR

(71) Applicant: THE UNIVERSITY OF QUEENSLAND, St Lucia (AU)

(72) Inventors: Abu Sina, St Lucia (AU); Matt Trau, St Lucia (AU); Laura Garcia Carrascosa, St Lucia (AU)

(73) Assignee: THE UNIVERSITY OF QUEENSLAND, St Lucia (AU)

( * ) Notice: Subject to any disclaimer, the term of this patent is extended or adjusted under 35 U.S.C. 154(b) by 1082 days.

(21) Appl. No.: 17/286,379

(22) PCT Filed: Oct. 17, 2019

(86) PCT No.: PCT/AU2019/051131
§ 371 (c)(1),
(2) Date: Apr. 16, 2021

(87) PCT Pub. No.: WO2020/077409
PCT Pub. Date: Apr. 23, 2020

(65) Prior Publication Data
US 2022/0033880 A1    Feb. 3, 2022

(30) Foreign Application Priority Data
Oct. 17, 2018   (AU) .............................. 2018903935

(51) Int. Cl.
*C12Q 1/6809*   (2018.01)
*C12Q 1/6886*   (2018.01)

(52) U.S. Cl.
CPC ......... *C12Q 1/6809* (2013.01); *C12Q 1/6886* (2013.01); *C12Q 2600/154* (2013.01)

(58) Field of Classification Search
CPC .................................................. C12Q 1/6809
See application file for complete search history.

(56) References Cited

U.S. PATENT DOCUMENTS

| | | |
|---|---|---|
| 4,816,567 A | 3/1989 | Cabilly et al. |
| 5,212,290 A | 5/1993 | Vogelstein et al. |
| 5,457,105 A | 10/1995 | Barker |
| 5,475,001 A | 12/1995 | Barker |
| 5,525,462 A | 6/1996 | Takarada et al. |
| 5,616,582 A | 4/1997 | Barker |
| 5,654,307 A | 8/1997 | Bridges et al. |
| 5,679,683 A | 10/1997 | Bridges et al. |
| 5,693,762 A | 12/1997 | Queen et al. |
| 5,747,498 A | 5/1998 | Schnur et al. |
| 5,760,041 A | 6/1998 | Wissner et al. |
| 5,770,599 A | 6/1998 | Gibson |
| 5,786,146 A | 7/1998 | Herman et al. |
| 5,804,396 A | 9/1998 | Plowman |
| 5,866,572 A | 2/1999 | Barker et al. |
| 5,891,996 A | 4/1999 | Mateo et al. |
| 5,972,602 A | 10/1999 | Hyland et al. |
| 6,002,008 A | 12/1999 | Wissner et al. |
| 6,017,704 A | 1/2000 | Herman et al. |
| 6,033,854 A | 3/2000 | Kurnit et al. |
| 6,084,095 A | 7/2000 | Bridges et al. |
| 6,114,117 A | 9/2000 | Hepp et al. |
| 6,127,120 A | 10/2000 | Graham et al. |
| 6,140,332 A | 10/2000 | Traxler et al. |
| 6,180,349 B1 | 1/2001 | Ginzinger et al. |
| 6,200,756 B1 | 3/2001 | Herman et al. |
| 6,235,883 B1 | 5/2001 | Jakobovits et al. |
| 6,265,171 B1 | 7/2001 | Herman et al. |
| 6,265,410 B1 | 7/2001 | Bridges et al. |
| 6,306,597 B1 | 10/2001 | Macevicz |
| 6,331,393 B1 | 12/2001 | Laird et al. |
| 6,344,317 B2 | 2/2002 | Urnovitz |
| 6,344,455 B1 | 2/2002 | Bridges et al. |
| 6,344,459 B1 | 2/2002 | Bridges et al. |
| 6,391,874 B1 | 5/2002 | Cockerill et al. |
| 6,399,602 B1 | 6/2002 | Barker et al. |
| 6,448,001 B2 | 9/2002 | Oku et al. |
| 6,455,534 B2 | 9/2002 | Bridges et al. |
| 6,521,620 B1 | 2/2003 | Bridges et al. |
| 6,528,632 B1 | 3/2003 | Catanzariti et al. |
| 6,596,726 B1 | 7/2003 | Bridges et al. |
| 6,602,863 B1 | 8/2003 | Bridges et al. |
| 6,713,484 B2 | 3/2004 | Bridges et al. |
| 6,797,470 B2 | 9/2004 | Barany et al. |

(Continued)

FOREIGN PATENT DOCUMENTS

| EP | 0659439 B1 | 10/2001 |
|---|---|---|
| KR | 10-2016-0009357 | 1/2016 |

(Continued)

OTHER PUBLICATIONS

Brotons et al. "Electrochemical detection of cytosine and 5-methylcytosine on Au(111) surfaces," Electrochemistry Communications, 2016, vol. 65, pp. 27-30.

Karymov et al. "DNA methylation-dependent chromatin fiber compaction in vivo and in vitro: requirement for linker histone," FASEB Journal, Dec. 2001, vol. 15, pp. 2631-2641.

Koo et al. "eMethylsorb: Rapid quantification of DNA methylation in cancer cells on screen-printed gold electrodes," Analyst, 2014, vol. 139, No. 23, pp. 6178-6184.

(Continued)

*Primary Examiner* — Albert M Navarro
(74) *Attorney, Agent, or Firm* — Casimir Jones, S.C.; Peter J. Schlueter

(57) ABSTRACT

Disclosed is an epigenetic biomarker that comprises clustered methylated genomic DNA which can self-assemble to form complexes that have distinct physicochemical properties relative to genomic DNA that lacks such clusters. Also disclosed are methods, systems, compositions and kits that takes advantage of these physicochemical properties for detecting clustered methylated genomic DNA including for determining likelihood of the presence of cancer.

9 Claims, 28 Drawing Sheets

Specification includes a Sequence Listing.

(56) References Cited

U.S. PATENT DOCUMENTS

| | | | |
|---|---|---|---|
| 7,011,944 | B2 | 3/2006 | Prudent et al. |
| 7,037,687 | B2 | 5/2006 | Williams et al. |
| 7,083,917 | B2 | 8/2006 | Barany et al. |
| 7,166,434 | B2 | 1/2007 | Barany et al. |
| 7,169,560 | B2 | 1/2007 | Lapidus et al. |
| 7,186,512 | B2 | 3/2007 | Martienssen et al. |
| 7,232,656 | B2 | 6/2007 | Balasubramanian et al. |
| 7,320,865 | B2 | 1/2008 | Barany et al. |
| 7,332,285 | B2 | 2/2008 | Barany et al. |
| 7,364,858 | B2 | 4/2008 | Barany et al. |
| 7,429,453 | B2 | 9/2008 | Barany et al. |
| 7,459,274 | B2 | 12/2008 | Lakey et al. |
| 7,553,627 | B2 | 6/2009 | Laird et al. |
| 7,598,035 | B2 | 10/2009 | Macevicz |
| 7,611,869 | B2 | 11/2009 | Fan |
| 7,645,596 | B2 | 1/2010 | Williams et al. |
| 7,700,324 | B1 | 4/2010 | Issa et al. |
| 7,769,400 | B2 | 8/2010 | Backholm et al. |
| 7,901,880 | B2 | 3/2011 | Jeddeloh et al. |
| 7,910,296 | B2 | 3/2011 | Jeddeloh et al. |
| 8,323,890 | B2 | 12/2012 | Laird et al. |
| 2005/0069879 | A1 | 3/2005 | Berlin |
| 2009/0155791 | A1 | 6/2009 | Wojdacz et al. |
| 2010/0144836 | A1 | 6/2010 | Van Engeland et al. |
| 2010/0203594 | A1 | 8/2010 | Segawa et al. |

FOREIGN PATENT DOCUMENTS

| | | |
|---|---|---|
| WO | WO-9630347 A1 | 10/1996 |
| WO | WO-9633978 A1 | 10/1996 |
| WO | WO-9633980 A1 | 10/1996 |
| WO | WO-9640210 A1 | 12/1996 |
| WO | WO-9738983 A1 | 10/1997 |
| WO | WO-9906396 A1 | 2/1998 |
| WO | WO-9814451 A1 | 4/1998 |
| WO | WO-9843960 A1 | 10/1998 |
| WO | WO-9850038 A1 | 11/1998 |
| WO | WO-9850433 A2 | 11/1998 |
| WO | WO-9906378 A1 | 2/1999 |
| WO | WO-9909016 A1 | 2/1999 |
| WO | WO-9924037 A1 | 5/1999 |
| WO | WO-2005012578 A1 | 2/2005 |
| WO | WO-2005111209 A1 | 11/2005 |
| WO | WO-2009021141 A1 | 2/2009 |
| WO | WO-2009049916 A2 | 4/2009 |
| WO | WO 2018/109212 | 6/2018 |
| WO | WO-2020077409 A1 | 4/2020 |
| WO | WO-2022031620 A2 | 2/2022 |

OTHER PUBLICATIONS

Lin et al. "Colorimetric Determination of DNA Methylation Based on the Strength of the Hydrophobic Interactions between DNA and Gold Nanoparticles," ACS Applied Materials & Interfaces, 2013, vol. 5, No. 22, pp. 12045-12051.

Sina et al. "Epigenetically reprogrammed methylation landscape drives the DNA self-assembly and serves as a universal cancer biomarker," Nature Communications, 2018, vol. 9, Article No. 4915, 13 pages.

International Search Report and Written Opinion for International (PCT) Patent Application No. PCT/AU2019/051131, dated Nov. 29, 2019, 11 pages.

Acevedo et al. Analysis of the mechanisms mediating tumor-specific changes in gene expression in human liver tumors. Cancer Res. 68:2641-2651 (2008).

Acosta-Silva et al., Mutual relationship between stacking and hydrogen bonding in DNA. Theoretical study of guanine-cytosine, guanine-5-methylcytosine, and their dimers. J Phys Chem B. 114(31):10217-10227 (2010).

Ahmed et al., Detection of aberrant protein phosphorylation in cancer using direct gold-protein affinity interactions. Biosens Bioelectron. 91:8-14 (2017).

Ashford, AiGene aims to remodel clinical trials with ctDNA tech for on-treatment response monitoring. GenomeWeb. Published Apr. 14, 2023.

Balic et al., High quality assessment of DNA methylation in archival tissues from colorectal cancer patients using quantitative high-resolution melting analysis. J. Mol. Diagn. 11(2):102-108 (2009).

Ball et al., Targeted and genome-scale strategies reveal gene-body methylation signatures in human cells. Nat Biotechnol. 27(4):361-368 (2009).

Behe et al., Effects of methylation on a synthetic polynucleotide: the B—Z transition in poly(dG-m5dC).poly(dG-m5dC). Proc Natl Acad Sci USA. 78(3):1619-1623 (1981).

Bibikova et al., High-throughput DNA methylation profiling using universal bead arrays. Genome Res. 16(3):383-393 (2006).

Camafeita et al., SERS of cytosine and its methylated derivatives on gold sols. J Raman Spectrosc. 26(2):149-154 (1995).

Chuang, What's Working: Where a company that develops cancer tests, other startups are finding funding in Colorado. The Colorado Sun (2023).

Colorado Oedit, Early-stage capital and retention grant; advanced industries accelerator grant program. Colorado Office of Economic Development & International Trade (OEDIT). Press-release (2023).

Colorado Oedit, Proof-of-concept award; advanced industries accelerator grant program. Colorado Office of Economic Development & International Trade (OEDIT). Letter and Press-release (2021).

Costello et al., Restriction landmark genome scanning. Methods Mol Biol. 200:53-70 (2002).

Cottrell et al. A real-time PCR assay for DNA-methylation using methylation-specific blockers. Nucleic Acids Res. 32:e10 (2004).

Cottrell et al. Discovery and validation of 3 novel DNA methylation markers of prostate cancer prognosis. J. Urology 177:1753-1758 (2007).

Davies et al., Ultra-high resolution imaging of DNA and nucleosomes using non-contact atomic force microscopy. FEBS Lett. 579(7):1702-1706 (2005).

Degraves et al., High-Sensitivity Quantitative PCR Platform. Biotechniques. 34(1):106-115 (2003).

Deiman et al. Characteristics and applications of nucleic acid sequence-based amplification (NASBA). Mol. Biotechnol. 20(2):163-179 (2002).

Deng et al., Targeted bisulfite sequencing reveals changes in DNA methylation associated with nuclear reprogramming. Nat Biotechnol. 27(4):353-360 (2009).

Derreumaux et al., Impact of CpG methylation on structure, dynamics and solvation of cAMP DNA responsive element. Nucleic Acids Res. 29(11):2314-2326 (2001).

Doluca et al., Molecular engineering of guanine-rich sequences: Z-DNA, DNA triplexes, and G-quadruplexes. Chem Rev. 113(5):3044-3083 (2013).

Eads et al., MethyLight: a high-throughput assay to measure DNA methylation. Nucleic Acid Res. 28(8):e32 (2000).

Elghanian et al., Selective colorimetric detection of polynucleotides based on the distance-dependent optical properties of gold nanoparticles. Science. 277(5329):1078-1081 (1997).

Fojt et al., Adsorption and two-dimensional condensation of 5-methylcytosine. Bioelectrochemistry. 75(2):89-94 (2009).

Frommer et al. A genomic sequencing protocol that yields a positive display of 5-methylcytosine residues in individual DNA strands. PNAS USA 89:1827-1831 (1992).

Fujii et al., Molecular structure of (m5 dC-dG)3: the role of the methyl group on 5-methyl cytosine in stabilizing Z-DNA. Nucleic Acids Res. 10(23):7879-7892 (1982).

Gasparac et al., Ultrasensitive electrocatalytic DNA detection at two- and three-dimensional nanoelectrodes. J Am Chem Soc. 126(39):12270-12271 (2004).

Gibson et al., A novel method for real time quantitative RT-PCR. Genome Research 6(10):995-1001 (1996).

Golub et al.; Molecular classification of cancer: class discovery and class prediction by gene expression monitoring. Science. 286(5439):531-537 (1999).

(56) References Cited

OTHER PUBLICATIONS

Gonzalgo et al., Rapid quantitation of methylation differences at specific sites using methylation-sensitive single nucleotide primer extension (Ms—SNuPE). Nucleic Acids Res. 25(12):2529-2531 (1997).
Guo et al., Identification of methylation haplotype blocks aids in deconvolution of heterogeneous tissue samples and tumor tissue-of-origin mapping from plasma DNA. Nat Genet. 49(4):635-642 (2017).
Hanley et al., The meaning and use of the area under a receiver operating characteristic (ROC) curve. Radiology. 143(1):29-36 (1982).
Harris, et al. Single-molecule DNA sequencing of a viral genome. Science. Apr. 4, 2008;320(5872):106-9. doi: 10.1126/science. 1150427.
Haskell, Press release: License agreement creates golden opportunity for cancer diagnostic technology. UniQuest Communications (2020).
Herman et al., Methylation-specific PCR: a novel PCR assay for methylation status of CpG islands. Proc Natl Acad Sci USA. 93(18):9821-9826 (1996).
Hihath et al., Effects of cytosine methylation on DNA charge transport. J Phys Condens Matter. 24(16):164204 (2012).
Hodges-Garcia et al., Cytosine methylation can induce local distortions in the structure of duplex DNA. Biochemistry. 31(33):7595-7599 (1992).
Hong et al., An electrochemical assay for DNA methylation based on 3D nanostructured gold electrode and methyl binding domain protein (Transducers 2015). IEEE Xplore. pp. 1545-1548 (2015).
Hossain et al., Electrochemical biosensing strategies for DNA methylation analysis. Biosensors and Bioelectronics. 94:63-73 (2017).
Jiang et al., Lengthening and shortening of plasma DNA in hepatocellular carcinoma patients. Proc Natl Acad Sci USA. 112(11):E1317-E1325 (2015).
Jimenez-Useche et al., The effect of DNA CpG methylation on the dynamic conformation of a nucleosome. Biophys J. 103(12):2502-2512 (2012).
Johns et al., Identification of the epitope for the epidermal growth factor receptor-specific monoclonal antibody 806 reveals that it preferentially recognizes an untethered form of the receptor. J Biol Chem. 279(29):30375-30384 (2004).
Kaur et al., Hydrophobicity of methylated DNA as a possible mechanism for gene silencing. Phys Biol. 9(6):065001 (2012).
Kelley et al., Orienting DNA helices on gold using applied electric fields. Langmuir. 14(24):6781-6784 (1998).
Kimura-Suda Base-dependent competitive adsorption of single-stranded DNA on gold. J Am Chem Soc. 125(30):9014-9015 (2003).
Klysik et al., Effects of 5 cytosine methylation on the B-Z transition in DNA restriction fragments and recombinant plasmids. J Mol Biol. 168(1):51-71 (1983).
Koga et al. Genome-wide screen of promoter methylation identifies novel markers in melanoma. Genome Res. 19:1462-1470 (2009).
Koo et al., Amplification-free detection of gene fusions in prostate cancer urinary samples using mRNA-Gold affinity interactions. Anal Chem. 88(13):6781-6788 (2016).
Koo et al., DNA-bare gold affinity interactions: mechanism and applications in biosensing. Analytical Methods. 7(17):7042-7054 (2015).
Koo et al., eMethylsorb: rapid quantification of DNA methylation in cancer cells on screen-printed gold electrodes. Analyst. 139(23):6178-84 (2014).
Koo et al., Poly(A) Extensions of miRNAs for Amplification-Free Electrochemical Detection on Screen-Printed Gold Electrodes. Anal Chem. 88(4):2000-2005 (2016).
Lee et al., Adsorption patterns of gold nanoparticles on methyl-terminated self-assembled monolayers. J Phys Chem C. 115(25):12501-12507 (2011).
Lee et al., Effects of DNA methylation on the structure of nucleosomes. J Am Chem Soc. 134(1):173-175 (2012).

Li et al., Colorimetric detection of DNA sequences based on electrostatic interactions with unmodified gold nanoparticles. Proc Natl Acad Sci USA. 101(39):14036-14039 (2004).
Li et al., Label-free colorimetric detection of specific sequences in genomic DNA amplified by the polymerase chain reaction. J Am Chem Soc. 126(35):10958-10961 (2004).
Margulies, et al. Genome Sequencing in Microfabricated High-density Picolitre Reactors. Nature. vol. No. 437, Issue No. 7057 (2005): 14 Pages.
McClelland et al., Effect of site-specific modification on restriction endonucleases and DNA modification methyltransferases. Nucleic Acids Res. 22(17):3640-3659 (1994).
Nicolaou et al., Calicheamicin ⊖1I: a rationally designed molecule with extremely potent and selective DNA cleaving properties and apoptosis inducing activity. Angew Chem IntlEd. Engl. 33:183-186 (1994).
Nolte. Branched DNA signal amplification for direct quantitation of nucleic acid sequences in clinical specimens. Adv. Clin. Chem. 33:201-235 (1998).
Ohno et al., Aggregation behavior in water of amphiphilic diblock copolymers bearing biocompatible phosphorylcholine and cholesteryl groups. Polymer Journal. 47:71-76 (2015).
Olek et al., The pre-implantation ontogeny of the H19 methylation imprint. Nature Genetics. 17(3):275-276 (1997).
Orlandi et al., Cloning immunoglobulin variable domains for expression by the polymerase chain reaction. Proc Natl Acad Sci USA. 86(10):3833-3837 (1989).
Peck et al., Energetics of B-to-Z transition in DNA. Proc Natl Acad Sci USA. 80(20):6206-6210 (1983).
Piana et al., The nature of the adsorption of nucleobases on the gold [111] surface. J Phys Chem B. 110(46):23467-23471 (2006).
Rauch et al., High-resolution mapping of DNA hypermethylation and hypomethylation in lung cancer. Proc Natl Acad Sci USA 105(1):252-257 (2008).
Rein et al., Identifying 5-methylcytosine and related modifications in DNA genomes. Nucleic Acids Res. 26(10):2255-2264 (1998).
Rich et al., Z-DNA: the long road to biological function. Nat Rev Genet. 4(7):566-572 (2003).
Russo, Electrochemical biosensor for point of care based monitoring of cancer progression using ctDNA methylscape as a biomarker. Session No. C48-06, Room-122B. Bioanalytical applications of electrochemical based sensors, Pittcon Conference and Exposition 2023.
Sadri et al. Rapid analysis of DNA methylation using new restriction enzyme sites created by bisulfite modification. Nucleic Acids Res. 24:5058-5059 (1996).
Sandhu, Protein engineering of antibodies. Crit Rev Biotechnol. 12(5-6):437-462 (1992).
Sato et al., Rapid aggregation of gold nanoparticles induced by non-cross-linking DNA hybridization. J Am Chem Soc. 125(27):8102-8103 (2003).
Schübeler, Function and information content of DNA methylation. Nature. 517(7534):321-326 (2015).
Severin et al., Cytosine methylation alters DNA mechanical properties. Nucleic Acids Res. 39(20):8740-8751 (2011).
Shimooka et al., Most methylation-susceptible DNA sequences in human embryonic stem cells undergo a change in conformation or flexibility upon methylation. Biochemistry. 52(8):1344-1353 (2013).
Sina et al., eMethylsorb: electrochemical quantification of DNA methylation at CpG resolution using DNA-gold affinity interactions. Chem Commun (Camb). 50(86):13153-13156 (2014).
Sina et al., Methylsorb: a simple method for quantifying DNA methylation using DNA-gold affinity interactions. Anal Chem. 86(20):10179-85 (2014).
Singer et al., Optimal humanization of 1B4, an anti-CD18 murine monoclonal antibody, is achieved by correct choice of human V-region framework sequences. J Immunol. 150(7):2844-2857 (1993).
Smith et al., DNA methylation: roles in mammalian development. Nat Rev Genet. 14(3):204-220 (2013).
Snyder et al., Cell-free DNA comprises an in vivo nucleosome footprint that informs its tissues-of-origin. Cell. 164(1-2):57-68 (2016).

(56) References Cited

OTHER PUBLICATIONS

Soleymani et al., Nanostructuring of patterned microelectrodes to enhance the sensitivity of electrochemical nucleic acids detection. Angew Chem Int Ed Engl. 48(45):8457-8460 (2009).
Soni, et al. Progress toward ultrafast DNA sequencing using solid-state nanopores. Clin Chem. Nov. 2007;53(11):1996-2001. Epub Sep. 21, 2007.
Storhoff et al., Sequence-dependent stability of DNA-modified gold nanoparticles. Langmuir. 18(17) 6666-6670 (2002).
Stragliotto et al., Multiple infusions of anti-epidermal growth factor receptor (EGFR) monoclonal antibody (EMD 55,900) in patients with recurrent malignant gliomas. Eur J Cancer. 32A(4):636-640 (1996).
Sun et al., Plasma DNA tissue mapping by genome-wide methylation sequencing for noninvasive prenatal, cancer, and transplantation assessments. Proc Natl Acad Sci USA. 112(40): E5503-E5512 (2015).
Suzuki et al., DNA methylation landscapes: provocative insights from epigenomics. Nat Rev Genet. 9(6):465-476 (2008).
Taub, aiGENE is proud to announce our partnership with the Department of the Air Force Material Command's competitive awards-based Small Business Innovation Research (SBIR) program. Air Force SBIR award (2023).
Taub et al., Novel "SMARTer" clinical trial design improves odds of approval and can reduce study size by over 80%: Modeling use of a ctDNA "optimizing diagnostic" for early therapy switching in immuno-oncology trials. medRxiv Preprint (2023). https://www.medrxiv.org/content/10.1101/2023.02.20.23286152v1.
Tost et al., DNA methylation analysis by pyrosequencing. Nat Protoc. 2(9):2265-2275 (2007).
Toyota et al., Identification of differentially methylated sequences in colorectal cancer by methylated CpG island amplification. Cancer Res. 59(10):2307-2312 (1999).
Tuab et al., Abstract P049: A simplified, potentially point-of-care (POC), electrode method detects changes in the amount of cfDNA/ctDNA and evaluates the response of advanced cancer patients to therapy. Cancer Prev Res (Phila). 16 (1_Supplement):P049 (2023).
Underhill et al. Fragment Length of Circulating Tumor DNA. Edited by David J. Kwiatkowski. PLOS Genetics 12(7):e1006162 (2016).
Ushijima et al. Methylation-Sensitive Representational Difference Analysis (MS-RDA). Methods Mol Biol 507:117-130 (2009).
Wang et al., Monitoring DNA immobilization and hybridization on surfaces by atomic force microscopy force measurements. Anal Chem. 73(10):2207-2212 (2001).
Wojdacz et al., Methylation-sensitive high resolution melting (MS-HRM): a new approach for sensitive and high-throughput assessment of methylation. Nucleic Acids Res. 35(6):e41 (2007).
Xia et al.; Colorimetric detection of DNA, small molecules, proteins, and ions using unmodified gold nanoparticles and conjugated polyelectrolytes. Proc Natl Acad Sci USA. 107(24):10837-10841 (2010).
Xiong et al COBRA: a sensitive and quantitative DNA methylation assay. Nucleic Acids Res. 25:2532-2534 (1997).
Yong, Cancer biomarkers: Written in blood. Nature. 511(7511):524-526 (2014).
Zhang et al., DNA hybridization "turns on" electro-catalysis at gold electrodes. Chem Commun (Camb). (11):1154-1156 (2007).
Zhang et al., Investigation of ordered ds-DNA monolayers on gold electrodes. J Phys Chem B. 106(43):11233-11239 (2002).
Zou et al., Sensitive Quantification of vimentin methylation with a novel methylation specific qInvader technology. Clinical Chemistry 56(6) Supplement, 2010 AACC poster presentation, D-144: A198 (2010).

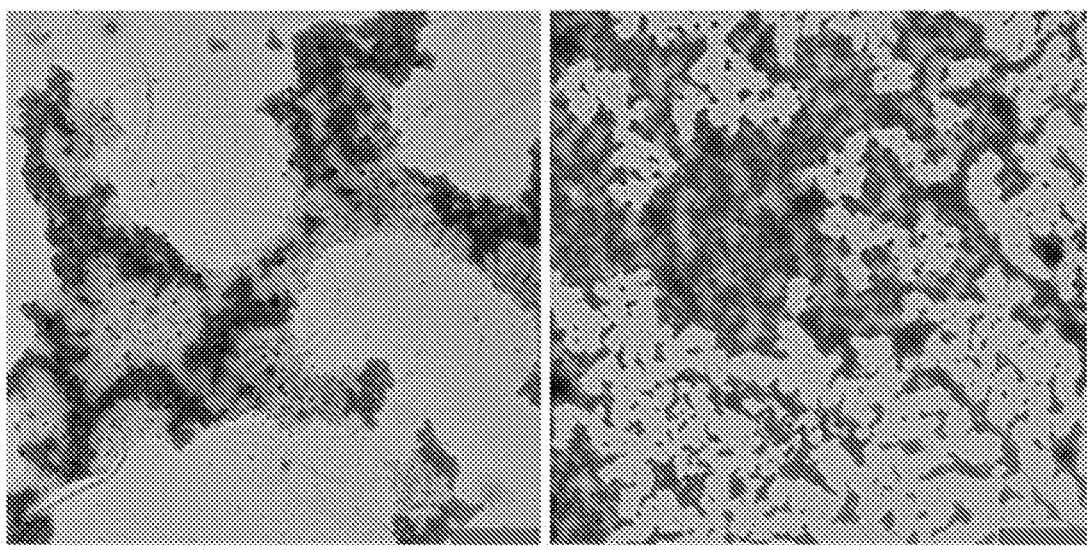
normal Prostate tissue DNA
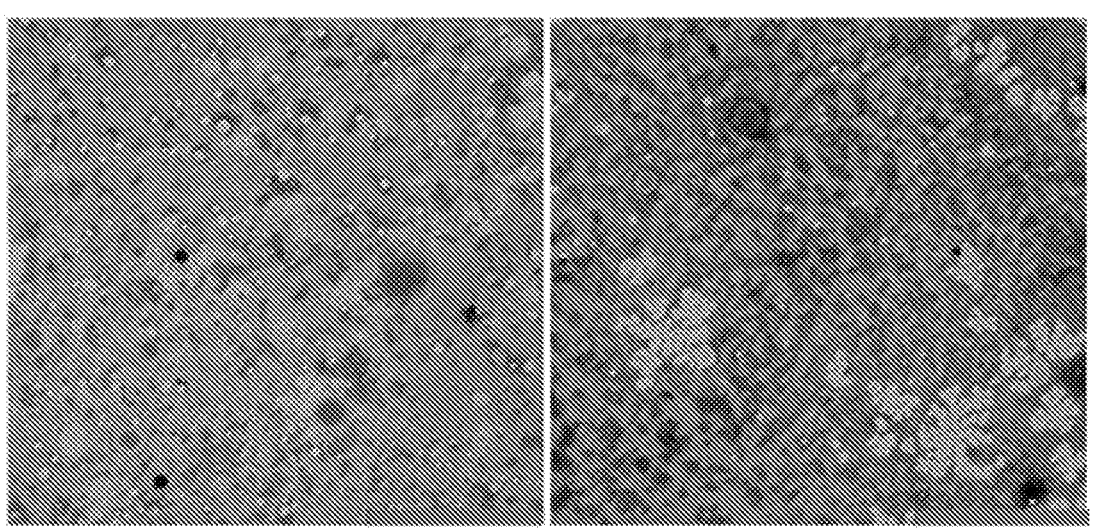
Prostate cancer tissue DNA
FIGURE 2

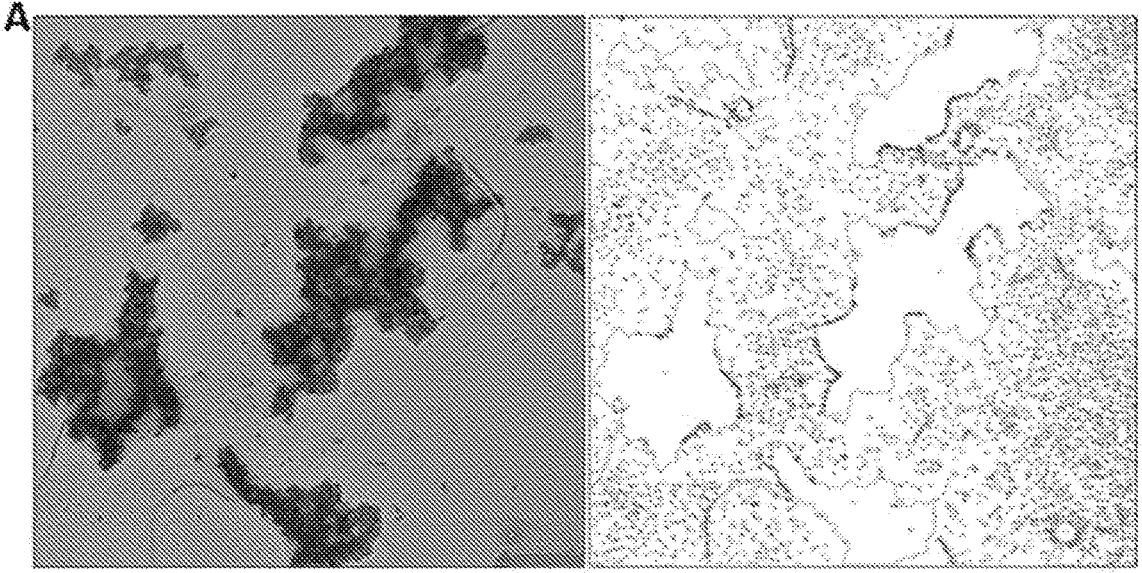
| Sample | Aggregates Count | Total Area (nm²) | Average Size (nm²) | %Area |
|---|---|---|---|---|
| gDNA (Normal Prostate tissue) | 5464 | 45341257.06 | 8298.18 | 25.369 |
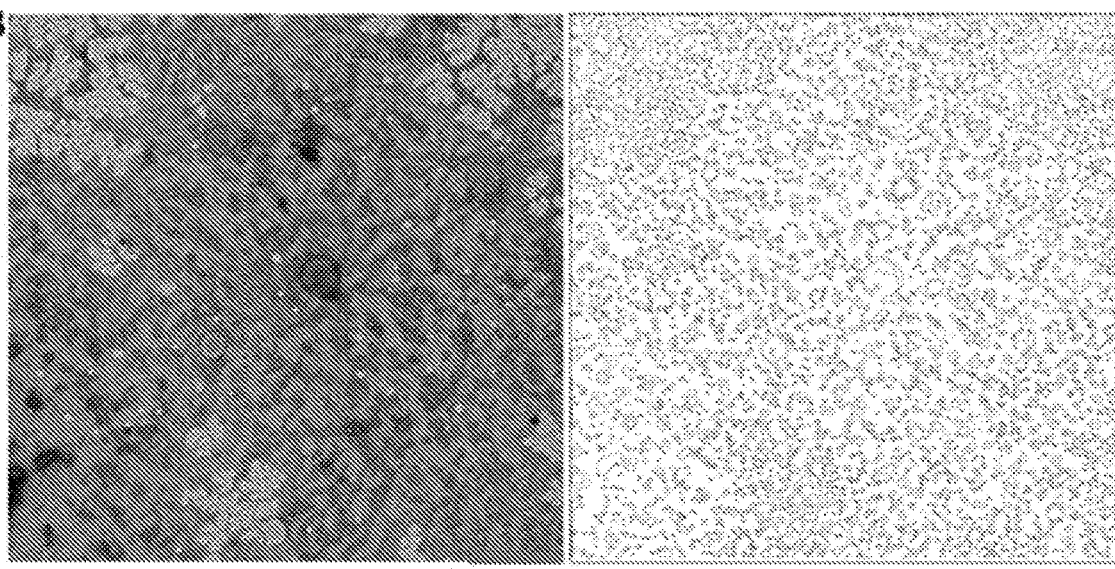
| Sample | Aggregates Count | Total Area (nm²) | Average Size (nm²) | %Area |
|---|---|---|---|---|
| gDNA (Cancer Prostate tissue) | 3933 | 6057435.111 | 1540.156 | 14.608 |
FIGURE 3

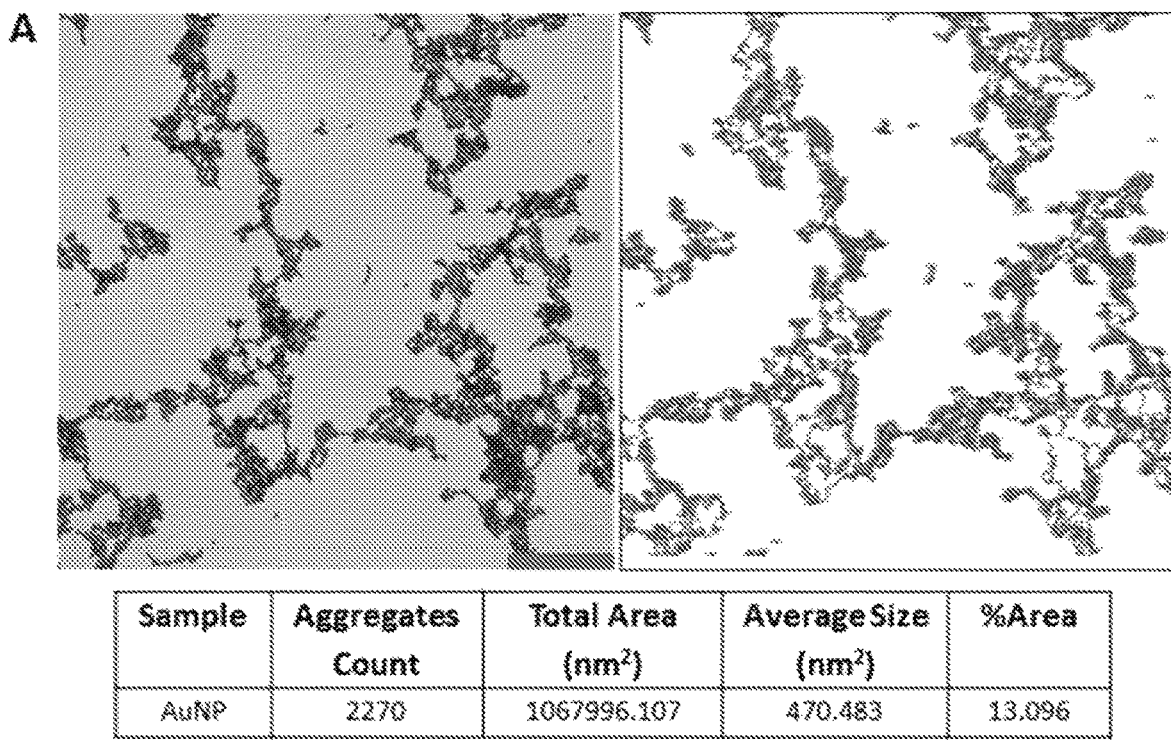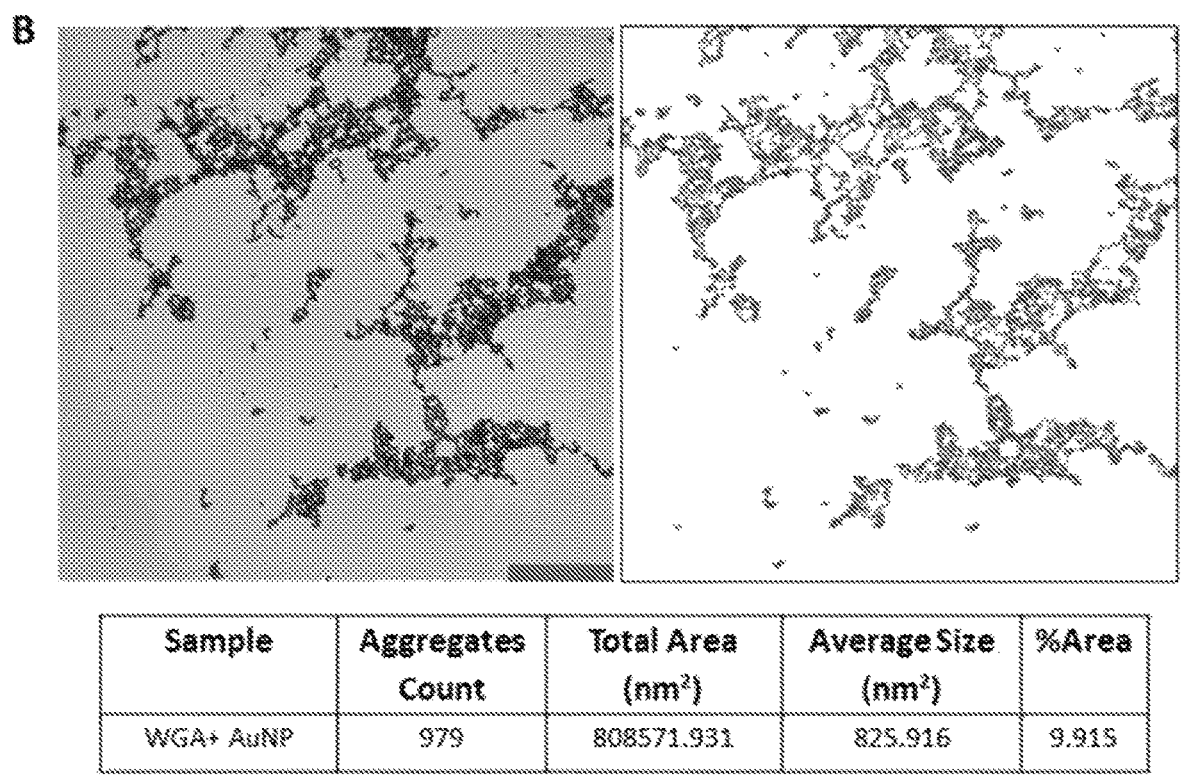
FIGURE 24

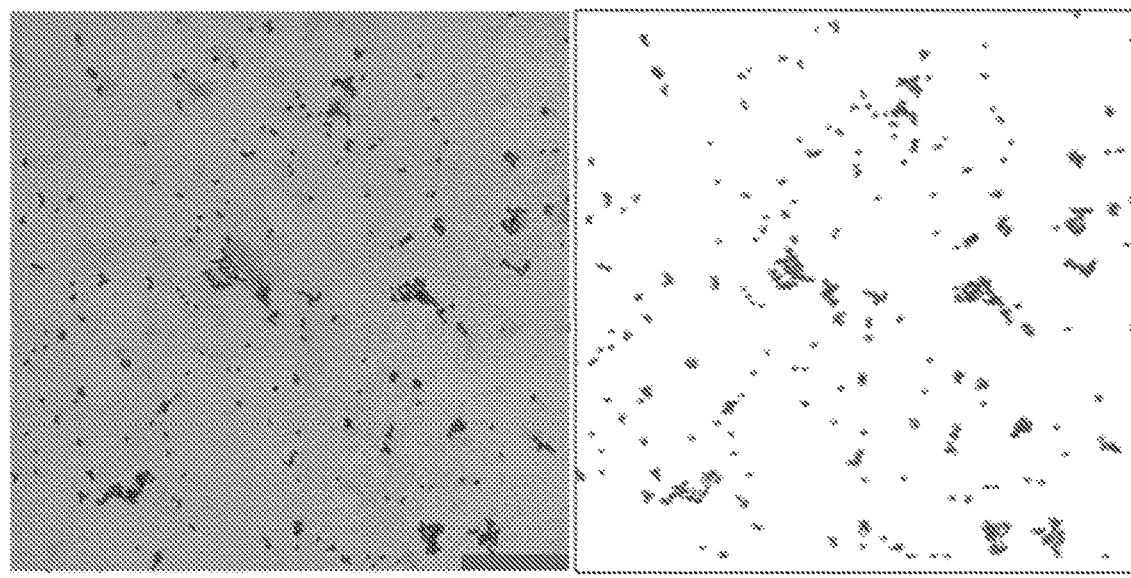
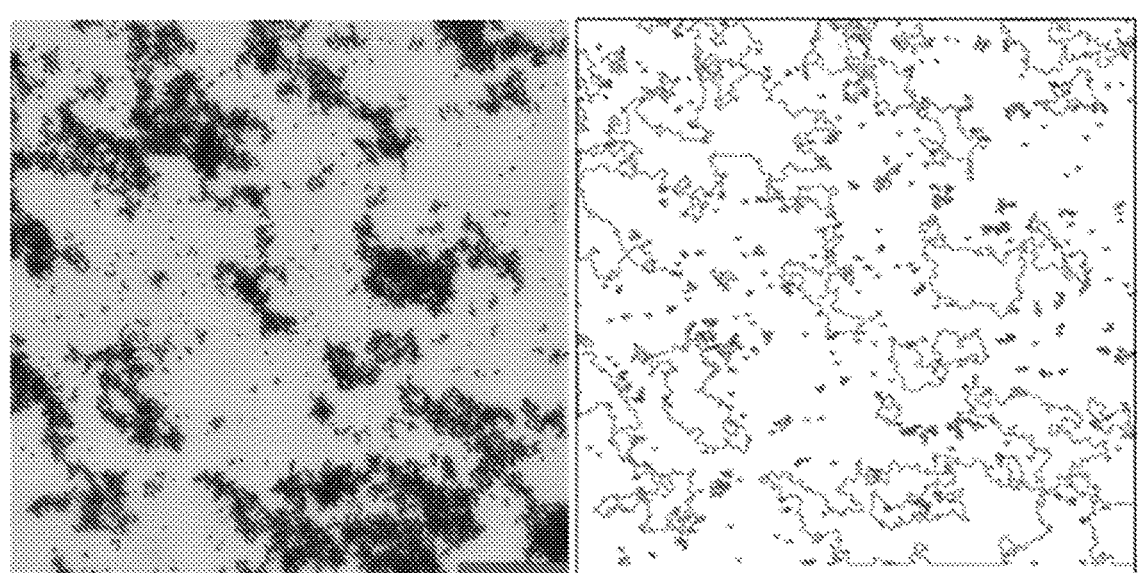
FIGURE 24 cont'd

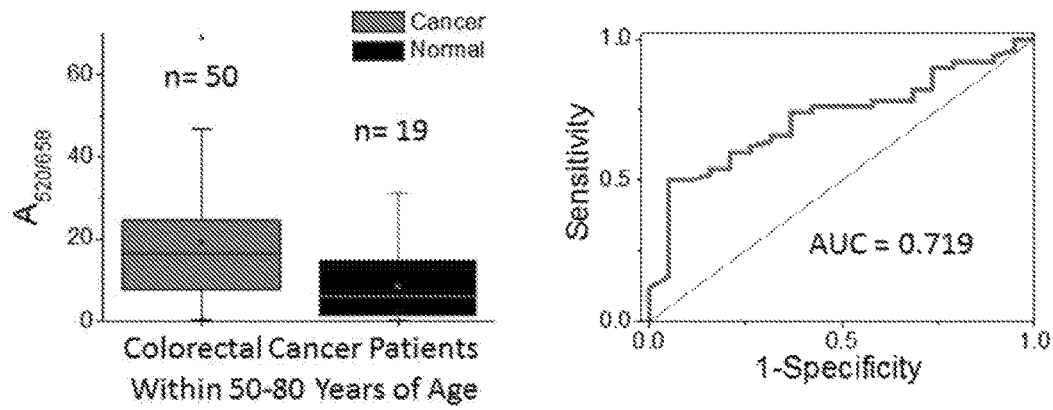

FIGURE 28

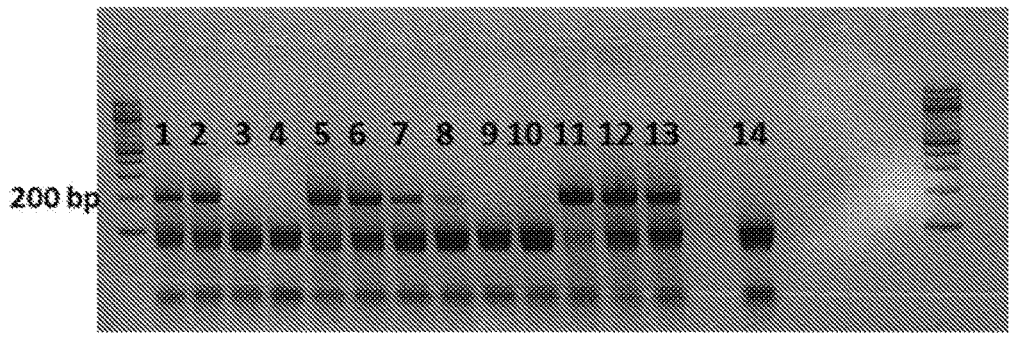

| Sample No | Sample Description | Sample DNA Concentration(ng/μl) | Mercaptohexanol (MCH) Concentration (ng/ μl) |
|---|---|---|---|
| 1 | BT474 Breast Cancer cell DNA | 100 | 10 |
| 2 | BT474 Breast Cancer cell DNA | 50 | 10 |
| 3 | BT474 Breast Cancer cell DNA | 10 | 10 |
| 4 | BT474 Breast Cancer cell DNA | 5 | 10 |
| 5 | Normal Breast Tissue DNA | 100 | 10 |
| 6 | Normal Breast Tissue DNA | 50 | 10 |
| 7 | Normal Breast Tissue DNA | 10 | 10 |
| 8 | Normal Breast Tissue DNA | 5 | 10 |
| 9 | No DNA | 0 | 10 |
| 10 | BT474 Breast Cancer cell DNA | 100 | 0 |
| 11 | Normal Breast Tissue DNA without adsorption (PCR positive Control) | 100 | 0 |
| 12 | BT474 Breast Cancer cell DNA without adsorption (PCR positive Control) | 100 | 0 |
| 13 | BT474 Breast Cancer cell DNA without adsorption (PCR positive Control) | 10 | 0 |
| 14 | No DNA in PCR (PCR negative Control) | 0 | 0 |

FIGURE 29

A
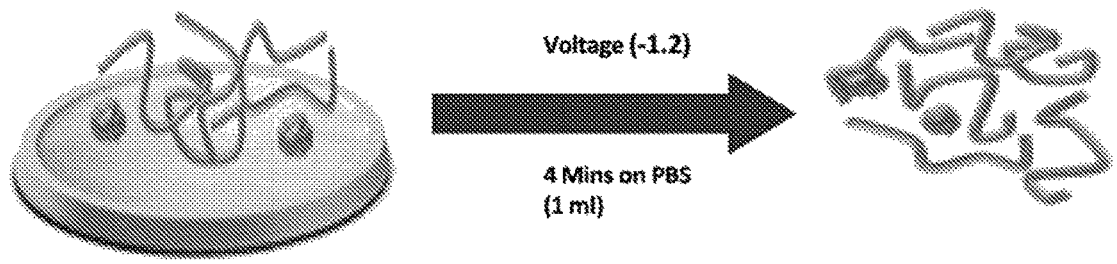
B
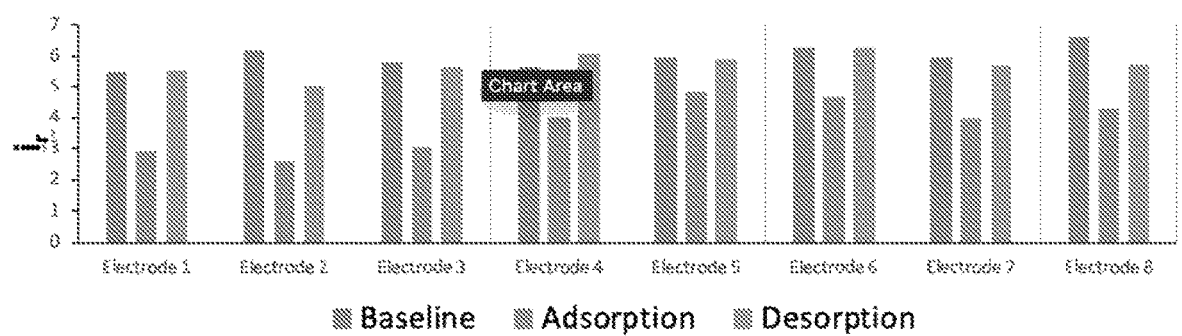
C
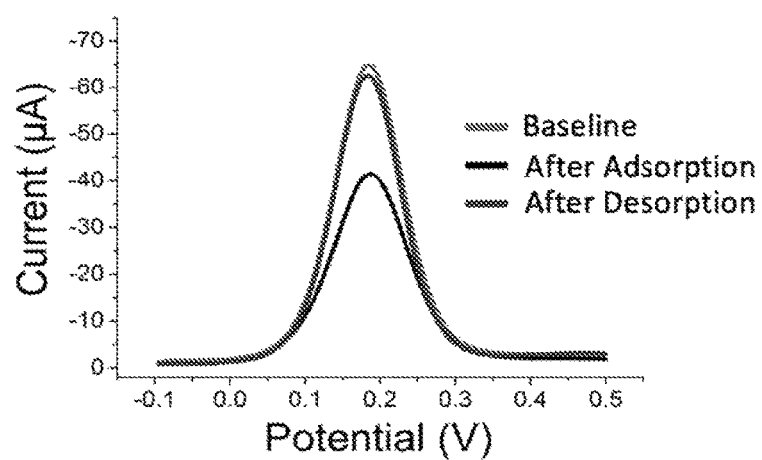
FIGURE 40

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Synthetic forward primer

<400> SEQUENCE: 1
tgcctggggc acccggctct t                                            21

<210> SEQ ID NO 2
<211> LENGTH: 22
<212> TYPE: DNA
<213> ORGANISM: Artificial Sequence
<220> FEATURE:
<223> OTHER INFORMATION: Synthetic reverse primer

<400> SEQUENCE: 2
tggggacgtc tgcccgccct ct                                           22

<210> SEQ ID NO 3
```

```
<211> LENGTH: 22
<212> TYPE: DNA
<213> ORGANISM: Artificial Sequence
<220> FEATURE:
<223> OTHER INFORMATION: Synthetic forward primer

<400> SEQUENCE: 3
acctgtgttc attcacatga gg                                          22

<210> SEQ ID NO 4
<211> LENGTH: 20
<212> TYPE: DNA
<213> ORGANISM: Artificial Sequence
<220> FEATURE:
<223> OTHER INFORMATION: Synthetic reverse primer

<400> SEQUENCE: 4
agagcttgtt ctggccgttt                                             20
```

EPIGENETIC BIOMARKER AND USES THEREFOR

CROSS-REFERENCE TO RELATED APPLICATIONS

This application is a national stage application under 35 U.S.C. 371 and claims the benefit of PCT Application No. PCT/AU2019/051131 having an international filing date of 17 Oct. 2019, which designated the United States, which PCT application claimed the benefit of Australian Provisional Application No. 2018903935 entitled "Epigenetic Biomarker and Uses therefor" filed 17 Oct. 2018, the contents of which each are incorporated herein by reference in their entirety.

REFERENCE TO SEQUENCE LISTING

This application contains a Sequence Listing submitted as an electronic text file named 10621-1-PUS_Seq_Listing_ST25.txt, having a size in bytes of 1.184 bytes, and created on Sep. 29, 2021. The information contained in this electronic file is hereby incorporated by reference in its entirety pursuant to 37 CFR § 1.52(e)(5).

FIELD OF THE INVENTION

This invention relates generally to an epigenetic biomarker. More particularly, the present invention relates to clustered methylated genomic DNA which can self-assemble to form complexes that have distinct physicochemical properties relative to genomic DNA that lacks such clusters. The present invention takes advantage of these physicochemical properties in methods, systems, compositions and kits for detecting clustered methylated genomic DNA including in methods for determining likelihood of the presence of cancer.

BACKGROUND OF THE INVENTION

DNA methylation is a key epigenetic change involving addition of a methyl group to cytosine nucleotides, and this modification is used by living systems to control genes and their genetic programs (Smith, Z. D. et al., 2013, *Nature Reviews Genetics* 14:204-220; Schubeler, D., 2015, *Nature* 517:321-326; Suzuki, M. M. et al., 2008, *Nature Reviews Genetics* 9:465-476). The unique levels and pattern of cytosine methylation across the entire genome defines the epigenetic state of the cell, reflects the tissue of origin and when epigenetic reprogramming occurs, it leads to fundamental changes in cell biology which may trigger the onset of diseases (Smith, Z. D. et al., 2013, supra; Schubeler, D., 2015, supra). An example of this is the transition of cells from a healthy state to malignant neoplasms during cancer (Suzuki, M. M. et al., 2008, supra). Epigenetic reprogramming in cancer represents a unique methylation landscape involving the net loss of global DNA methylation together with a concomitant increase in the levels of methylcytosines at regions often involved in regulatory roles (e.g., promoter regions), in which CpG sites are abundant and clustered within a short span (Suzuki, M. M. et al., 2008, supra). Given the versatile nature of cancer leaving different biomarkers for different cancer types, the methylation landscape (hereafter referred to as "methylscape") of genomes that are epigenetically reprogrammed is found to be a common feature exhibited by most cancer types and therefore can serve as a universal cancer biomarker. However, there is no appropriate platform to detect this cancer methylscape biomarker, which could significantly improve the current strategies for cancer diagnosis, stratification, prognosis and responses to therapy.

DNA is one of the best-known naturally occurring organic polymers in nature and recent studies have found that methylation could impact many physicochemical properties of DNA polymer in solution including DNA structure (Hodges-Garcia, Y. et al., 1992, *Biochemistry-Us* 31:7595-7599; Lee, J. Y. et al., 2011, *Journal of the American Chemical Society* 134:173-175), flexibility (Derreumaux, S. et al., 2001, *Nucleic Acids Res* 29:2314-2326; Geahigan, K. B. et al., 2000, *Biochemistry-Us* 39:4939-4946; Severin, P. M. et al., 2011, *Nucleic Acids Res*, gkr578) and three dimensional conformation (Jimenez-Useche, I. et al., 2012, *Biophysical journal* 103:2502-2512; Rich, A. et al., 2003, *Nature Reviews Genetics* 4:566-572; Shimooka, Y. et al., 2013, *Biochemistry-Us* 52:1344-1353). This was mainly attributed to the hydrophobic nature and larger size of individual methylcytosines in comparison to the regular cytosine (Kaur, P. et al., 2012, *Physical biology* 9:065001). However, these studies used model DNA systems and therefore broad changes in the physicochemical properties of DNA polymer occurring at the whole genome level during cancer epigenetic reprogramming largely remained unknown. This knowledge could therefore open new opportunities to precisely detect the methylscape biomarker of cancer genomes by analyzing their physicochemical properties alone.

SUMMARY OF THE INVENTION

The present invention is based in part on the determination that certain physicochemical properties of isolated genomic DNA are fundamentally different between normal and epigenetically reprogrammed cancer genomes, which enable the development of platforms for detecting methylscape biomarker. In particular, it has been determined that genomic DNA derived from normal cells shows greater tendency towards aggregation in aqueous solutions than genomic DNA derived from cancer cells. The present inventors have found in this regard that genomic DNA derived from cancer cells forms significantly smaller aggregates or complexes than DNA from normal cells. It is proposed that this is caused by the hydrophobic properties of methylated cytosines leading to different DNA polymer conformations in solution, depending on their levels, and particularly, on their patterning—whether they are evenly distributed or enriched in clusters across the genome, which is analogous to patterning effects on polymer solvation. In this regard, it is known that copolymers with block or clustered distributions of their monomers exhibit widely different physicochemical properties than copolymers with a random or even distribution (Alexandridis, P. & Lindman, B. "Amphiphilic block copolymers: self-assembly and applications." (Elsevier, 2000)).

The present inventors have also found that the different solvation properties of cancer and normal epigenomes significantly influence their affinity towards solid supports such as bare metals including gold. Notably, they have found that the affinity of genomic DNA towards these solid supports is influenced by their methylation level and patterning. The present inventors have also found that, in addition to the solvation properties, this interaction is modulated by different affinity of methylated nucleotides (e.g., methylated cytosines) and non-methylated nucleotide (e.g., cytosines), and as a function of their clustered or dispersed patterning (i.e., methylation landscape) across the genome, which in turn, can determine the clinicopathological state of the DNA. These findings have been reduced to practice in methods, systems, compositions and kits for detecting cancer methylscape biomarker, including for determining likelihood of the presence of cancer.

Accordingly, the present invention provides in one aspect an isolated nucleic acid complex comprising a plurality of genomic DNA molecules each comprising a clustered distribution of methylated nucleotides (e.g., methylated cytosines), wherein the complex is formed by self-assembly of the DNA molecules under aqueous conditions.

Another aspect of the present invention provides systems, suitably for detecting clustered methylated DNA, including the nucleic acid complex broadly described above and elsewhere herein. These systems generally comprise: (1) a biological sample comprising a nucleic acid complex that comprises a plurality of genomic DNA molecules each comprising a clustered distribution of methylated nucleotides (e.g., methylated cytosines), wherein the complex is formed by self-assembly of the DNA molecules under aqueous conditions; and (2) a sensor, which is in communication with the biological sample, for detecting the presence or level of the nucleic acid complex.

In yet another aspect, the present invention provides conjugates, suitably for detecting clustered methylated DNA, including the nucleic acid complex broadly described above and elsewhere herein. These conjugates generally comprise: (a) a nucleic acid that comprises a plurality of genomic DNA molecules each comprising a clustered distribution of methylated nucleotides (e.g., methylated cytosines), wherein the complex is formed by self-assembly of the DNA molecules under aqueous conditions; and (b) an affinity agent for which the nucleic acid complex has affinity. The affinity agent may be selected from antigen-binding molecules that bind specifically with the nucleic acid complex and solid supports to which hydrophobic moieties (e.g., methylated nucleotides such as methylated cytosines) adsorb under the aqueous conditions.

Yet another aspect of the present method provides methods of detecting clustered methylated nucleic acid in a biological sample. These methods generally comprise, consist or consist essentially of: detecting in the biological sample a nucleic acid complex that comprises a plurality of genomic DNA molecules each comprising a clustered distribution of methylated nucleotides (e.g., methylated cytosines), wherein the complex is formed by self-assembly of the DNA molecules under aqueous conditions. The nucleic acid complex may be detected by contacting the biological sample with an affinity agent for which the nucleic acid complex has affinity. The affinity agent may be selected from antigen-binding molecules that bind specifically with the nucleic acid complex and solid supports to which hydrophobic moieties (e.g., methylated nucleotides such as methyl cytosines) adsorb under the aqueous conditions.

Still another aspect of the present invention provides methods of isolating a nucleic acid complex from a biological sample, wherein the complex comprises a plurality of genomic DNA molecules each comprising a clustered distribution of methylated nucleotides (e.g., methylated cytosines), and is formed by self-assembly of the DNA molecules under aqueous conditions. These methods generally comprise, consist or consist essentially of contacting the biological sample with an affinity agent (e.g., as broadly described above and elsewhere herein) for which the nucleic acid complex has affinity to form a conjugate and separating the conjugate from the biological sample. In some embodiments, the methods further comprise separating the nucleic acid complex from the affinity agent (e.g., by elution).

A further aspect of the present invention provides methods of nucleic acid analysis. These methods generally comprise, consist or consist essentially of: isolating a nucleic acid complex comprising a plurality of genomic DNA molecules each comprising a clustered distribution of methylated nucleotides (e.g., methylated cytosines), wherein the complex is formed by self-assembly of the DNA molecules under aqueous conditions; and analyzing a feature of the nucleic acid complex. The feature may be a nucleotide sequence of the nucleic acid complex. In representative examples of this type, the nucleotide sequence is analyzed by nucleic acid hybridization, nucleic acid amplification (e.g., polymerase chain reaction (PCR), linear amplification, rolling circle replication and QB replication) and/or nucleotide sequencing (e.g., Sanger sequencing, pyrosequencing, nanopore sequencing and Next Generation sequencing). In some of the same and other embodiments, the nucleic acid complex is analyzed by any one or more of microarray analysis, a polymerase chain reaction (PCR)-based analysis including methylation-specific PCR (MSP), bisulfite treatment, hybridization with allele-specific probes, enzymatic mutation detection, ligation chain reaction (LCR), oligonucleotide ligation assay (OLA), flow-cytometric heteroduplex analysis, chemical cleavage of mismatches, mass spectrometry, single strand conformation polymorphism (SSCP), denaturing gradient gel electrophoresis (DGGE), temperature gradient gel electrophoresis (TGGE), restriction fragment polymorphisms, serial analysis of gene expression (SAGE), DNA sequencing, or combinations thereof. In some of the same and other embodiments, the nucleic acid complex is analyzed by a methylation analysis assay, including for example, bisulfite genomic sequencing, MSP, melting curve methylation-specific PCR (McMS-PCR), multiplex ligation-dependent probe amplification (MLPA) with or without bisulfite treatment, digestion of genomic DNA with methylation-sensitive restriction enzyme, multiplexed PCR with gene specific primers (MSRE-PCR), bisulfite conversion-specific methylation-specific PCR (BS-MSP), methylation-sensitive single-nucleotide primer extension conformation (MS-SNuPE), methylation-sensitive single-strand conformation analysis (MS-SSCA), melting curve combined bisulfite restriction analysis (McCOBRA), enzymatic regional methylation assay (ERMA), quantitative PCR sequencing and oligonucleotide-based microarray systems, pyrosequencing, and Meth-DOP-PCR, or a combination between a modified degenerate oligonucleotide primed PCR (DOP-PCR) and MSP.

In another aspect, the present invention provides methods of determining the likelihood of the presence or absence of cancer in a subject. These methods generally comprise, consist or consist essentially of detecting in a biological sample obtained from the subject a nucleic acid complex that comprises a plurality of genomic DNA molecules each comprising a clustered distribution of methylated nucleotides (e.g., methylated cytosines), wherein the complex is formed by self-assembly of the DNA molecules under aqueous conditions, thereby determining the likely presence or absence of cancer in the subject. In some embodiments, the nucleic acid complex is detected by contacting the biological sample with an affinity agent for which the nucleic acid complex has affinity. In some of the same and other embodiments, the nucleic acid complex is detected by exposing the biological sample to electromagnetic radiation and detecting a physical feature that is indicative of the nucleic acid complex. In some of the same and other embodiments, the nucleic acid complex is detected by electrochemical detection.

Another aspect of the present invention provides methods of determining the presence in a biological sample of clustered methylated genomic DNA that comprises a clustered distribution of methylated nucleotides (e.g., methylated cytosines). These methods generally comprise, consist or consist essentially of: contacting the biological sample with a solid support, as described for example above and elsewhere herein, to which clustered hydrophobic moieties (e.g., clustered methylated nucleotides such as clustered methylated cytosines) adsorb more strongly than non-clustered hydrophobic moieties (e.g., non-clustered methylated nucleotides such as non-clustered methylated cytosines) under aqueous conditions; and detecting the presence of a conjugate comprising genomic DNA and the solid support, thereby determining the presence of clustered methylated genomic DNA in the biological sample. In some embodiments, the conjugate is detected by colorimetric detection, as broadly described above and elsewhere herein. In some embodiments, the conjugate is detected by electrochemical detection, as broadly described above and elsewhere herein.

In yet another aspect, the present invention provides systems, suitably for detecting clustered methylated DNA, as broadly described above and elsewhere herein. These systems generally comprise: (1) a biological sample comprising a clustered methylated genomic DNA that comprises a clustered distribution of methylated nucleotides (e.g., methylated cytosines); and (2) a sensor, which is in communication with the biological sample, for detecting the presence or level of the clustered methylated genomic DNA. Suitably, the sensor is selected from one or more of: an antigen-binding molecule that binds specifically with the clustered methylated genomic DNA, a light based sensor, a spectrometer, a refractometer, a particle sizer, an x-ray, a monochromator, an absorption detector, a reflectance detector, a transmission detector, a conductivity sensor, an electrode, a resistive pulse sensor, a camera, a microscope, a particle size analyzer, an optical detector, a solid support to which hydrophobic moieties adsorb under the aqueous conditions, a colloidal particle or a biosensor. In some embodiments, the sensor comprises a microscope (e.g., a transmission electron microscope). In some embodiments, the sensor comprises a solid support as broadly described above and elsewhere herein.

In still another aspect, the present invention provides conjugates, suitably for detecting clustered methylated DNA, as broadly described above and elsewhere herein. These conjugates generally comprise: (a) a clustered methylated genomic DNA that comprises a clustered distribution of methylated nucleotides (e.g., methylated cytosines); and (b) an affinity agent for which the clustered methylated genomic DNA has affinity. The affinity agent may be selected from antigen-binding molecules that bind specifically with clustered methylated DNA, solid supports to which hydrophobic moieties (e.g., methylated nucleotides) adsorb under the aqueous conditions, as broadly described above and elsewhere herein, including colloidal particles and electrodes as broadly described above and elsewhere herein.

A further aspect of the present invention provides methods of isolating clustered methylated genomic DNA from a biological sample, wherein the genomic DNA comprises a clustered distribution of methylated nucleotides (e.g., methylated cytosines). These methods generally comprise, consist or consist essentially of: contacting the biological sample with an affinity agent for which the genomic DNA has affinity to form a conjugate and separating the conjugate from the biological sample. In some embodiments, these methods further comprise separating the genomic DNA from the affinity agent. In illustrative examples of this type, the genomic DNA is separated from the affinity agent by elution. The affinity agent may be selected from antigen-binding molecules that bind specifically with the nucleic acid complex, solid supports to which hydrophobic moieties (e.g., methylated nucleotides such as methylated cytosines) adsorb under the aqueous conditions, as broadly described above and elsewhere herein, including colloidal particles and electrodes as broadly described above and elsewhere herein.

Still another aspect of the present invention provides methods of nucleic acid analysis. These methods generally comprise, consist or consist essentially of: isolating a clustered methylated genomic DNA from a biological sample as broadly described above and elsewhere herein, wherein the genomic DNA comprises a clustered distribution of methylated nucleotides (e.g., methylated cytosines); and analyzing a feature of the genomic DNA. In some embodiments, the feature is the nucleotide sequence of the genomic DNA.

Yet another aspect of the present invention provides methods of determining the likelihood of the presence or absence of cancer in a subject. These methods generally comprise, consist or consist essentially of: contacting a biological sample obtained from the subject with an affinity agent, as broadly described above and elsewhere herein, for which genomic DNA that comprises a clustered distribution of methylated nucleotides (e.g., methylated cytosines) has affinity; and detecting the presence or absence of a conjugate comprising the genomic DNA and the affinity agent, and optionally the methylation status and/or one or more ancillary cancer biomarkers of the genomic DNA, to thereby determine the likely presence or absence of cancer in the subject.

A further aspect of the present invention provides kits for detecting clustered methylated genomic DNA or complex thereof, and/or of determining the likelihood of the presence or absence of cancer in a subject. These kits generally comprise, consist or consist essentially of: a sensor for detecting the presence or level of clustered methylated genomic DNA or complex thereof, as broadly described above and elsewhere herein; optionally together with instructional material. In some embodiments, the sensor is selected from any one or more of: an antigen-binding molecule that binds specifically with the clustered methylated genomic DNA or complex thereof, a light based sensor, a spectrometer, a refractometer, an x-ray, a monochromator, an absorption detector, a reflectance detector, a transmission detector, a conductivity sensor, an electrode, a resistive pulse sensor, a camera, a microscope, a particle size analyzer, an optical detector, a solid support to which hydrophobic moieties adsorb under the aqueous conditions, a colloidal particle or a biosensor.

In another aspect, the present invention provides methods of treating cancer. These methods generally comprise, consist or consist essentially of: analyzing a biological sample obtained from a subject for the presence or absence of clustered methylated genomic DNA or complex thereof, and optionally the methylation status and/or one or more ancillary cancer biomarkers of the clustered methylated genomic DNA; and exposing the subject to a treatment regimen for treating the cancer if the analysis indicates the likely presence of cancer in the subject, or not exposing the subject to a treatment regimen for treating the cancer if the analysis indicates the likely absence of cancer in the subject. In various embodiments, the biological sample may be analyzed at the point of care or is sent to a laboratory to conduct the analysis.

Yet another aspect of the present invention provides methods for monitoring efficacy of a treatment regimen in a subject with a cancer. These methods generally comprise, consist or consist essentially of: analyzing a biological sample obtained from a subject exposed to a treatment regimen for the presence, absence or level of clustered methylated genomic DNA or complex thereof, and optionally the methylation status and/or one or more ancillary cancer biomarkers of the clustered methylated genomic DNA; and monitoring the subject over a period of time for a change in the clustered methylated genomic DNA or complex thereof, and optionally the methylation status of the clustered methylated genomic DNA, wherein a change or otherwise in the methylscape of the genomic DNA molecule or complex thereof in the biological sample over the period of time is indicative of treatment efficacy.

In any of the above aspects, the biological sample is suitably selected from tissue and fluid samples. In specific embodiments, the biological sample is a biological fluid, representative examples of which include: whole blood; lysed whole blood; serum; plasma; urine; sputum; sweat; follicular fluid; synovial fluid; amniotic fluid; a nasopharyngeal aspirate; a bronchial aspirate; semen and cerebrospinal fluid. In other embodiments, the biological sample comprises a tissue sample (e.g., prepared by any suitable procedure non-limiting examples of which include peeling cells using adhesive tape, scraping, biopsy touch preparations etc.). Exemplary tissues include lymph node, esophagus, lung, lung washes, BAL (bronchoalveolar lavage), thyroid, skin, breast, ovary, endometrium, uterus, pancreas, spleen, thymus, bone marrow, colon, stomach, bladder, brain, salivary gland, prostate, testicles and liver.

In any of the above aspects, the genomic DNA may be isolated from a cell, i.e., contained within a cell, or from a biological fluid (e.g., blood or fraction thereof such as plasma). In some embodiments, the genomic DNA is circulating tumor DNA (ctDNA), cell-free DNA (cfDNA) or extracellular vesicular DNA (evDNA). In other embodiments, the genomic DNA is cellular genomic DNA (i.e., not from a biological fluid), also referred to herein as cellular gDNA).

BRIEF DESCRIPTION OF THE DRAWINGS

FIG. 2 is a photographic representation showing additional TEM images of cellular gDNA derived from A) normal prostate tissue and b) prostate cancer tissue. Scale bars are 2000 nm for all the figures.

FIG. 3 is a photographic and tabular representation showing ImageJ analysis for TEM image of cellular gDNA from a) normal tissue and b) prostate cancer tissue. Scale bars are 2000 nm for all the figures

FIG. 24 is a photographic and tabular representation showing ImageJ analysis for TEM image for AuNP and its interaction with cellular gDNA having different methylation status. (A) AuNP (B) AUNP with WGA DNA (C) AuNP with BT474 DNA (D) AuNP with Jurkat 100% methylated DNA. Scale bars are 500 nm for all the figures.

FIG. 28 is a graphical representation showing a box plot and an ROC curve. The box plot shows the mean relative absorbance values A520/658 of AuNP-cfDNA solution for cfDNA samples derived from the plasma of colorectal cancer patients or healthy donors within 50-80 years of age. The ROC analysis is shown on the right. In the box and whisker plots, the middle lines of the boxes represent the median (50th percentile) and the terminal line of the boxes represents the 25th to 75th percentile. The whiskers represent the lowest and the highest value.

FIG. 29 is a photographic and tabular representation of a gel image showing that the desorbed DNA undergoes successful PCR amplification.

FIG. 40 is a schematic and graphical representation depicting electrochemical desorption of hypomethylated cancer BT474 cellular gDNA. The graph represents the baseline current for the bare gold electrodes (blue bar, No DNA), current after adsorbing BT474 cancer DNA onto the gold electrodes (orange bar) and the current after desorbing the same DNA from the gold electrodes.

Figure 1:
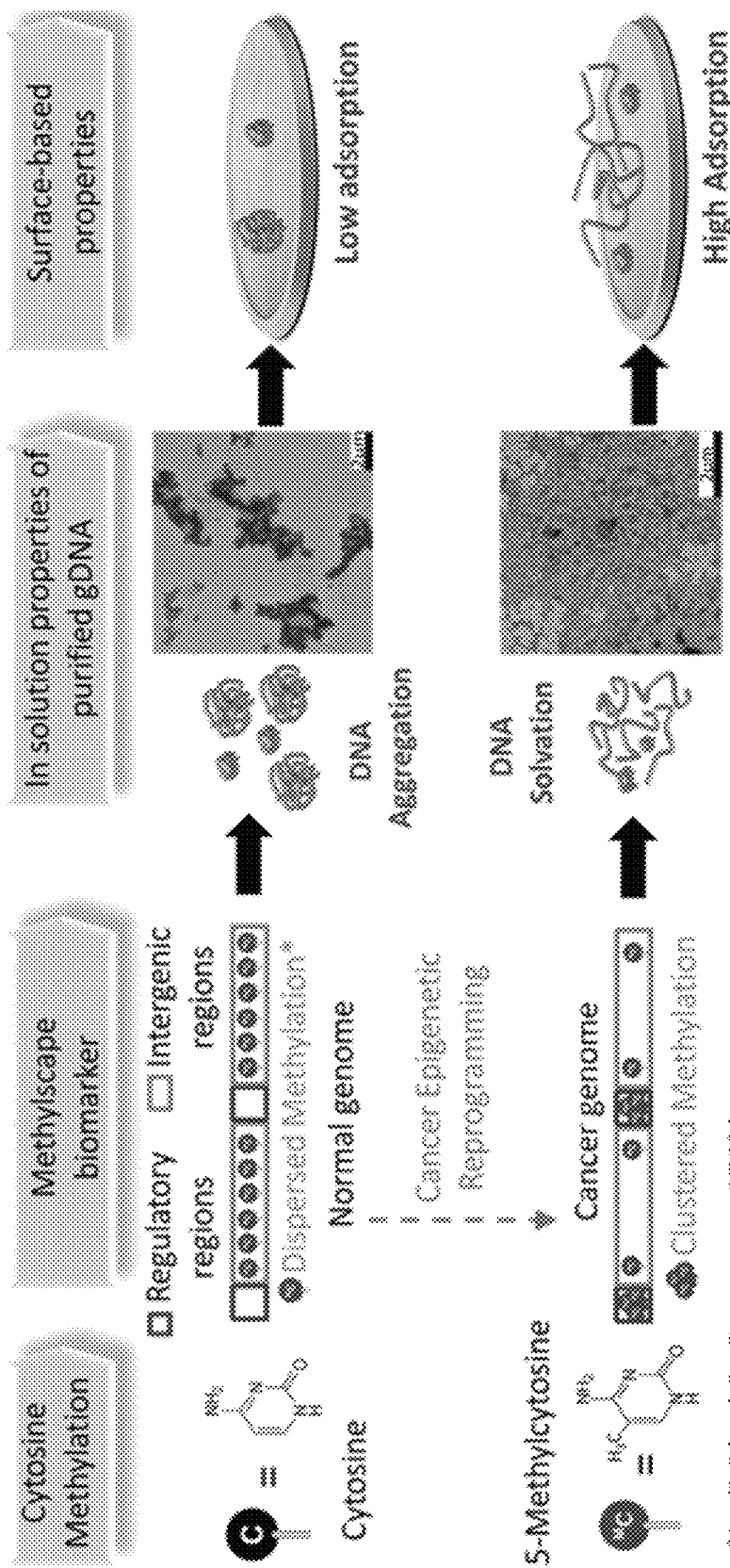
FIG. 1 is a schematic and photographic representation showing that epigenetic reprogramming of the DNA methylation landscape in cancer modulates the solution and surface-based properties of genomic DNA. Scheme: While DNAs from normal cells contain large levels of dispersed methylcytosines, the DNAs from cancer cells are hypomethylated across the genome and tend to cluster most of the methylcytosines into CpG rich regulatory regions. This distinct methylation landscape leads to different solvation properties in solution, which in turn modulates their adsorption towards gold surface. Inset: TEM image showing the different solvation of DNA genome derived from the prostate tissue of a cancer patient and a healthy individual.

Some figures and text contain color representations or entities. Color illustrations are available from the Applicant upon request or from an appropriate Patent Office. A fee my be imposed if obtained from a Patent Office.

DETAILED DESCRIPTION OF THE INVENTION

1. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much 15, 14, 13, 12, 11, 10, 9, 8, 7, 6, 5, 4, 3, 2 or 1% to a reference quantity, level, value, number, frequency, percentage, dimension, size, amount, weight or length.

The term "adsorption" means a type of adhesion taking place at a surface in contact with molecules resulting in the accumulation of the molecules at the surface.

The term "affinity" means the strength of the sum total of noncovalent interactions between a single binding site of a molecule (for example, a genomic DNA molecule of complex thereof) and its binding partner (for example, a solid support). The affinity of a molecule X for its partner Y can generally be represented by the dissociation constant ($K_D$). Affinity can be measured by common methods known in the art, such as, for example, immunoblot, ELISA KD, KinEx A, biolayer interferometry (BLI), or surface plasmon resonance devices.

As used herein, "and/or" refers to and encompasses any and all possible combinations of one or more of the associated listed items, as well as the lack of combinations when interpreted in the alternative (or).

The term "amphipathic" refers to a substance (e.g., a polymer) having hydrophobic and hydrophilic moieties, wherein the hydrophobic moieties of the substance orient into a hydrophobic phase, and the hydrophilic moieties orient toward an aqueous phase.

By "antigen-binding molecule" is meant a molecule that has binding affinity for a target antigen. It will be understood that this term extends to immunoglobulins, immunoglobulin fragments and non-immunoglobulin derived protein frameworks that exhibit antigen-binding activity. Representative antigen-binding molecules that are useful in the practice of the present invention include polyclonal and monoclonal antibodies as well as their fragments (such as Fab, Fab', $F(ab')_2$, Fv), single chain (scFv) and domain antibodies (including, for example, shark and camelid antibodies), and fusion proteins comprising an antibody, and any other modified configuration of the immunoglobulin molecule that comprises an antigen binding/recognition site. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called α, δ, ε, γ, and μ, respectively. The subunit structures and three-dimensional configurations of different classes of immunoglobulins are well known. Antigen-binding molecules also encompass dimeric antibodies, as well as multivalent forms of antibodies. In some embodiments, the antigen-binding molecules are chimeric antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, for example, U.S. Pat. No. 4,816,567; and Morrison et al., 1984, *Proc. Natl. Acad. Sci. USA* 81:6851-6855). Also contemplated, are humanized antibodies, which are generally produced by transferring complementarity determining regions (CDRs) from heavy and light variable chains of a non-human (e.g., rodent, preferably mouse) immunoglobulin into a human variable domain. Typical residues of human antibodies are then substituted in the framework regions of the non-human counterparts. The use of antibody components derived from humanized antibodies obviates potential problems associated with the immunogenicity of non-human constant regions. General techniques for cloning non-human, particularly murine, immunoglobulin variable domains are described, for example, by Orlandi et al. (1989, *Proc. Natl. Acad. Sci. USA* 86: 3833). Techniques for producing humanized monoclonal antibodies are described, for example, by Jones et al. (1986, *Nature* 321: 522), Carter et al. (1992, *Proc. Natl. Acad. Sci. USA* 89: 4285), Sandhu (1992, *Crit. Rev. Biotech.* 12: 437), Singer et al. (1993, *J. Immun.* 150: 2844), Sudhir (ed., Antibody Engineering Protocols, Humana Press, Inc. 1995), Kelley ("Engineering Therapeutic Antibodies," in Protein Engineering: Principles and Practice Cleland et al. (eds.), pages 399-434 (John Wiley & Sons, Inc. 1996), and by Queen et al., U.S. Pat. No. 5,693,762 (1997). Humanized antibodies include "primatized" antibodies in which the antigen-binding region of the antibody is derived from an antibody produced by immunizing macaque monkeys with the antigen of interest. Also contemplated as antigen-binding molecules are humanized antibodies.

As used herein, the term "aqueous conditions" refers to a solution comprised in whole, or in part, water. In some embodiments, the solution has at least or about 60%, 65%, 70%, 75%, 80%, 85%, 90%, 95%, 96%, 97%, 98%, 99% (vol/vol) water. In some of the same and other embodiments, the solution contains acids and/or bases, such as inorganic acids and/or bases. Additionally, the aqueous solution may contain one or more salts or ions, such as inorganic salts or ions. In some embodiments, the solution has a pH of about 3 to about 10, such as a pH of about 3, about 4, about 5, about 6, about 7, about 8, about 9. In some embodiments, the solution has a pH of about 7. In some embodiments, the solution comprises SSC 5× (0.75M NaCl, 0.075M sodium citrate). In particular embodiments, the solution comprises SSC 5× (0.75M NaCl, 0.075M sodium citrate) and has a pH of about 7.

As described herein, the term "bead" refers to a solid support particle. The bead may be organic or inorganic. The bead may be porous or non-porous and substantially non-soluble in an aqueous medium. The bead may be solid, semi-solid, gel or a mixture thereof. The bead may be in the form of a plate, a chip, a fiber, a mesh, a pin, a membrane, such as a nitrocellulose membrane; a container; and a cell or cell membrane. The bead may be coated, for example, with a hydrogel to minimize non-specific binding and self-aggregation. The beads may be of any suitable size that can be used for the methods, compositions and systems disclosed herein. The beads can have any suitable size range but generally have dimensions that fall within the scope of microparticles or nanoparticles. Exemplary bead materials include without limitation latex, glass, metal, ceramic, plastic, such as polycarbonate, polypropylene, polystyrene, nylon, paper, silicon, cellulose, nitrocellulose, agarose, dextran, polyacrylamide and the like or combinations thereof.

As use herein, the term "binds", "specifically binds to" or is "specific for" refers to measurable and reproducible interactions such as binding between a target and an antigen-binding molecule, which is determinative of the presence of the target in the presence of a heterogeneous population of molecules including biological molecules. For example, an antigen-binding molecule that binds to or specifically binds to a target (which can be an epitope) is an antigen-binding molecule that binds this target with greater affinity, avidity, more readily, and/or with greater duration than it binds to other targets. In one embodiment, the extent of binding of an antigen-binding molecule to an unrelated target is less than about 10% of the binding of the antibody to the target as measured, e.g., by a radioimmunoassay (RIA). In certain embodiments, an antigen-binding molecule that specifically binds to a target has a dissociation constant (Kd) of ≤1 µM, ≤100 nM, ≤10 nM, ≤1 nM, or ≤0.1 nM.

The term "biomarker" typically refers to any molecule or a combination of molecules that may provide biological information about the physiological state of a subject. In some cases, the presence or absence of the biomarker may be informative. In some other cases, the level of the biomarker may be informative.

"Biological sample", "sample", and "test sample" are used interchangeably herein to refer to any material, biological fluid, tissue, or cell obtained or otherwise derived from an individual. This includes blood (including whole blood, leukocytes, peripheral blood mononuclear cells, buffy coat, plasma, and serum), sputum, tears, mucus, sweat, nasal washes, nasal aspirate, breath, urine, semen, saliva, meningeal fluid, amniotic fluid, glandular fluid, lymph fluid, bronchial aspirate, synovial fluid, joint aspirate, cells, a cellular extract, secretions of the gastrointestinal tract, ascitic fluid, pleural fluid, intraocular fluid, fluid from a hydrocele (e.g. of the testis), fluid from a cyst, pancreatic secretions, intestinal secretions, aspiration fluids from breast and thyroid, etc. and cerebrospinal fluid. This also includes experimentally separated fractions of all of the preceding. For example, a blood sample can be fractionated into serum or into fractions containing particular types of blood cells, such as red blood cells or white blood cells (leukocytes). If desired, a sample can be a combination of samples from an individual, such as a combination of a tissue and fluid sample. The term "biological sample" also includes materials containing homogenized solid material, such as from a stool sample, a tissue sample (e.g., a sample of a tissue that associates with a cancer), or a tissue biopsy (e.g., a biopsy of a tissue that associates with a cancer), for example. The term "biological sample" also includes materials derived from a tissue culture or a cell culture. Any suitable methods for obtaining a biological sample can be employed; exemplary methods include, e.g., peeling cells using adhesive tape, scraping, phlebotomy, swab (e.g., buccal swab), biopsy touch preparations and fine needle aspirate biopsy procedure. Exemplary tissues include lymph node, esophagus, lung, lung washes, BAL (bronchoalveolar lavage), thyroid, skin, breast, ovary, endometrium, uterus, pancreas, spleen, thymus, bone marrow, colon, stomach, bladder, brain, salivary gland, prostate, testicles and liver. Samples can also be collected, e.g., by micro dissection (e.g., laser capture micro dissection (LCM) or laser micro dissection (LMD)), bladder wash, smear (e.g., a PAP smear), or ductal lavage. A "biological sample" obtained or derived from an individual includes any such sample that has been processed in any suitable manner after being obtained from the individual. In specific embodiments, the biological sample is a tumor sample. In some embodiments, the biological sample comprises any one or more of cellular genomic DNA (cellular gDNA), cell-free DNA (cfDNA), circulating tumor DNA (ctDNA) and extracellular vesicular DNA (evDNA).

The terms "cancer" and "cancerous" refer to or describe the physiological condition in subjects that is typically characterized by unregulated cell growth, with potential to invade locally and/or spread to other parts of the body (metastasize). The term "cancer" is generally used interchangeably with "tumor" herein (unless a tumor is specifically referred to as a "benign" tumor, which is an abnormal mass of cells that lacks the ability to invade neighboring tissue or metastasize), and encompasses malignant solid tumors (e.g., carcinomas, sarcomas) and malignant growths in which there may be no detectable solid tumor mass (e.g., certain hematologic malignancies). Non-limiting examples of cancers include but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenström's macroglobulinemia, and heavy chain disease. In some embodiments, cancers are epithelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

As used herein, the term "cancer biomarker" refers to a biomarker characteristic of a tumor or cancer cell or tissue but not a normal cell or tissue. The biomarker characteristic includes, but is not limited to: (1) methylation status; (2) a nucleic acid sequence; and (3) a mutation or single-nucleotide polymorphism (SNP), which region, sequence or mutation/SNP that can be associated with subjects having cancer or a stage of cancer, as compared with those not having cancer. In the context of the present invention, an "ancillary cancer biomarker" excludes methylation status and is suitably selected from a nucleic acid sequence and a mutation or SNP, which can be associated with subjects having cancer or a stage of cancer, as compared with those not having cancer.

The term "cell-free DNA (cfDNA)" refers to DNA in a sample that when collected, was not contained within a cell. cfDNAs can comprise both normal cell and cancer cell-derived DNA. cfDNA is commonly obtained from blood or plasma ("circulation"). cfDNAs may be released into the circulation through secretion or cell death processes, e.g., cellular necrosis or apoptosis. Some cfDNA is circulating tumor DNA.

The term "chemotherapy" refers to a therapy of a human or animal with one or more chemotherapeutic agents, which inhibit or abrogate cell growth and cell division, namely, the therapy is taken as a cell proliferation inhibitor or is used for inducing cell death (cell apoptosis). Compared with normal cells, cancer cells grow and divide uncontrollably so that the chemotherapy should be more effective to the cancer cells.

"Chemotherapeutic agent" includes compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafarnib (SCH 66336), sorafenib (NEXAVAR®, Bayer Labs), gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (Angew Chem. Intl. Ed. Engl. 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-α, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG.sub.1 .lamda. antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. Eur. J. Cancer 32A:636-640 (1996)); EMD7200 (matuzumab) a humanized EGFR antibody directed against EGFR that competes with both EGF and TGF-α for EGFR binding (EMD/Merck); human EGFR antibody, HuMax-EGFR (GenMab); fully human antibodies known as E1.1, E2.4, E2.5, E6.2, E6.4, E2.11, E6.3 and E7.6.3 and described in U.S. Pat. No. 6,235,883; MDX-447 (Medarex Inc); and mAb 806 or humanized mAb 806 (Johns et al., J. Biol. Chem. 279(29): 30375-30384 (2004)). The anti-EGFR antibody may be conjugated with a cytotoxic agent, thus generating an immunoconjugate (see, e.g., EP659439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quin-azolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol)-; (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(-dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6[5[[[2methylsulfonyl) ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d] pyrimidines; curcumin (diferuloyl methane, 4,5-bis(4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804, 396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN BioTherapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor α (TNF-α) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T-cell costimulation blockers such as abatacept (Orencia), Interleukin 6 (IL-6) blockers such as tocilizumab (ACTEMERA®); Interleukin 13 (IL-13) blockers such as lebrikizumab; Interferon α (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/P2 blockers such as Anti-lymphotoxin a (LTa); radioactive isotopes (e.g., $At^{21}$, $I^{131}$, $I^{125}$, $Y^{90}$, $Re^{186}$, $Re^{188}$, $Sm^{153}$, $Bi^{212}$, $p^{32}$, $Pb^{212}$ and radioactive isotopes of Lu); miscellaneous investigational agents such as thioplatin, PS-341, phenylbutyrate, ET-18-OCH3, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhea, metastatic bone pain, headache and migraine, postoperative pain, mild-to-moderate pain due to inflammation and tissue injury, pyrexia, ileus, and renal colic.

The term "circulating tumor DNA (ctDNA)" or "circulating cancer DNA" refers to the fraction of cell-free DNA (cfDNA) that originates from a tumor.

As used herein, the terms "clustered distribution of methylated nucleotides" and "DNA methylation cluster" are used interchangeably herein to refer to a region of genomic DNA that comprises a higher frequency of methylated nucleotides than a flanking or adjacent region of genomic DNA. In some embodiments, a clustered distribution of methylated nucleotides refers to a region of genomic DNA that has at least about 2, 3, 4, 5, 6, 7, 8, 9, 10, 15, 20, 30, 40, 50, 100, 200, 300, 400, 500 or even more than 1000 times the frequency of methylated nucleotides than a flanking or adjacent region of genomic DNA. In specific examples of this type, the flanking region is an unmethylated region. In some embodiments, at least about 10%, 20%, 30%, 40%, 50%, 60%, 70%, 80%, 90%, 95%, or even about 100% of the nucleotides of a DNA methylation cluster are methylated. The DNA methylation cluster may be less than 100 bp; 100-200 bp, 200-300 bp, 300-500 bp, 500-750 bp; 750-1000 bp; 100 or more bp in length. In specific embodiments, at least about 10%, 20%, 30%, 40%, 50%, 60%, 70%, 80%, 90%, 95% or even about 100%, of the cytosines in a respective CpG cluster are methylated.

The term "clustered methylated genomic DNA", as used herein refers to genomic DNA that comprises a mosaic DNA methylation pattern that includes a DNA methylation cluster and at least one region that flanks the DNA methylation cluster, which comprises a lower frequency of methylated nucleotides than the DNA methylation cluster. In some embodiments, the at least one flanking region comprises a frequency of methylated cytosines that is no more than about $\frac{1}{2}$, $\frac{1}{3}$, $\frac{1}{4}$, $\frac{1}{5}$, $\frac{1}{6}$, $\frac{1}{7}$, $\frac{1}{8}$, $\frac{1}{9}$, $\frac{1}{10}$, $\frac{1}{20}$, $\frac{1}{30}$, $\frac{1}{40}$, $\frac{1}{50}$ or $\frac{1}{100}$ of the frequency of methylated cytosines in a respective CpG cluster.

As used herein, the term "colloidal particle" refers to particles, including nanoparticles and microparticles, that are capable of dispersing without settling, to form a colloidal dispersion.

The term "complex" refers to an assemblage or aggregate of molecules (e.g., nucleic acid molecules such as genomic DNA molecules) in direct and/or indirect contact with one another. In specific embodiments, "contact", or more particularly, "direct contact" means two or more molecules are close enough so that attractive noncovalent interactions, such as Van der Waal forces, hydrogen bonding, ionic and hydrophobic interactions, and the like, dominate the interaction of the molecules. In such embodiments, a complex of molecules (e.g., nucleic acid molecules such as genomic DNA molecules) is formed under conditions such that the complex is thermodynamically favored (e.g., compared to a non-aggregated, or non-complexed, state of its component molecules). In specific embodiments, the complex is a particle.

Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. For example, the phrase "an isolated nucleic acid complex comprising a plurality of genomic DNA molecules each comprising a clustered distribution of methylated nucleotides" indicates that the isolated nucleic acid complex requires the plurality of said genomic DNA molecules but may or may not include other elements including for example other nucleic acid molecules (e.g., other genomic DNA molecules) that do not comprise a clustered distribution of methylated nucleotides. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present.

As used herein, the term "conjugate" refers to the association between molecules. The association can be direct or indirect. For example, a conjugate between a nucleic acid (e.g., a genomic DNA molecule) and a protein (e.g., an antigen-binding molecule, or substrate as described for example herein) can be direct, e.g., by covalent bond, or indirect, e.g., by non-covalent bond (e.g. electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like).

As used herein "CpG dinucleotide" refers to a nucleic acid region where a cytosine nucleotide occurs next to a guanine nucleotide in the linear sequence of bases along its length.

As used herein, the term "CpG cluster" refers to genomic DNA in which CpG dinucleotides are overrepresented as compared to their average occurrence within a given genome. In many genes, a CpG cluster may begin just upstream of a promoter and extend downstream into a transcribed region. The CpG cluster may also surround the 5' region of the coding region of the gene as well as the 3' region of the coding region. CpG clusters can be found in multiple regions of a gene like upstream of coding regions in a regulatory region including a promoter region; within the coding regions (e.g., exons); downstream of coding regions in, for example, enhancer regions; or within introns. In some embodiments, a CpG cluster has a GC percentage that is greater than 50% and with an observed/expected CpG ratio that is greater than 60%. The CpG cluster may be less than 100 bp; 100-200 bp, 200-300 bp, 300-500 bp, 500-750 bp; 750-1000 bp; 100 or more bp in length. In specific embodiments, at least about 10%, 20%, 30%, 40%, 50%, 60%, 70%, 80%, 90%, or even about 100%, of the cytosines in a respective CpG cluster are methylated. In these embodiments, the CpG cluster is typically flanked by at least one region that comprises a lower frequency of methylated nucleotides than a respective CpG cluster.

The terms "correlate" and "correlating" generally refers to determining a relationship between one type of data with another or with a state. In various embodiments, correlating a methylscape physical or physicochemical feature or feature panel, and optionally a methylation status of methylscape genomic DNA, with the presence or absence of a condition (e.g., a condition selected from a healthy condition, carcinoma, a particular stage of carcinoma, or a particular severity of carcinoma) comprises determining the presence, absence or level of a methylscape physical or physicochemical feature or feature panel, and optionally a methylation status of methylscape genomic DNA, in a biological sample obtained from a subject that suffers from that condition; or in persons known to be free of that condition. In specific embodiments, a profile of methylscape physical or physicochemical features or feature panels, and optionally methylation statuses of methylscape genomic DNA levels, absences or presences is correlated to a global probability or a particular outcome, using receiver operating characteristic (ROC) curves.

The term "cytotoxic agent" as used herein refers to any agent that is detrimental to cells (e.g., causes cell death, inhibits proliferation, or otherwise hinders a cellular function). Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof. Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A, inhibitors of fatty acid biosynthesis, cell cycle signaling inhibitors, HDAC inhibitors, proteasome inhibitors, and inhibitors of cancer metabolism. In some embodiments, the cytotoxic agent is a taxane. In representative examples of this type, the taxane is paclitaxel or docetaxel. In some embodiments, the cytotoxic agent is a platinum agent. In some embodiments, the cytotoxic agent is an antagonist of EGFR. In representative examples of this type, the antagonist of EGFR is N-(3-ethynylphenyl)-6,7-bis(2-methoxyethoxy)quinazolin-4-amine (e.g., erlotinib). In some embodiments, the cytotoxic agent is a RAF inhibitor. In non-limiting examples of this type, the RAF inhibitor is a BRAF and/or CRAF inhibitor. In other non-limiting examples, the RAF inhibitor is vemurafenib. In one embodiment the cytotoxic agent is a PI3K inhibitor.

As used herein, the term "cytotoxic therapy" refers to therapies that induce cellular damage including but not limited to radiation, chemotherapy, photodynamic therapy, radiofrequency ablation, anti-angiogenic therapy, and combinations thereof. A cytotoxic therapeutic may induce DNA damage when applied to a cell.

The term "detection" includes any means of detecting, including direct and indirect detection.

"DNA methylation" refers to the addition of a methyl moiety to a nucleotide base, where the methyl moiety is not present in a recognized typical nucleotide base. Thus, a "methylated nucleotide" refers to the presence of a methyl moiety on a nucleotide base, where the methyl moiety is not present in a recognized typical nucleotide base. For example, cytosine does not contain a methyl moiety on its pyrimidine ring, however 5-methylcytosine contains a methyl moiety at position 5 of its pyrimidine ring. In this respect, cytosine is not a methylated nucleotide and 5-methylcytosine is a methylated nucleotide. Methylation of cytosine can occur in cytosines in other sequence contexts, for example 5'-CHG-3' and 5'-CHH-3', where H is adenine, cytosine or thymine. Cytosine methylation can also be in the form of 5-hydroxymethylcytosine. Methylation of DNA can include methylation of non-cytosine nucleotides, such as N6-methyladenine.

As used herein, the term "electrochemical detection" refers to a detection of an electrochemically detectable property of the analyte by electrochemical means, such as an electrochemical detection reaction. Thus, for example, the electrochemical detection reaction may be detected by comparing one or more electrode potentials, such as a potential of a working electrode with the potential of one or more further electrodes such as a counter electrode or a reference electrode. The detection may be analyte specific. The detection may be a qualitative and/or a quantitative detection. Representative electrochemical detection techniques (e.g., differential pulse voltammetry, Impedance, cyclic voltammetry) involve initial measurement of a baseline electrical signal (e.g., current, voltage, impedance, capacitance, charge, conductivity, resistance, or a combination thereof) from a working electrode comprising an electroconductive material in presence of an electrolyte solution, adding a sample comprising an analyte to the working electrode, and measuring a sample electrical signal (e.g., current, voltage, impedance, capacitance, charge, conductivity, resistance, or a combination thereof) from the working electrode, wherein the sample electrical signal is suitably normalized with the baseline electrical signal to determine the level of interaction between the analyte and the electroconductive material.

The term "elute" or "eluting" or "elution" refers to releasing of a molecule (e.g., a nucleic acid molecule of interest) from a substrate. This release may be facilitated by using or altering certain solution conditions, whereby a buffer (referred to as an "elution buffer") or buffer component competes with the molecule of interest for binding to the substrate, or by electrochemical desorption, nanoscopic shear force (e.g., nanoshearing), mechanical agitation, sonication, nucleic acid digestion or cleavage agents (e.g., restriction endonucleases), protein digestive enzymes (pepsin, trypsin), or any combination thereof.

As used herein, the term "epigenome" refers to changes to genetic material that are not reflected at the sequence level such as DNA methylation and chromatin restructuring or remodeling. Thus, the term "epigenetic" refers to the state or condition of DNA with respect to changes in function without a change in the nucleotide sequence. Such changes are referred to in the art as "epigenetic modifications", and tend to result in expression or silencing of genes. The term "epigenetic biomarker", as used herein, refers to functionally relevant changes to a nucleic acid sequence, other than a change in the underlying nucleotide sequence itself, which modulates expression of the nucleic acid sequence. Examples of mechanisms that produce such changes are DNA methylation and histone modification, each of which alters how genes are expressed without altering the underlying DNA sequence. In specific embodiments, the "epigenetic biomarker" refers to a clustered methylated genomic DNA. Suitably, such DNA molecules self-assemble to form a complex, typically a particulate complex, under aqueous conditions.

As used herein, the term "extracellular vesicle" refers to a cell-derived vesicle comprising a membrane that encloses an internal space. Extracellular vesicles comprise all membrane-bound vesicles that have a smaller diameter than the cell from which they are derived. Generally extracellular vesicles range in diameter from 20 nm to 1000 nm, and can comprise various macromolecular cargo either within the internal space, displayed on the external surface of the extracellular vesicle, and/or spanning the membrane. The cargo can comprise nucleic acids (e.g., gDNA), proteins, carbohydrates, lipids, small molecules, and/or combinations thereof. By way of example and without limitation, extracellular vesicles include apoptotic bodies, fragments of cells, vesicles derived from cells by direct or indirect manipulation (e.g., by serial extrusion or treatment with alkaline solutions), vesiculated organelles, and vesicles produced by living cells (e.g., by direct plasma membrane budding or fusion of the late endosome with the plasma membrane). Extracellular vesicles can be derived from a living or dead organism, explanted tissues or organs, and/or cultured cells.

The term "extracellular vesicular DNA (evDNA)" refers to the fraction of DNA (e.g., gDNA) that originates from an extracellular vesicle.

As used herein, the term "gene" refers to a genomic DNA sequence that comprises a coding sequence associated with the production of a polypeptide or polynucleotide product (e.g., microRNA, ribosomal RNA, transfer RNA). The methylation level of a gene as used herein, encompasses the methylation level of sequences which are known or predicted to affect expression of the gene, including the promoter, enhancer, and transcription factor binding sites. As used herein, the term "enhancer" refers to a cis-acting region of DNA that is located up to 1 Mbp (upstream or downstream) of a gene.

The term "genomic DNA" of "gDNA", as used herein, refers to any DNA that is derived from a genome. The genomic DNA may be isolated from a cell, i.e., contained within a cell, or from a biological fluid (e.g., blood or fraction thereof such as plasma). The term "genomic DNA" includes within its scope circulating tumor DNA (ctDNA), cell-free DNA (cfDNA) and extracellular vesicular DNA (evDNA).

As used herein, "instructional material" includes a publication, a recording, a diagram, or any other medium of expression which can be used to communicate the usefulness of the compositions and methods of the invention. The instructional material of the kit of the invention may, for example, be affixed to a container which contains the therapeutic or diagnostic agents of the invention or be shipped together with a container which contains the therapeutic or diagnostic agents of the invention.

The term "methylation landscape" as used herein refers to a map or pattern of DNA methylation of a genome or part thereof. The methylation landscape of genomic DNA may comprise largely evenly dispersed (uniform) methylation throughout the genome with typically short regions (e.g., CpG clusters) that are unmethylated. This pattern of DNA methylation is typically representative of normal or non-disease genomic DNA. Alternatively, the methylation landscape of genomic DNA may comprise a mosaic or patterned DNA methylation comprising regions of methylated DNA interspersed with regions that are unmethylated, representative examples of which include clustered methylated genomic DNA, as described herein. This pattern of DNA methylation is typically representative of cancer genomes, which is referred to herein as "cancer methylscape".

As used herein, a "methylation state", "methylation profile", and "methylation status" of a nucleic acid molecule refers to the presence of absence of one or more methylated nucleotide bases in the nucleic acid molecule. These terms include within their scope methylation characteristics of a target site such as, but not limited to, a gene, gene region, or CpG cluster at a particular locus relevant to methylation (e.g., at one or more particular CpG dinucleotides). Such characteristics include, but are not limited to, whether any of the nucleotides (e.g., cytosines) within this target site are methylated, location of methylated nucleotide(s) (e.g., methylated cytosine(s)), ratio or percentage of methylated nucleotide(s) (e.g., methylated cytosine(s)) at any particular contiguous sequence of nucleotides, and allelic differences in methylation due to, e.g., difference in the origin of the alleles.

The term "microparticle" refers to a particle having a characteristic dimension of less than about 1 millimeter and at least about 1 micrometer, where the characteristic dimension of the particle is the smallest cross-sectional dimension of the particle.

The term "noble metal" as used herein refers to a metallic element that is resistant to corrosion in moist air. Non-limiting examples of noble metals include Copper (Cu), Ruthenium (Ru), Rhodium (Rh), Palladium (Pd), Silver (Ag), Rhenium (Re), Osmium (Os), Iridium (Ir), Platinum (Pt), Gold (Au), Mercury (Hg), or combinations thereof.

The term "nanoparticle" refers to a particle having a characteristic dimension of less than about 1 micrometer and at least about 1 nanometer, where the characteristic dimension of the particle is the smallest cross-sectional dimension of the particle.

As used herein, the term "packaging material" refers to a physical structure housing the components of a kit.

The terms "particle" refers to a small object, fragment, or piece of a substance that may be a single element, inorganic material, organic material, or mixture thereof. Examples of particles include polymeric particles, single-emulsion particles, double-emulsion particles, coacervates, liposomes, microparticles, nanoparticles, macroscopic particles, pellets, crystals, aggregates, composites, pulverized, milled, or otherwise disrupted matrices, and cross-linked protein or polysaccharide particles, each of which have an average characteristic dimension of about less than about 1 mm and at least 1 nm, where the characteristic dimension, or "critical dimension", of the particle is the smallest cross-sectional dimension of the particle. A particle may be composed of a single substance or multiple substances. In certain embodiments, the particle is a nanoparticle. In certain embodiments, the particle is a microparticle.

As used herein, the term "self-assemble" or "self-assembly" refers to the ability of self-assembling molecules (e.g., nucleic acid molecules such as genomic DNA molecules) described herein to form a complex under a specified condition (e.g., aqueous conditions) and/or in response to at least an environmental or external stimulus, including for example, a particular pH, temperature, light (including a particular wavelength of light), humidity, and/or ionic strength. In some embodiments, the formation of a self-assembled complex can be spontaneous (e.g., the self-assembly process occurs within about 15 minutes, within about 10 minutes, within about 5 minutes or less). In some embodiments, the formation of a self-assembled complex can occur over a longer period of time, for example, over a period of about 30 minutes, about 1 hour, about 2 hours or more.

The term "single nucleotide polymorphism" or "SNP" refers to a variation in a single nucleotide that occurs at a specific position in a genome, where each variation is present to some appreciable degree within the population comprising the genome. It is to be understood that within the context of the present invention, the terms "mutation" and "point mutation" are meant to include and/or refer to SNPs.

The term "solid support" refers to any substrate having a surface to which molecules may be attached, directly or indirectly, through either covalent or non-covalent bonds. The solid support may include any substrate material that is capable of providing physical support for the molecules and/or complexes of the invention that are attached to the surface. The material is generally capable of enduring conditions related to the attachment of the molecules and/or complexes of the invention to the surface and any subsequent treatment, handling, or processing encountered during the performance of an assay. The materials may be naturally occurring, synthetic, or a modification of a naturally occurring material.

The terms "subject", "patient", "host" or "individual" used interchangeably herein, refer to any subject, particularly a vertebrate subject, and even more particularly a mammalian subject, for whom diagnosis, therapy or prophylaxis is desired. Suitable vertebrate animals that fall within the scope of the invention include, but are not restricted to, any member of the subphylum Chordata including primates (e.g., humans, monkeys and apes, and includes species of monkeys such from the genus *Macaca* (e.g., cynomolgus monkeys such as *Macaca fascicularis*, and/or rhesus monkeys (*Macaca mulatta*)) and baboon (*Papio ursinus*), as well as marmosets (species from the genus *Callithrix*), squirrel monkeys (species from the genus *Saimiri*) and tamarins (species from the genus *Saguinus*), as well as species of apes such as chimpanzees (Pan troglodytes)), rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as canaries, budgerigars etc.), marine mammals (e.g., dolphins, whales), reptiles (e.g., snakes, frogs, lizards), and fish. A preferred subject is one who has or is suspected of having cancer. In specific embodiments, the subject is a human. However, it will be understood that the aforementioned terms do not imply that symptoms are present.

The term "treating" as used herein, unless otherwise indicated, means reversing, alleviating, inhibiting the progress of, or preventing, either partially or completely, the growth of the cancer, tumor metastasis, or other cancer-causing or neoplastic cells in a patient. The term "treating" as used herein, unless otherwise indicated, also means alleviating, inhibiting the progress of, or preventing, either partially or completely, the symptoms associated with a cancer, such as organ failure, pain or any other symptoms known to persons skilled in the art as being associated with a cancer. The term "treatment" as used herein, unless otherwise indicated, refers to the act of treating.

As used herein, the term "treatment regimen" refers to prophylactic and/or therapeutic (i.e., after onset of a specified condition) treatments, unless the context specifically indicates otherwise. The term "treatment regimen" encompasses natural substances and pharmaceutical agents (i.e., "drugs") as well as any other treatment regimen including but not limited to dietary treatments, physical therapy, exercise regimens, surgical interventions, radiation therapy and combinations thereof.

The term "tumor", as used herein, refers to any neoplastic cell growth and proliferation, whether malignant or benign, and all pre-cancerous and cancerous cells and tissues.

The term "tumor sample" as used herein means a sample comprising tumor material obtained from a cancerous patient. The term encompasses clinical samples, for example tissue obtained by surgical resection and tissue obtained by biopsy, such as for example a core biopsy or a fine needle biopsy. The term also encompasses samples comprising tumor cells obtained from sites other than the primary tumor, e.g., circulating tumor cells, as well as preserved tumor samples, such as formalin-fixed, paraffin-embedded tumor samples or frozen tumor samples. The term encompasses cells that are the progeny of the patient's tumor cells, e.g., cell culture samples derived from primary tumor cells or circulating tumor cells. The term encompasses samples that may comprise protein or nucleic acid material shed from tumor cells in vivo, e.g., bone marrow, blood, plasma, serum, and the like. The term also encompasses samples that have been enriched for tumor cells or otherwise manipulated after their procurement and samples comprising polynucleotides and/or polypeptides that are obtained from a patient's tumor material.

The term "unmethylated" as used herein refers to low degrees of methylation, preferably less than 20%, 10%, %, 2% or 1%. Also included within the term "unmethylated" is the complete absence of methylation or the absence of detectable methylation.

Each embodiment described herein is to be applied mutatis mutandis to each and every embodiment unless specifically stated otherwise.

2. Epigenetic Biomarker

The present invention is predicated in part on the determination that the methylscape of genomic DNA in cancer changes the physicochemical properties of the genomic DNA in such a way that it facilitates self-assembly of genomic DNA molecules under aqueous conditions to form nucleic acid complexes and increases the affinity of the genomic DNA molecules for solid supports to which hydrophobic moieties (e.g., methylated nucleotides such as methylated cytosines), including clustered hydrophobic moieties (e.g., clustered methylated nucleotides such as clustered methylated cytosines) adsorb under aqueous conditions. The present invention takes advantage of these findings to provide various methods, systems, conjugates, compositions and kits for detecting cancer methylscape biomarker, including for determining likelihood of the presence of cancer, as described hereafter.

2.1 Detection of Epigenetic Biomarker

Accordingly, the present invention provides an isolated nucleic acid complex comprising a plurality of genomic DNA molecules (also referred to herein as "cancer methylscape genomic DNA molecules"), each cancer methylscape genomic DNA molecule comprising a clustered distribution of methylated nucleotides (e.g., methylated cytosines), wherein the complex is formed by self-assembly of the DNA molecules under aqueous conditions. Suitably, the methylated nucleotides (e.g., methylated cytosines) are in at least one CpG cluster. In illustrative examples of this type, at least about 10%, 20%, 30%, 40%, 50%, 60%, 70%, 80%, 90%, or even about 100%, of the nucleotides (e.g., cytosines) in a respective CpG cluster are methylated. Typically, the CpG cluster is flanked by at least one region that comprises a lower frequency of methylated nucleotides (e.g., methylated cytosines) than a respective CpG cluster. For example, the at least one flanking region may comprise a frequency of methylated nucleotides (e.g., methylated cytosines) that is no more than about ½, ⅓, ¼, ⅕, ⅙, ⅐, ⅛, ⅑, 1/10, 1/20, 1/30, 1/40, 1/50 or 1/100 of the frequency of methylated nucleotides (e.g., methylated cytosines) in a respective CpG cluster. Suitably, the genomic DNA molecules are amphipathic.

The cancer methylscape genomic DNA molecules may have a length of between 50 and 50,000 base pairs. For example, the genomic DNA molecules may be up to 300, up to 400, up to 500, up to 1000, up to 2,000, up to 3,000, up to 4,000, up to 5,000, up to 10,000, up to 15,000, or even up to 20,000 base pairs in length. In some of the same embodiments, the genomic DNA molecules may be at least 25, at least 50, at least 75, at least 100, or at least 200 base pairs in length.

The nucleic acid complex (also referred to herein as "cancer methylscape nucleic acid complex") is significantly smaller than a nucleic acid complex formed from self-assembly of normal or non-diseased methylscape genomic DNA (also referred to herein as "normal methylscape nucleic acid complex"). In specific embodiments, the cancer methylscape nucleic acid complex has a size that is less than about 50%, 40%, 30%, 20%, 10%, 5% or 1% of the size of a normal methylscape nucleic acid complex (e.g., prepared under the same conditions as the cancer methylscape nucleic acid complex). For example, the cancer methylscape nucleic acid complex typically has a size that falls within the scope of microparticles or nanoparticles. For example the nucleic acid complex may have a size of about 10 $nm^2$ to about 2000 $nm^2$, 50 $nm^2$ to about 2000 $nm^2$, 100 $nm^2$ to about 2000 $nm^2$, 500 $nm^2$ to about 2000 $nm^2$, or 1000 $nm^2$ to about 2000 $nm^2$, under aqueous conditions.

The cancer methylscape genomic DNA molecule and/or nucleic acid complex are typically present in a biological sample obtained from a subject. In some embodiments, the biological sample is a tissue sample (e.g., a tissue biopsy sample) or a fluid sample (e.g., blood). In some instances, the biological sample is a cell-free biological sample. In some instances, the biological sample is a circulating tumor DNA sample. In specific embodiments, the biological sample is a cell free biological sample containing circulating tumor DNA.

In particular embodiments, the cancer methylscape genomic DNA molecule and/or nucleic acid complex is obtained from a fluid sample. In non-limiting examples of this type, the fluid sample comprises blood or other fluid samples of biological origin including, but not limited to, peripheral blood, sera, plasma, ascites, urine, cerebrospinal fluid (CSF), sputum, saliva, bone marrow, synovial fluid, aqueous humor, amniotic fluid, cerumen, breast milk, bronchioalveolar lavage fluid, semen, prostatic fluid, Cowper's fluid or pre-ejaculatory fluid, female ejaculate, sweat, tears, cyst fluid, pleural and peritoneal fluid, pericardial fluid, ascites, lymph, chyme, chyle, bile, interstitial fluid, menses, pus, sebum, vomit, vaginal secretions/flushing, synovial fluid, mucosal secretion, stool water, pancreatic juice, lavage fluids from sinus cavities, bronchopulmonary aspirates, blastocyl cavity fluid, or umbilical cord blood. In some embodiments, the biological fluid is blood, a blood derivative or a blood fraction, e.g., serum or plasma. In a specific embodiment, a sample comprises a plasma sample. In another embodiment, a serum sample is used. In another embodiment, a sample comprises urine. The fluid sample may encompass a sample that has been manipulated in any way after their procurement, such as by centrifugation, filtration, precipitation, dialysis, chromatography, treatment with reagents, washed, or enriched for certain cell populations.

In some embodiments, the cancer methylscape genomic DNA molecule and/or nucleic acid complex is obtained from a tissue sample. In some instances, a tissue corresponds to any cell(s). Different types of tissue correspond to different types of cells (e.g., intestine, liver, lung, blood, connective tissue, and the like), but also healthy cells vs. tumor cells or to tumor cells at various stages of cancer, or to displaced malignant tumor cells. In some embodiments, a tissue sample further encompasses a clinical sample, and also includes cells in culture, cell supernatants, organs, and the like. Samples also comprise fresh-frozen and/or formalin-fixed, paraffin-embedded tissue blocks, such as blocks prepared from clinical or pathological biopsies, prepared for pathological analysis or study by immunohistochemistry.

The present invention also provides systems, which are suitable for detecting cancer methylscape genomic DNA molecule and/or nucleic acid complex. These systems generally comprise: (1) a biological sample comprising a cancer methylscape genomic DNA molecule or nucleic acid complex; and (2) a sensor, which is in communication with the biological sample, for detecting the presence or level of the genomic DNA molecule and/or nucleic acid complex.

Suitably, the sensor is selected from one or more of: an antigen-binding molecule that binds specifically with the nucleic acid complex, a light based sensor, a spectrometer, a refractometer, a monochromator, an x-ray, an absorption detector, a reflectance detector, a transmission detector, a conductivity sensor, an electrode, a resistive pulse sensor, a camera, a microscope, a particle size analyzer, an optical detector, a solid support to which hydrophobic moieties adsorb under the aqueous conditions, a colloidal particle or a biosensor.

In some embodiments, the nucleic acid complex is detected by exposing the biological sample to electromagnetic radiation and detecting a physical feature that is indicative of the nucleic acid complex. In non-limiting examples of this type. the physical feature is selected from size, shape or aggregation status of the nucleic acid complex. For example, the size may be about 10 $nm^2$ to about 2000 $nm^2$, 50 $nm^2$ to about 2000 $nm^2$, 100 $nm^2$ to about 2000 $nm^2$, 500 $nm^2$ to about 2000 $nm^2$, or 1000 $nm^2$ to about 2000 $nm^2$, in the aqueous conditions. In some embodiments, the electromagnetic radiation includes light. In some of the same and other embodiments, the electromagnetic radiation includes at least one of an x-ray radiation, a microwave radiation, an infrared light, a radio frequency signal or an ultraviolet light. In some of the same and other embodiments, the physical feature is detected by receiving electromagnetic radiation (e.g., scattered, refracted, phase-shifted, or emitted electromagnetic radiation, particle beams, visible light, etc.) from the nucleic acid complex. In illustrative examples of this type, the physical feature is detected by microscopy and the sensor suitably includes a microscope (e.g., transmission electron microscope).

The sensor may comprise an affinity agent for which the cancer methylscape genomic DNA molecule or nucleic acid complex has affinity. In these embodiments, the affinity agent and the cancer methylscape genomic DNA molecule or nucleic acid complex form a conjugate that is detectable by various means, including immunoassay, visual or colorimetric detection and electrochemical detection. Suitably, the affinity agent is selected from antigen-binding molecules that bind specifically with the nucleic acid complex and solid supports to which hydrophobic moieties (e.g., methylated nucleotides such as methylated cytosines) adsorb under the aqueous conditions.

In embodiments in which the affinity agent is an antigen-binding molecule, the conjugate is typically detected by immunoassay. A variety of immunoassay techniques, including competitive and non-competitive immunoassays, can be used including, without limitation, western blot, immunoprecipitation, flow cytometry, enzyme immunoassays (EIA), such as enzyme multiplied immunoassay technique (EMIT), enzyme-linked immunosorbent assay (ELISA), IgM antibody capture ELISA (MAC ELISA), and microparticle enzyme immunoassay (META), capillary electrophoresis immunoassays (CEIA), radio-immunoassays (MA), immunoradiometric assays (IRMA), fluorescence polarization immunoassays (FPIA), and chemiluminescence assays (CL). If desired, such immunoassays can be automated. Immunoassays can also be used in conjunction with laser induced fluorescence. Liposome immunoassays, such as flow-injection liposome immunoassays and liposome immunosensors, are also suitable for use in the present invention. In addition, nephelometry assays, in which, for example, the formation of biomolecular complexes results in increased light scatter that is converted to a peak rate signal as a function of the marker concentration, are suitable for use in the systems and methods of the present invention. In specific embodiments, the conjugate is detected by ELISA, RIA, fluoro immunoassay (FIA) or soluble particle immune assay (SPIA).

In embodiments in which the affinity agent is a solid support, the solid support is preferably one to which clustered hydrophobic moieties (e.g., clustered methylated nucleotides such as methylated cytosines) adsorb under aqueous conditions. In exemplary embodiments, the solid support to which hydrophobic moieties (e.g., methylated nucleotides such as methylated cytosines) adsorb more strongly than hydrophilic moieties under aqueous conditions. In some of the same and other embodiments, the solid support is one to which clustered hydrophobic moieties (e.g., clustered methylated nucleotides such as clustered methylated cytosines) adsorb more strongly than non-clustered hydrophobic moieties (e.g., non-clustered methylated nucleotides such as non-clustered methylated cytosines) under aqueous conditions. Non-limiting solid supports may be selected from organic polymers such as polystyrene and its derivatives, polyacrylates and polymethacrylates and their derivatives, polyurethanes, nylon, polyethylene, polypropylene, polybutylene and copolymers of these materials, polysaccharides and hydrogels such as agarose, cellulose, dextran, Sephadex, Sephacryl, chitosan, inorganic supports such as silica gels, silica particles, glass, metal, semi-metal oxides, and supports with metal surfaces. In representative examples, the solid support is selected from a polymer bead, an agarose bead, a polystyrene bead, an acrylamide bead, a solid core bead, a porous bead, a paramagnetic bead, glass bead, controlled pore bead, a microtiter well, a cyclo-olefin copolymer substrate, a membrane, a plastic substrate, nylon, a Langmuir-Blodgett film, glass, a germanium substrate, a silicon substrate, a silicon wafer chip, a flow through chip, a microbead, a nanoparticle, a polytetrafluoroethylene substrate, a polystyrene substrate, a metal substrate such as a gold (Au) substrate, a silver (Ag) substrate; a tin (Sn) substrate, a rhodium (Rh) substrate, a ruthenium (Ru) substrate, a palladium (Pd) substrate, an osmium (Os) substrate, an iridium (Ir) substrate, a platinum (Pt) substrate, a titanium (Ti) substrate, an aluminum (Al) substrate, a chromium (Cr), a copper (Cu) substrate, a magnesium (Mg) substrate, a carbon substrate, a silicon substrate such as p-type doped silicon substrate, n-type doped silicon substrate, and gallium arsenide. In any of the above embodiments, the solid support may be a colloidal particle. In non-limiting examples of this type, the colloidal particle comprises a metal substrate such as a gold (Au) substrate, a silver (Ag) substrate; a tin (Sn) substrate, a rhodium (Rh) substrate, a ruthenium (Ru) substrate, a palladium (Pd) substrate, an osmium (Os) substrate, an iridium (Ir) substrate, a platinum (Pt) substrate, a titanium (Ti) substrate, an aluminum (Al) substrate, a chromium (Cr), a copper (Cu) substrate, a magnesium (Mg) substrate, a carbon substrate, a silicon substrate such as p-type doped silicon substrate, n-type doped silicon substrate, and gallium arsenide. In some embodiments, the solid support is a noble metal.

In certain embodiments, the solid support permits colorimetric or visual detection of a cancer methylscape genomic DNA molecule and/or nucleic acid complex and the sensor suitably comprises a colloidal particle (e.g., a colloidal particle made from gold, silver, platinum, copper, metal composites, other soft metals, core-shell structure particles, or hollow gold nanosphere) that comprises a substrate or surface to which hydrophobic moieties (e.g., methylated nucleotides such as methylated cytosines) adsorb under aqueous conditions.

In some embodiments, the solid support permits electrochemical detection of a cancer methylscape genomic DNA molecule and/or nucleic acid complex. The electrochemical detection may comprise: exposing the biological sample to a working electrode that comprises an electro-conductive material to which hydrophobic moieties (e.g., methylated nucleotides such as methyl cytosines) adsorb under aqueous conditions; applying a potential to the working electrode; and detecting an electrical signal from the working electrode that is indicative of adsorption of the nucleic acid complex to the electroconductive material, wherein the electrical signal is selected from the group consisting of current, voltage, impedance, capacitance, charge, conductivity, resistance, or a combination thereof. For example, the electroconductive material may be selected from: noble metals (e.g., gold, platinum, palladium, silver, osmium, indium, rhodium, ruthenium); alloys of noble metals (e.g., gold-palladium, silver-platinum, etc.); conducting polymers (e.g., polypyrole (PPY)); non-noble metals (e.g., copper, nickel, aluminum, tin, titanium, indium, tungsten, platinum); metal oxides (e.g., zinc oxide, tin oxide, nickel oxide, indium tin oxide, titanium oxide, nitrogen-doped titanium oxide (Ti-OxNy); metal silicides (e.g., nickel silicide, platinum silicide); metal nitrides (titanium nitride (TiN), tungsten nitride (WN) or tantalum nitride (TaN), carbon (nanotubes, fibers, graphene and amorphous) or combinations of any of the above. Such electro-conductive materials are highly conductive and form strong bonds with nucleic acids, suitably methylated nucleic acids. The surface of an electro-conductive material may be further coated with a material, which maintains the electrode's high conductivity, but facilitates binding with nucleic acids, suitably methylated nucleic acids. For example, a nitrogen containing electro-conductive material (e.g., TiN, WN or TaN) can bind with an amine functional group of the nucleic acid.

Accordingly, in some embodiments, the sensor comprises an electrode comprising an electro-conductive material to which hydrophobic moieties (e.g., methylated nucleotides such as methylated cytosines) adsorb under aqueous conditions. In representative examples of this type, the electrode is a working electrode that is part of an electrical detection unit comprising an electrical circuit configured for detecting an electrical signal from the working electrode, wherein the electrical signal is selected from the group consisting of current or voltage, or a derived parameter such as impedance, capacitance, charge, conductivity, resistance, or a combination thereof. Thus the present invention encompasses the use of electrochemical detection of the cancer methylscape genomic DNA molecules and complexes of the invention. In specific embodiments, the electrochemical detection involves the use of a working electrode (e.g., an amperometric electrode) and a reference electrode (e.g., a counter reference electrode), whereby a constant potential is applied to the working electrode leading to an reduction-oxidation (redox) reaction that can be quantified as a recordable electric current. In representative examples of this type, a redox probe may be present in the biological sample. The redox probe may be a transition metal species, wherein the transition metal can adopt two valence states (e.g., a metal ion (M) being able to adopt M(II) and M(III) states). In some embodiments, the redox probe contains a metal ion, wherein the metal of the metal ion is selected from iron, ruthenium, iridium, osmium, cobalt, tungsten and molybdenum. In illustrative examples of this type, the redox probe is selected from $Fe(CN)_6^{3-/4-}$, $Fe(NH_3)_6^{3+/2+}$, $Fe(phen)_3^{3+/2+}$, $Fe(bipy)_2^{3+/2+}$, $Fe(bipy)_3^{3+/2+}$, $Ru_3^{+/2+}$, $RuO_4^{3-/2-}$, $Ru(CN)_6^{3-/4-}$, $Ru(NH_3)_6^{3+/2+}$, $Ru(en)_3^{3+/2+}$, $Ru(NH_3)_5$ $(Py)^{3+/2+}$, $Ir^{4+/3+}$, $Ir(Cl)_6^{2-/3-}$, $Ir(Br)_6^{2-/3-}$, $Os(bipy)_2^{3+/2+}$, $Os(bipy)_3^{3+/2+}$, $OxCl_6^{2-/3-}$, $Co(NH_3)_6^{3+/2+}$, $W(CN)_6^{3-/4-}$, $Mo(CN)_6^{3-/4-}$, optionally substituted ferrocene, polyferrocene, quinones, such as p-benzoquinone and hydroquinone and phenol. In specific embodiments, the redox probe is an iron-containing species in which iron is in Fe(II) and/or Fe(III) states. For example, the redox probe may be $Fe(CN)_6^{3-/4-}$. The redox probe may be present in the biological sample in an amount of from 0.1 mM to 100 mM, optionally from 0.5 mM to 10 mM, optionally from 0.5 mM to 2 mM, optionally from 0.5 mM to 1.5 mM, optionally about 1 mM.

In related embodiments, the present invention provides methods for detecting cancer DNA (e.g., cellular gDNA, ctDNA, cfDNA, evDNA, etc. derived from a cancer cell or tissue, or cancer subject; e.g., comprising cancer methylscape DNA). These methods generally comprise: exposing a biological sample comprising cancer DNA to a solid support to which hydrophobic moieties adsorb under aqueous conditions; and detecting a signal that is indicative of adsorption of cancer DNA to the solid support, wherein the signal is different to a signal generated when normal DNA (e.g., cellular gDNA, ctDNA, cfDNA, evDNA, etc. derived from a normal, healthy or non-cancerous cell, tissue or subject; e.g., comprising normal methylscape DNA) is exposed and/or adsorbed to the solid support.

In other related embodiments, the present invention provides methods for determining the presence of cancer DNA (e.g., cellular gDNA, ctDNA, cfDNA, evDNA, etc. derived from a cancer cell or tissue, or cancer subject; e.g., comprising cancer methylscape DNA) or normal DNA (e.g., cellular gDNA, ctDNA, cfDNA, evDNA, etc. derived from a normal, healthy or non-cancerous cell, tissue or subject; e.g., comprising normal methylscape DNA) in a biological sample. These methods generally comprise: exposing a biological sample comprising DNA (e.g., cellular gDNA, ctDNA, cfDNA, evDNA, etc.) to a solid support to which hydrophobic moieties adsorb under aqueous conditions; and detecting a first signal that is indicative of adsorption of cancer DNA to the solid support or a second signal that is indicative of exposure and/or adsorption of normal, healthy DNA or non-cancer DNA to the solid support, wherein the first and second signals are different, and determining whether the biological sample comprises cancer DNA or normal, healthy or non-cancer DNA based upon detection of the first or second signal.

In representative examples of this type, the solid support permits colorimetric or visual detection of DNA adsorbed thereto. In these examples, the methods suitably further comprise detecting a colorimetric or visual signal.

Accordingly, in some embodiments, the present invention provides methods for detecting cancer DNA (e.g., cellular gDNA, ctDNA, cfDNA, evDNA, etc. derived from a cancer cell or tissue, or cancer subject; e.g., comprising cancer methylscape DNA). These methods generally comprise: exposing a biological sample comprising cancer DNA to a solid support to which hydrophobic moieties adsorb under aqueous conditions; and detecting a colorimetric or visual signal that is indicative of adsorption of cancer DNA to the solid support, wherein the colorimetric or visual signal is different to a colorimetric or visual signal generated when normal DNA (e.g., cellular gDNA, ctDNA, cfDNA, evDNA, etc. derived from a normal, healthy or non-cancerous cell, tissue or subject; e.g., comprising normal methylscape DNA) is exposed and/or adsorbed to the solid support.

In related embodiments, the present invention provides methods for determining the presence of cancer DNA (e.g., cellular gDNA, ctDNA, cfDNA, evDNA, etc. derived from a cancer cell or tissue, or cancer subject; e.g., comprising cancer methylscape DNA) or normal DNA (e.g., cellular gDNA, ctDNA, cfDNA, evDNA, etc. derived from a normal, healthy or non-cancerous cell, tissue or subject; e.g., comprising normal methylscape DNA) in a biological sample. These methods generally comprise: exposing a biological sample comprising DNA (e.g., cellular gDNA, ctDNA, cfDNA, evDNA, etc.) to a solid support to which hydrophobic moieties adsorb under aqueous conditions; and detecting a first colorimetric or visual signal that is indicative of adsorption of cancer DNA to the solid support or a second colorimetric or visual signal that is indicative of exposure and/or adsorption of normal DNA to the solid support, wherein the first and second colorimetric or visual signals are different, and determining whether the biological sample comprises cancer DNA or normal, healthy or non-cancer DNA based upon detection of the first or second colorimetric or visual signal.

In other representative examples, the solid support permits electrochemical detection of DNA adsorbed thereto. In these examples, the methods suitably further comprise detecting an electrical signal.

Accordingly, in some embodiments, the present invention provides methods for detecting cancer DNA (e.g., cellular gDNA, ctDNA, cfDNA, evDNA, etc. derived from a cancer cell or tissue, or cancer subject; e.g., comprising cancer methylscape DNA). These methods generally comprise: exposing a biological sample comprising cancer DNA to a working electrode that comprises an electro-conductive material; applying a potential to the working electrode; and detecting an electrical signal from the working electrode that is indicative of adsorption of cancer DNA to the electroconductive material, wherein the electrical signal is different to an electrical signal generated from the working electrode when normal DNA (e.g., cellular gDNA, ctDNA, cfDNA, evDNA, etc. derived from a normal, healthy or non-cancerous cell, tissue or subject; e.g., comprising normal methylscape DNA) is adsorbed the electroconductive material.

In related embodiments, the present invention provides methods for determining the presence of cancer DNA (e.g., cellular gDNA, ctDNA, cfDNA, evDNA, etc. derived from a cancer cell or tissue, or cancer subject; e.g., comprising cancer methylscape DNA) or normal DNA (e.g., cellular gDNA, ctDNA, cfDNA, evDNA, etc. derived from a normal, healthy or non-cancerous cell, tissue or subject; e.g., comprising normal methylscape DNA) in a biological sample. These methods generally comprise: exposing a biological sample comprising DNA (e.g., cellular gDNA, ctDNA, cfDNA, evDNA, etc.) to a working electrode that comprises an electro-conductive material; applying a potential to the working electrode; and detecting a first electrical signal from the working electrode that is indicative of adsorption of cancer DNA to the electroconductive material or a second electrical signal from the working electrode that is indicative of adsorption of normal DNA to the electroconductive material, wherein the first and second electrical signals are different, and determining whether the biological sample comprises cancer DNA or normal, healthy or non-cancer DNA based upon detection of the first or second electrical signal.

2.2 Analysis of Epigenetic Biomarker

The present invention extends to methods of analyzing a cancer methylscape genomic DNA molecule that is detected in a biological sample. These analytical methods are suitably used for further characterizing the cancer methylscape genomic DNA molecule (e.g., CpG cluster-containing region/fragment) in determining the likelihood of the presence of a cancer or cancer subtype in a subject, the prognosis of a subject having a cancer, and the progression or regression of a cancer in subject following administration of a therapeutic agent.

In some embodiments, the analytical methods comprise isolating the cancer methylscape genomic DNA molecule and/or nucleic acid complex of the present invention from a biological sample. The cancer methylscape genomic DNA molecule and/or nucleic acid complex may be isolated using any methodology disclosed herein or known in the art, including for example centrifugation such as density gradient centrifugation and differential centrifugation, exclusion chromatography, and affinity isolation such as affinity capture, including immunosorbent capture (e.g., immunoprecipitation), affinity chromatography, microfluidic separation, flow cytometry, or combination thereof.

In specific embodiments, the cancer methylscape genomic DNA molecule and/or nucleic acid complex are isolated using an affinity agent as described herein by contacting the biological sample with the affinity agent to form a conjugate that comprises the cancer methylscape genomic DNA molecule and/or nucleic acid and the conjugate and separating the conjugate from the biological sample. If desired, the cancer methylscape genomic DNA molecule and/or nucleic acid complex may be separated or displaced from the affinity agent suitably by elution, which disrupts the binding interaction between cancer methylscape genomic DNA molecule and/or nucleic acid complex and the affinity agent. Non-limiting elution strategies include pH (e.g., increased pH with a base such as sodium bicarbonate, decreased pH with an acids such as acetic acid, trichloroacetic acid, sulfosalicylic acid, HCl, formic acid, and common pH elution buffers such as 100 mM glycine·HCl, pH 2.5, 3.0, 100 mM citric acid, pH 3.0, 50, 100 mM triethylamine or triethanolamine, pH 11.5, 150 mM ammonium hydroxide, pH 10.5), photochemical reduction (e.g., using UV light), endonuclease cleavage of methylated DNA; a displacer or displacing agent, competitive elution (e.g., >0.1M counter ligand or analog), ionic strength and/or chaotropic effects (e.g., NaCl, KCl, 3.5, 4.0 M magnesium chloride pH 7.0 in 10 mM Tris, 5M lithium chloride in 10 mM phosphate buffer pH 7.2, 2.5M sodium iodide pH 7.5, 0.2, 3.0M sodium thiocyanate), surfactant, detergent, a concentrated inorganic salt, denaturing (e.g., 2, 6M guanidine·HCl, 2, 8M urea, 1% deoxycholate, 1% SDS), an organic solvent (e.g., alcohol, chloroform, ethanol, methanol, acetonitrile, hexane, DMSO, 10% dioxane, 50% ethylene glycol pH 8, 11.5 (also chaotropic)), radiation or heat (increased temperature), conformational change, disulfide bond reducers (2-mercaptoethanol, dithiothreitol, tris(2-carboxylethyl)phosphine), enzyme inactivation, chaotropic agents (e.g., urea, guanidinium chloride, lithium perchlorate), electrochemical desorption, nanoscopic shear force (e.g., nanoshearing), mechanical agitation, sonication, nucleic acid digestion or cleavage agents (e.g., restriction endonucleases), and protein digestive enzymes (pepsin, trypsin), and combinations thereof. In illustrative examples of this type, the cancer methylscape genomic DNA molecule and/or nucleic acid complex may be separated or displaced from the affinity agent using an elution buffer.

In specific embodiments, the affinity agent is a solid support selected from a metal (e.g., a noble metal, alloy of noble metal, non-noble metal, metal oxide, metal silicide, metal nitride, or combination thereof), a carbon-based solid support, a silicon-based solid support, or a combination thereof, and the cancer methylscape genomic DNA molecule and/or nucleic acid complex is displaced from the solid support using a displacing agent that binds to the solid support, suitably with greater affinity than the cancer methylscape genomic DNA molecule and/or nucleic acid complex. The displacing agent may be selected from: organic thiols (e.g., alkanethiols; omega-functionalized alkanethiols including those comprising omega groups of hydroxyl, nitrile, carboxylic acid, ethylene oxide, diethylene oxide, triethylene oxide, tetraethylene oxide, pentaethylene oxide, or polyethylene oxide; cysteine; cystamine; thiol-amines; and aromatic thiols such as benzene thiol (BenzSH) and dithiol (Benz2SH), 1-naphalenethiol (NaphSH), phenylthiol (PhSH) and 2-nanpthalenethiol (2-NaphSH); phosphonic acids; phosphinic acids; disulfides; selenols and arsenates. In some embodiments, the displacing agent is an omega-functionalized alkanethiol, wherein the omega group is a hydroxyl group and the alkanethiol has a chain length ranging from $C_4$ to $C_{20}$, and in some embodiments $C_6$. In representative examples of this type, the displacing agent is selected from 6-mercapto-1-hexanol (MCH), 2-mercaptoethanol (MCE) and 11-mercapto-1-undecanol (MCU). In preferred embodiments, the solid support (e.g., a particle such as a microparticle or nanoparticle) comprises a noble metal, suitably gold, and the displacing agent is an omega-functionalized alkanethiol, suitably any one of MCH, MCE or MCU, or combination thereof.

In some cases, the DNA solution is cleared of proteins and other contaminants e.g., by digestion with proteinase K. The DNA is then recovered from the solution. In such cases, this is carried out by means of a variety of methods including salting out, organic extraction or binding of the DNA to a solid phase support. In some instances, the choice of method is affected by several factors including time, expense and required quantity of DNA.

In certain instances, a miniprep system is employed to isolate the cancer methylscape genomic DNA molecule and/or nucleic acid complex of the present invention from a biological sample. The miniprep system may comprise a column, which is suitably a microspin column, having a matrix comprising an affinity agent as broadly described above and elsewhere herein. In representative examples of this type, the affinity agent is a solid support, which is suitably a metal-based solid support (e.g., a noble metal, alloy of noble metal, non-noble metal, metal oxide, metal silicide, metal nitride, or combination thereof), a carbon-based solid support, a silicon-based solid support, or a combination thereof. In preferred embodiments, the solid support is a noble metal (e.g., gold). In representative examples of this type the solid support is a particle (e.g., microparticle or nanoparticle) comprising a metal surface (e.g., a noble metal such as gold). The miniprep system may further comprise a pre-filter (e.g., a disc of porous, sintered polyethylene, polypropylene, cellulose absorbent paper or polypropylene mesh) for removing insoluble material (e.g., flocculant cellular debris generated from cell lysis). In certain instances, the miniprep system further comprises a depth filter (e.g., a glass microfiber filter of cellulose paper) that reduces residual contaminant flow-through from the pre-filter. A sample containing cancer methylscape genomic DNA molecule and/or nucleic acid complex of the present invention is suitably loaded onto the system and the sample is caused to flow through the column via gravity flow or centrifugation. In embodiments in which the system comprises a pre-filter and optionally a depth filter, flocculants including cell debris are captured by the pre-filter and optionally the depth filter. If desired, the column is washed using a suitable washing solution to remove soluble impurities and the cancer methylscape genomic DNA molecule and/or nucleic acid complex is eluted or displaced from the affinity agent of the matrix by loading the column with an elution buffer, which suitably comprises a displacing agent (e.g., an omega-functionalized alkanethiol, suitably any one of MCH, MCE or MCU, or combination thereof).

In some embodiments, methylation analysis is carried on the isolated cancer methylscape genomic DNA. The analysis may be carried out by any means known in the art. A variety of methylation analysis procedures are known in the art and may be used to practice the methods disclosed herein. These assays allow for determination of the methylation state of one or a plurality of CpG sites within a sample. In addition, these methods may be used for absolute or relative quantification of methylated nucleic acids. Such methylation assays involve, among other techniques, two major steps. The first step is a methylation specific reaction or separation, such as (i) bisulfite treatment, (ii) methylation specific binding, or (iii) methylation specific restriction enzymes. The second major step involves (i) amplification and detection, or (ii) direct detection, by a variety of methods such as (a) PCR (sequence-specific amplification) such as TaqMan™, (b) DNA sequencing of untreated and bisulfite-treated DNA, (c) sequencing by ligation of dye-modified probes (including cyclic ligation and cleavage), (d) pyrosequencing, (e) single-molecule sequencing, (f) mass spectroscopy, or (g) Southern blot analysis.

Additionally, restriction enzyme digestion of PCR products amplified from bisulfite-converted DNA may be used, e.g., the method described by Sadri and Hornsby (1996, *Nucleic Acids Res.* 24:5058-5059), or COBRA (Combined Bisulfite Restriction Analysis) (Xiong and Laird, 1997, *Nucleic Acids Res.* 25:2532-2534). COBRA analysis is a quantitative methylation assay useful for determining DNA methylation levels at specific gene loci in small amounts of genomic DNA. Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (1992, *Proc. Nat. Acad. Sci. USA* 89: 1827-1831). PCR amplification of the bisulfite converted DNA is then performed using primers specific for the CpG sites of interest, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels.

In some embodiments, the methylation profile of selected CpG sites is determined using Methylation-Specific PCR (MSP). MSP allows for assessing the methylation status of virtually any group of CpG sites within a CpG island, independent of the use of methylation-sensitive restriction enzymes (Herman et al., 1996, *Proc. Nat. Acad. Sci. USA* 93: 9821-9826; U.S. Pat. Nos. 5,786,146, 6,017,704, 6,200,756, 6,265,171 (Herman and Baylin); U.S. Pat. Pub. No. 2010/0144836 (Van Engeland et al.)). Briefly, DNA is modified by a deaminating agent such as sodium bisulfite to convert unmethylated, but not methylated cytosines to uracil, and subsequently amplified with primers specific for methylated vs. unmethylated DNA.

In some embodiments, the methylation profile of selected CpG sites is determined using MethyLight and/or Heavy Methyl Methods. The MethyLight and Heavy Methyl assays are a high-throughput quantitative methylation assay that utilizes fluorescence-based real-time PCR (TaqMan™) technology that requires no further manipulations after the PCR step (Eads, C. A. et al., 2000, *Nucleic Acid Res.* 28: e 32; Cottrell et al., 2007, *J. Urology* 177: 1753, U.S. Pat. No. 6,331,393 (Laird et al.)). Briefly, the MethyLight process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed either in an "unbiased" (with primers that do not overlap known CpG methylation sites) PCR reaction, or in a "biased" (with PCR primers that overlap known CpG dinucleotides) reaction. In some cases, sequence discrimination occurs either at the level of the amplification process or at the level of the fluorescence detection process, or both. In some cases, the MethyLight assay is used as a quantitative test for methylation patterns in the genomic DNA sample, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the "MSP" technique), or with oligonucleotides covering potential methylation sites.

Quantitative MethyLight uses bisulfite to convert genomic DNA and the methylated sites are amplified using PCR with methylation independent primers. Detection probes specific for the methylated and unmethylated sites with two different fluorophores provides simultaneous quantitative measurement of the methylation. The Heavy Methyl technique begins with bisulfate conversion of DNA. Next specific blockers prevent the amplification of unmethylated DNA. Methylated genomic DNA does not bind the blockers and their sequences will be amplified. The amplified sequences are detected with a methylation specific probe. (Cottrell et al, 2004, *Nuc. Acids Res.* 32:e 10, the contents of which is hereby incorporated by reference in its entirety).

The Methylation-sensitive Single Nucleotide Primer Extension (Ms-SNuPE) technique is a quantitative method for assessing methylation differences at specific CpG sites based on bisulfite treatment of DNA, followed by single-nucleotide primer extension (Gonzalgo and Jones, 1997, *Nucleic Acids Res.* 25: 2529-2531). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest. In some cases, small amounts of DNA are analyzed (e.g., micro-dissected pathology sections), and the method avoids utilization of restriction enzymes for determining the methylation status at CpG sites.

In some embodiments, methods for detecting methylation include randomly shearing or randomly fragmenting the genomic DNA, cutting the DNA with a methylation-dependent or methylation-sensitive restriction enzyme and subsequently selectively identifying and/or analyzing the cut or uncut DNA. Selective identification can include, for example, separating cut and uncut DNA (e.g., by size) and quantifying a sequence of interest that was cut or, alternatively, that was not cut. See, e.g., U.S. Pat. No. 7,186,512. Alternatively, the method can encompass amplifying intact DNA after restriction enzyme digestion, thereby only amplifying DNA that was not cleaved by the restriction enzyme in the area amplified. See, e.g., U.S. Pat. Nos. 7,910,296; 7,901,880; and 7,459,274. In some embodiments, amplification can be performed using primers that are gene specific.

For example, there are methyl-sensitive enzymes that preferentially or substantially cleave or digest at their DNA recognition sequence if it is non-methylated. Thus, an unmethylated DNA sample is cut into smaller fragments than a methylated DNA sample. Similarly, a hypermethylated DNA sample is not cleaved. In contrast, there are methyl-sensitive enzymes that cleave at their DNA recognition sequence only if it is methylated. Methyl-sensitive enzymes that digest unmethylated DNA suitable for use in methods of the technology include, but are not limited to, HpaII, HhaI, MaeII, BstUI and AciI. In some instances, an enzyme that is used is HpaII that cuts only the unmethylated sequence CCGG. In other instances, another enzyme that is used is HhaI that cuts only the unmethylated sequence GCGC. Combinations of two or more methyl-sensitive enzymes that digest only unmethylated DNA are also used. Suitable enzymes that digest only methylated DNA include, but are not limited to, DpnI, which only cleaves at fully methylated 5'-GATC sequences, and McrBC, an endonuclease, which cleaves DNA containing modified cytosines (5-methylcytosine or 5-hydroxymethylcytosine or N4-methylcytosine) and cuts at recognition site 5' . . . Pu$^m$C(N$_{40-3000}$) Pu$^m$C . . . 3'. Cleavage methods and procedures for selected restriction enzymes for cutting DNA at specific sites are well known to the skilled person.

In some instances, a methylation-dependent restriction enzyme is a restriction enzyme that cleaves or digests DNA at or in proximity to a methylated recognition sequence, but does not cleave DNA at or near the same sequence when the recognition sequence is not methylated. Methylation-dependent restriction enzymes include those that cut at a methylated recognition sequence (e.g., DpnI) and enzymes that cleave at a sequence near but not at the recognition sequence (e.g., McrBC). For example, McrBC's recognition sequence is 5' R$^m$C (N$_{40-3000}$) R$^m$C 3' where "R" is a purine and "$^m$C" is a methylated cytosine and "N$_{40-3000}$" indicates the distance between the two R$^m$C half sites for which a restriction event has been observed. Exemplary methylation-dependent restriction enzymes include, e.g., McrBC, McrA, MrrA, BisI, GlaI and DpnI.

In some cases, a methylation-sensitive restriction enzyme is a restriction enzyme that cleaves DNA at or in proximity to an unmethylated recognition sequence but does not cleave at or in proximity to the same sequence when the recognition sequence is methylated. Exemplary methylation-sensitive restriction enzymes are described in, e.g., McClelland et al. (1994, *Nucleic Acids Res.* 22(17): 3640-59). Suitable methylation-sensitive restriction enzymes that do not cleave DNA at or near their recognition sequence when a cytosine within the recognition sequence is methylated at position C5 include, e.g., AatII, AciI, AcdI, AgeI, AluI, AscI, AseI, AsiSI, BbeI, BsaAI, BsaHI, BsiEI, BsiWI, BsrFI, BssHII, BssKI, BstBI, BstNI, BstUI, ClaI, EaeI, EagI, FauI, FseI, HhaI, HinPII, HinCII, HpaII, Hpy99I, HpyCH4IV, KasI, MboI, MluI, MapAII, MspI, NaeI, NarI, NotI, PmlI, PstI, PvuI, RsrII, SacII, SapI, Sau3AI, SfI, SfoI, SgrAI, SmaI, SnaBI, TscI, XmaI, and ZraI. Suitable methylation-sensitive restriction enzymes that do not cleave DNA at or near their recognition sequence when an adenosine within the recognition sequence is methylated at position N6 include, e.g., MboI.

In alternative embodiments, adaptors are optionally added to the ends of the randomly fragmented DNA, the DNA is then digested with a methylation-dependent or methylation-sensitive restriction enzyme, and intact DNA is subsequently amplified using primers that hybridize to the adaptor sequences. In this case, a second step is performed to determine the presence, absence or quantity of a particular gene in an amplified pool of DNA. In some embodiments, the DNA is amplified using real-time, quantitative PCR.

In other embodiments, the methods comprise quantifying the average methylation density in a target sequence within a population of genomic DNA. In some embodiments, the method comprises contacting genomic DNA with a methylation-dependent restriction enzyme or methylation-sensitive restriction enzyme under conditions that allow for at least some copies of potential restriction enzyme cleavage sites in the locus to remain uncleaved; quantifying intact copies of the locus; and comparing the quantity of amplified product to a control value representing the quantity of methylation of control DNA, thereby quantifying the average methylation density in the locus compared to the methylation density of the control DNA.

In some instances, the quantity of methylation of a locus of DNA is determined by providing a sample of genomic DNA comprising the locus, cleaving the DNA with a restriction enzyme that is either methylation-sensitive or methylation-dependent, and then quantifying the amount of intact DNA or quantifying the amount of cut DNA at the DNA locus of interest. The amount of intact or cut DNA will depend on the initial amount of genomic DNA containing the locus, the amount of methylation in the locus, and the number (i.e., the fraction) of nucleotides in the locus that are methylated in the genomic DNA. The amount of methylation in a DNA locus can be determined by comparing the quantity of intact DNA or cut DNA to a control value representing the quantity of intact DNA or cut DNA in a similarly-treated DNA sample. The control value can represent a known or predicted number of methylated nucleotides. Alternatively, the control value can represent the quantity of intact or cut DNA from the same locus in another (e.g., normal, non-diseased) cell or a second locus.

By using at least one methylation-sensitive or methylation-dependent restriction enzyme under conditions that allow for at least some copies of potential restriction enzyme cleavage sites in the locus to remain uncleaved and subsequently quantifying the remaining intact copies and comparing the quantity to a control, average methylation density of a locus can be determined. If the methylation-sensitive restriction enzyme is contacted to copies of a DNA locus under conditions that allow for at least some copies of potential restriction enzyme cleavage sites in the locus to remain uncleaved, then the remaining intact DNA will be directly proportional to the methylation density, and thus may be compared to a control to determine the relative methylation density of the locus in the sample. Similarly, if a methylation-dependent restriction enzyme is contacted to copies of a DNA locus under conditions that allow for at least some copies of potential restriction enzyme cleavage sites in the locus to remain uncleaved, then the remaining intact DNA will be inversely proportional to the methylation density, and thus may be compared to a control to determine the relative methylation density of the locus in the sample. Such assays are disclosed in, e.g., U.S. Pat. No. 7,910,296.

The methylated CpG island amplification (MCA) technique is a method that can be used to screen for altered methylation patterns in genomic DNA, and to isolate specific sequences associated with these changes (Toyota et al., 1999, Cancer Res. 59: 2307-2312, U.S. Pat. No. 7,700,324 (Issa et al.)). Briefly, restriction enzymes with different sensitivities to cytosine methylation in their recognition sites are used to digest genomic DNAs from primary tumors, cell lines, and normal tissues prior to arbitrarily primed PCR amplification. Fragments that show differential methylation are cloned and sequenced after resolving the PCR products on high-resolution polyacrylamide gels. The cloned fragments are then used as probes for Southern analysis to confirm differential methylation of these regions.

Additional methylation detection methods include those methods described in, e.g., U.S. Pat. Nos. 7,553,627; 6,331,393; U.S. patent Ser. No. 12/476,981; U.S. Patent Publication No. 2005/0069879; Rein, et al., 1998, Nucleic Acids Res. 26(10): 2255-64; and Olek et al., 1997, Nat. Genet. 17(3) 275-6.

In other embodiments, the methylation status of selected CpG sites is determined using Methylation-Sensitive High Resolution Melting (HRM). (see, Wojdacz and Dobrovic, 2007, Nucleic Acids Res. 35(6): e41; Wojdacz et al., 2008, Nat. Prot. 3(12): 1903-1908; Balic et al., 2009, J. Mol. Diagn. 11 102-108; and US Pat. Pub. No. 2009/0155791 (Wojdacz et al.)).

In still other embodiments, the methylation status of selected CpG locus is determined using a primer extension assay, including an optimized PCR amplification reaction that produces amplified targets for analysis using mass spectrometry. The assay can also be done in multiplex. Mass spectrometry is a particularly effective method for the detection of polynucleotides associated with the differentially methylated regulatory elements. The presence of the polynucleotide sequence is verified by comparing the mass of the detected signal with the expected mass of the polynucleotide of interest. The relative signal strength, e.g., mass peak on a spectra, for a particular polynucleotide sequence indicates the relative population of a specific allele, thus enabling calculation of the allele ratio directly from the data. This method is described in detail in PCT Pub. No. WO 2005/012578A1 (Beaulieu et al.). For methylation analysis, the assay can be adopted to detect bisulfite introduced methylation dependent C to T sequence changes. These methods are particularly useful for performing multiplexed amplification reactions and multiplexed primer extension reactions (e.g., multiplexed homogeneous primer mass extension (hME) assays) in a single well to further increase the throughput and reduce the cost per reaction for primer extension reactions.

Other methods for DNA methylation analysis include restriction landmark genomic scanning (RLGS, Costello et al., 2002, Meth. Mol Biol, 200, 53-70), methylation-sensitive-representational difference analysis (MS-RDA, Ushijima and Yamashita, 2009, Methods Mol Biol 507, 1 17-130). Comprehensive high-throughput arrays for relative methylation (CHARM) techniques are described in WO 2009/021141 (Feinberg and Irizarry). The Roche® NimbleGen® microarrays including the Chromatin Immunoprecipitation-on-chip (ChIP-chip) or methylated DNA immunoprecipitation-on-chip (MeDIP-chip). These tools have been used for a variety of cancer applications including melanoma, liver cancer and lung cancer (Koga et al., 2009, Genome Res. 19: 1462-1470; Acevedo et al., 2008, Cancer Res. 68: 2641-2651; Rauch et al., 2008, Proc. Nat. Acad. Sci. USA 105: 252-257). Others have reported bisulfate conversion, padlock probe hybridization, circularization, amplification and next generation or multiplexed sequencing for high throughput detection of methylation (Deng et al., 2009, Nat. Biotechnol. 27: 353-360; Ball et al., 2009, Nat. Bio-

*technol* 27, 361-368; U.S. Pat. No. 7,611,869 (Fan)). As an alternative to bisulfate oxidation, Bayeyt et al. have reported selective oxidants that oxidize 5-methylcytosine, without reacting with thymidine, which are followed by PCR or pyro sequencing (WO 2009/049916 (Bayeyt et al.).

In some instances, quantitative amplification methods (e.g., quantitative PCR or quantitative linear amplification) are used to quantify the amount of intact DNA within a locus flanked by amplification primers following restriction digestion. Methods of quantitative amplification are disclosed in, e.g., U.S. Pat. Nos. 6,180,349; 6,033,854; and 5,972,602, as well as in, e.g., DeGraves, et al., 2003, *Biotechniques* 34(1): 106-15; Deiman B, et al., 2002, *Mol. Biotechnol.* 20(2):163-79; and Gibson et al., 1996, *Genome Research* 6: 995-1001.

Following reaction or separation of nucleic acid in a methylation specific manner, the nucleic acid in some cases are subjected to sequence-based analysis. For example, once it is determined that one particular genomic sequence from a sample is hypermethylated or hypomethylated compared to its counterpart, the amount of this genomic sequence can be determined. Subsequently, this amount can be compared to a standard control value and used to determine the presence of cancer in the sample. In many instances, it is desirable to amplify a nucleic acid sequence using any of several nucleic acid amplification procedures which are well known in the art. Nucleic acid amplification or detection methods are known to the skilled person, such as those described in U.S. Pat. No. 5,525,462 (Takarada et al.); U.S. Pat. No. 6,114,117 (Hepp et al.); U.S. Pat. No. 6,127,120 (Graham et al.); U.S. Pat. No. 6,344,317 (Urnovitz); U.S. Pat. No. 6,448,001 (Oku); U.S. Pat. No. 6,528,632 (Catanzariti et al.); and PCT Pub. No. WO 2005/111209 (Nakajima et al.).

In some embodiments, the nucleic acids are amplified by PCR amplification using methodologies known to one skilled in the art. One skilled in the art will recognize, however, that amplification can be accomplished by any known method, such as ligase chain reaction (LCR), Q-replicas amplification, rolling circle amplification, transcription amplification, self-sustained sequence replication, nucleic acid sequence-based amplification (NASBA), each of which provides sufficient amplification. Branched-DNA technology is also optionally used to qualitatively demonstrate the presence of a sequence of the technology, which represents a particular methylation pattern, or to quantitatively determine the amount of this particular genomic sequence in a sample. Nolte reviews branched-DNA signal amplification for direct quantitation of nucleic acid sequences in clinical samples (Nolte, 1998, *Adv. Clin. Chem.* 33:201-235).

In some embodiments, amplified sequences are also measured using invasive cleavage reactions such as the Invader® technology (Zou et al., 2010, *Association of Clinical Chemistry (AACC) poster presentation on* Jul. 28, 2010, "Sensitive Quantification of Methylated Markers with a Novel Methylation Specific Technology; and U.S. Pat. No. 7,011,944 (Prudent et al.)).

Suitable next generation sequencing technologies are widely available. Examples include the 454 Life Sciences platform (Roche, Branford, Conn.) (Margulies et al. 2005 Nature, 437, 376-380); Illumina's Genome Analyzer, GoldenGate Methylation Assay, or Infinium Methylation Assays, i.e., Infinium HumanMethylation 27K BeadArray or VeraCode GoldenGate methylation array (Illumina, San Diego, Calif.; Bibkova et al. 2006, Genome Res. 16, 383-393; U.S. Pat. Nos. 6,306,597 and 7,598,035 (Macevicz); U.S. Pat. No. 7,232,656 (Balasubramanian et al.)); QX200™ Droplet Digital™ PCR System from Bio-Rad; or DNA Sequencing by Ligation, SOLiD System (Applied Biosystems/Life Technologies; U.S. Pat. Nos. 6,797,470, 7,083,917, 7,166,434, 7,320,865, 7,332,285, 7,364,858, and 7,429,453 (Barany et al.); the Helicos True Single Molecule DNA sequencing technology (Harris et al., 2008 Science, 320, 106-109; U.S. Pat. Nos. 7,037,687 and 7,645,596 (Williams et al.); U.S. Pat. No. 7,169,560 (Lapidus et al.); U.S. Pat. No. 7,769,400 (Harris)), the single molecule, real-time (SMRT™) technology of Pacific Biosciences, and sequencing (Soni and Meller, 2007, *Clin. Chem.* 53: 1996-2001); semiconductor sequencing (Ion Torrent; Personal Genome Machine); DNA nanoball sequencing; sequencing using technology from Dover Systems (Polonator), and technologies that do not require amplification or otherwise transform native DNA prior to sequencing (e.g., Pacific Biosciences and Helicos), such as nanopore-based strategies (e.g., Oxford Nanopore, Genia Technologies, and Nabsys). These systems allow the sequencing of many nucleic acid molecules isolated from a specimen at high orders of multiplexing in a parallel fashion. Each of these platforms allow sequencing of clonally expanded or non-amplified single molecules of nucleic acid fragments. Certain platforms involve, for example, (i) sequencing by ligation of dye-modified probes (including cyclic ligation and cleavage), (ii) pyrosequencing, and (iii) single-molecule sequencing.

Pyrosequencing is a nucleic acid sequencing method based on sequencing by synthesis, which relies on detection of a pyrophosphate released on nucleotide incorporation. Generally, sequencing by synthesis involves synthesizing, one nucleotide at a time, a DNA strand complimentary to the strand whose sequence is being sought. Study nucleic acids may be immobilized to a solid support, hybridized with a sequencing primer, incubated with DNA polymerase, ATP sulfurylase, luciferase, apyrase, adenosine 5' phosphosulfate and luciferin. Nucleotide solutions are sequentially added and removed. Correct incorporation of a nucleotide releases a pyrophosphate, which interacts with ATP sulfurylase and produces ATP in the presence of adenosine 5' phosphosulfate, fueling the luciferin reaction, which produces a chemiluminescent signal allowing sequence determination. Machines for pyrosequencing and methylation specific reagents are available from Qiagen, Inc. (Valencia, Calif.). See also Tost and Gut, 2007, Nat. Prot. 2 2265-2275.

In certain embodiments, the methylation values measured for cancer methylscape genomic DNA, which may include one or more methylation panels, are mathematically combined and the combined value is correlated to the underlying diagnostic question. In some instances, methylated biomarker values are combined by any appropriate state of the art mathematical method. Well-known mathematical methods for correlating a biomarker combination to a disease status employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. The skilled artisan will have no problem in selecting an appropriate method to evaluate an epigenetic biomarker or biomarker combination. In one embodiment, the method used in a correlating methylation status of an epigenetic biomarker or biomarker combination, e.g. to diagnose cancer or a cancer subtype, is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression), and Principal Components Analysis.

3. Kits/Article of Manufacture

The present invention further encompasses kits for detecting cancer methylscape genomic DNA, including cancer methylscape nucleic acid complexes. In some instances the kits may comprise a sensor for detecting the presence or level of cancer methylscape genomic DNA and/or nucleic acid complex. The sensor may be selected from any one or more of: an antigen-binding molecule that binds specifically with the clustered methylated genomic DNA or complex thereof, a light based sensor, a spectrometer, a refractometer, an x-ray, a monochromator, an absorption detector, a reflectance detector, a transmission detector, a conductivity sensor, an electrode, a resistive pulse sensor, a camera, a microscope, a particle size analyzer, an optical detector, a solid support to which hydrophobic moieties adsorb under the aqueous conditions, a colloidal particle or a biosensor, as described for example above and elsewhere herein. In some instances, the kits further contain positive (e.g., cancer methylscape genomic DNA and/or nucleic acid complex) and negative control (e.g., normal or non-diseased methylscape genomic DNA and or nucleic acid complexes).

The kits may further contain reagents for characterizing the methylation profile of the cancer methylscape genomic DNA, optionally together with instructional material. In some instances, the kit comprises a plurality of primers or probes to detect or measure the methylation status/levels of one or more samples. Reagents for detection of methylation include, e.g., sodium bisulfite, nucleic acids including primers and oligonucleotides designed to hybridize to an epigenetic biomarker sequence or to the product of an epigenetic biomarker sequence if the biomarker sequence is not methylated (e.g., containing at least one C-U conversion), and/or a methylation-sensitive or methylation-dependent restriction enzyme. In some cases, the kits provide solid supports in the form of an assay apparatus that is adapted to use in the assay. In some instances, the kits further comprise detectable labels, optionally linked to a polynucleotide, e.g., a probe, in the kit.

In some embodiments, the kit includes a packaging material. In some instances, the packaging material maintains sterility of the kit components, and is made of material commonly used for such purposes (e.g., paper, corrugated fiber, glass, plastic, foil, ampules, etc.). Other materials useful in the performance of the assays are included in the kits, including test tubes, transfer pipettes, and the like. In some cases, the kits also include written instructions for the use of one or more of these reagents in any of the assays described herein.

In some embodiments, kits also include a buffering agent (e.g., for facilitating self-assembly of methylscape genomic DNA into nucleic acid complexes), a preservative, or a protein/nucleic acid stabilizing agent. In some cases, kits also include other components of a reaction mixture as described herein. For example, kits include one or more aliquots of thermostable DNA polymerase as described herein, and/or one or more aliquots of dNTPs. In some cases, kits also include control samples of known amounts of template DNA molecules harboring the individual alleles of a locus. In some embodiments, the kit includes a negative control sample, e.g., a sample that does not contain DNA molecules harboring the individual alleles of a locus. In some embodiments, the kit includes a positive control sample, e.g., a sample containing known amounts of one or more of the individual alleles of a locus.

4. Methods of Detection and Diagnosis

The present invention also provides methods of determining the likelihood of the presence of cancer in a subject by detecting the presence or absence of cancer methylscape genomic DNA and/or a complex thereof in a biological sample obtained from the subject, as described for example in Section 2 and elsewhere herein. In some instances, a physical or physicochemical feature of methylscape genomic DNA (also referred to herein as "methylscape physical or physicochemical feature") in the sample is compared to a reference methylscape physical or physicochemical feature, to thereby determine the likelihood of the presence or absence of cancer. The methylscape physical feature may include size, shape or aggregation status of the methylscape nucleic acid complex. In some instances, the physicochemical feature comprises affinity of the methylscape genomic DNA and/or nucleic acid complex for a solid support. Thresholds may be selected that provide an acceptable ability to predict diagnosis, likelihood, prognostic risk, treatment success, etc. As used herein, the term "likelihood" is used as a measure of whether subjects with a particular methylscape physical or physicochemical feature or feature panel actually have cancer (or not) based on a given mathematical model. An increased likelihood for example may be relative or absolute and may be expressed qualitatively or quantitatively. For instance, an increased risk may be identified simply by determining a methylscape physical or physicochemical feature or feature panel in a biological sample obtained from a subject and placing the subject in an "increased risk" category, based upon previous population studies in which a methylscape physical or physicochemical feature or feature panel has been determined for cancer and healthy subjects. Alternatively, a numerical expression of a subject's increased risk may be determined based upon an analysis of the subject's methylscape physical or physicochemical feature or feature panel per se. In some embodiments, increased risk may be determined by further analyzing the methylation status of methylscape genomic DNA. Alternatively or in addition, increased risk may be determined by further analyzing an ancillary cancer biomarker such as a nucleic acid sequence or a mutation/SNP, which correlate with likely presence of cancer or a stage of cancer.

In illustrative examples, receiver operating characteristic (ROC) curves are calculated by plotting the value of a variable versus its relative frequency in two populations in which a first population has a first condition (e.g., cancer) or risk and a second population has a second condition (e.g., healthy) or risk (called arbitrarily, for example, "cancer" and "healthy condition", "a first stage or severity of cancer" and "a second stage or severity of cancer", or "low risk" and "high risk").

A distribution of methylscape physical or physicochemical features or feature panels, and optionally methylation status and/or one or more ancillary cancer biomarkers of methylscape genomic DNA, for subjects with and without a disease will likely overlap. Under such conditions, a test does not absolutely distinguish a first condition and a second condition with 100% accuracy, and the area of overlap indicates where the test cannot distinguish the first condition and the second condition. A threshold is selected, above which (or below which, depending on how methylscape physical or physicochemical features or feature panels, and optionally methylation status and/or one or more ancillary cancer biomarkers of methylscape genomic DNA, change with a specified condition or prognosis) the test is considered to be "positive" and below which the test is considered to be "negative." The area under the ROC curve (AUC) provides the C-statistic, which is a measure of the probability that the perceived measurement will allow correct identification of a condition (see, e.g., Hanley et al., 1982. Radiology 143: 29-36). The term "area under the curve" or "AUC" refers to the area under the curve of a receiver operating characteristic (ROC) curve, both of which are well known in the art. AUC measures are useful for comparing the accuracy of a classifier across the complete data range. Classifiers with a greater AUC have a greater capacity to classify unknowns correctly between two groups of interest (e.g., a healthy condition methylscape physical or physicochemical feature or feature panel and a cancer methylscape physical or physicochemical features or feature panel). ROC curves are useful for plotting the performance of a particular feature (e.g., a methylscape physical or physicochemical features or feature panel described herein and/or any item of additional biomedical information) in distinguishing or discriminating between two populations (e.g., cases having a cancer and controls without the cancer). Typically, the feature data across the entire population (e.g., the cases and controls) are sorted in ascending order based on the value of a single feature. Then, for each value for that feature, the true positive and false positive rates for the data are calculated. The sensitivity is determined by counting the number of cases above the value for that feature and then dividing by the total number of cases. The specificity is determined by counting the number of controls below the value for that feature and then dividing by the total number of controls. Although this definition refers to scenarios in which a feature is elevated in cases compared to controls, this definition also applies to scenarios in which a feature is lower in cases compared to the controls (in such a scenario, samples below the value for that feature would be counted). ROC curves can be generated for a single feature as well as for other single outputs, for example, a combination of two or more features can be mathematically combined (e.g., added, subtracted, multiplied, etc.) to produce a single value, and this single value can be plotted in a ROC curve. Additionally, any combination of multiple features (e.g., one or more methylscape physical or physicochemical features and optionally methylation status and/or one or more ancillary cancer biomarkers of methylscape genomic DNA), in which the combination derives a single output value, can be plotted in a ROC curve. These combinations of features may comprise a test. The ROC curve is the plot of the sensitivity of a test against the specificity of the test, where sensitivity is traditionally presented on the vertical axis and specificity is traditionally presented on the horizontal axis. Thus, "AUC ROC values" are equal to the probability that a classifier will rank a randomly chosen positive instance higher than a randomly chosen negative one. An AUC ROC value may be thought of as equivalent to the Mann-Whitney U test, which tests for the median difference between scores obtained in the two groups considered if the groups are of continuous data, or to the Wilcoxon test of ranks.

Alternatively, or in addition, thresholds may be established by obtaining an earlier methylscape physical or physicochemical feature or feature panel result, and optionally methylation status and/or one or more ancillary cancer biomarkers of methylscape genomic DNA result, from the same patient, to which later results may be compared. In these embodiments, the individual in effect acts as their own "control group." In cancer methylscape physical or physicochemical feature levels that increase with condition severity or prognostic risk, an increase over time in the same patient can indicate a worsening of the condition or a failure of a treatment regimen, while a decrease over time can indicate remission of the condition or success of a treatment regimen.

In some embodiments, a positive likelihood ratio, negative likelihood ratio, odds ratio, and/or AUC or receiver operating characteristic (ROC) values are used as a measure of a method's ability to predict risk or likelihood, or to diagnose a disease or condition. As used herein, the term "likelihood ratio" is the probability that a given test result would be observed in a subject with a condition of interest divided by the probability that that same result would be observed in a patient without the condition of interest. Thus, a positive likelihood ratio is the probability of a positive result observed in subjects with the specified condition divided by the probability of a positive results in subjects without the specified condition. A negative likelihood ratio is the probability of a negative result in subjects without the specified condition divided by the probability of a negative result in subjects with specified condition. As used herein, the term "probability" refers to the probability of class membership for a sample as determined by a given mathematical model and is construed to be equivalent likelihood in this context. The term "odds ratio", as used herein, refers to the ratio of the odds of an event occurring in one group (e.g., a healthy condition group) to the odds of it occurring in another group (e.g., a cancer group, or a group with particular stage or severity of cancer), or to a data-based estimate of that ratio.

In some embodiments, a methylscape physical or physicochemical feature or feature panel, and optionally a methylation status and/or one or more ancillary cancer biomarkers of methylscape genomic DNA, is selected to discriminate between subjects with a first condition and subjects with a second condition with at least about 50%, 55% 60%, 65%, 70%, 75%, 80%, 85%, 90%, 95% accuracy or having a C-statistic of at least about 0.50, 0.55, 0.60, 0.65, 0.70, 0.75, 0.80, 0.85, 0.90, 0.95.

In the case of a positive likelihood ratio, a value of 1 indicates that a positive result is equally likely among subjects in both the "condition" and "control" groups; a value greater than 1 indicates that a positive result is more likely in the condition group; and a value less than 1 indicates that a positive result is more likely in the control group. In this context, "condition" is meant to refer to a group having one characteristic (e.g., the presence of a healthy condition, cancer, or a particular stage or severity of cancer) and "control" group lacking the same characteristic.

In the case of a negative likelihood ratio, a value of 1 indicates that a negative result is equally likely among subjects in both the "condition" and "control" groups; a value greater than 1 indicates that a negative result is more likely in the "condition" group; and a value less than 1 indicates that a negative result is more likely in the "control" group. In the case of an odds ratio, a value of 1 indicates that a positive result is equally likely among subjects in both the "condition" and "control" groups; a value greater than 1 indicates that a positive result is more likely in the "condition" group; and a value less than 1 indicates that a positive result is more likely in the "control" group.

In the case of an AUC ROC value, this is computed by numerical integration of the ROC curve. The range of this value can be 0.5 to 1.0. A value of 0.5 indicates that a classifier (e.g., a DNA methylation status and/or one or more ancillary cancer biomarkers) is no better than a 50% chance to classify unknowns correctly between two groups of interest, while 1.0 indicates the relatively best diagnostic accuracy. In certain embodiments, a methylscape physical or physicochemical feature or feature panel, and optionally a methylation status and/or one or more ancillary cancer biomarkers of methylscape genomic DNA, is selected to exhibit a positive or negative likelihood ratio of at least about 1.5 or more or about 0.67 or less, at least about 2 or more or about 0.5 or less, at least about 5 or more or about 0.2 or less, at least about 10 or more or about 0.1 or less, or at least about 20 or more or about 0.05 or less.

In certain embodiments, a methylscape physical or physicochemical feature or feature panel, and optionally a methylation status and/or one or more ancillary cancer biomarkers of methylscape genomic DNA, is selected to exhibit an odds ratio of at least about 2 or more or about 0.5 or less, at least about 3 or more or about 0.33 or less, at least about 4 or more or about 0.25 or less, at least about 5 or more or about 0.2 or less, or at least about 10 or more or about 0.1 or less.

In certain embodiments, a methylscape physical or physicochemical feature or feature panel, and optionally a methylation status and/or one or more ancillary cancer biomarkers of methylscape genomic DNA, is selected to exhibit an AUC ROC value of greater than 0.5, preferably at least 0.6, more preferably 0.7, still more preferably at least 0.8, even more preferably at least 0.9, and most preferably at least 0.95.

In some cases, multiple thresholds may be determined in so-called "tertile", "quartile", or "quintile" analyses. In these methods, for example, the "diseased (e.g., cancer)" and "control groups" (or "high risk" and "low risk") groups are considered together as a single population, and are divided into 3, 4, or 5 (or more) "bins" having equal numbers of individuals. The boundary between two of these "bins" may be considered "thresholds." A risk (of a particular diagnosis or prognosis for example) can be assigned based on which "bin" a test subject falls into.

In other embodiments, particular thresholds for the methylscape physical or physicochemical feature or feature panel, and optionally methylation status and/or one or more ancillary cancer biomarkers of methylscape genomic DNA, are not relied upon to determine if the methylscape physical or physicochemical feature or feature panel, and optionally methylation status and/or one or more ancillary cancer biomarkers of methylscape genomic DNA, obtained from a subject are correlated to a particular diagnosis or prognosis. For example, a temporal change in the methylscape physical or physicochemical feature or feature panel, and optionally the methylation status and/or one or more ancillary cancer biomarkers of methylscape genomic DNA, can be used to rule in or out one or more particular diagnoses and/or prognoses. Alternatively, the methylscape physical or physicochemical feature or feature panel, and optionally the methylation status and/or one or more ancillary cancer biomarkers of methylscape genomic DNA, is correlated to a condition, disease, prognosis, treatment efficacy etc., by the presence or absence of a methylscape physical or physicochemical feature or feature panel, and optionally the methylation status and/or one or more ancillary cancer biomarkers of methylscape genomic DNA, in a particular assay format. In the case of methylscape physical or physicochemical feature panel, and optionally methylation status and/or one or more ancillary cancer biomarkers of methylscape genomic DNA, the present invention may utilize an evaluation of the entire profile of features to provide a single result value (e.g., a "panel response" value expressed either as a numeric score or as a percentage risk).

In certain embodiments, a methylscape physical or physicochemical feature or feature panel, and optionally the methylation status and/or one or more ancillary cancer biomarkers of methylscape genomic DNA, is selected to assist in distinguishing a pair of groups (i.e., assist in assessing whether a subject has an increased likelihood of being in one group or the other group of the pair) selected for example from "healthy condition" and "cancer", "a first stage or severity of cancer" and "a second stage or severity of cancer", or "low risk" and "high risk" with at least about 70%, 80%, 85%, 90% or 95% sensitivity, suitably in combination with at least about 70% 80%, 85%, 90% or 95% specificity. In some embodiments, both the sensitivity and specificity are at least about 75%, 80%, 85%, 90% or 95%.

The phrases "assessing the likelihood" and "determining the likelihood", as used herein, refer to methods by which the skilled artisan can predict the presence or absence of a condition (e.g., a condition selected from healthy condition, cancer, a particular stage of cancer, or a particular severity of cancer) in a patient. The skilled artisan will understand that this phrase includes within its scope an increased probability that a condition is present or absence in a patient; that is, that a condition is more likely to be present or absent in a subject. For example, the probability that an individual identified as having a specified condition actually has the condition may be expressed as a "positive predictive value" or "PPV." Positive predictive value can be calculated as the number of true positives divided by the sum of the true positives and false positives. PPV is determined by the characteristics of the predictive methods of the present invention as well as the prevalence of the condition in the population analyzed. The statistical algorithms can be selected such that the positive predictive value in a population having a condition prevalence is in the range of 70% to 99% and can be, for example, at least 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In other examples, the probability that an individual identified as not having a specified condition actually does not have that condition may be expressed as a "negative predictive value" or "NPV." Negative predictive value can be calculated as the number of true negatives divided by the sum of the true negatives and false negatives. Negative predictive value is determined by the characteristics of the diagnostic or prognostic method, system, or code as well as the prevalence of the disease in the population analyzed. The statistical methods and models can be selected such that the negative predictive value in a population having a condition prevalence is in the range of about 70% to about 99% and can be, for example, at least about 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In some embodiments, a subject is determined as having a significant likelihood of having or not having a specified condition. By "significant likelihood" is meant that the subject has a reasonable probability (0.6, 0.7, 0.8, 0.9 or more) of having, or not having, a specified condition (e.g., healthy condition, cancer, a stage of cancer or severity of cancer).

The methylscape genomic DNA analysis methods of the present invention permit the generation of data sets that can be evaluated using informatics approaches. Informatics analytical methods are known, and software is available to those in the art, e.g., cluster analysis (Pirouette, Informetrix), class prediction (SIMCA-P, Umetrics), principal components analysis of a computationally modeled dataset (SIMCA-P, Umetrics), 2D cluster analysis (GeneLinker Platinum, Improved Outcomes Software), and metabolic pathway analysis (biotech.icmb.utexas.edu). The choice of software packages offers specific tools for questions of interest (Kennedy et al., Solving Data Mining Problems Through Pattern Recognition. Indianapolis: Prentice Hall PTR, 1997; Golub et al., (2999) Science 286:531-7; Eriksson et al., Multi and Megavariate Analysis Principles and Applications: Umetrics, Umea, 2001). In general, any suitable mathematic analysis can be used to evaluate the methylscape physical or physicochemical feature or feature panel, and optionally the methylation status and/or one or more ancillary cancer biomarkers of methylscape genomic DNA, with respect to a condition selected from healthy condition, cancer, a particular stage of cancer, or a particular severity of cancer. For example, methods such as multivariate analysis of variance, multivariate regression, and/or multiple regression can be used to determine relationships between dependent variables (e.g., clinical measures) and independent variables (e.g., methylscape physical or physicochemical feature or feature panel, and optionally the methylation status and/or one or more ancillary cancer biomarkers of methylscape genomic DNA). Clustering, including both hierarchical and non-hierarchical methods, as well as nonmetric Dimensional Scaling can be used to determine associations or relationships among variables and among changes in those variables.

In addition, principal component analysis is a common way of reducing the dimension of studies and can be used to interpret the variance-covariance structure of a data set. Principal components may be used in such applications as multiple regression and cluster analysis. Factor analysis is used to describe the covariance by constructing "hidden" variables from the observed variables. Factor analysis may be considered an extension of principal component analysis, where principal component analysis is used as parameter estimation along with the maximum likelihood method. Furthermore, simple hypothesis such as equality of two vectors of means can be tested using Hotelling's T squared statistic.

5. Method of Treatment

The detection and diagnostic methods of the present invention are also suitable for identifying patients that may require treatment; that is, patient stratification. Thus, the present invention further provides methods of treating cancer. These methods typically comprise analyzing a biological sample obtained from a subject for the presence or absence of a cancer methylscape genomic DNA molecule or complex thereof, and optionally the methylation status and/or one or more ancillary cancer biomarkers of methylscape genomic DNA; and exposing the subject to a treatment regimen for treating the cancer if the analysis indicates the likely presence of cancer in the subject, or not exposing the subject to a treatment regimen for treating the cancer if the analysis indicates the likely absence of cancer in the subject. The biological samples can be analyzed at the point of care or they can be sent to laboratories to conduct the analysis.

Following diagnosis, treatment is often decided according to the type of cancer, its anatomical location in the subject and its size (i.e., its stage). The "stage" of a cancer is a descriptor (usually numbers I to IV) of how much the cancer has spread. The stage often takes into account the size of a primary and/or secondary tumor, how deep it has penetrated, whether it has invaded adjacent organs, if and how many lymph nodes it has metastasized to, and whether it has spread to distant organs. Staging of a cancer is important because the stage at diagnosis is a predictor of survival, and treatments are often changed based on the stage.

Thus, the present invention contemplates exposing the subject to a treatment regimen if the subject tests positive for the presence or likelihood of the presence of the cancer. Non-limiting examples of such treatment regimens include surgery, cytotoxic therapy, nucleic acid therapy and immunotherapy. Non-limiting examples of treatment regimens include the administration of cancer therapy agents cytotoxic agents, gene therapy agents, DNA therapy agents, viral therapy agents, RNA therapy agents, immunotherapeutic agents, bone marrow transplantation agents, nanotherapy agents, or a combination of the foregoing. The cancer therapy agent may be in the form of adjuvant or neoadjuvant therapy. In some embodiments, the cancer therapy agent is a small molecule enzymatic inhibitor or anti-metastatic agent. In some embodiments, the cancer therapy agent is a side-effect limiting agent (e.g., agents intended to lessen the occurrence and/or severity of side effects of treatment, such as anti-nausea agents, etc.). In some embodiments, the cancer therapy agent is a radiotherapy agent. In some embodiments, the cancer therapy agent is an agent that targets PI3K/AKT/mTOR pathway, HSP90 inhibitor, tubulin inhibitor, apoptosis inhibitor, and/or chemopreventative agent. In some embodiments, the cancer therapy agent is an immunotherapeutic, e.g., a blocking antibody, ipilimumab (also known as MDX-010, MDX-101, or Yervoy®), tremelimumab (also known as ticilimumab or CP-675,206), an antagonist directed against B7-H3 (also known as CD276), e.g., a blocking antibody, MGA271, an antagonist directed against a TGF-β, e.g., metelimumab (also known as CAT-192), fresolimumab (also known as GC1008), or LY2157299, a T cell (e.g., a cytotoxic T cell or CTL) expressing a chimeric antigen receptor (CAR), a T cell comprising a dominant-negative TGF-β receptor, e.g., a dominant-negative TGF-β type II receptor, an agonist directed against CD137 (also known as TNFRSF9, 4-1BB, or ILA), e.g., an activating antibody, urelumab (also known as BMS-663513), an agonist directed against CD40, e.g., an activating antibody, CP-870893, an agonist directed against OX40 (also known as CD134), e.g., an activating antibody, administered in conjunction with an anti-OX40 antibody (e.g., AgonOX), an agonist directed against CD27, e.g., an activating antibody, CDX-1127, indoleamine-2,3-dioxygenase (IDO), 1-methyl-D-tryptophan (also known as 1-D-MT), an antibody-drug conjugate (in some embodiments, comprising mertansine or monomethyl auristatin E (MMAE)), an anti-NaPi2b antibody-MMAE conjugate (also known as DNIB0600A or RG7599), trastuzumab emtansine (also known as T-DM1, ado-trastuzumab emtansine, or KADCYLA®, Genentech), DMUC5754A, an antibody-drug conjugate targeting the endothelin B receptor (EDNBR), e.g., an antibody directed against EDNBR conjugated with MMAE, an angiogenesis inhibitor, an antibody directed against a VEGF, e.g., VEGF-A, bevacizumab (also known as AVASTIN®, Genentech), an antibody directed against angiopoietin 2 (also known as Ang2), MEDI3617, an antineoplastic agent, an agent targeting CSF-1R (also known as M-CSFR or CD115), anti-CSF-1R (also known as IMC-CS4), an interferon, for example IFN-α or IFN-γ, Roferon-A, GM-CSF (also known as recombinant human granulocyte macrophage colony stimulating factor, rhu GM-CSF, sargramostim, or Leukine®), IL-2 (also known as aldesleukin or Proleukin®), IL-12, an antibody targeting CD20 (in some embodiments, the antibody targeting CD20 is obinutuzumab (also known as GA101 or Gazyva®) or rituximab), an antibody targeting GITR (in some embodiments, the antibody targeting GITR is TRX518), in conjunction with a cancer vaccine (in some embodiments, the cancer vaccine is a peptide cancer vaccine, which in some embodiments is a personalized peptide vaccine; in some embodiments the peptide cancer vaccine is a multivalent long peptide, a multi-peptide, a peptide cocktail, a hybrid peptide, or a peptide-pulsed dendritic cell vaccine (see, e.g., Yamada et al., Cancer Sci, 104:14-21, 2013)), in conjunction with an adjuvant, a TLR agonist, e.g., Poly-ICLC (also known as Hiltonol®), LPS, MPL, or CpG ODN, TNF-α, IL-1, HMGB1, an IL-10 antagonist, an IL-4 antagonist, an IL-13 antagonist, an HVEM antagonist, an ICOS agonist, e.g., by administration of ICOS-L, or an agonistic antibody directed against ICOS, an agent targeting CX3CL1, an agent targeting CXCL10, an agent targeting CCL5, an LFA-1 or ICAM1 agonist, a Selectin agonist, a targeted therapeutic agent, an inhibitor of B-Raf, vemurafenib (also known as Zelboraf®), dabrafenib (also known as Tafinlar®), erlotinib (also known as Tarceva®), an inhibitor of a MEK, such as MEK1 (also known as MAP2K1) or MEK2 (also known as MAP2K2). cobimetinib (also known as GDC-0973 or XL-518), trametinib (also known as Mekinist®), an inhibitor of K-Ras, an inhibitor of c-Met, onartuzumab (also known as MetMAb), an inhibitor of Alk, AF802 (also known as CH5424802 or alectinib), an inhibitor of a phosphatidylinositol 3-kinase (PI3K), BKM120, idelalisib (also known as GS-1101 or CAL-101), perifosine (also known as KRX-0401), an Akt, MK2206, GSK690693, GDC-0941, an inhibitor of mTOR, sirolimus (also known as rapamycin), temsirolimus (also known as CCI-779 or Torisel®), everolimus (also known as RAD001), ridaforolimus (also known as AP-23573, MK-8669, or deforolimus), OSI-027, AZD8055, INK128, a dual PI3K/mTOR inhibitor, XL765, GDC-0980, BEZ235 (also known as NVP-BEZ235), BGT226, GSK2126458, PF-04691502, PF-05212384 (also known as PKI-587). The cancer therapy agent may be one or more of the cytotoxic or chemotherapeutic agents described herein.

6. Method of Monitoring Treatment

The present invention can also be used to monitor the efficacy of treatment for a cancer. Thus, the present invention further provides methods for monitoring efficacy of a treatment regimen in a subject with a cancer. These methods typically comprise analyzing a biological sample obtained from a subject exposed to a treatment regimen for the presence, absence or level of a cancer methylscape genomic DNA molecule or complex thereof, and optionally the methylation status and/or one or more ancillary cancer biomarkers of the methylscape genomic DNA; and monitoring the subject over a period of time for a change in the methylscape of the genomic DNA molecule or complex thereof using the detection methods of the present invention, wherein a change or otherwise in the methylscape of the genomic DNA molecule or complex thereof over the period of time is indicative of treatment efficacy.

In some embodiments, the methods comprise the analysis of a series of biological samples obtained over a period of time using a similar source of biological sample. In another embodiment, the method comprises analyzing a series of biological samples obtained over a period of time from different sources from the same subject or by analyzing a series of biological samples obtained over a period of time from a combination of the same and different sources from the same subject.

Particular Embodiments of the Invention

1. An isolated nucleic acid complex comprising a plurality of genomic DNA molecules each comprising a clustered distribution of methylated nucleotides (e.g., methylated cytosines), wherein the complex is formed by self-assembly of the DNA molecules under aqueous conditions.

2. An isolated nucleic acid complex comprising genomic DNA comprising a plurality of genomic DNA molecules individual ones of which comprise a clustered distribution of methylated nucleotides (e.g., methylated cytosines), wherein the complex is formed by self-assembly of the DNA molecules under aqueous conditions.

3. The complex of embodiment 1 or embodiment 2, wherein the methylated nucleotides (e.g., methylated cytosines) are in at least one CpG cluster.

4. The complex of embodiment 3, wherein at least about 10%, 20%, 30%, 40%, 50%, 60%, 70%, 80%, 90%, or even about 100%, of the nucleotides (e.g., cytosine) in a respective CpG cluster are methylated.

5. The complex of embodiment 3 or embodiment 4, wherein the CpG cluster is flanked by at least one region that comprises a lower frequency of methylated nucleotides (e.g., methylated cytosines) than a respective CpG cluster.

6. The complex of embodiment 5, wherein the at least one flanking region comprises a frequency of methylated nucleotides (e.g., methylated cytosines) that is no more than about ½, ⅓, ¼, ⅕, ⅙, ⅐, ⅛, ⅑, ¹⁄₁₀, ¹⁄₂₀, ¹⁄₃₀, ¹⁄₄₀, ¹⁄₅₀ or ¹⁄₁₀₀ of the frequency of methylated nucleotides (e.g., methylated cytosines) in a respective CpG cluster.

7. The complex of any one of embodiments 1 to 6, wherein the genomic DNA molecules have a length of up to 300, up to 400, up to 500, up to 1000, up to 2,000, up to 3,000, up to 4,000, up to 5,000, up to 10,000, up to 15,000, or even up to 20,000 base pairs.

8. The complex of any one of embodiments 1 to 7, wherein the genomic DNA molecules have a length of at least 25, at least 50, at least 75, at least 100, or at least 200 base pairs.

9. The complex of any one of embodiments 1 to 8, wherein the complex has a size of about 10 $nm^2$ to about 2000 $nm^2$, 50 $nm^2$ to about 2000 $nm^2$, 100 $nm^2$ to about 2000 $nm^2$, 500 $nm^2$ to about 2000 $nm^2$, or 1000 $nm^2$ to about 2000 $nm^2$, in the aqueous conditions.

10. The complex of any one of embodiments 1 to 9, wherein the genomic DNA molecules are amphipathic.

11. A system comprising
  a biological sample comprising a nucleic acid complex that comprises a plurality of genomic DNA molecules each comprising a clustered distribution of methylated nucleotides (e.g., methylated cytosines), wherein the complex is formed by self-assembly of the DNA molecules under aqueous conditions; and
  a sensor, which is in communication with the biological sample, for detecting the presence or level of the nucleic acid complex.

12. A system comprising:
a biological sample comprising a nucleic acid complex comprising genomic DNA comprising a plurality of genomic DNA molecules individual ones of which comprise a clustered distribution of methylated nucleotides (e.g., methylated cytosines), wherein the complex is formed by self-assembly of the DNA molecules under aqueous conditions; and
a sensor, which is in communication with the biological sample, for detecting the presence or level of the nucleic acid complex.

13. The system of embodiment 11 or embodiment 12, wherein the sensor is selected from one or more of: an antigen-binding molecule that binds specifically with the nucleic acid complex, a light based sensor, a spectrometer, a refractometer, a particle sizer, an x-ray, a monochromator, an absorption detector, a reflectance detector, a transmission detector, a conductivity sensor, an electrode, a resistive pulse sensor, a camera, a microscope, a particle size analyzer, an optical detector, a solid support to which hydrophobic moieties adsorb under the aqueous conditions, a colloidal particle or a biosensor.

14. The system of any one of embodiments 11 to 13, wherein the sensor comprises a microscope.

15. The system of embodiment 14, wherein the microscope is a transmission electron microscope.

16. The system of any one of embodiments 11 to 15, wherein the sensor comprises a solid support to which hydrophobic moieties (e.g., methylated nucleotides such as methylated cytosines) adsorb under the aqueous conditions.

17. The system of any one of embodiments 11 to 15, wherein the sensor comprises a solid support to which clustered hydrophobic moieties (e.g., clustered methylated nucleotides such as clustered methylated cytosines) adsorb under the aqueous conditions.

18. The system of any one of embodiments 11 to 15, wherein the sensor comprises a solid support to which hydrophobic moieties (e.g., methylated nucleotides such as methylated cytosines) adsorb more strongly than hydrophilic moieties under the aqueous conditions.

19. The system of any one of embodiments 11 to 15, wherein the sensor comprises a solid support to which clustered hydrophobic moieties (e.g., clustered methylated nucleotides such as clustered methylated cytosines) adsorb more strongly than non-clustered hydrophobic moieties (e.g., non-clustered methylated nucleotides such as non-clustered methylated cytosines) under the aqueous conditions.

20. The system of any one of embodiments 16 to 19, wherein the solid support is selected from organic polymers such as polystyrene and its derivatives, polyacrylates and polymethacrylates and their derivatives, polyurethanes, nylon, polyethylene, polypropylene, polybutylene and copolymers of these materials, polysaccharides and hydrogels such as agarose, cellulose, dextran, Sephadex, Sephacryl, chitosan, inorganic supports such as silica gels, silica particles, glass, metal, semi-metal oxides, and supports with metal surfaces.

21. The system of embodiment 20, wherein the solid support is selected from a polymer bead, an agarose bead, a polystyrene bead, an acrylamide bead, a solid core bead, a porous bead, a paramagnetic bead, glass bead, controlled pore bead, a microtiter well, a cyclo-olefin copolymer substrate, a membrane, a plastic substrate, nylon, a Langmuir-Blodgett film, glass, a germanium substrate, a silicon substrate, a silicon wafer chip, a flow through chip, a microbead, a nanoparticle, a polytetrafluoroethylene substrate, a polystyrene substrate, a metal substrate such as a gold (Au) substrate, a silver (Ag) substrate; a tin (Sn) substrate, a rhodium (Rh) substrate, a ruthenium (Ru) substrate, a palladium (Pd) substrate, an osmium (Os) substrate, an iridium (Ir) substrate, a platinum (Pt) substrate, a titanium (Ti) substrate, an aluminum (Al) substrate, a chromium (Cr), a copper (Cu) substrate, a magnesium (Mg) substrate, a carbon substrate, a silicon substrate such as p-type doped silicon substrate, n-type doped silicon substrate, and gallium arsenide.

22. The system of embodiment 20 or embodiment 21, wherein the solid support is a colloidal particle.

23. The system of embodiment 22, wherein the colloidal particle comprises a metal substrate such as a gold (Au) substrate, a silver (Ag) substrate; a tin (Sn) substrate, a rhodium (Rh) substrate, a ruthenium (Ru) substrate, a palladium (Pd) substrate, an osmium (Os) substrate, an iridium (Ir) substrate, a platinum (Pt) substrate, a titanium (Ti) substrate, an aluminum (Al) substrate, a chromium (Cr), a copper (Cu) substrate, a magnesium (Mg) substrate, a carbon substrate, a silicon substrate such as p-type doped silicon substrate, n-type doped silicon substrate, and gallium arsenide.

24. The system of any one of embodiments 11 to 23, wherein the sensor comprises an electrode that comprises an electro-conductive material to which hydrophobic moieties (e.g., methylated nucleotides such as methylated cytosines) adsorb under the aqueous conditions.

25. The system of embodiment 24, wherein the electro-conductive material is selected from gold, platinum, palladium, silver, carbon, alloys thereof, and composites thereof.

26. The system of embodiment 24 or embodiment 25, wherein the electrode is a working electrode that is part of an electrical detection unit comprising an electrical circuit configured for detecting an electrical signal from the working electrode, wherein the electrical signal is selected from the group consisting of current or voltage, or a derived parameter such as impedance, capacitance, charge, conductivity, resistance, or a combination thereof.

27. A conjugate comprising:
a nucleic acid that comprises a plurality of genomic DNA molecules each comprising a clustered distribution of methylated nucleotides (e.g., methylated cytosines), wherein the complex is formed by self-assembly of the DNA molecules under aqueous conditions; and
an affinity agent for which the nucleic acid complex substrate has affinity.

28. A conjugate comprising:
a nucleic acid complex comprising genomic DNA comprising a plurality of genomic DNA molecules individual ones of which comprise a clustered distribution of methylated nucleotides (e.g., methylated cytosines), wherein the complex is formed by self-assembly of the DNA molecules under aqueous conditions; and
an affinity agent for which the nucleic acid complex substrate has affinity.

29. The conjugate of embodiment 27 or embodiment 28, wherein the affinity agent is an antigen-binding molecule that binds specifically with the nucleic acid complex.

30. The conjugate of embodiment 29, wherein the affinity agent is a solid support to which hydrophobic moieties (e.g., methylated nucleotides such as methylated cytosines) adsorb under the aqueous conditions.

31. The conjugate of embodiment 29, wherein the affinity agent is a solid support to which clustered hydrophobic moieties (e.g., clustered methylated nucleotides such as clustered methylated cytosines) adsorb under the aqueous conditions.

32. The conjugate of embodiment 29, wherein the affinity agent is a solid support to which hydrophobic moieties (e.g., methylated nucleotides such as methylated cytosines) adsorb more strongly than hydrophilic moieties under the aqueous conditions.

33. The conjugate of embodiment 29, wherein the affinity agent is a solid support to which clustered hydrophobic moieties (e.g., clustered methylated nucleotides such as clustered methylated cytosines) adsorb more strongly than non-clustered hydrophobic moieties (e.g., non-clustered methylated nucleotides such as non-clustered methylated cytosines) under the aqueous conditions.

34. The conjugate of any one of embodiments 30 to 33, wherein the solid support is selected from organic polymers such as polystyrene and its derivatives, polyacrylates and polymethacrylates and their derivatives, polyurethanes, nylon, polyethylene, polypropylene, polybutylene and copolymers of these materials, polysaccharides and hydrogels such as agarose, cellulose, dextran, Sephadex, Sephacryl, chitosan, inorganic supports such as silica gels, silica particles, glass, metal, semi-metal oxides, and supports with metal surfaces.

35. The conjugate of embodiment 34, wherein the solid support is selected from a polymer bead, an agarose bead, a polystyrene bead, an acrylamide bead, a solid core bead, a porous bead, a paramagnetic bead, glass bead, controlled pore bead, a microtiter well, a cyclo-olefin copolymer substrate, a membrane, a plastic substrate, nylon, a Langmuir-Blodgett film, glass, a germanium substrate, a silicon substrate, a silicon wafer chip, a flow through chip, a microbead, a nanoparticle, a polytetrafluoroethylene substrate, a polystyrene substrate, a metal substrate such as a gold (Au) substrate, a silver (Ag) substrate; a tin (Sn) substrate, a rhodium (Rh) substrate, a ruthenium (Ru) substrate, a palladium (Pd) substrate, an osmium (Os) substrate, an iridium (Ir) substrate, a platinum (Pt) substrate, a titanium (Ti) substrate, an aluminum (Al) substrate, a chromium (Cr), a copper (Cu) substrate, a magnesium (Mg) substrate, a carbon substrate, a silicon substrate such as p-type doped silicon substrate, n-type doped silicon substrate, and gallium arsenide 36. The conjugate of any one of embodiments 30 to 35, wherein the solid support is a colloidal particle.

37. The conjugate of embodiment 36, wherein the colloidal particle comprises a metal substrate such as a gold (Au) substrate, a silver (Ag) substrate; a tin (Sn) substrate, a rhodium (Rh) substrate, a ruthenium (Ru) substrate, a palladium (Pd) substrate, an osmium (Os) substrate, an iridium (Ir) substrate, a platinum (Pt) substrate, a titanium (Ti) substrate, an aluminum (Al) substrate, a chromium (Cr), a copper (Cu) substrate, a magnesium (Mg) substrate, a carbon substrate, a silicon substrate such as p-type doped silicon substrate, n-type doped silicon substrate, and gallium arsenide.

38. A method of detecting clustered methylated nucleic acid in a biological sample, the method comprising: detecting in the biological sample a nucleic acid complex that comprises a plurality of genomic DNA molecules each comprising a clustered distribution of methylated nucleotides (e.g., methylated cytosines), wherein the complex is formed by self-assembly of the DNA molecules under aqueous conditions.

39. A method of detecting clustered methylated nucleic acid in a biological sample, the method comprising: detecting in the biological sample a nucleic acid complex comprising genomic DNA comprising a plurality of genomic DNA molecules individual ones of which comprise a clustered distribution of methylated nucleotides (e.g., methylated cytosines), wherein the complex is formed by self-assembly of the DNA molecules under aqueous conditions.

40. The method of embodiment 38 or embodiment 39, wherein nucleic acid complex is detected by contacting the biological sample with an affinity agent for which the nucleic acid complex has affinity.

41. The method of embodiment 40, wherein the affinity agent is an antigen-binding molecule that binds specifically with the nucleic acid complex.

42. The method of embodiment 40, wherein the affinity agent is a solid support to which hydrophobic moieties (e.g., methylated nucleotides such as methylated cytosines) adsorb under the aqueous conditions.

43. The method of embodiment 40, wherein the affinity agent is a solid support to which clustered hydrophobic moieties (e.g., clustered methylated nucleotides such as clustered methylated cytosines) adsorb under the aqueous conditions.

44. The method of embodiment 40, wherein the affinity agent is a solid support to which hydrophobic moieties (e.g., methylated nucleotides such as methylated cytosines) adsorb more strongly than hydrophilic moieties under the aqueous conditions.

45. The method of embodiment 40, wherein the affinity agent is a solid support to which clustered hydrophobic moieties (e.g., clustered methylated nucleotides such as clustered methylated cytosines) adsorb more strongly than non-clustered hydrophobic moieties (e.g., non-clustered methylated nucleotides such as non-clustered methylated cytosines) under the aqueous conditions.

46. The method of any one of embodiment 42 to 45, wherein the solid support is selected from organic polymers such as polystyrene and its derivatives, polyacrylates and polymethacrylates and their derivatives, polyurethanes, nylon, polyethylene, polypropylene, polybutylene and copolymers of these materials, polysaccharides and hydrogels such as agarose, cellulose, dextran, Sephadex, Sephacryl, chitosan, inorganic supports such as silica gels, silica particles, glass, metal, semi-metal oxides, and supports with metal surfaces.

47. The method of embodiment 46, wherein the solid support is selected from a polymer bead, an agarose bead, a polystyrene bead, an acrylamide bead, a solid core bead, a porous bead, a paramagnetic bead, glass bead, controlled pore bead, a microtiter well, a cyclo-olefin copolymer substrate, a membrane, a plastic substrate, nylon, a Langmuir-Blodgett film, glass, a germanium substrate, a silicon substrate, a silicon wafer chip, a flow through chip, a microbead, a nanoparticle, a polytetrafluoroethylene substrate, a polystyrene substrate, a metal substrate such as a gold (Au) substrate, a silver (Ag) substrate; a tin (Sn) substrate, a rhodium (Rh) substrate, a ruthenium (Ru) substrate, a palladium (Pd) substrate, an osmium (Os) substrate, an iridium (Ir) substrate, a platinum (Pt) substrate, a titanium (Ti) substrate, an aluminum (Al) substrate, a chromium (Cr), a copper (Cu) substrate, a magnesium (Mg) substrate, a carbon substrate, a silicon substrate such as p-type doped silicon substrate, n-type doped silicon substrate, and gallium arsenide 48. The method of any one of embodiments 42 to 47, wherein the solid support is a colloidal particle.

49. The method of embodiment 48, wherein the colloidal particle comprises a metal substrate such as a gold (Au)

substrate, a silver (Ag) substrate; a tin (Sn) substrate, a rhodium (Rh) substrate, a ruthenium (Ru) substrate, a palladium (Pd) substrate, an osmium (Os) substrate, an iridium (Ir) substrate, a platinum (Pt) substrate, a titanium (Ti) substrate, an aluminum (Al) substrate, a chromium (Cr), a copper (Cu) substrate, a magnesium (Mg) substrate, a carbon substrate, a silicon substrate such as p-type doped silicon substrate, n-type doped silicon substrate, and gallium arsenide.

50. The method of embodiment 38 or embodiment 39, wherein the nucleic acid complex is detected by exposing the biological sample to electromagnetic radiation and detecting a physical feature that is indicative of the nucleic acid complex.

51. The method of embodiment 50, wherein the physical feature is selected from size, shape or aggregation status of the nucleic acid complex.

52. The method of embodiment 51, wherein the size is about 10 nm$^2$ to about 2000 nm$^2$, 50 nm$^2$ to about 2000 nm$^2$, 100 nm$^2$ to about 2000 nm$^2$, 500 nm$^2$ to about 2000 nm$^2$, or 1000 nm$^2$ to about 2000 nm$^2$, in the aqueous conditions.

53. The method of any one of embodiments 50 to 52, wherein the electromagnetic radiation includes light.

54. The method of any one of embodiments 50 to 53, wherein the electromagnetic radiation includes at least one of an x-ray radiation, a microwave radiation, an infrared light, a radio frequency signal or an ultraviolet light.

55. The method of any one of embodiments 50 to 54, wherein the physical feature is detected by receiving electromagnetic radiation from the nucleic acid complex.

56. The method of embodiment 55, wherein the received electromagnetic radiation comprises scattered, refracted, phase-shifted, or emitted electromagnetic radiation or particle beams.

57. The method of embodiment 55 or embodiment 56, wherein the received electromagnetic radiation comprises visible light.

58. The method of any one of embodiments 50 to 57, wherein the physical feature is detected by microscopy.

59. The method of embodiment 58, wherein the microscopy comprises transmission electron microscopy.

60. The method of any one of embodiments 50 to 59, wherein the physical feature is detected by colorimetric detection.

61. The method of embodiment 60, wherein the colorimetric detection is facilitated by contacting the biological sample with a colloidal particle comprising a substrate to which hydrophobic moieties (e.g., methylated nucleotides such as methylated cytosines) adsorb under the aqueous conditions.

62. The method of embodiment 60, wherein the colorimetric detection is facilitated by contacting the biological sample with a colloidal particle comprising a substrate to which clustered hydrophobic moieties (e.g., clustered methylated nucleotides such as clustered methylated cytosines) adsorb under the aqueous conditions.

63. The method of embodiment 60, wherein the colorimetric detection is facilitated by contacting the biological sample with a colloidal particle comprising a substrate to which hydrophobic moieties (e.g., methylated nucleotides such as methylated cytosines) adsorb more strongly than hydrophilic moieties under the aqueous conditions.

64. The method of embodiment 60, wherein the colorimetric detection is facilitated by contacting the biological sample with a colloidal particle comprising a substrate to which clustered hydrophobic moieties (e.g., clustered methylated nucleotides such as clustered methylated cytosines) adsorb more strongly than non-clustered hydrophobic moieties (e.g., non-clustered methylated nucleotides such as non-clustered methylated cytosines) under the aqueous conditions.

65. The method of any one of embodiments 57 to 60, wherein the substrate comprises a metal substrate such as a gold (Au) substrate, a silver (Ag) substrate; a tin (Sn) substrate, a rhodium (Rh) substrate, a ruthenium (Ru) substrate, a palladium (Pd) substrate, an osmium (Os) substrate, an iridium (Ir) substrate, a platinum (Pt) substrate, a titanium (Ti) substrate, an aluminum (Al) substrate, a chromium (Cr), a copper (Cu) substrate, a magnesium (Mg) substrate, a carbon substrate, a silicon substrate such as p-type doped silicon substrate, n-type doped silicon substrate, and gallium arsenide.

66. The method of embodiment 38 or embodiment 39, wherein the nucleic acid complex is detected by electrochemical detection.

67. The method of embodiment 66, wherein the electrochemical detection comprises exposing the biological sample to a working electrode that comprises an electroconductive material to which hydrophobic moieties (e.g., methylated nucleotides such as methylated cytosines) adsorb under the aqueous conditions; applying a potential to the working electrode; and detecting an electrical signal from the working electrode that is indicative of adsorption of the nucleic acid complex to the electroconductive material, wherein the electrical signal is selected from the group consisting of current, voltage, impedance, capacitance, charge, conductivity, resistance, or a combination thereof.

68. The method of embodiment 67, wherein the electroconductive material is selected from gold, platinum, palladium, silver, carbon, alloys thereof, and composites thereof.

69. A method of isolating a nucleic acid complex from a biological sample, wherein the complex comprises a plurality of genomic DNA molecules each comprising a clustered distribution of methylated nucleotides (e.g., methylated cytosines), and is formed by self-assembly of the DNA molecules under aqueous conditions, the method comprising contacting the biological sample with an affinity agent for which the nucleic acid complex has affinity to form a conjugate and separating the conjugate from the biological sample.

70. A method of isolating a nucleic acid complex from a biological sample, wherein the nucleic complex comprises genomic DNA comprising a plurality of genomic DNA molecules individual ones of which comprise a clustered distribution of methylated nucleotides (e.g., methylated cytosines), wherein the complex is formed by self-assembly of the DNA molecules under aqueous conditions, the method comprising contacting the biological sample with an affinity agent for which the nucleic acid complex has affinity to form a conjugate and separating the conjugate from the biological sample.

71. The method of embodiment 69 or embodiment 70, further comprising separating the nucleic acid complex from the affinity agent.

72. The method of embodiment 71, wherein the nucleic acid complex is separated from the affinity agent by elution.

73. The method of any one of embodiments 69 to 72, wherein the affinity agent is an antigen-binding molecule that binds specifically with the nucleic acid complex.

74. The method of any one of embodiments 69 to 72, wherein the affinity agent is a solid support to which hydrophobic moieties (e.g., methylated nucleotides such as methylated cytosines) adsorb under the aqueous conditions.

75. The method of any one of embodiments 69 to 72, wherein the affinity agent is a solid support to which clustered hydrophobic moieties (e.g., clustered methylated nucleotides such as clustered methylated cytosines) adsorb under the aqueous conditions.

76. The method of any one of embodiments 69 to 72, wherein the affinity agent is a solid support to which hydrophobic moieties (e.g., methylated nucleotides such as methylated cytosines) adsorb more strongly than hydrophilic moieties under the aqueous conditions.

77. The method of any one of embodiments 69 to 72, wherein the affinity agent is a solid support to which clustered hydrophobic moieties (e.g., clustered methylated nucleotides such as clustered methylated cytosines) adsorb more strongly than non-clustered hydrophobic moieties (e.g., non-clustered methylated nucleotides such as non-clustered methylated cytosines) under the aqueous conditions.

78. The method of any one of embodiments 74 to 77, wherein the solid support is selected from organic polymers such as polystyrene and its derivatives, polyacrylates and polymethacrylates and their derivatives, polyurethanes, nylon, polyethylene, polypropylene, polybutylene and copolymers of these materials, polysaccharides and hydrogels such as agarose, cellulose, dextran, Sephadex, Sephacryl, chitosan, inorganic supports such as silica gels, silica particles, glass, metal, semi-metal oxides, and supports with metal surfaces.

79. The method of embodiment 78, wherein the solid support is selected from a polymer bead, an agarose bead, a polystyrene bead, an acrylamide bead, a solid core bead, a porous bead, a paramagnetic bead, glass bead, controlled pore bead, a microtiter well, a cyclo-olefin copolymer substrate, a membrane, a plastic substrate, nylon, a Langmuir-Blodgett film, glass, a germanium substrate, a silicon substrate, a silicon wafer chip, a flow through chip, a microbead, a nanoparticle, a polytetrafluoroethylene substrate, a polystyrene substrate, a metal substrate such as a gold (Au) substrate, a silver (Ag) substrate; a tin (Sn) substrate, a rhodium (Rh) substrate, a ruthenium (Ru) substrate, a palladium (Pd) substrate, an osmium (Os) substrate, an iridium (Ir) substrate, a platinum (Pt) substrate, a titanium (Ti) substrate, an aluminum (Al) substrate, a chromium (Cr), a copper (Cu) substrate, a magnesium (Mg) substrate, a carbon substrate, a silicon substrate such as p-type doped silicon substrate, n-type doped silicon substrate, and gallium arsenide 80. The method of any one of embodiments 74 to 79, wherein the solid support is a colloidal particle.

81. The method of embodiment 80, wherein the colloidal particle comprises a metal substrate such as a gold (Au) substrate, a silver (Ag) substrate; a tin (Sn) substrate, a rhodium (Rh) substrate, a ruthenium (Ru) substrate, a palladium (Pd) substrate, an osmium (Os) substrate, an iridium (Ir) substrate, a platinum (Pt) substrate, a titanium (Ti) substrate, an aluminum (Al) substrate, a chromium (Cr), a copper (Cu) substrate, a magnesium (Mg) substrate, a carbon substrate, a silicon substrate such as p-type doped silicon substrate, n-type doped silicon substrate, and gallium arsenide.

82. A method of nucleic acid analysis, the method comprising: isolating a nucleic acid complex (e.g., naked or as part of a conjugate as herein described) comprising a plurality of genomic DNA molecules each comprising a clustered distribution of methylated nucleotides (e.g., methylated cytosines), wherein the complex is formed by self-assembly of the DNA molecules under aqueous conditions; and analyzing a feature of the nucleic acid complex.

83. A method of nucleic acid analysis, the method comprising: isolating a nucleic complex (e.g., naked or as part of a conjugate as herein described) which comprises genomic DNA comprising a plurality of genomic DNA molecules individual ones of which comprise a clustered distribution of methylated nucleotides (e.g., methylated cytosines), wherein the complex is formed by self-assembly of the DNA molecules under aqueous conditions; and analyzing a feature of the nucleic acid complex.

84. The method of embodiment 82 or embodiment 83, wherein the feature is a nucleotide sequence of the nucleic acid complex.

85. The method of embodiment 84, wherein the nucleotide sequence is analyzed by nucleic acid hybridization, nucleic acid amplification and/or nucleotide sequencing.

86. The method of embodiment 85, wherein the nucleic acid amplification is selected from polymerase chain reaction (PCR), linear amplification, rolling circle replication and QB replication.

87. The method of embodiment 85, wherein the nucleotide sequencing is selected from Sanger sequencing, pyrosequencing, nanopore sequencing and Next Generation sequencing.

88. The method of any one of embodiments 82 to 87, wherein nucleic acid complex is analyzed by any one or more of microarray analysis, a polymerase chain reaction (PCR)-based analysis including methylation-specific PCR (MSP), bisulfite treatment, hybridization with allele-specific probes, enzymatic mutation detection, ligation chain reaction (LCR), oligonucleotide ligation assay (OLA), flow-cytometric heteroduplex analysis, chemical cleavage of mismatches, mass spectrometry, single strand conformation polymorphism (SSCP), denaturing gradient gel electrophoresis (DGGE), temperature gradient gel electrophoresis (TGGE), restriction fragment polymorphisms, serial analysis of gene expression (SAGE), DNA sequencing, or combinations thereof.

89. The method of any one of embodiments 82 to 88, wherein the nucleic acid complex is analyzed by a methylation analysis assay, including for example, bisulfite genomic sequencing, MSP, melting curve methylation-specific PCR (McMS-PCR), multiplex ligation-dependent probe amplification (MLPA) with or without bisulfite treatment, digestion of genomic DNA with methylation-sensitive restriction enzyme, multiplexed PCR with gene specific primers (MSRE-PCR), bisulfite conversion-specific methylation-specific PCR (BS-MSP), methylation-sensitive single-nucleotide primer extension conformation (MS-SNuPE), methylation-sensitive single-strand conformation analysis (MS-SSCA), melting curve combined bisulfite restriction analysis (McCOBRA), enzymatic regional methylation assay (ERMA), quantitative PCR sequencing and oligonucleotide-based microarray systems, pyrosequencing, and Meth-DOP-PCR, or a combination between a modified degenerate oligonucleotide primed PCR (DOP-PCR) and MSP.

90. A method of determining the likelihood of the presence or absence of cancer in a subject, the method comprising detecting in a biological sample obtained from the subject a nucleic acid complex that comprises a plurality of genomic DNA molecules each comprising a clustered distribution of methylated nucleotides (e.g., methylated cytosines), wherein the complex is formed by self-assembly of the DNA molecules under aqueous conditions, thereby determining the likely presence or absence of cancer in the subject.

91. A method of determining the likelihood of the presence or absence of cancer in a subject, the method comprising detecting in a biological sample obtained from the subject a nucleic complex that comprises genomic DNA comprising a plurality of genomic DNA molecules individual ones of which comprise a clustered distribution of methylated nucleotides (e.g., methylated cytosines), wherein the complex is formed by self-assembly of the DNA molecules under aqueous conditions, thereby determining the likely presence or absence of cancer in the subject.

92. The method of embodiment 90 or embodiment 91, wherein nucleic acid complex is detected by contacting the biological sample with an affinity agent for which the nucleic acid complex has affinity.

93. The method of embodiment 92, wherein the affinity agent is an antigen-binding molecule that binds specifically with the nucleic acid complex.

94. The method of embodiment 92, wherein the affinity agent is a solid support to which hydrophobic moieties (e.g., methylated nucleotides such as methylated cytosines) adsorb under the aqueous conditions.

95. The method of embodiment 92, wherein the affinity agent is a solid support to which clustered hydrophobic moieties (e.g., clustered methylated nucleotides such as clustered methylated cytosines) adsorb under the aqueous conditions.

96. The method of embodiment 92, wherein the affinity agent is a solid support to which hydrophobic moieties (e.g., methylated nucleotides such as methylated cytosines) adsorb more strongly than hydrophilic moieties under the aqueous conditions.

97. The method of embodiment 92, wherein the affinity agent is a solid support to which clustered hydrophobic moieties (e.g., clustered methylated nucleotides such as methylated cytosines) adsorb more strongly than non-clustered hydrophobic moieties (e.g., non-clustered methylated nucleotides such as non-clustered methylated cytosines) under the aqueous conditions.

98. The method of any one of embodiments 94 to 97, wherein the solid support is selected from organic polymers such as polystyrene and its derivatives, polyacrylates and polymethacrylates and their derivatives, polyurethanes, nylon, polyethylene, polypropylene, polybutylene and copolymers of these materials, polysaccharides and hydrogels such as agarose, cellulose, dextran, Sephadex, Sephacryl, chitosan, inorganic supports such as silica gels, silica particles, glass, metal, semi-metal oxides, and supports with metal surfaces.

99. The method of embodiment 98, wherein the solid support is selected from a polymer bead, an agarose bead, a polystyrene bead, an acrylamide bead, a solid core bead, a porous bead, a paramagnetic bead, glass bead, controlled pore bead, a microtiter well, a cyclo-olefin copolymer substrate, a membrane, a plastic substrate, nylon, a Langmuir-Blodgett film, glass, a germanium substrate, a silicon substrate, a silicon wafer chip, a flow through chip, a microbead, a nanoparticle, a polytetrafluoroethylene substrate, a polystyrene substrate, a metal substrate such as a gold (Au) substrate, a silver (Ag) substrate; a tin (Sn) substrate, a rhodium (Rh) substrate, a ruthenium (Ru) substrate, a palladium (Pd) substrate, an osmium (Os) substrate, an iridium (Ir) substrate, a platinum (Pt) substrate, a titanium (Ti) substrate, an aluminum (Al) substrate, a chromium (Cr), a copper (Cu) substrate, a magnesium (Mg) substrate, a carbon substrate, a silicon substrate such as p-type doped silicon substrate, n-type doped silicon substrate, and gallium arsenide 100. The method of any one of embodiments 94 to 99, wherein the solid support is a colloidal particle.

101. The method of embodiment 100, wherein the colloidal particle comprises a metal substrate such as a gold (Au) substrate, a silver (Ag) substrate; a tin (Sn) substrate, a rhodium (Rh) substrate, a ruthenium (Ru) substrate, a palladium (Pd) substrate, an osmium (Os) substrate, an iridium (Ir) substrate, a platinum (Pt) substrate, a titanium (Ti) substrate, an aluminum (Al) substrate, a chromium (Cr), a copper (Cu) substrate, a magnesium (Mg) substrate, a carbon substrate, a silicon substrate such as p-type doped silicon substrate, n-type doped silicon substrate, and gallium arsenide.

102. The method of any one of embodiments 90 or embodiment 91, wherein the nucleic acid complex is detected by exposing the biological sample to electromagnetic radiation and detecting a physical feature that is indicative of the nucleic acid complex.

103. The method of embodiment 102, wherein the physical feature is selected from size, shape or aggregation status of the nucleic acid complex.

104. The method of embodiment 103, wherein the size is about 10 $nm^2$ to about 2000 $nm^2$, 50 $nm^2$ to about 2000 $nm^2$, 100 $nm^2$ to about 2000 $nm^2$, 500 $nm^2$ to about 2000 $nm^2$, or 1000 $nm^2$ to about 2000 $nm^2$, in the aqueous conditions.

105. The method of any one of embodiments 102 to 104, wherein the electromagnetic radiation includes light.

106. The method of any one of embodiments 102 to 105, wherein the electromagnetic radiation includes at least one of an x-ray radiation, a microwave radiation, an infrared light, a radio frequency signal or an ultraviolet light.

107. The method of any one of embodiments 102 to 106, wherein the physical feature is detected by receiving electromagnetic radiation from the nucleic acid complex.

108. The method of embodiment 107, wherein the received electromagnetic radiation comprises scattered, refracted, phase-shifted, or emitted electromagnetic radiation or particle beams.

109. The method of embodiment 107 or embodiment 108, wherein the received electromagnetic radiation comprises visible light.

110. The method of any one of embodiments 102 to 109, wherein the physical feature is detected by microscopy.

111. The method of embodiment 110, wherein the microscopy comprises transmission electron microscopy.

112. The method of any one of embodiments 102 to 111, wherein the physical feature is detected by colorimetric detection.

113. The method of embodiment 112, wherein the colorimetric detection is facilitated by contacting the biological sample with a colloidal particle comprising a substrate to which hydrophobic moieties (e.g., methylated cytosines) adsorb under the aqueous conditions.

114. The method of embodiment 112, wherein the colorimetric detection is facilitated by contacting the biological sample with a colloidal particle comprising a substrate to which clustered hydrophobic moieties (e.g., clustered methylated nucleotides such as clustered methylated cytosines) adsorb under the aqueous conditions.

115. The method of embodiment 112, wherein the colorimetric detection is facilitated by contacting the biological sample with a colloidal particle comprising a substrate to which hydrophobic moieties (e.g., methylated nucleotides such as methylated cytosines) adsorb more strongly than hydrophilic moieties under the aqueous conditions.

116. The method of embodiment 112, wherein the colorimetric detection is facilitated by contacting the biological sample with a colloidal particle comprising a substrate to which clustered hydrophobic moieties (e.g., clustered methylated nucleotides such as methylated cytosines) adsorb more strongly than non-clustered hydrophobic moieties (e.g., non-clustered methylated nucleotides such as non-clustered methylated cytosines) under the aqueous conditions.

117. The method of any one of embodiments 113 to 116, wherein the substrate comprises a metal substrate such as a gold (Au) substrate, a silver (Ag) substrate; a tin (Sn) substrate, a rhodium (Rh) substrate, a ruthenium (Ru) substrate, a palladium (Pd) substrate, an osmium (Os) substrate, an iridium (Ir) substrate, a platinum (Pt) substrate, a titanium (Ti) substrate, an aluminum (Al) substrate, a chromium (Cr), a copper (Cu) substrate, a magnesium (Mg) substrate, a carbon substrate, a silicon substrate such as p-type doped silicon substrate, n-type doped silicon substrate, and gallium arsenide.

118. The method of embodiment 117, wherein the nucleic acid complex is detected by electrochemical detection.

119. The method of embodiment 118, wherein the electrochemical detection comprises exposing the biological sample to a working electrode that comprises an electroconductive material to which hydrophobic moieties (e.g., methylated nucleotides such as methylated cytosines) adsorb under the aqueous conditions; applying a potential to the working electrode; and detecting an electrical signal from the working electrode that is indicative of adsorption of the nucleic acid complex to the electroconductive material, wherein the electrical signal is selected from the group consisting of current, voltage, impedance, capacitance, charge, conductivity, resistance, or a combination thereof.

120. The method of embodiment 119, wherein the electroconductive material is selected from gold, platinum, palladium, silver, carbon, alloys thereof, and composites thereof.

121. The system or method of any preceding embodiment, wherein the biological sample is suitably selected from tissue (e.g., lymph node, esophagus, lung, lung washes, BAL (bronchoalveolar lavage), thyroid, skin, breast, ovary, endometrium, uterus, pancreas, spleen, thymus, bone marrow, colon, stomach, bladder, brain, salivary gland, prostate, testicles and liver) and fluid samples.

122. The system or method of embodiment 121, wherein the biological sample is a biological fluid.

123. The system or method of embodiment 122, wherein the biological fluid is selected from whole blood; lysed whole blood; serum; plasma; urine; sputum; sweat; follicular fluid; synovial fluid; amniotic fluid; a nasopharyngeal aspirate; a bronchial aspirate; semen and cerebrospinal fluid.

124. A method of determining the presence in a biological sample of clustered methylated genomic DNA that comprises a clustered distribution of methylated nucleotides (e.g., methylated cytosines), the method comprising: contacting the biological sample with a solid support to which clustered hydrophobic moieties (e.g., clustered methylated cytosines) adsorb more strongly than non-clustered hydrophobic moieties (e.g., non-clustered methylated nucleotides such as non-clustered methylated cytosines) under aqueous conditions and detecting the presence of a conjugate comprising genomic DNA and the solid support, thereby determining the presence of clustered methylated genomic DNA in the biological sample.

125. The method of embodiment 124, wherein the methylated nucleotides (e.g., methylated cytosines) are in at least one CpG cluster.

126. The method of embodiment 125, wherein at least about 10%, 20%, 30%, 40%, 50%, 60%, 70%, 80%, 90%, or even about 100%, of the nucleotides (e.g., cytosines) in a respective CpG cluster are methylated.

127. The method of embodiment 125 or embodiment 126, wherein the CpG cluster is flanked by at least one region that comprises a lower frequency of methylated nucleotides (e.g., methylated cytosines) than a respective CpG cluster.

128. The method of embodiment 127, wherein the at least one flanking region comprises a frequency of methylated nucleotides (e.g., methylated cytosines) that is no more than about 1/2, 1/3, 1/4, 1/5, 1/6, 1/7, 1/8, 1/9, 1/10, 1/20, 1/30, 1/40, 1/50 or 1/100 of the frequency of methylated nucleotides (e.g., methylated cytosines) in a respective CpG cluster.

129. The method of any one of embodiments 124 to 128, wherein the genomic DNA has a length of up to 300, up to 400, up to 500, up to 1000, up to 2,000, up to 3,000, up to 4,000, up to 5,000, up to 10,000, up to 15,000, or even up to 20,000 base pairs.

130. The method of any one of embodiments 124 to 129, wherein the genomic DNA has a length of at least 25, at least 50, at least 75, at least 100, or at least 200 base pairs.

131. The method of any one of embodiments 124 to 130, wherein the genomic DNA is in the form of nucleic acid complex that comprises a plurality of genomic DNA molecules each comprising a clustered distribution of methylated nucleotides (e.g., methylated cytosines) (e.g., wherein the nucleic acid complex that comprises genomic DNA comprising a plurality of genomic DNA molecules individual ones of which comprise a clustered distribution of methylated nucleotides (e.g., methylated cytosines), wherein the complex is formable by self-assembly of the DNA molecules under aqueous conditions.

132. The method of embodiment 131, wherein the complex has a size that of about 10 $nm^2$ to about 2000 $nm^2$, 50 $nm^2$ to about 2000 $nm^2$, 100 $nm^2$ to about 2000 $nm^2$, 500 $nm^2$ to about 2000 $nm^2$, or 1000 $nm^2$ to about 2000 $nm^2$, in the aqueous conditions.

133. The method of any one of embodiments 124 to 132, wherein the genomic DNA is amphipathic.

134. The method of any one of embodiments 124 to 133, wherein the solid support is selected from organic polymers such as polystyrene and its derivatives, polyacrylates and polymethacrylates and their derivatives, polyurethanes, nylon, polyethylene, polypropylene, polybutylene and copolymers of these materials, polysaccharides and hydrogels such as agarose, cellulose, dextran, Sephadex, Sephacryl, chitosan, inorganic supports such as silica gels, silica particles, glass, metal, semi-metal oxides, and supports with metal surfaces.

135. The method of any one of embodiments 124 to 134, wherein the solid support is selected from a polymer bead, an agarose bead, a polystyrene bead, an acrylamide bead, a solid core bead, a porous bead, a paramagnetic bead, glass bead, controlled pore bead, a microtiter well, a cyclo-olefin copolymer substrate, a membrane, a plastic substrate, nylon, a Langmuir-Blodgett film, glass, a germanium substrate, a silicon substrate, a silicon wafer chip, a flow through chip, a microbead, a nanoparticle, a polytetrafluoroethylene substrate, a polystyrene substrate, a metal substrate such as a gold (Au) substrate, a silver (Ag) substrate; a tin (Sn) substrate, a rhodium (Rh) substrate, a ruthenium (Ru) substrate, a palladium (Pd) substrate, an osmium (Os) substrate, an iridium (Ir) substrate, a platinum (Pt) substrate, a titanium (Ti) substrate, an aluminum (Al) substrate, a chromium (Cr), a copper (Cu) substrate, a magnesium (Mg) substrate, a carbon substrate, a silicon substrate such as p-type doped silicon substrate, n-type doped silicon substrate, and gallium arsenide 136. The method of any one of embodiments 124 to 135, wherein the solid support is a colloidal particle.

137. The method of embodiment 136, wherein the colloidal particle comprises a metal substrate such as a gold (Au) substrate, a silver (Ag) substrate; a tin (Sn) substrate, a rhodium (Rh) substrate, a ruthenium (Ru) substrate, a palladium (Pd) substrate, an osmium (Os) substrate, an iridium (Ir) substrate, a platinum (Pt) substrate, a titanium (Ti) substrate, an aluminum (Al) substrate, a chromium (Cr), a copper (Cu) substrate, a magnesium (Mg) substrate, a carbon substrate, a silicon substrate such as p-type doped silicon substrate, n-type doped silicon substrate, and gallium arsenide.

138. The method of any one of embodiments 124 to 137, wherein the conjugate is detected by colorimetric detection.

139. The method of any one of embodiments 124 to 138, wherein the conjugate is detected by electrochemical detection.

140. The method of embodiment 139, wherein the electrochemical detection comprises exposing the biological sample to a working electrode that comprises an electroconductive material to which clustered hydrophobic moieties (e.g., clustered methylated nucleotides such as clustered methylated cytosines) adsorb more strongly than non-clustered hydrophobic moieties (e.g., non-clustered methylated nucleotides such as non-clustered methylated cytosines) under aqueous conditions; applying a potential to the working electrode; and detecting an electrical signal from the working electrode that is indicative of adsorption of the nucleic acid complex to the electroconductive material, wherein the electrical signal is selected from the group consisting of current, voltage, impedance, capacitance, charge, conductivity, resistance, or a combination thereof.

141. The method of embodiment 140, wherein the electroconductive material is selected from gold, platinum, palladium, silver, carbon, alloys thereof, and composites thereof.

142. A system, suitably for detecting clustered methylated DNA, the system comprising: (1) a biological sample comprising a clustered methylated genomic DNA that comprises a clustered distribution of methylated nucleotides (e.g., methylated cytosines); and (2) a sensor, which is in communication with the biological sample, for detecting the presence or level of the clustered methylated genomic DNA.

143. The system of embodiment 142, wherein the sensor is selected from one or more of: an antigen-binding molecule that binds specifically with the clustered methylated genomic DNA, a light based sensor, a spectrometer, a refractometer, a particle sizer, an x-ray, a monochromator, an absorption detector, a reflectance detector, a transmission detector, a conductivity sensor, an electrode, a resistive pulse sensor, a camera, a microscope, a particle size analyzer, an optical detector, a solid support to which hydrophobic moieties adsorb under the aqueous conditions, a colloidal particle or a biosensor.

144. The system of embodiment 142 or embodiment 143, wherein the sensor comprises a microscope (e.g., a transmission electron microscope).

145. The system of embodiment 142 or embodiment 143, wherein the sensor comprises a solid support to which hydrophobic moieties (e.g., methylated nucleotides such as methylated cytosines) adsorb under the aqueous conditions.

146. The system of embodiment 142 or embodiment 143, wherein the sensor comprises a solid support to which clustered hydrophobic moieties (e.g., clustered methylated nucleotides such as clustered methylated cytosines) adsorb under the aqueous conditions.

147. The system of embodiment 142 or embodiment 143, wherein the sensor comprises a solid support to which hydrophobic moieties (e.g., methylated nucleotides such as methylated cytosines) adsorb more strongly than hydrophilic moieties under the aqueous conditions.

148. The system of embodiment 142 or embodiment 143, wherein the sensor comprises a solid support to which clustered hydrophobic moieties (e.g., clustered methylated nucleotides such as clustered methylated cytosines) adsorb more strongly than non-clustered hydrophobic moieties (e.g., non-clustered methylated nucleotides such as non-clustered methylated cytosines) under the aqueous conditions.

149. The system of any one of embodiments 145 to 148, wherein the solid support is selected from organic polymers such as polystyrene and its derivatives, polyacrylates and polymethacrylates and their derivatives, polyurethanes, nylon, polyethylene, polypropylene, polybutylene and copolymers of these materials, polysaccharides and hydrogels such as agarose, cellulose, dextran, Sephadex, Sephacryl, chitosan, inorganic supports such as silica gels, silica particles, glass, metal, semi-metal oxides, and supports with metal surfaces.

150. The system of embodiment 149, wherein the solid support is selected from a polymer bead, an agarose bead, a polystyrene bead, an acrylamide bead, a solid core bead, a porous bead, a paramagnetic bead, glass bead, controlled pore bead, a microtiter well, a cyclo-olefin copolymer substrate, a membrane, a plastic substrate, nylon, a Langmuir-Blodgett film, glass, a germanium substrate, a silicon substrate, a silicon wafer chip, a flow through chip, a microbead, a nanoparticle, a polytetrafluoroethylene substrate, a polystyrene substrate, a metal substrate such as a gold (Au) substrate, a silver (Ag) substrate; a tin (Sn) substrate, a rhodium (Rh) substrate, a ruthenium (Ru) substrate, a palladium (Pd) substrate, an osmium (Os) substrate, an iridium (Ir) substrate, a platinum (Pt) substrate, a titanium (Ti) substrate, an aluminum (Al) substrate, a chromium (Cr), a copper (Cu) substrate, a magnesium (Mg) substrate, a carbon substrate, a silicon substrate such as p-type doped silicon substrate, n-type doped silicon substrate, and gallium arsenide.

151. The system of any one of embodiments 145 to 150, wherein the solid support is a colloidal particle.

152. The system of embodiment 151, wherein the colloidal particle comprises a metal substrate such as a gold (Au) substrate, a silver (Ag) substrate; a tin (Sn) substrate, a rhodium (Rh) substrate, a ruthenium (Ru) substrate, a palladium (Pd) substrate, an osmium (Os) substrate, an iridium (Ir) substrate, a platinum (Pt) substrate, a titanium (Ti) substrate, an aluminum (Al) substrate, a chromium (Cr), a copper (Cu) substrate, a magnesium (Mg) substrate, a carbon substrate, a silicon substrate such as p-type doped silicon substrate, n-type doped silicon substrate, and gallium arsenide.

153. The system of any one of embodiments 142 to 152, wherein the sensor comprises an electrode that comprises an electro-conductive material to which hydrophobic moieties (e.g., methylated nucleotides such as methylated cytosines) adsorb under the aqueous conditions.

154. The system of embodiment 153, wherein the electroconductive material is selected from gold, platinum, palladium, silver, carbon, alloys thereof, and composites thereof.

155. The system of embodiment 153 or embodiment 154, wherein the electrode is a working electrode that is part of an electrical detection unit comprising an electrical circuit configured for detecting an electrical signal from the working electrode, wherein the electrical signal is selected from the group consisting of current or voltage, or a derived parameter such as impedance, capacitance, charge, conductivity, resistance, or a combination thereof.

156. A conjugate, suitably for detecting clustered methylated DNA, the conjugate comprising: (a) a clustered methylated genomic DNA that comprises a clustered distribution of methylated nucleotides (e.g., methylated cytosines); and (b) an affinity agent for which the clustered methylated genomic DNA has affinity.

157. The conjugate of embodiment 156, wherein the affinity agent is an antigen-binding molecule that binds specifically with clustered methylated DNA.

158. The conjugate of embodiment 156, wherein the affinity agent is a solid support to which hydrophobic moieties (e.g., methylated nucleotides such as methylated cytosines) adsorb under the aqueous conditions.

159. The conjugate of embodiment 156, wherein the affinity agent is a solid support to which clustered hydrophobic moieties (e.g., clustered methylated nucleotides such as clustered methylated cytosines) adsorb under the aqueous conditions.

160. The conjugate of embodiment 156, wherein the affinity agent is a solid support to which hydrophobic moieties (e.g., methylated nucleotides such as methylated cytosines) adsorb more strongly than hydrophilic moieties under the aqueous conditions.

161. The conjugate of embodiment 156, wherein the affinity agent is a solid support to which clustered hydrophobic moieties (e.g., clustered methylated nucleotides such as clustered methylated cytosines) adsorb more strongly than non-clustered hydrophobic moieties (e.g., non-clustered methylated nucleotides such as non-clustered methylated cytosines) under the aqueous conditions.

162. The conjugate of any one of embodiments 158 to 161, wherein the solid support is selected from organic polymers such as polystyrene and its derivatives, polyacrylates and polymethacrylates and their derivatives, polyurethanes, nylon, polyethylene, polypropylene, polybutylene and copolymers of these materials, polysaccharides and hydrogels such as agarose, cellulose, dextran, Sephadex, Sephacryl, chitosan, inorganic supports such as silica gels, silica particles, glass, metal, semi-metal oxides, and supports with metal surfaces.

163. The conjugate of embodiment 162, wherein the solid support is selected from a polymer bead, an agarose bead, a polystyrene bead, an acrylamide bead, a solid core bead, a porous bead, a paramagnetic bead, glass bead, controlled pore bead, a microtiter well, a cyclo-olefin copolymer substrate, a membrane, a plastic substrate, nylon, a Langmuir-Blodgett film, glass, a germanium substrate, a silicon substrate, a silicon wafer chip, a flow through chip, a microbead, a nanoparticle, a polytetrafluoroethylene substrate, a polystyrene substrate, a metal substrate such as a gold (Au) substrate, a silver (Ag) substrate; a tin (Sn) substrate, a rhodium (Rh) substrate, a ruthenium (Ru) substrate, a palladium (Pd) substrate, an osmium (Os) substrate, an iridium (Ir) substrate, a platinum (Pt) substrate, a titanium (Ti) substrate, an aluminum (Al) substrate, a chromium (Cr), a copper (Cu) substrate, a magnesium (Mg) substrate, a carbon substrate, a silicon substrate such as p-type doped silicon substrate, n-type doped silicon substrate, and gallium arsenide 164. The conjugate of any one of embodiments 158 to 163, wherein the solid support is a colloidal particle.

165. The conjugate of embodiment 164, wherein the colloidal particle comprises a metal substrate such as a gold (Au) substrate, a silver (Ag) substrate; a tin (Sn) substrate, a rhodium (Rh) substrate, a ruthenium (Ru) substrate, a palladium (Pd) substrate, an osmium (Os) substrate, an iridium (Ir) substrate, a platinum (Pt) substrate, a titanium (Ti) substrate, an aluminum (Al) substrate, a chromium (Cr), a copper (Cu) substrate, a magnesium (Mg) substrate, a carbon substrate, a silicon substrate such as p-type doped silicon substrate, n-type doped silicon substrate, and gallium arsenide.

166. A method of isolating clustered methylated genomic DNA from a biological sample, wherein the genomic DNA comprises a clustered distribution of methylated nucleotides (e.g., methylated cytosines), the method comprising contacting the biological sample with an affinity agent for which the genomic DNA has affinity to form a conjugate and separating the conjugate from the biological sample.

167. The method of embodiment 166, further comprising separating the genomic DNA from the affinity agent.

168. The method of embodiment 167, wherein the genomic DNA is separated from the affinity agent by elution.

169. The method of any one of embodiments 166 to 168, wherein the affinity agent is an antigen-binding molecule that binds specifically with the nucleic acid complex.

170. The method of any one of embodiments 166 to 168, wherein the affinity agent is a solid support to which hydrophobic moieties (e.g., methylated nucleotides such as methylated cytosines) adsorb under the aqueous conditions.

171. The method of any one of embodiments 166 to 168, wherein the affinity agent is a solid support to which clustered hydrophobic moieties (e.g., clustered methylated nucleotides such as clustered methylated cytosines) adsorb under the aqueous conditions.

172. The method of any one of embodiments 166 to 168, wherein the affinity agent is a solid support to which hydrophobic moieties (e.g., methylated nucleotides such as methylated cytosines) adsorb more strongly than hydrophilic moieties under the aqueous conditions.

173. The method of any one of embodiments 166 to 168, wherein the affinity agent is a solid support to which clustered hydrophobic moieties (e.g., clustered methylated nucleotides such as clustered methylated cytosines) adsorb more strongly than non-clustered hydrophobic moieties (e.g., non-clustered methylated nucleotides such as non-clustered methylated cytosines) under the aqueous conditions.

174. The method of any one of embodiments 170 to 173, wherein the solid support is selected from organic polymers such as polystyrene and its derivatives, polyacrylates and polymethacrylates and their derivatives, polyurethanes, nylon, polyethylene, polypropylene, polybutylene and copolymers of these materials, polysaccharides and hydrogels such as agarose, cellulose, dextran, Sephadex, Sephacryl, chitosan, inorganic supports such as silica gels, silica particles, glass, metal, semi-metal oxides, and supports with metal surfaces.

175. The method of embodiment 174, wherein the solid support is selected from a polymer bead, an agarose bead, a polystyrene bead, an acrylamide bead, a solid core bead, a porous bead, a paramagnetic bead, glass bead, controlled pore bead, a microtiter well, a cyclo-olefin copolymer substrate, a membrane, a plastic substrate, nylon, a Langmuir- Blodgett film, glass, a germanium substrate, a silicon substrate, a silicon wafer chip, a flow through chip, a microbead, a nanoparticle, a polytetrafluoroethylene substrate, a polystyrene substrate, a metal substrate such as a gold (Au) substrate, a silver (Ag) substrate; a tin (Sn) substrate, a rhodium (Rh) substrate, a ruthenium (Ru) substrate, a palladium (Pd) substrate, an osmium (Os) substrate, an iridium (Ir) substrate, a platinum (Pt) substrate, a titanium (Ti) substrate, an aluminum (Al) substrate, a chromium (Cr), a copper (Cu) substrate, a magnesium (Mg) substrate, a carbon substrate, a silicon substrate such as p-type doped silicon substrate, n-type doped silicon substrate, and gallium arsenide 176. The method of any one of embodiments 170 to 175, wherein the solid support is a colloidal particle.

177. The method of embodiment 176, wherein the colloidal particle comprises a metal substrate such as a gold (Au) substrate, a silver (Ag) substrate; a tin (Sn) substrate, a rhodium (Rh) substrate, a ruthenium (Ru) substrate, a palladium (Pd) substrate, an osmium (Os) substrate, an iridium (Ir) substrate, a platinum (Pt) substrate, a titanium (Ti) substrate, an aluminum (Al) substrate, a chromium (Cr), a copper (Cu) substrate, a magnesium (Mg) substrate, a carbon substrate, a silicon substrate such as p-type doped silicon substrate, n-type doped silicon substrate, and gallium arsenide.

178. A method of nucleic acid analysis, the method comprising: isolating a clustered methylated genomic DNA from a biological sample according to the method of any one of embodiments 166 to 177, wherein the genomic DNA comprises a clustered distribution of methylated cytosines; and analyzing a feature of the genomic DNA.

179. The method of embodiment 178, wherein the feature is the nucleotide sequence of the genomic DNA.

180. The method of embodiment 179, wherein the nucleotide sequence is analyzed by nucleic acid hybridization, nucleic acid amplification and/or nucleotide sequencing.

181. The method of embodiment 180, wherein the nucleic acid amplification is selected from polymerase chain reaction (PCR), linear amplification, rolling circle replication and QB replication.

182. The method of embodiment 180, wherein the nucleotide sequencing is selected from Sanger sequencing, pyrosequencing, nanopore sequencing and Next Generation sequencing.

183. The method of any one of embodiments 178 to 182, wherein genomic DNA is analyzed by any one or more of microarray analysis, a polymerase chain reaction (PCR)-based analysis including methylation-specific PCR (MSP), bisulfite treatment, hybridization with allele-specific probes, enzymatic mutation detection, ligation chain reaction (LCR), oligonucleotide ligation assay (OLA), flow-cytometric heteroduplex analysis, chemical cleavage of mismatches, mass spectrometry, single strand conformation polymorphism (SSCP), denaturing gradient gel electrophoresis (DGGE), temperature gradient gel electrophoresis (TGGE), restriction fragment polymorphisms, serial analysis of gene expression (SAGE), DNA sequencing, or combinations thereof.

184. The method of any one of embodiments 178 to 183, wherein the genomic DNA is analyzed by a methylation analysis assay, including for example, bisulfite genomic sequencing, MSP, melting curve methylation-specific PCR (McMS-PCR), multiplex ligation-dependent probe amplification (MLPA) with or without bisulfite treatment, digestion of genomic DNA with methylation-sensitive restriction enzyme, multiplexed PCR with gene specific primers (MSRE-PCR), bisulfite conversion-specific methylation-specific PCR (BS-MSP), methylation-sensitive single-nucleotide primer extension conformation (MS-SNuPE), methylation-sensitive single-strand conformation analysis (MS-SSCA), melting curve combined bisulfite restriction analysis (McCOBRA), enzymatic regional methylation assay (ERMA), quantitative PCR sequencing and oligo-nucleotide-based microarray systems, pyrosequencing, and Meth-DOP-PCR, or a combination between a modified degenerate oligonucleotide primed PCR (DOP-PCR) and MSP.

185. A method of determining the likelihood of the presence or absence of cancer in a subject, the method comprising: contacting a biological sample obtained from the subject with an affinity agent for which genomic DNA that comprises a clustered distribution of methylated nucleotides (e.g., methylated cytosines) has affinity; and detecting the presence or absence of a conjugate comprising the genomic DNA and the affinity agent, and optionally the methylation status and/or one or more ancillary cancer biomarkers of the clustered methylated genomic DNA, to thereby determine the likely presence or absence of cancer in the subject.

186. The method of embodiment 185, wherein the affinity agent is an antigen-binding molecule that binds specifically with clustered methylated genomic DNA.

187. The method of embodiment 185, wherein the affinity agent is an antigen-binding molecule that binds specifically with the nucleic acid complex.

188. The method of embodiment 185, wherein the affinity agent is a solid support to which hydrophobic moieties (e.g., methylated nucleotides such as methylated cytosines) adsorb under the aqueous conditions.

189. The method of embodiment 185, wherein the affinity agent is a solid support to which clustered hydrophobic moieties (e.g., clustered methylated nucleotides such as clustered methylated cytosines) adsorb under the aqueous conditions.

190. The method of embodiment 185, wherein the affinity agent is a solid support to which hydrophobic moieties (e.g., methylated nucleotides such as methylated cytosines) adsorb more strongly than hydrophilic moieties under the aqueous conditions.

191. The method of embodiment 185, wherein the affinity agent is a solid support to which clustered hydrophobic moieties (e.g., clustered methylated nucleotides such as clustered methylated cytosines) adsorb more strongly than non-clustered hydrophobic moieties (e.g., non-clustered methylated nucleotides such as non-clustered methylated cytosines) under the aqueous conditions.

192. The method of any one of embodiments 188 to 191, wherein the solid support is selected from organic polymers such as polystyrene and its derivatives, polyacrylates and polymethacrylates and their derivatives, polyurethanes, nylon, polyethylene, polypropylene, polybutylene and copolymers of these materials, polysaccharides and hydrogels such as agarose, cellulose, dextran, Sephadex, Sephacryl, chitosan, inorganic supports such as silica gels, silica particles, glass, metal, semi-metal oxides, and supports with metal surfaces.

193. The method of embodiment 192, wherein the solid support is selected from a polymer bead, an agarose bead, a polystyrene bead, an acrylamide bead, a solid core bead, a porous bead, a paramagnetic bead, glass bead, controlled pore bead, a microtiter well, a cyclo-olefin copolymer substrate, a membrane, a plastic substrate, nylon, a Langmuir-Blodgett film, glass, a germanium substrate, a silicon substrate, a silicon wafer chip, a flow through chip, a microbead, a nanoparticle, a polytetrafluoroethylene substrate, a polystyrene substrate, a metal substrate such as a gold (Au) substrate, a silver (Ag) substrate; a tin (Sn) substrate, a rhodium (Rh) substrate, a ruthenium (Ru) substrate, a palladium (Pd) substrate, an osmium (Os) substrate, an iridium (Ir) substrate, a platinum (Pt) substrate, a titanium (Ti) substrate, an aluminum (Al) substrate, a chromium (Cr), a copper (Cu) substrate, a magnesium (Mg) substrate, a carbon substrate, a silicon substrate such as p-type doped silicon substrate, n-type doped silicon substrate, and gallium arsenide 194. The method of any one of embodiments 188 to 193, wherein the solid support is a colloidal particle.

195. The method of embodiment 194, wherein the colloidal particle comprises a metal substrate such as a gold (Au) substrate, a silver (Ag) substrate; a tin (Sn) substrate, a rhodium (Rh) substrate, a ruthenium (Ru) substrate, a palladium (Pd) substrate, an osmium (Os) substrate, an iridium (Ir) substrate, a platinum (Pt) substrate, a titanium (Ti) substrate, an aluminum (Al) substrate, a chromium (Cr), a copper (Cu) substrate, a magnesium (Mg) substrate, a carbon substrate, a silicon substrate such as p-type doped silicon substrate, n-type doped silicon substrate, and gallium arsenide.

196. The system or method according to any preceding embodiments, wherein the biological sample is selected from tissue (e.g., lymph node, esophagus, lung, lung washes, BAL (bronchoalveolar lavage), thyroid, skin, breast, ovary, endometrium, uterus, pancreas, spleen, thymus, bone marrow, colon, stomach, bladder, brain, salivary gland, prostate, testicles and liver) and fluid samples.

197. The system or method according to any preceding embodiments, wherein the biological sample is a biological fluid.

198. The system or method of embodiment 197, wherein the biological fluid is selected from whole blood; lysed whole blood; serum; plasma; urine; sputum; sweat; follicular fluid; synovial fluid; amniotic fluid; a nasopharyngeal aspirate; a bronchial aspirate; semen and cerebrospinal fluid.

199. A kit for detecting clustered methylated genomic DNA or complex thereof, the kit comprising a sensor for detecting the presence or level of clustered methylated genomic DNA or complex thereof, optionally together with instructional material.

200. The kit of embodiment 199, wherein the sensor is selected from any one or more of: an antigen-binding molecule that binds specifically with the clustered methylated genomic DNA or complex thereof, a light based sensor, a spectrometer, a refractometer, an x-ray, a monochromator, an absorption detector, a reflectance detector, a transmission detector, a conductivity sensor, an electrode, a resistive pulse sensor, a camera, a microscope, a particle size analyzer, an optical detector, a solid support to which hydrophobic moieties adsorb under the aqueous conditions, a colloidal particle or a biosensor.

201. The kit of embodiment 199 or embodiment 200, further containing a positive and/or negative control genomic DNA or complex thereof.

202. A method of treating cancer, comprising analyzing a biological sample obtained from a subject for the presence or absence of clustered methylated genomic DNA or complex thereof, and optionally the methylation status and/or one or more ancillary cancer biomarkers of the clustered methylated genomic DNA; and exposing the subject to a treatment regimen for treating the cancer if the analysis indicates the likely presence of cancer in the subject, or not exposing the subject to a treatment regimen for treating the cancer if the analysis indicates the likely absence of cancer in the subject.

203. The method of embodiment 202, wherein the biological sample is analyzed at the point of care.

204. The method of embodiment 202, wherein the biological sample is sent to a laboratory to conduct the analysis.

205. A method for monitoring efficacy of a treatment regimen in a subject with a cancer, the method comprising analyzing a biological sample obtained from a subject exposed to a treatment regimen for the presence, absence or level of clustered methylated genomic DNA or complex thereof, and optionally the methylation status and/or one or more ancillary cancer biomarkers of the clustered methylated genomic DNA; and monitoring the subject over a period of time for a change in the clustered methylated genomic DNA or complex thereof, and optionally the methylation status of the clustered methylated genomic DNA, wherein a change or otherwise in the methylscape of the genomic DNA molecule or complex thereof in the biological sample over the period of time is indicative of treatment efficacy.

206. The complex, conjugate, system, method or kit of any preceding embodiment, wherein the genomic DNA is cellular genomic DNA (cellular gDNA).

207. The complex, conjugate, system, method or kit of any preceding embodiment, wherein the genomic DNA is cell-free DNA (cfDNA).

208. The complex, conjugate, system, method or kit of any preceding embodiment, wherein the genomic DNA is circulating tumor DNA (ctDNA).

209. The complex, conjugate, system, method or kit of any preceding embodiment, wherein the genomic DNA is extracellular vesicular DNA (evDNA).

210. A method for detecting cancer DNA (e.g., cellular gDNA, ctDNA, cfDNA, evDNA, etc. derived from a cancer cell or tissue, or cancer subject; e.g., comprising cancer methylscape DNA), the method comprising: exposing a biological sample comprising cancer DNA to a solid support to which hydrophobic moieties adsorb under aqueous conditions; and detecting a signal that is indicative of adsorption of cancer DNA to the solid support, wherein the signal is different to a signal generated when normal DNA (e.g., cellular gDNA, ctDNA, cfDNA, evDNA, etc. derived from a normal, healthy or non-cancerous cell, tissue or subject; e.g., comprising normal methylscape DNA) is exposed and/or adsorbed to the solid support.

211. A method for determining the presence of cancer DNA (e.g., cellular gDNA, ctDNA, cfDNA, evDNA, etc. derived from a cancer cell or tissue, or cancer subject; e.g., comprising cancer methylscape DNA) or normal DNA (e.g., cellular gDNA, ctDNA, cfDNA, evDNA, etc. derived from a normal, healthy or non-cancerous cell, tissue or subject; e.g., comprising normal methylscape DNA) in a biological sample, the method comprising: exposing a biological sample comprising DNA (e.g., cellular gDNA, ctDNA, cfDNA, evDNA, etc.) to a solid support to which hydrophobic moieties adsorb under aqueous conditions; and detecting a first signal that is indicative of adsorption of cancer DNA to the solid support or a second signal that is indicative of exposure and/or adsorption of normal DNA to the solid support, wherein the first and second signals are different, and determining whether the biological sample comprises cancer DNA or normal DNA based upon detection of the first or second signal.

212. The method of embodiment 210 or embodiment 211, wherein the solid support permits colorimetric or visual detection of DNA adsorbed thereto.

213. The method of embodiment 212, further comprising detecting a colorimetric or visual signal.

214. A method for detecting cancer DNA (e.g., cellular gDNA, ctDNA, cfDNA, evDNA, etc. derived from a cancer cell or tissue, or cancer subject; e.g., comprising cancer methylscape DNA), the method comprising: exposing a biological sample comprising cancer DNA to a solid support to which hydrophobic moieties adsorb under aqueous conditions; and detecting a colorimetric or visual signal that is indicative of adsorption of cancer DNA to the solid support, wherein the colorimetric or visual signal is different to a colorimetric or visual signal generated when normal DNA (e.g., cellular gDNA, ctDNA, cfDNA, evDNA, etc. derived from a normal, healthy or non-cancerous cell, tissue or subject; e.g., comprising normal methylscape DNA) is exposed and/or adsorbed to the solid support.

215. A method for determining the presence of cancer DNA (e.g., cellular gDNA, ctDNA, cfDNA, evDNA, etc. derived from a cancer cell or tissue, or cancer subject; e.g., comprising cancer methylscape DNA) or normal DNA (e.g., cellular gDNA, ctDNA, cfDNA, evDNA, etc. derived from a normal, healthy or non-cancerous cell, tissue or subject; e.g., comprising normal methylscape DNA) in a biological sample, the method comprising: exposing a biological sample comprising DNA (e.g., cellular gDNA, ctDNA, cfDNA, evDNA, etc.) to a solid support to which hydrophobic moieties adsorb under aqueous conditions; and detecting a first colorimetric or visual signal that is indicative of adsorption of cancer DNA to the solid support or a second colorimetric or visual signal that is indicative of exposure and/or adsorption of normal DNA to the solid support, wherein the first and second colorimetric or visual signals are different, and determining whether the biological sample comprises cancer DNA or normal DNA based upon detection of the first or second colorimetric or visual signal.

216. The method of any one of embodiments 210 to 215, wherein the solid support is selected from organic polymers such as polystyrene and its derivatives, polyacrylates and polymethacrylates and their derivatives, polyurethanes, nylon, polyethylene, polypropylene, polybutylene and copolymers of these materials, polysaccharides and hydrogels such as agarose, cellulose, dextran, Sephadex, Sephacryl, chitosan, inorganic supports such as silica gels, silica particles, glass, metal, semi-metal oxides, and supports with metal surfaces.

217. The method of embodiment 216, wherein the solid support is selected from a polymer bead, an agarose bead, a polystyrene bead, an acrylamide bead, a solid core bead, a porous bead, a paramagnetic bead, glass bead, controlled pore bead, a microtiter well, a cyclo-olefin copolymer substrate, a membrane, a plastic substrate, nylon, a Langmuir-Blodgett film, glass, a germanium substrate, a silicon substrate, a silicon wafer chip, a flow through chip, a microbead, a nanoparticle, a polytetrafluoroethylene substrate, a polystyrene substrate, a metal substrate such as a gold (Au) substrate, a silver (Ag) substrate; a tin (Sn) substrate, a rhodium (Rh) substrate, a ruthenium (Ru) substrate, a palladium (Pd) substrate, an osmium (Os) substrate, an iridium (Ir) substrate, a platinum (Pt) substrate, a titanium (Ti) substrate, an aluminum (Al) substrate, a chromium (Cr), a copper (Cu) substrate, a magnesium (Mg) substrate, a carbon substrate, a silicon substrate such as p-type doped silicon substrate, n-type doped silicon substrate, and gallium arsenide 218. The method of any one of embodiments 216 to 217, wherein the solid support is a colloidal particle.

219. The method of embodiment 210 or embodiment 211, wherein the solid support permits electrochemical detection of DNA adsorbed thereto.

220. The method of embodiment 219, further comprising detecting an electrical signal.

221. A method for detecting cancer DNA (e.g., cellular gDNA, ctDNA, cfDNA, evDNA, etc. derived from a cancer cell or tissue, or cancer subject; e.g., comprising cancer methylscape DNA), the method comprising: exposing a biological sample comprising cancer DNA to a working electrode that comprises an electro-conductive material; applying a potential to the working electrode; and detecting an electrical signal from the working electrode that is indicative of adsorption of cancer DNA to the electroconductive material, wherein the electrical signal is different to an electrical signal generated from the working electrode when a corresponding normal DNA (e.g., cellular gDNA, ctDNA, cfDNA or evDNA, etc. derived from a normal, healthy or non-cancerous cell, tissue or subject; e.g., comprising normal methylscape DNA) is adsorbed the electroconductive material.

222. A method for determining the presence of cancer DNA (e.g., cellular gDNA, ctDNA, cfDNA, evDNA, etc. derived from a cancer cell or tissue, or cancer subject; e.g., comprising cancer methylscape DNA) or a corresponding normal DNA (e.g., cellular gDNA, ctDNA, cfDNA or evDNA, etc. derived from a normal, healthy or non-cancerous cell, tissue or subject; e.g., comprising normal methylscape DNA) in a biological sample, the method comprising: exposing a biological sample comprising DNA (e.g., cellular gDNA, ctDNA, cfDNA, evDNA, etc.) to a working electrode that comprises an electro-conductive material; applying a potential to the working electrode; and detecting a first electrical signal from the working electrode that is indicative of adsorption of cancer DNA to the electroconductive material or a second electrical signal from the working electrode that is indicative of adsorption of the corresponding normal DNA to the electroconductive material, wherein the first and second electrical signals are different, and determining whether the biological sample comprises cancer DNA or the corresponding normal DNA based upon detection of the first or second electrical signal.

223. The method of embodiment 221 or embodiment 222, wherein the electro-conductive material is selected from gold, platinum, palladium, silver, carbon, alloys thereof, and composites thereof.

224. The method of any one of embodiments 223 to 224, wherein the electrical signal is selected from the group consisting of current, voltage, impedance, capacitance, charge, conductivity, resistance, or a combination thereof.

225. The method of any one of embodiments 210 to 224, wherein the biological sample is selected from tissue and fluid samples.

226. The method of any one of embodiments 210 to 224, wherein the biological sample is a biological fluid.

227. The method of embodiment 226, wherein the biological fluid is selected from whole blood; lysed whole blood; serum; plasma; urine; sputum; sweat; follicular fluid; synovial fluid; amniotic fluid; a nasopharyngeal aspirate; a bronchial aspirate; semen and cerebrospinal fluid.

228. The method of any one of embodiments 210 to 227, wherein the cancer DNA and corresponding normal DNA is cellular genomic DNA (cellular gDNA).

229. The method of any one of embodiments 210 to 227, wherein the cancer DNA and corresponding normal DNA is cell-free DNA (cfDNA).

230. The method of any one of embodiments 210 to 227, wherein the cancer DNA and corresponding normal DNA is circulating tumor DNA (ctDNA).

231. The method of any one of embodiments 210 to 227, wherein the cancer DNA and corresponding normal DNA is extracellular vesicular DNA (evDNA).

232. The method of any one of embodiments 210 to 231, further comprising analyzing a feature of the cancer DNA if present in the biological sample.

233. The method of embodiment 232, further comprising separating the cancer DNA from the solid support or electroconductive material.

234. The method of embodiment 232 or embodiment 233, wherein the feature is a nucleotide sequence of the cancer DNA.

235. The method of embodiment 234, wherein the nucleotide sequence is analyzed by nucleic acid hybridization, nucleic acid amplification and/or nucleotide sequencing.

236. The method of embodiment 235, wherein the nucleic acid amplification is selected from polymerase chain reaction (PCR), linear amplification, rolling circle replication and QB replication.

237. The method of embodiment 235, wherein the nucleotide sequencing is selected from Sanger sequencing, pyrosequencing, nanopore sequencing and Next Generation sequencing.

238. The method of any one of embodiments 232 to 237, wherein the cancer DNA is analyzed by any one or more of microarray analysis, a polymerase chain reaction (PCR)-based analysis including methylation-specific PCR (MSP), bisulfite treatment, hybridization with allele-specific probes, enzymatic mutation detection, ligation chain reaction (LCR), oligonucleotide ligation assay (OLA), flow-cytometric heteroduplex analysis, chemical cleavage of mismatches, mass spectrometry, single strand conformation polymorphism (SSCP), denaturing gradient gel electrophoresis (DGGE), temperature gradient gel electrophoresis (TGGE), restriction fragment polymorphisms, serial analysis of gene expression (SAGE), DNA sequencing, or combinations thereof.

239. The method of any one of embodiments 232 to 238, wherein the cancer DNA is analyzed by a methylation analysis assay, including for example, bisulfite genomic sequencing, MSP, melting curve methylation-specific PCR (McMS-PCR), multiplex ligation-dependent probe amplification (MLPA) with or without bisulfite treatment, digestion of genomic DNA with methylation-sensitive restriction enzyme, multiplexed PCR with gene specific primers (MSRE-PCR), bisulfite conversion-specific methylation-specific PCR (BS-MSP), methylation-sensitive single-nucleotide primer extension conformation (MS-SNuPE), methylation-sensitive single-strand conformation analysis (MS-SSCA), melting curve combined bisulfite restriction analysis (McCOBRA), enzymatic regional methylation assay (ERMA), quantitative PCR sequencing and oligonucleotide-based microarray systems, pyrosequencing, and Meth-DOP-PCR, or a combination between a modified degenerate oligonucleotide primed PCR (DOP-PCR) and MSP.

240. A method of isolating cancer DNA, the method comprising contacting the biological sample with a solid support to which hydrophobic moieties adsorb under aqueous conditions to form a conjugate comprising the solid support and the cancer DNA and separating the conjugate from the biological sample.

241. A method of determining the likelihood of the presence or absence of cancer in a subject, the method comprising: contacting a biological sample obtained from the subject with a solid support to which hydrophobic moieties adsorb under aqueous conditions; and detecting the presence or absence of a conjugate comprising the cancer DNA and the solid support, and optionally the methylation status and/or one or more ancillary cancer biomarkers of the cancer DNA, to thereby determine the likely presence or absence of cancer in the subject.

242. A method of treating cancer, comprising determining the likelihood of the presence or absence of cancer in a subject, and optionally the methylation status and/or one or more ancillary cancer biomarkers of the cancer DNA according to the method of embodiment 241; and exposing the subject to a treatment regimen for treating the cancer if the analysis indicates the likely presence of cancer in the subject, or not exposing the subject to a treatment regimen for treating the cancer if the analysis indicates the likely absence of cancer in the subject.

In order that the invention may be readily understood and put into practical effect, particular preferred embodiments will now be described by way of the following non-limiting examples.

EXAMPLES

Example 1

In Solution and Surface-Based Self-Assembly of Epigenomes as a Function of Global Methylation Levels The present inventors hypothesized that different methylation landscape of normal and cancerous epigenomes may impact their physicochemical and self-assembly properties in aqueous solutions, and as they interact with solid surfaces (FIG. 1). To investigate this hypothesis, they first undertook experiments to visualize (using transmission electron microscopy (TEM)) the purified genomic DNA extracted from normal and malignant prostate tissue isolated from a healthy individual and a metastatic cancer patient, respectively. Initial observations of DNA isolated from the cancerous sample put in evidence a uniform coating across the surface, as compared to the normal DNA sample, which showed tendency to create larger aggregates (FIGS. 1 and 2). Digital image analysis showed that the size of aggregates in DNA derived from normal prostate tissue DNA is approximately 8298 nm$^2$, with some of the individual aggregates reaching up to micron sizes (approx. 8 µm$^2$). In contrast, the average size of aggregates in cancer tissue DNA is 1540 nm$^2$ with most of them within the nanometer size (see, FIG. 3).

Figure 4:
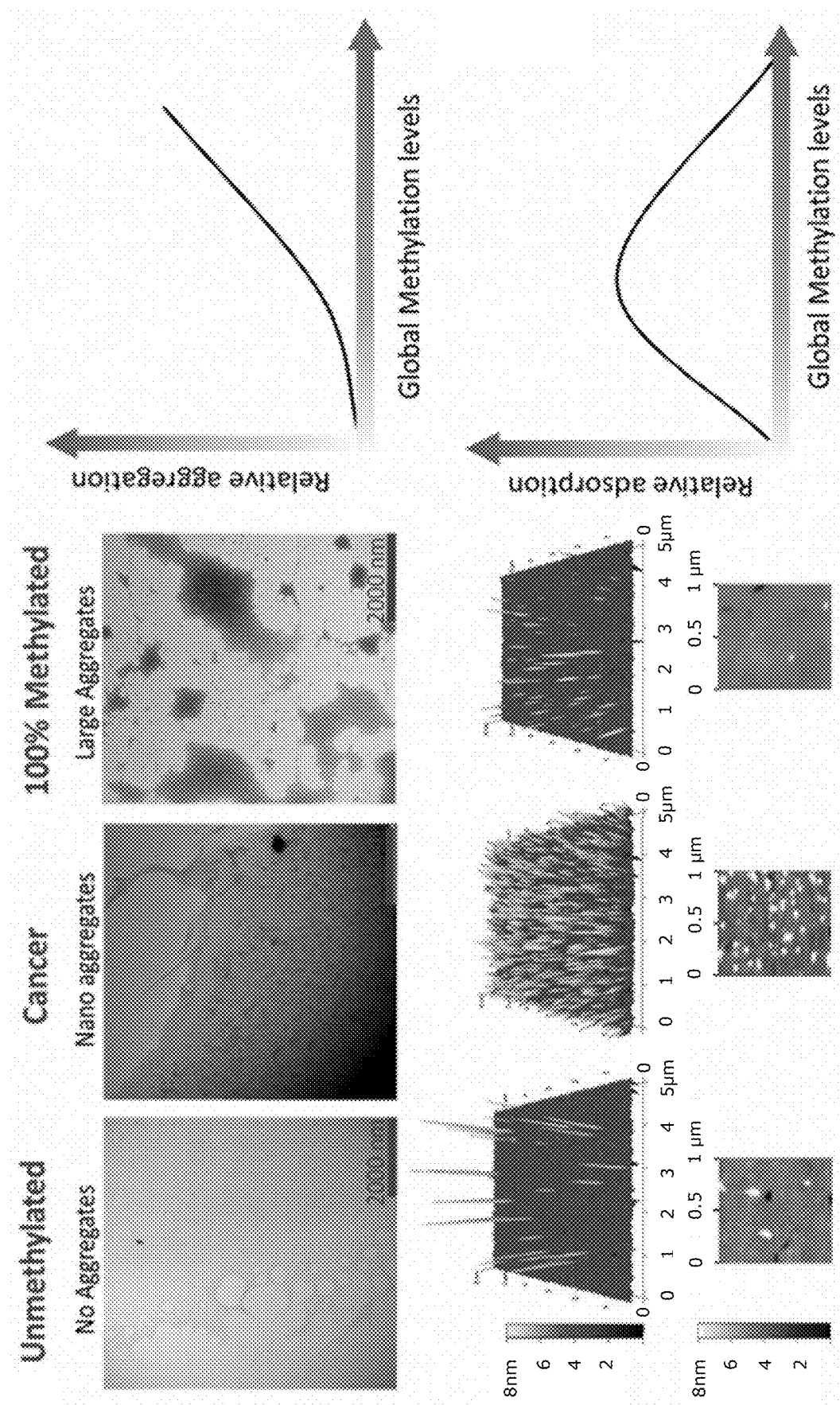
FIG. 4 is a photographic, schematic and graphical representation showing how different methylation levels and methylation patterns modulate the solution and surface-based properties of genomic DNA. (Top-left) TEM image showing the different solvation of DNA based on their different methylation status. i) fully unmethylated WGA DNA ii) moderately methylated DNA from BT474 cancer cells iii) 100% CpG methylated Jurkat DNA. (Top-right) the solvation trend of DNA with increasing methylation levels. (Bottom-left) AFM image showing the interaction behavior of genomic DNAs with the gold surface based on their different methylation status. WGA and 100% methylated Jurkat DNA shows very low adsorption, whereas BT474 DNA shows very high adsorption. (Bottom-right) surface adsorption trend of genomic DNA with increasing global methylation levels.
Figure 5:
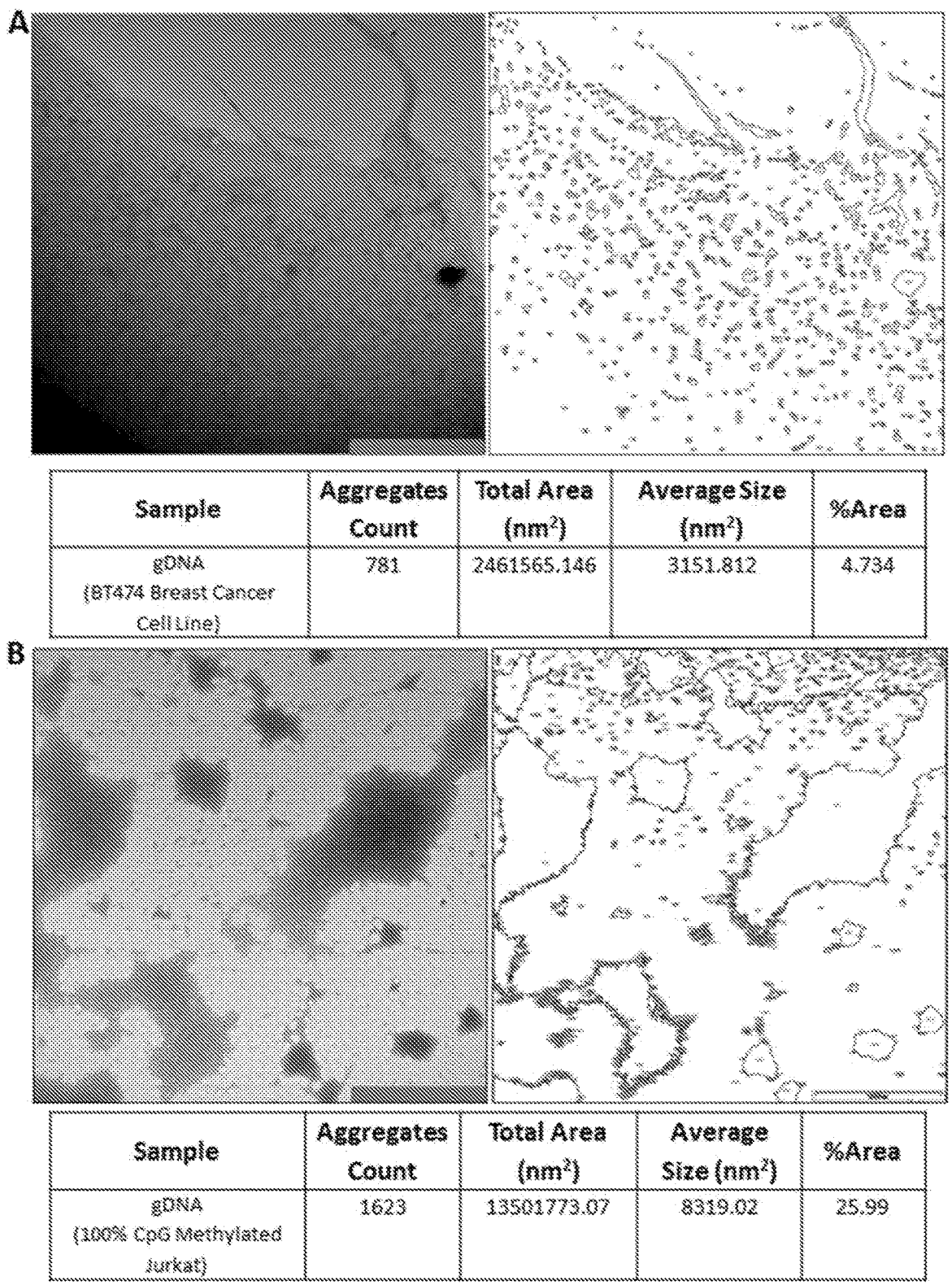
FIG. 5 is a photographic and tabular representation showing ImageJ analysis for TEM image of DNA with different methylation status. A) cellular gDNA from BT474 breast cancer cell line B) 100% CpG methylated Jurkat DNA. Scale bars are 2000 nm for all the figures.
Figure 6:
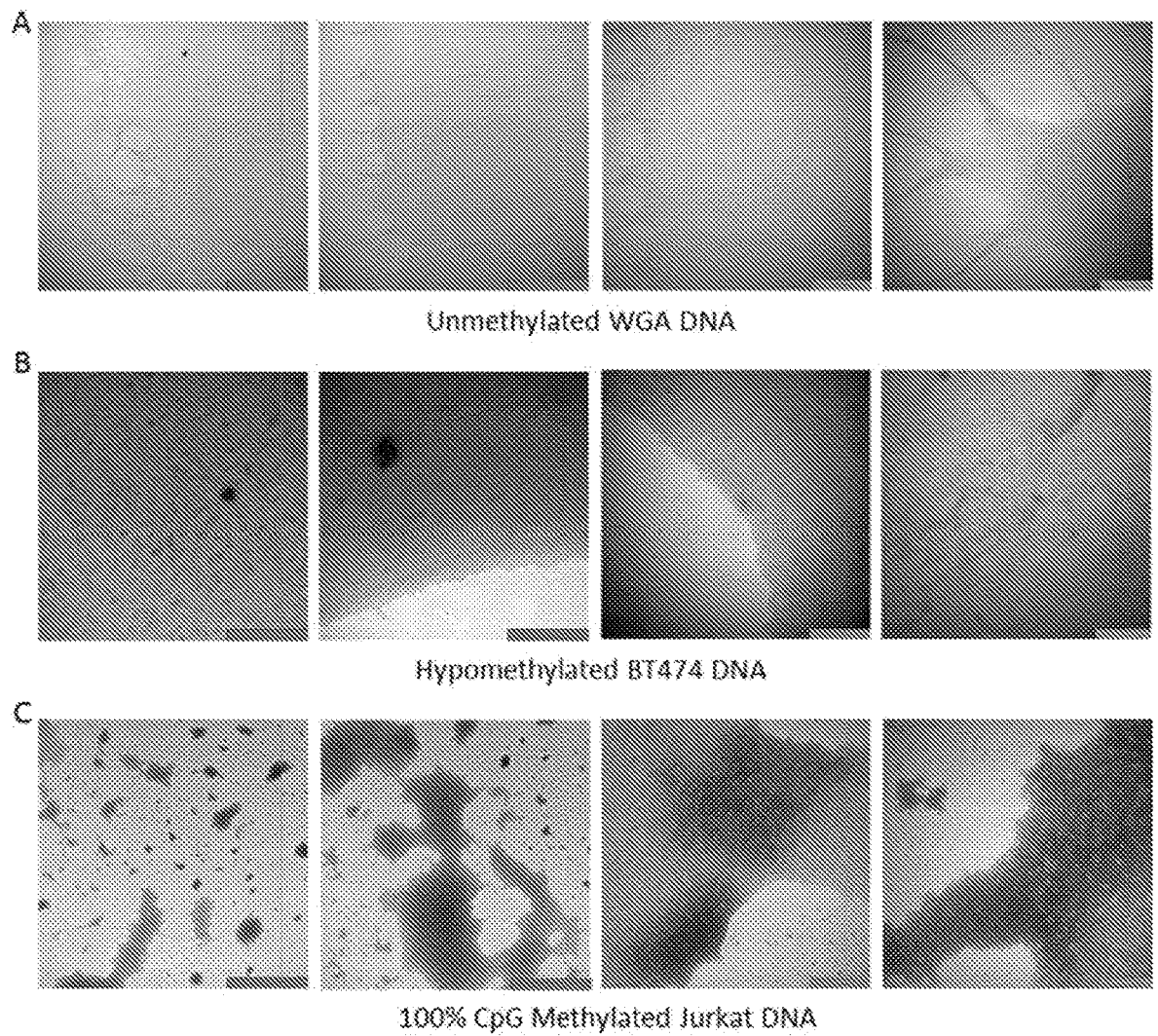
FIG. 6 is a photographic representation showing additional TEM images of cellular gDNA with different methylation status. A) Unmethylated WGA DNA B) Hypomethylated BT474 breast cancer cell line DNA (43% global methylation) C) 100% Methylated Jurkat DNA. Scale bars are 2000 nm (red) 1000 nm (blue) and 500 nm (orange) for all the figures.

To further investigate the methylation dependent self-assembly properties of epigenomes in solution, the present invention visualized an additional set of control samples with defined DNA methylation characteristics: (i) a DNA derived from the BT474 breast cancer cell line, which has approximately 43% global methylation levels (see methods section for calculation details); (ii) a fully unmethylated epigenome generated by whole genome amplification (WGA) of the BT474 DNA, which is a process that erases all methylation marks but preserves the genetic sequence; and (iii) a commercially available 100% methylated DNA sample (M-Jurkat), which has been enzymatically manipulated to have all CpG sites methylated. The TEM Images depicted in FIG. 4 shows that the unmethylated WGA DNA coated the surface in a uniform manner, but as the sample becomes methylated, nanometer-sized domains begin to emerge (FIG. 4, WGA verses BT474) with the 100% methylated sample exhibiting large, micron-sized aggregates. The average size of aggregates for BT474 and 100% methylated Jurkat DNA was found to be approximately 3151 nm$^2$ and 8319 nm$^2$ respectively (see, FIG. 5). Interestingly, the TEM image of the fully methylated DNA largely resembles that of normal genome (FIG. 1) and this could be due to the fact that normal genomes also feature large levels of global methylation. Overall, the TEM data suggest a trend towards increased aggregation with increased global methylation content of DNA epigenomes in solution (FIG. 4, top-right). It is known that methyl group is highly hydrophobic, and hydrophobic forces are indeed vastly involved in aggregation processes of polymers. Moreover, hydrophobic driven methylation-dependent conformational changes of DNA have already been reported in the literature (Kaur, P. et al., 2012, *Physical Biology* 9:065001). Thus, the present inventors posited that the presence of very high methylation levels in the fully methylated—and in normal DNAs—likely makes the DNA polymer highly hydrophobic in nature and thus favors the aggregation process in solution. Additional TEM experiments with these DNA (WGA, BT474 and 100% Methylated Jurkat DNA) were also performed, and technical replicates of different samples of the same DNA (analyzed on different days) continued to display the same surface-interaction effects, suggesting a consistent phenomenon unrelated to sample manipulation or imaging (see, FIG. 6 for additional TEM images).

Following these observations, the present inventors envisioned that the distinct nanometer-sized morphologies of cancer vs. normal genomes—which accrued from their methylation-dependent solvation properties—would have an impact on DNA-adsorption processes, as they interact and self-assemble onto metal surfaces such as gold. While the relative gold-affinities of canonical DNA bases is well known (Ohno, S. et al., 2015, *Polymer Journal* 47:71-76; Kimura-Suda, H. et al., 2003, *Journal of the American Chemical Society* 125:9014-9015; Sina, A. A. I. et al., 2014, *Analytical chemistry* 86:10179-10185; Storhoff, J. J. et al., 2002, *Langmuir* 18:6666-6670), the effect of methylcytosines on DNA adsorption has been widely overlooked owing to generalized use of short synthetic oligos or amplified DNA samples that have lost their methylation information during the amplification process.

To evaluate the effect of methylation on DNA-gold adsorption, the same three DNAs (i.e., WGA, BT474 and 100% Methylated Jurkat) were first adsorbed onto ultra-flat gold substrates (Roughness (R)=259.4 µm) and visualized under Atomic Force Microscope (AFM). To date, there are few experiments involving DNA adsorbed onto gold surfaces, and in most cases, they involve the use of DNA chemically anchored onto gold by one end (Kelley, S. O. et al., 1998, *Langmuir* 14:6781-6784; Wang, J. et al., 2001, *Analytical chemistry* 73:2207-2212). Alternatively they employed DNA sequences (e.g., short oligos or fragments generated by PCR amplification reactions) (Davies, E. et al., 2005, *FEBS letters* 579:1702-1706; Zhang, R.-Y. et al., 2002, *The Journal of Physical Chemistry B* 106:11233-11239) which did not incorporate any methylation information. Hence, to the best of the inventors' knowledge, there are no AFM reports involving adsorption of intact genomic DNA onto the gold surfaces, nor comparing full genomes with different methylation landscapes.

Figure 7:
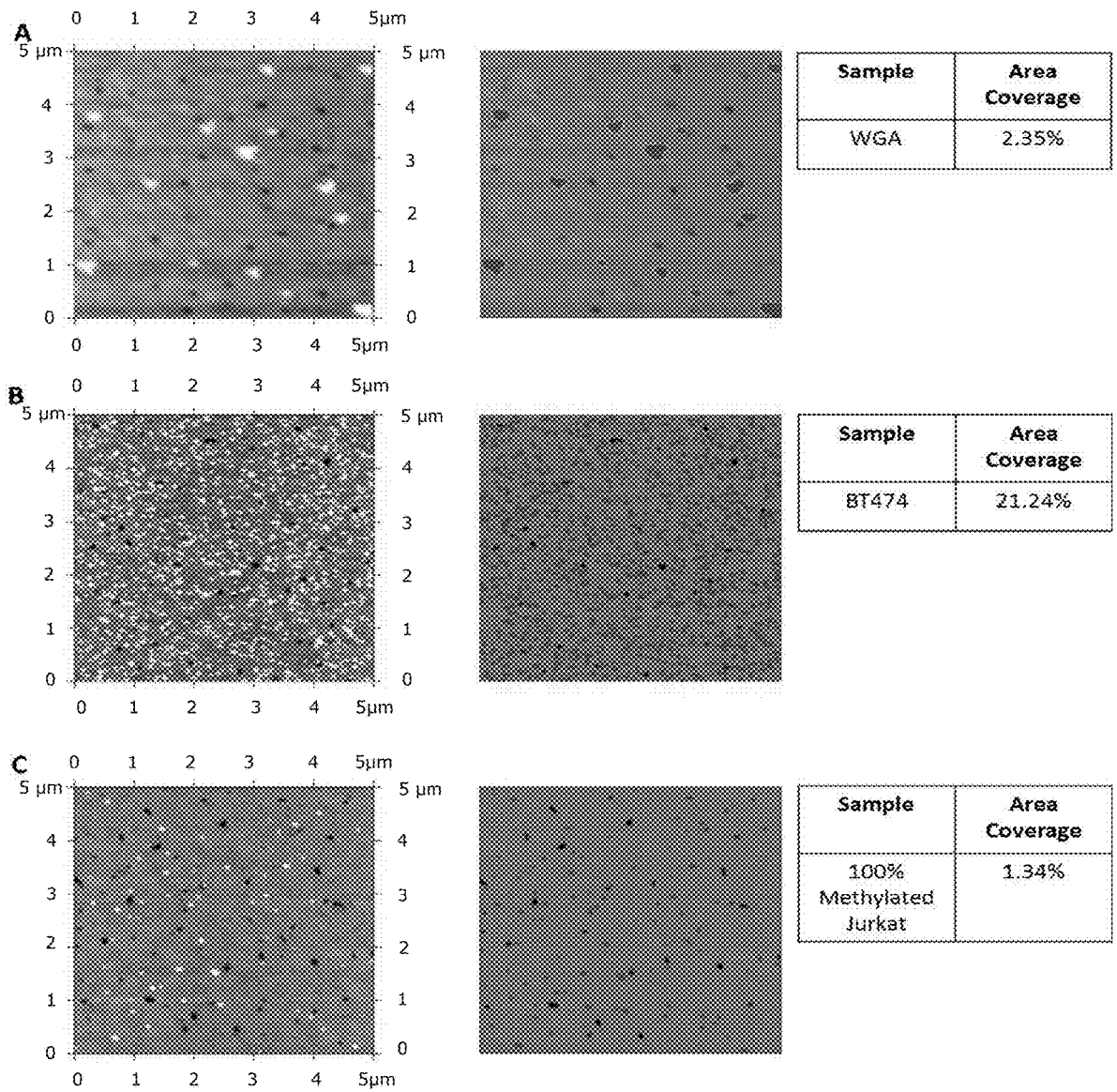
FIG. 7 is a photographic and tabular representation showing 2D-AFM image of DNA with different methylation status. Right tables shows the approximate % area coverage obtained from ImageJ analysis.

As shown in the AFM images of FIG. 4, unmethylated WGA DNA gave a scattered low-adsorption profile. This observation is in-line with previous reports of unmethylated or amplified double-stranded DNA which also displayed very low adsorption competence towards gold surfaces (Li, H. et al., 2004, *Journal of the American Chemical Society* 126:10958-10961). The present inventors also observed that, as the genomic DNA became methylated (i.e., BT474 DNA), the surface-adsorption process became significantly favoured, resulting in high saturation of the gold surface (FIG. 4). However, when the DNA was highly methylated (i.e., 100% methylated DNA), minimal attachment of the epigenome to the gold surface occurred. This suggests that the surface-adsorption kinetics of fully methylated samples is unfavourable—presumably due to the self-assembly of large aggregates of DNA in solution, which would limit the available surface-area of the sample and potentially block sample-surface interaction sites. ImageJ analysis of AFM images of these DNA shows that the approximate area coverage for WGA and 100% Methylated Jurkat DNA is 2.80% and 1.34%, respectively (FIG. 7). In contrast, the approximate area coverage for BT474 DNA is 21.24%, suggesting that there is a parabolic adsorption trend of DNA towards gold surface with increasing methylation levels (FIG. 4, down right).

Example 2

Figure 8:
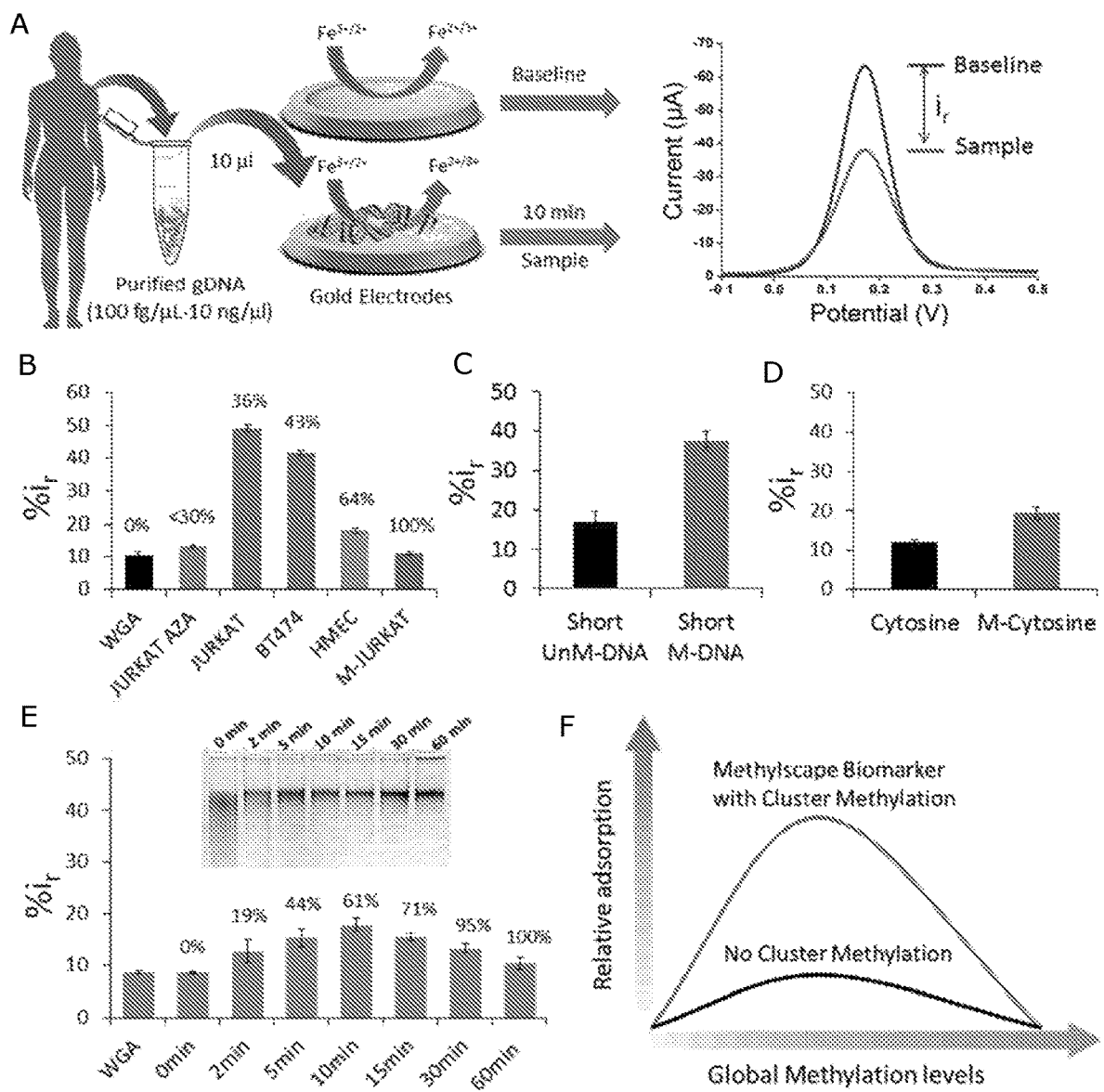
FIG. 8 is a schematic and graphical representation depicting the role of methylation on DNA-gold affinity. (A) Methodological approach for the electrochemical quantification of DNA adsorption on gold electrodes. First, the DPV current from the bare gold electrode was measured to get the baseline signal. The purified DNA extracted from cell line, tissue or plasma samples were then adsorbed onto the gold electrodes and the DPV current was measured to get the sample signal. The difference between the baseline and the sample signal is the ir value, which is normalized to % ir for better understanding. The % ir for a given DNA sample directly correlates with the adsorption level of DNA on gold electrodes. (B) Relative current (% ir) mean values for the unmethylated WGA DNA (black), Aza treated demethylated Jurkat DNA (Blue), cellular gDNA from BT474 and Jurkat cancer cells (red), HMEC cellular gDNA from primary mammary cells (green) and 100% methylated cellular gDNA from Jurkat cells (Brown). (C) Bar Graph of relative current (% ir) mean values for the adsorption of 140 bp methylated (red) and unmethylated (black) DNA fragments. (D) Bar graph of relative current (% ir) mean values for the adsorption of individual cytosines (black) and methylcytosines (red) nucleotides. (E) Relative current (% ir) mean values for various genomic DNAs prepared from WGA DNA by enzymatic reaction at different time points. Sample methylation levels are provided above each bar. Inset: electrophoresis gel of the enzymatically methylated DNA samples digested with methylation sensitive HpaII restriction enzyme. (F) Effect of cluster methylation towards adsorption. Each data point for the FIGS. 8B, 8C, 8D and 8E represents the average of three separate trials, and error bars represent the standard deviation of measurements (% RSD=<5% for n=3).

Methylcytosines Enhance Gold-Adsorption of Methylated DNA Fragments and Genomic DNAs To obtain greater insight on the methylation-dependent adsorption behavior of DNA, electrochemical assays were used to quantitatively assess the adsorption levels of DNA fragments and whole genomes with various methylation levels (FIG. 8). The electrochemical assay involved the direct adsorption of 5 µL of purified cellular gDNA (10 ng/µL concentration in SSC5× buffer at neutral pH) onto gold electrodes for 10 mins. Subsequently, the adsorption competence was measured by Differential Pulse voltammetry (DPV) in presence of the $[Fe(CN)_6]^{3-/4-}$ redox system (FIG. 8, see methods section for details). Upon adsorption of DNA on gold electrodes, $[Fe(CN)_6]^{3-/4-}$ redox system generates a Faradaic current signal, which is proportionally lower than the bare electrode signals (Koo, K. M. et al., 2014, *Analyst* 139:6178-6184; Sina, A. A. I. et al., 2014, *Chemical Communications* 50:13153-13156; Zhang, J. et al., 2007, *Chemical Communications*, 1154-1156) (i.e., the greater the DNA adsorption is, the larger the relative current signal difference will be, % $i_r$, with respect to the original baseline. The present inventors have previously used this redox system to quantify gold-adsorbed DNA (Koo, K. M. et al., 2014, supra; Sina, A. A. I. et al., 2014, supra) and RNA (Koo, K. M. et al., 2016, *Analytical Chemistry* 88:6781-6788; Koo, K. M. et al., 2016, *Analytical chemistry* 88:2000-2005) with excellent precision, and to discriminate between short DNA sequences with single-base differences under optimized conditions.

Figure 9:
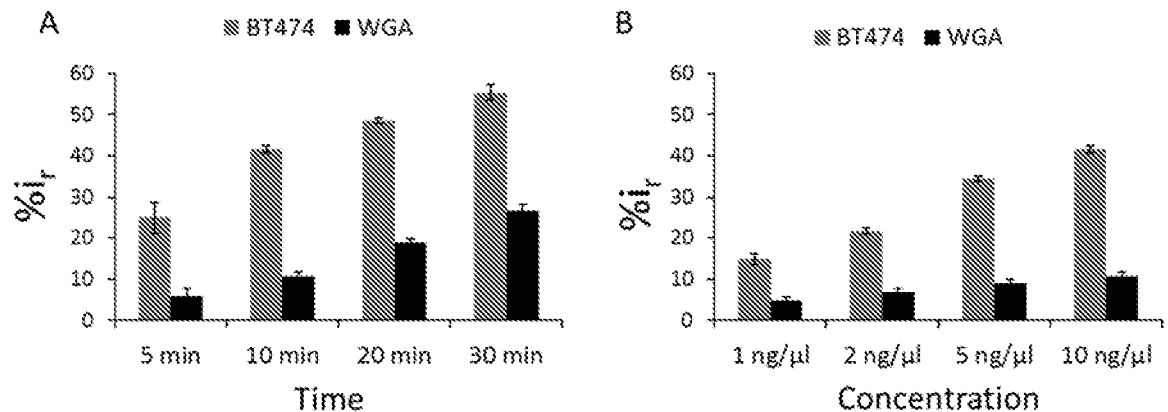
FIG. 9 is a graphical representation showing optimization of the operating parameters for cell line DNA. Mean values of the relative DPV current obtained for the adsorption of WGA and BT474 cell derived DNA at (A) different time (DNA concentration, 10 ng/μL) and (B) different concentration (adsorption time, 10 min). Each bar represents the average of three separate trials (n=3). Error bars represent the standard deviation of measurements (relative standard deviation (% RSD) was found to be <5% for n=3).

Using this approach, the present inventors tested a collection of genomic DNAs with (i) no methylation (ii) significant hypomethylation (iii) moderate methylation, (iv) large CpG Methylation (v), and 100% CpG methylation. The unmethylated and fully methylated DNA genomes were the same DNAs (i.e., WGA, and 100% methylated Jurkat) that were tested in the inventors' previous TEM and AFM experiments. The hypomethylated DNA used for this experiments was cellular gDNA derived from Jurkat cancer cells grown in the presence of 5-azacytidine—a demethylation drug that generates DNA with an average of <30% global methylation. For moderately methylated DNA, BT474 and Jurkat cancer cell derived DNA were used, which have 43% and 36% global methylation, respectively and for largely methylated DNA, Human Mammalian Epithelial cell (HMEC) line DNA was used, representing the normal phenotype (global methylation=64%). In agreement with the inventors' previous AFM data, the BT474 and Jurkat DNA provided significantly higher adsorption levels as reflected by approximately 20-40% larger relative current than the unmethylated, normal and the 100% methylated genomic DNA (FIG. 8B, % $i_r^{BT474}$=41.58±0.87, % $i_r^{Jurkat}$=49.24±1.17 vs % $i_r^{WGA}$=10.58±1.09, % $i_r^{HMEC}$=18.18±0.81, % $i_r^{M-Jurkat}$=11.28±0.49; for optimization experiments, see, FIG. 9). Largely methylated HMEC DNA and the fully methylated DNA, led to poor adsorption, and so did demethylated aza-Jurkat genomes, whose levels were slightly larger than the unmethylated WGA version, but still far lower than the cancer derived BT474 and Jurkat DNA (FIG. 8B). These data also indicate that the adsorption of genomic DNA towards gold surface varies with the number of methylcytosines present in the genome. Within this sample dataset, adsorption appears to display a parabolic trend with the increase of global methylation percentage (FIG. 8F); with the highest values for methylation percentages typical of cancer-derived DNA To better ascertain the role of methylcytosines in DNA-gold adsorption, another set of experiments was performed with short DNA fragments and individual nucleotides with different methylation status. In a first suite of experiments, the adsorption behavior of 1 ng/µL of ds-DNA fragment (140 bp long) encompassing a cluster of either eight methylcytosines (M-DNA) was compared to cytosines (UM-DNA) at neutral pH for 20 min. These two DNAs exhibited markedly different adsorption trend (FIG. 8C) with the M-DNA showing 20% larger relative current signal difference than UM-DNA (i.e., % $i_r^{M-DNA}$=37.47±0.2.51 vs % $i_r^{UM-DNA}$ 17.15±2.50). This outcome suggests that the small methylated DNA fragments have larger gold-DNA adsorption than the unmethylated fragments. It is proposed that this is due to a higher affinity of methylcytosine towards gold in comparison to the unmethylated cytosine nucleotide. To confirm this point, a similar experiment was performed with 1 µM solution of methylated (M-dCTP) and unmethylated (dCTP) individual cytosine nucleotides. A significantly higher adsorption was also observed for M-dCTP (FIG. 8D) in this case (i.e., % $i_r^{M-dCTP}$=19.45±1.45 vs % $i_r^{dCTP}$=12.01±0.78). These data indicate that methylation can modulate DNA adsorption onto gold surfaces in a dynamic way, where adsorption of small fragments and individual nucleotides is enhanced by the presence of methylcytosines. However, in case of whole genomes, methylation appears to only favour adsorption until it reaches a certain methylation value; and once a methylation maxima is exceeded, self-assembly of DNA in solution no longer favors the epigenome-surface interactions. This is presumably due to the formation of large aggregates, as noted in FIG. 1, which are more likely to appear for highly methylated DNA samples, but not for cancer-derived DNA.

Figure 10:
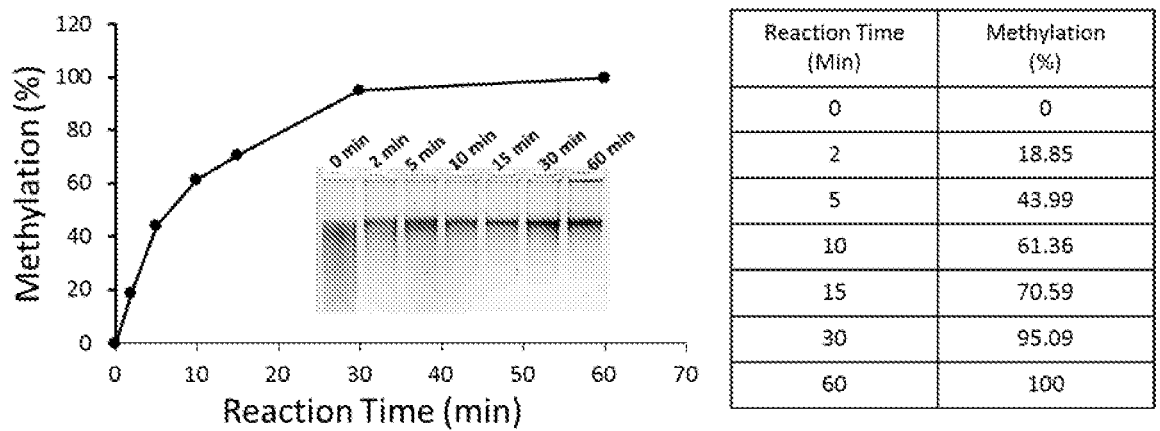
FIG. 10 is a graphical, photographic and tabular representation showing ImageJ analysis of the electrophoresis gel picture showing the methylation levels for each of the samples treated with M.SssI enzyme with different reaction time (methylation level is assumed 100% for 60 min reaction times as suggested by the manufacturer instruction for the kit used).

To evaluate this hypothesis and further investigate the reason for this methylation maxima self-assembly trend, the present inventors designed a time-point whole genome methylation-dependent adsorption experiment. They treated the unmethylated DNA (WGA) with the M.SssI CpG methyltransferase which attaches methyl groups to cytosines in CpG dinucleotides. By incubating this unmethylated genomic template with M.SssI for increasing time periods, a series of DNA genomes was generated with increasing methylation content. The outcome of this enzymatic treatment was confirmed by digestion using methylation sensitive HpaII restriction enzyme. ImageJ analysis of gel picture for HpaII enzyme digestion experiment (FIG. 8E, inset) allowed rough estimation of the methylation levels for each sample treated with M.SssI at a given time-point (see, FIG. 10 for details). The results of this experiment indicated that increasing methylation levels led to increased epigenome-surface interaction as measured by electrochemical DPV assays until a methylation threshold was reached. Beyond this threshold, sample adsorption onto the gold surface was compromised and adsorption levels began to decrease (FIG. 8E). Interestingly, it was not possible to recapitulate the overall adsorption value generated by the cancerous BT474, or Jurkat epigenome samples. For example, the BT474 sample with overall methylation levels in the range of 43% led to adsorption levels approximately two and half-times larger than the maxima achieved with the M.SsI samples (i.e., % $i_r^{BT474}$=41.58±0.87 vs % $i_r^{10mins}$=17.9±1.2). This observation suggest that although BT474 DNA have similar methylation levels as the DNAs obtained from 5-10 min M.SsI samples, it would portray a specific methylation pattern that would favour DNA adsorption significantly, to a degree unseen in any other tested DNA sample, regardless of their global methylation content. The present inventors hypothesize that this would be caused by the presence of "methylscape" biomarker (i.e., regions with high levels of clustered methylation separated by large intergenic tracks of unmethylated regions) in cancer genomes where the distribution of methylcytosines is significantly different than the DNAs methylated with the M.SsI enzyme. This is because this enzyme attaches methyl group across the genome in random fashion rather than in clustered regions. Therefore, this methylscape biomarker, which is typical of cancer DNAs and not present in DNAs from healthy individuals, would drive a unique self-assembly process, and regardless of their global methylation content, creates a distinctive adsorption footprint (As shown in FIG. 8F) that can be used to infer their clinicopathological state.

Example 3

Methylscape Biosensing can Discriminate Normal and Cancerous Samples

From the above experiments, the present inventors hypothesized that the cluster methylation (also called regional hypermethylation) present in cancer genomes represented an ideal configuration for maximizing epigenome-surface adsorption. A corollary of this proposition is that the unique self-assembly process of cancerous epigenomes, due to their methylation landscape distribution, could be exploited to detect "methylscape" biomarker using biosensing applications.

Figure 11:
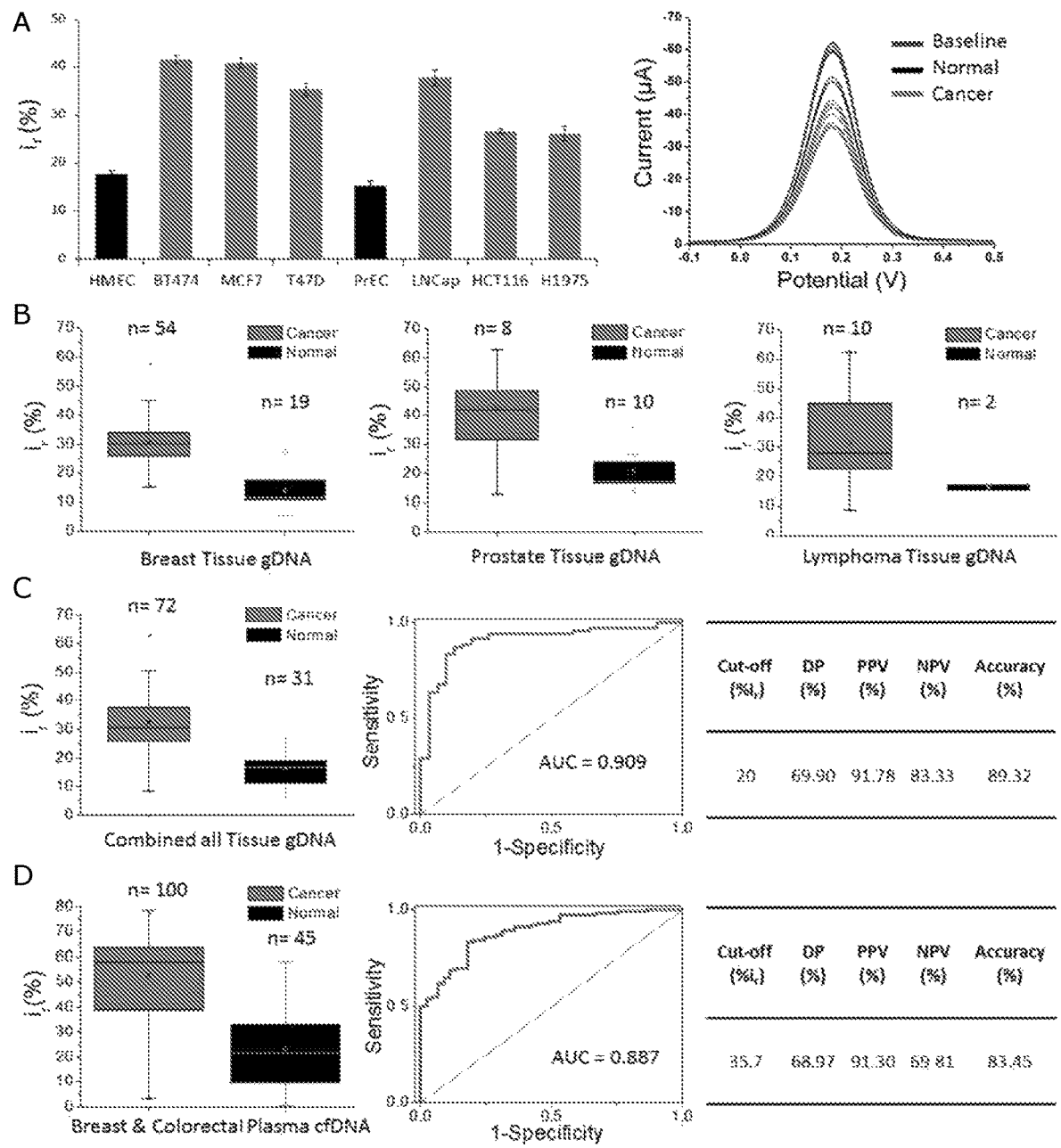
FIG. 11 is a graphical and tabular representation depicting practical application of methylscape approach. (A) Differential affinity/adsorption of cellular gDNAs as a function of their cancer and normal origin. Bars represent the relative current (% ir) mean values for DNA genomes derived from various normal (Black Bars: Human Mammalian Epithelial Cell (HMEC), Prostate Epithelial cell (PrEC)) and cancer cell lines (Red Bars: Breast cancer: BT474, MCF7, T47D, LNCap prostate cancer, HCT116 colorectal cancer and H-1975 lung cancer). Each data point represents the average of three separate trials, and error bars represent the standard deviation of measurements (% RSD=<5% for n=3). Right Panel: Corresponding DPV graphs for all cell line DNAs and their respective baseline. (B) Box plot showing mean relative current (% ir) values generated by electrochemical detection of genomic DNAs extracted from various tissues (breast, prostate and lymph node) derived from 31 healthy individuals and 72 cancer patients. (C) The combined data for all the tissue samples, Right: the ROC analysis and diagnostic test evaluation shows the Disease Prevalence (DP), positive predictive values (PPV), negative predictive values (NPV) and accuracy of the method. (D) Box plot showing relative current (% ir) mean values generated by electrochemical detection for genomic DNAs extracted from plasma samples derived from 45 healthy individuals and 100 breast cancer patients, Right: the ROC analysis and diagnostic test evaluation shows the Disease Prevalence (DP), positive predictive values (PPV), negative predictive values (NPV) and accuracy of the method.

To investigate the possibility of developing a simple method for cancer detection based on the different physico-chemical properties of DNA, the present inventors used an electrochemical DPV assay to analyze various epigenomes extracted from breast (BT474, MCF7 and T47D), prostate (LNCap), lung (H1975) and colorectal (HCT116) cancer cell lines, and compared them to DNA isolated from healthy breast (HMEC) or prostate (PrEC) cells. Notably, DNA genomes from breast cancer or prostate cancer cells provided approximately 2.5-fold higher relative current than their respective normal breast (HMEC) and prostate (PrEC) cell lines, as did the other epigenomes isolated from lung (H1975) and colorectal (HCT116) cancer cells (FIG. 11A).

Figure 12:
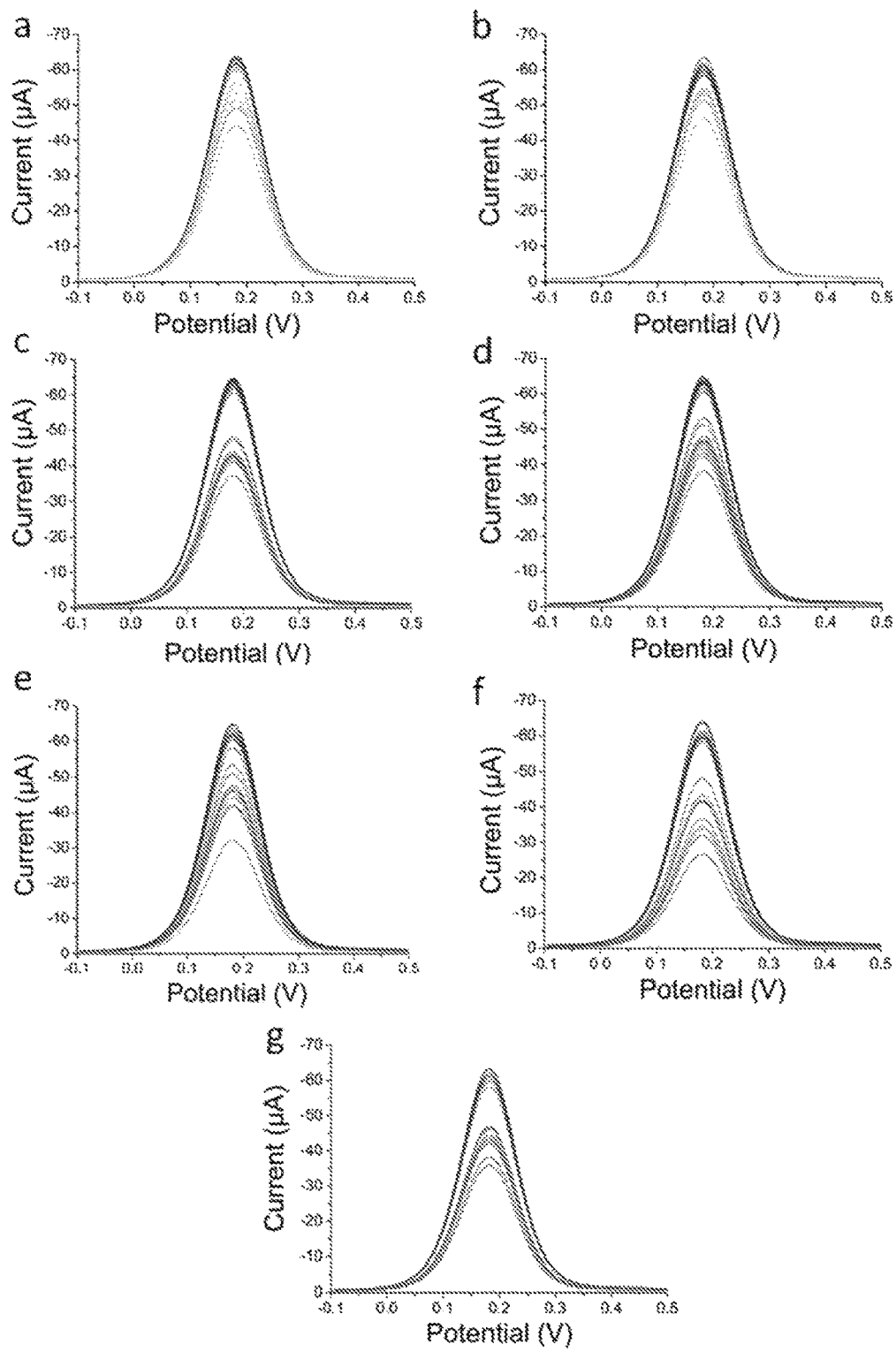
FIG. 12 is a graphical representation showing DPV signals for the adsorption of cellular gDNA derived from 31 normal breast tissues (green), 54 breast cancer tissues (red), and their corresponding baselines (blue). a) Normal Samples 1-15 b) Normal Samples 16-31 c) Patient Sample 1-11 d) Patient Samples 12-22 e) Patient Samples 22-33 f) Patient Samples 34-45 g) Patient sample 34-54.
Figure 13:
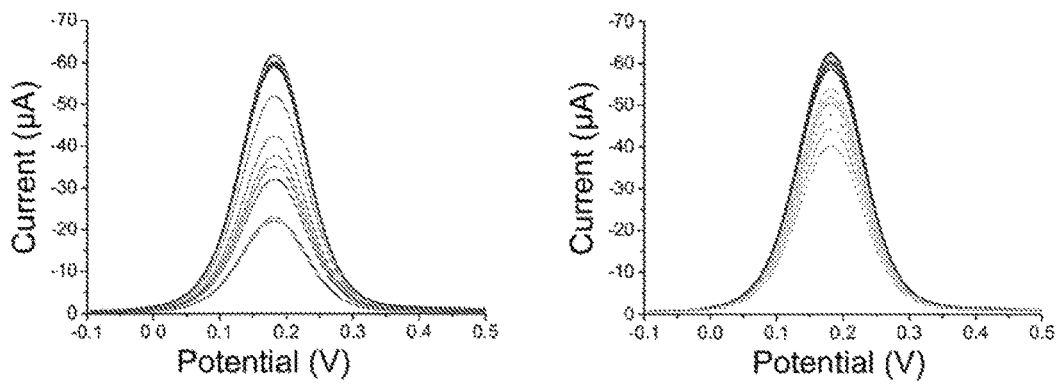
FIG. 13 is a graphical representation showing DPV signals for the adsorption of cellular gDNA derived from 8 prostate cancer tissues (red), 10 normal prostate tissues (green) and their corresponding baselines (blue).
Figure 14:
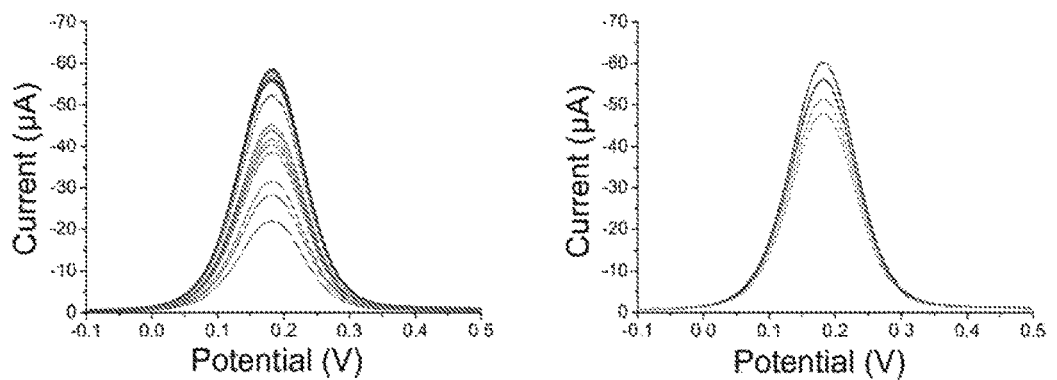
FIG. 14 is a graphical representation showing DPV signals for the adsorption of cellular gDNA derived from 10 lymphoma cancer tissues (red), 2 normal lymphoma tissues (green) and their corresponding baselines (blue).

To determine the applicability of this approach for cancer detection in clinical specimens, the present inventors analyzed 72 epigenomes extracted from patient tumor tissues of different cancer types (54 ER+ breast, 8 prostate, and 10 lymphoma cancer tissues), and compared their adsorption levels to 31 epigenomes extracted from matching tissues types of healthy individuals (19 normal breast, 10 normal prostate and 2 normal lymph node tissues). FIG. 11B shows the individual box plot representing relative DPV current values for the cellular gDNA samples extracted from breast (ER+), prostate and follicular lymphoma cancer tissues verses matching tissues from healthy individuals (see, FIGS. 12 to 14 for original DPVs and Table 1 to 4 for clinical information). Significant differences in cellular gDNA adsorption levels were observed between normal and cancer samples when they are compared by tissue type (FIG. 11B) or when all cancer types were combined (FIG. 11C). The combined box plot (FIG. 11C) for the adsorption experiments of all three types of cancer and normal samples shows that 75% of cancer samples have a relative DPV current (% ir) value of more than 25 units, whereas 75% of cellular gDNA derived from normal tissues provide relative current values lower than 20 units. Statistical significance was determined by pairwise comparisons between normal and cancer samples using Student's t-test for each of the box plots. P value of the t test (Table 5) clearly shows that the normal and cancer samples are significantly different with 95% confidence. Moreover, the ROC curve (FIG. 11C) for the range of tissue samples tested shows high-specificity for cancer detection (AUC=0.909). Statistical diagnostic efficacy test at cut-off value % ir=20 shows that the present biosensing method has high accuracy (89.32%) with high positive (PPV) and negative (NPV) predictive values (Table—FIG. 11C, PPV=91.78%, NPV=83.33%, see more details in Table 6). Notably, most of the samples used in this study were isolated from patient and normal individuals with the age above 40 years (see, Tables 1 to 4). For the breast and prostate cancer samples, comparison with the normal samples was performed among individuals of the same gender. This way, the analysis is not biased by gender or age associated DNA methylation changes among individual's DNA. Finally, to validate the methylation dependent adsorption changes of genomic DNA, the present inventors quantified the global methylation levels of some of the patient and normal DNA samples (See Method section for details). As shown in Tables 1 to 4, most of the patient DNA samples have moderate or low methylation levels—in the range of 30-50 percent while the normal DNA samples have higher level of global methylation—on average of 50-75 percent. These data are consistent with the present inventors' initial hypothesis that the adsorption of genomic DNA onto the gold surface is significantly modulated by the global methylation levels and patterning that defines the proposed methylscape biomarker.

Example 4

Methylscape Biosensing Applications Using Circulating-Free Plasma DNA

Figure 15:
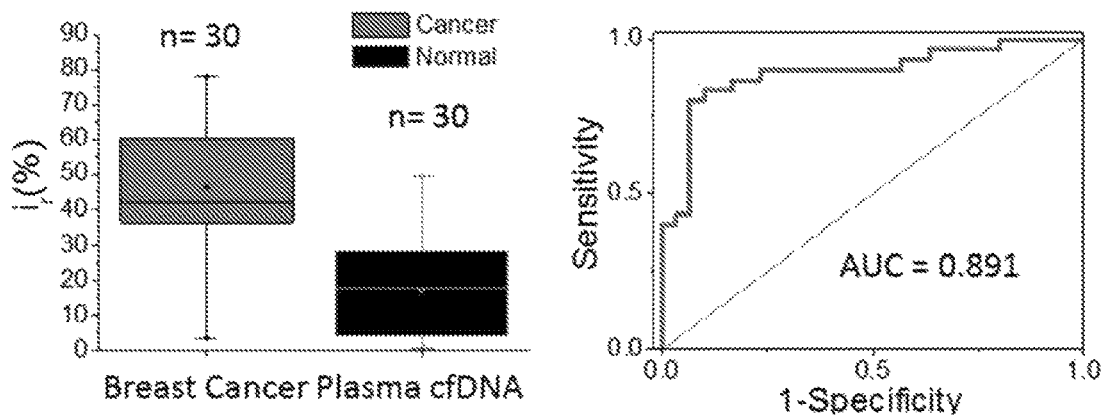
FIG. 15 is a graphical representation showing a box plot and an ROC curve. The box plot shows the mean relative current values generated by electrochemical detection of plasma cfDNAs extracted from 30 normal and 30 breast cancer patients. The ROC analysis is shown on the right. In the box and whisker plots, the middle lines of the boxes represent the median (50th percentile) and the terminal line of the boxes represents the 25th to 75th percentile. The whiskers represent the lowest and the highest value.
Figure 16:
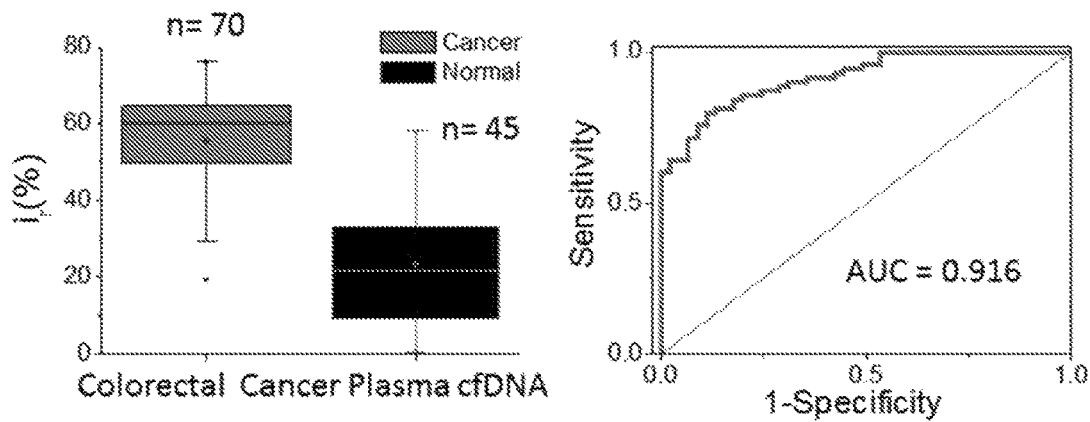
FIG. 16 is a graphical representation showing a box plot and an ROC curve. The box plot shows the mean relative current values generated by electrochemical detection of plasma cfDNAs extracted from 45 normal and 70 colorectal cancer patients. The ROC analysis are shown on the right. In the box and whisker plots, the middle lines of the boxes represent the median (50th percentile) and the terminal line of the boxes represents the 25th to 75th percentile. The whiskers represent the lowest and the highest value.
Figure 17:
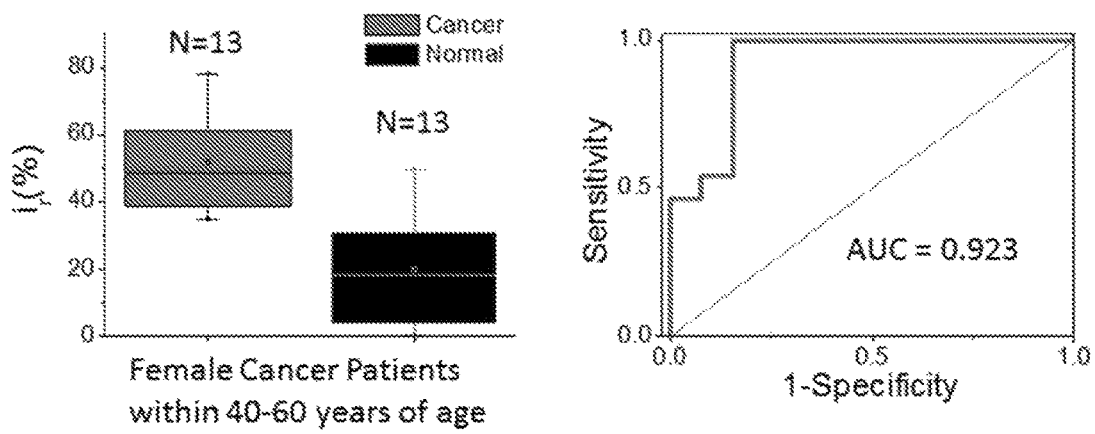
FIG. 17 is a graphical representation showing a box plot and an ROC curve. The box plot shows the mean relative current values generated by electrochemical detection of plasma cfDNAs extracted from 13 normal and 13 female cancer patients with the age above 40 years. The ROC analysis is shown on the right. In the box and whisker plots, the middle lines of the boxes represent the median (50th percentile) and the terminal line of the boxes represents the 25th to 75th percentile. The whiskers represent the lowest and the highest value.
Figure 18:
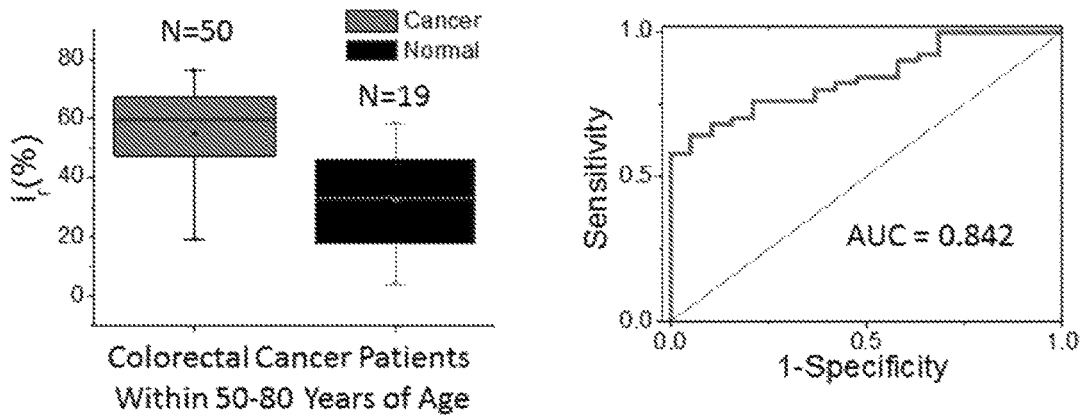
FIG. 18 is a graphical representation showing a box plot and an ROC curve. The box plot shows the mean relative current values generated by electrochemical detection of plasma cfDNAs extracted from 19 healthy individuals and 50 colorectal cancer patients within 50-80 years of age. The ROC analysis is shown on the right. In the box and whisker plots, the middle lines of the boxes represent the median (50th percentile) and the terminal line of the boxes represents the 25th to 75th percentile. The whiskers represent the lowest and the highest value.
Figure 19:
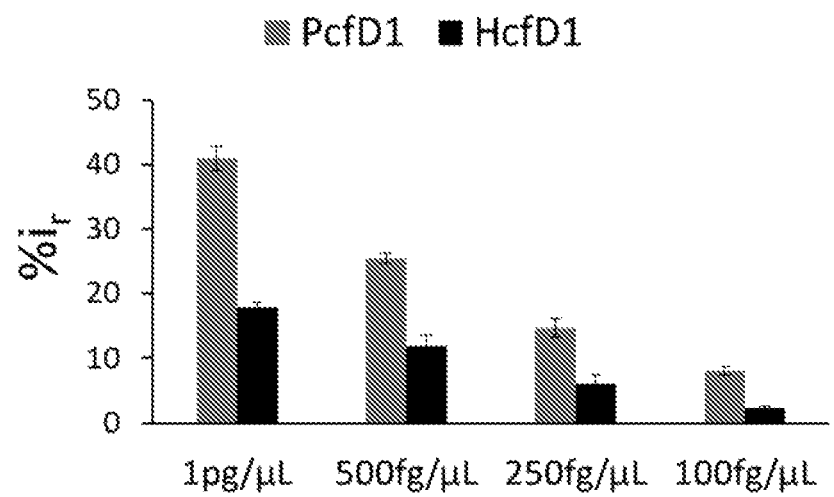
FIG. 19 is a graphical representation demonstrating sensitivity for the detection of DNA methylation landscape in cfDNA. Mean values of the relative DPV current obtained for the adsorption of 5 μl of cfDNA samples derived from the blood plasma of patient (#1) and healthy (#1) individuals. Each bar represents the average of three separate trials (n=3). Error bars represent the standard deviation of measurements (relative standard deviation (% RSD) was found to be <5% for n=3).
Figure 20:
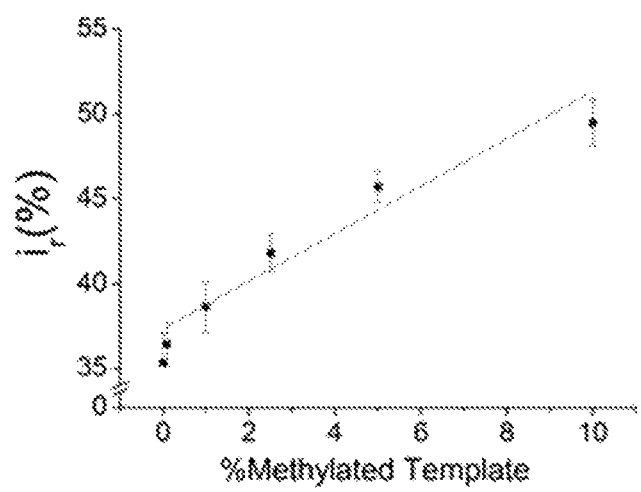
FIG. 20 is a graphical representation showing relative adsorption (% ir) vs % Methylated template DNA plot showing that the adsorption of normal cfDNA increases with the increased amount of clustered methylated DNA spiked in the normal cfDNA sample solution. Each point represents the average of three separate trials (n=3). Error bars represent the standard deviation of measurements (relative standard deviation (% RSD) was found to be <5% for n=3).

While the results of the above experiments demonstrated that the self-assembly of an epigenome from tissue samples and its subsequent adsorption onto surfaces can represent a simple approach to detect the methylscape biomarker, this strategy requires surgical resection or needle biopsy of the primary tumor to isolate the biological material. To develop a non-invasive assay, the present inventors sought to analyze circulating free DNA (cfDNA) isolated from plasma samples of 100 breast (ER+) and colorectal cancer patients and compared their adsorption with normal plasma cfDNA derived from 45 healthy individuals (see, Tables 7 to 9 for clinical information). In this case, only 5 μg (concentration: 1 μg/μL) of plasma derived patient cfDNA were sufficient, and adsorption was carried out for 10 minutes, followed by electrochemical measurements. Similar to previous experiments, the cfDNA extracted from cancer patients showed higher relative current (% $i_r$) than cfDNA samples derived from the plasma of healthy individuals (FIG. 11D, % $i_r$=>35 for 75% of cancer samples and % $i_r$=<35 for 75% of normal samples). The P-values clearly indicate that the normal and cancer samples are significantly different with 95% confidence (see, Table 5). The area under the ROC curve (AUC=0.887) is also similar to that observed for tissue samples. Statistical diagnostic efficacy test at cut-off value % $i_r$=35.7 shows that the present biosensing method has high accuracy (83.45%) with high positive and negative predictive values (Table-FIG. 11D, PPV=91.30%, NPV=69.81%, see, more details in Table 10). A separate study with only breast and colorectal samples also showed very high sensitivity and specificity (see, FIGS. 15 and 16 for details). To eliminate any bias towards gender and age of the patients, the present inventors also performed the age and gender matched analysis using the cfDNA samples. In particular, they compared 13 samples from 40-60 years old breast cancer female patients with 13 samples of healthy individual within the same gender and age range. The box-plot presented in FIG. 17 shows that the adsorption value of patient samples are clearly distinguishable from the normal sample (Area under the ROC curve is 0.923). The present inventors have also compared samples from 50 colorectal cancer patients with 19 samples from healthy individuals within the age range of 50-80 years. As shown in FIG. 18, cfDNA from colorectal cancer patients provided higher gold adsorption in comparison to the normal samples (Area under the ROC curve is 0.842). These data clearly indicate that the biosensing of cfDNA is not biased by gender and age related methylation changes in the genome. Notably, the use of cfDNA for detection allows ultra-low sample input requirements. Optimization of assay conditions enabled detection from as low as 500 fg of purified cfDNA input (see, FIG. 19). To further test the sensitivity of the electrochemical assay, another experiment was designed which involved spiking of different proportion of a cluster methylated DNA template into the normal plasma derived cfDNA solution. This experiment is important because it is noted in the literature that cfDNA variant allele frequency (VAF) is below 10% and in some cases even below 1% in the plasma samples of cancer patient. Thus to address this question, the present inventors wished to explore whether the electrochemical assay was sensitive enough to detect very low percentage of cluster methylated template DNA in presence of large numbers of normal cfDNA sequences. The inventors thus used short and cluster methylated template DNA (in line with the DNA used in the experiment for FIG. 8C) and spiked this DNA in normal cfDNA solution at different proportion (0%, 0.1%, 1%, 2.5%, 5%, 10%). As shown in the FIG. 20, the relative adsorption of cfDNA increased with the increase of methylated template DNA in the solution and can detect low loading of methylated DNA fragments.

Example 5

Naked Eye Detection of Cancer Using AuNPs

While the electrochemical assay showed excellent sensitivity and specificity, it required specialized equipment for detection; hence, the present inventors sought to develop alternative strategies, which could provide instant or rapid results to facilitate real-time clinical decision-making, such as colorimetric detection using gold nanoparticles (AuNP). AuNP solutions can exhibit unusual optical properties as function of their size, shape or agglomeration status—all of which can be tuned to detect the presence of DNA (Elghanian, R. et al., 1997, *Science* 277:1078-1081; Li, H. et al., 2004, *Proceedings of the National Academy of Sciences of the United States of America* 101:14036-14039; Lin, Y.-Z. et al., 2013, *ACS applied materials & interfaces* 5:12045-12051; Sato, K. et al., 2003, *Journal of the American Chemical Society* 125:8102-8103; Xia, F. et al., 2010, *Proceedings of the National Academy of Sciences* 107:10837-10841). For DNA analysis, salt-induced aggregation of AuNP is arguably the most suitable format for detection, due to excellent sensitivity, reproducibility and ease of performance (Koo, K. M. et al., 2015, *Analytical Methods* 7:7042-7054). In this approach, the AuNP aggregates upon addition of salt unless they are protected by previously adsorbed DNA molecules. This aggregation process can be detected by naked eye as a visual colour change of the AuNP solution from reddish to blue due to the red shift of the localized nanoparticles' surface plasmon band (Lin, Y.-Z. et al., 2013, supra; Koo, K. M. et al., 2015, supra).

Figure 21:
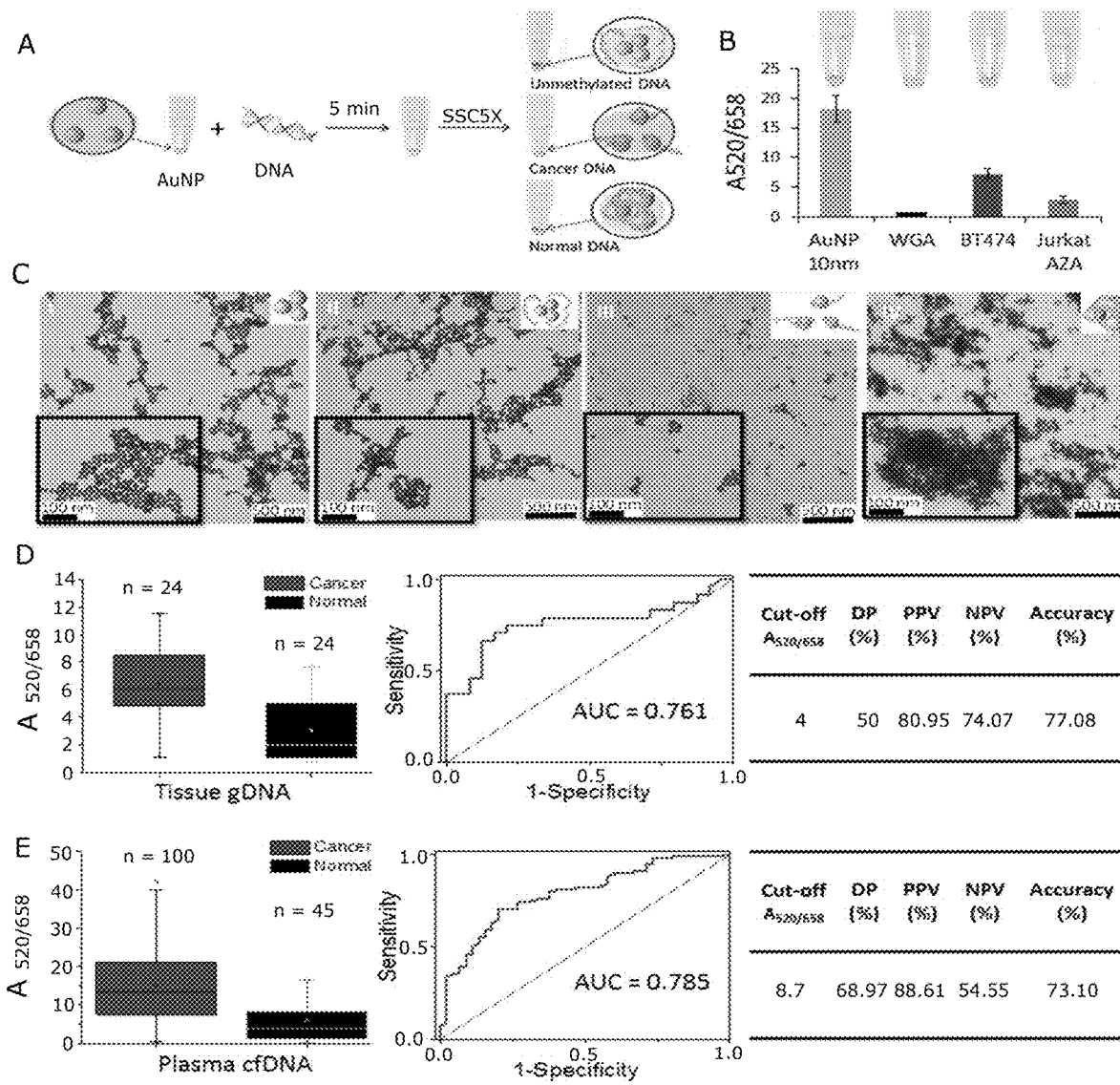
FIG. 21 is a schematic, photographic, graphical and tabular representation depicting naked eye detection of cancer using AuNPs. (A) Schematic of the assay and proposed mechanism for different DNA types. (B) Mean relative absorbance values A520/658 of 10 nm tannic-capped AuNP (pink) and AuNP-cellular gDNA solution for unmethylated WGA (black), BT474 breast cancer cell line (red), and Aza treated Jurkat (light blue). Inset, the representative coloured solution. (C) TEM images of AuNPs alone (I) and AuNP-cellular gDNA solution for WGA (II), BT474 (III) and M-Jurkat (IV) (no salt was added). (D) Box plot showing the mean relative absorbance values A520/658 of AuNP-cellular gDNA solution for cancer and normal cells extracted from breast, prostate and lymph node tissues, Right: The ROC analysis and diagnostic test evaluation shows the Disease Prevalence (DP), positive predictive values (PPV), negative predictive values (NPV) and accuracy of the method. (E) Box plot showing the mean relative absorbance values A520/658 of AuNP-cellular gDNA solution for DNA samples derived from plasma samples of breast and colorectal cancer patients or healthy donors, Right: The ROC analysis and diagnostic test evaluation shows the Disease Prevalence (DP), positive predictive values (PPV), negative predictive values (NPV) and accuracy of the method.
Figure 22:
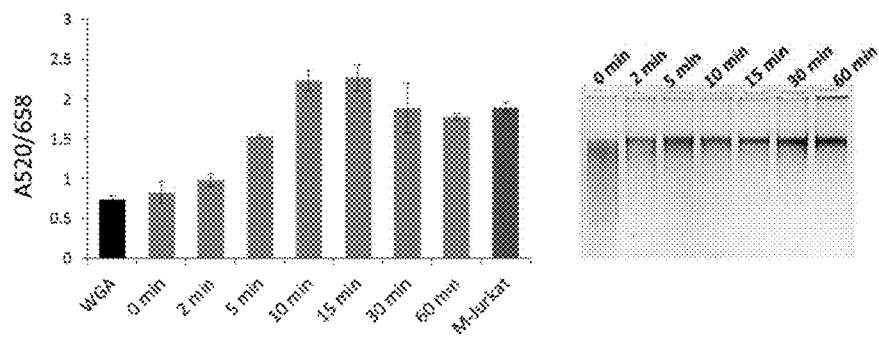
FIG. 22 is a graphical and photographic representation showing the effect of non-clustered CpG methylation on gold-DNA adsorption. Relative absorbance (A520/658) values for unmethylated (WGA), fully methylated (Jurkat) DNAs, and various genomic DNAs prepared from WGA DNA by enzymatic reaction using the M.SssI CpG methyltransferase enzyme for increasing time periods up to 60 min. Each bar represents the average of three separate trials (n=3). Error bars represent the standard deviation of measurements (relative standard deviation (% RSD) was found to be <5% for n=3). The inset panel shows an electrophoresis gel of the enzymatically methylated DNA samples digested with methylation sensitive HpaII restriction enzyme.

To assess the efficacy of the present approach in detecting methylscape biomarker using colloidal gold, 50 ng of purified DNA was incubated with AuNPs for 5 min, followed by the addition of salt (SSC 5×) to induce aggregation (see, FIG. 21A and Methods for details). Measurement of the spectral shift generated upon salt addition, showed approximately 6.5 units higher relative absorbance ($A_{658/520}$) for BT474 DNA compared to the unmethylated WGA (i.e., $A_{658/520}^{BT474}$=7.23±0.85, vs. $A_{658/520}^{WGA}$=0.74±0.04, FIG. 21B). The assay was also sensitive enough to identify 5-azacytidine treated Jurkat DNA (FIG. 21B). Of note, any of the genomic DNAs artificially methylated by the M.SssI CpG methyltransferase and also the 100% methylated Jurkat DNA showed very poor ability to stabilize the AuNPs in solution (FIG. 22)—an observation in-line with the inventors' previous data and concordant with the inventors' methylation maxima self-assembly model.

Figure 23:
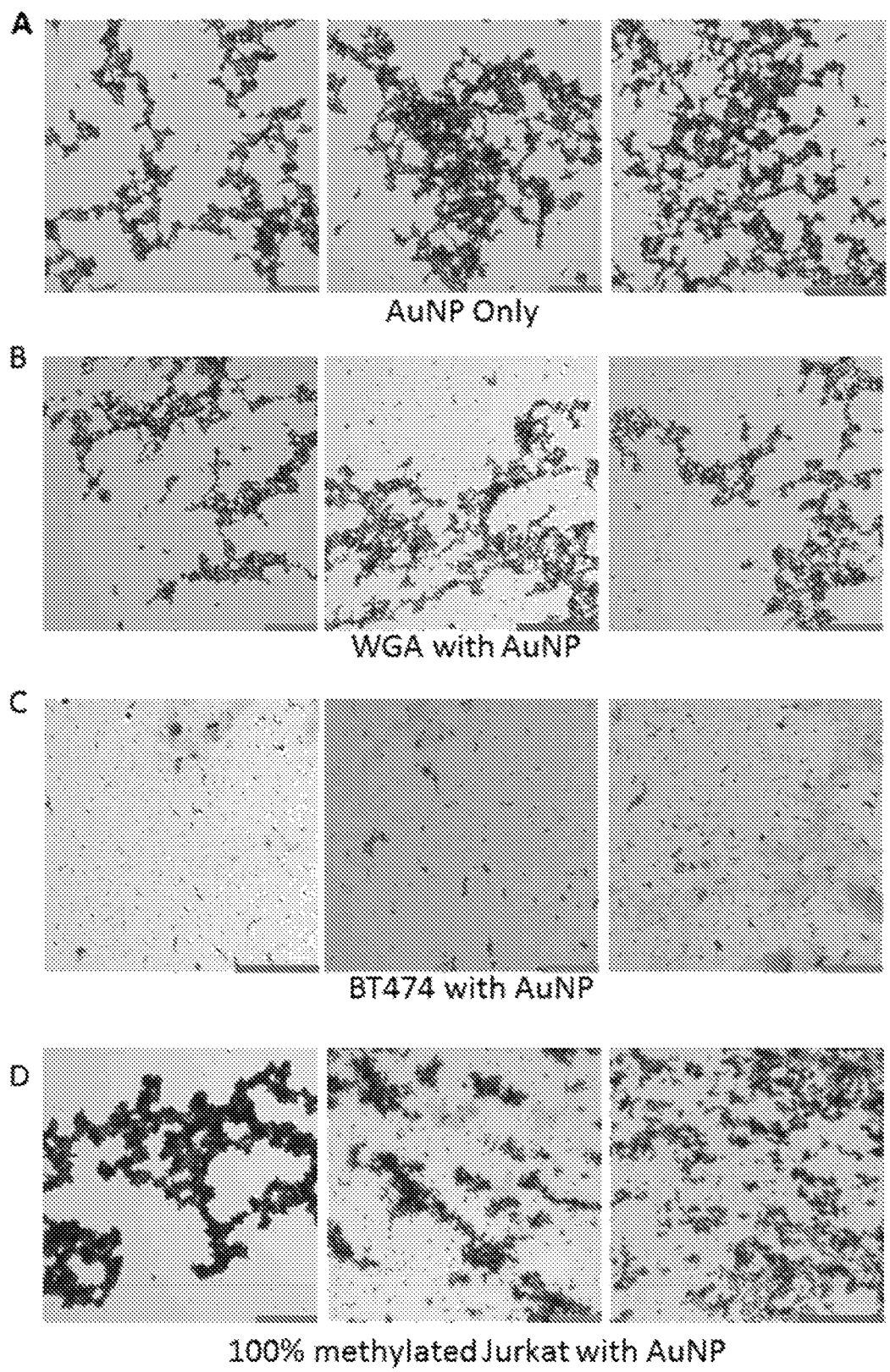
FIG. 23 is a photographic representation showing TEM images for gold nanoparticles and their interaction with DNA. Scale bars are 2000 nm (red) 1000 nm (blue) and 500 nm (orange) for all the figures.

To further investigate how the self-assembly of different epigenomes affects their interactions with AuNPs, TEM was used to visualize DNA-AuNPs interactions before addition of salt (FIGS. 21C and 23). As shown in Images I (AuNP alone) and II (AuNP and WGA), the presence of unmethylated DNA (WGA) had minimal effects on the dispersion pattern of AuNP, suggesting limited interaction of unmethylated template with colloidal gold. In contrast, the presence of moderately methylated DNA isolated from BT474 cells (FIG. 21C, Image III) favoured a dispersed distribution of AuNPs. It was hypothesized that the larger ability of BT474 DNA to stabilize AuNPs is due to the particular methylation landscape and high affinity of this type of DNA template towards gold surfaces, which would stabilize the gold nanoparticles and prevent their aggregation. Interestingly, fully methylated Jurkat DNA (FIG. 21C, Image IV) appeared to interact strongly with AuNPs whereas in the case of flat gold surface, it poorly interacted (FIG. 4, AFM and TEM). The present inventors propose that the difference in interaction between AuNPs and solid surfaces is associated with the ability of colloidal gold particles to move around DNA aggregates. This would allow them to perfuse the methylated-DNA aggregate to find methylcytosine-rich spots for interaction. However, because of the large numbers of AuNPs interacting with fully methylated DNA, this system displays the AuNPs in close proximity to each other and ultimately collapsed into large colloidal aggregates upon salt addition—probably by a crosslinking aggregation mechanism. The average DNA-AuNP aggregate size obtained from ImageJ analysis (FIG. 24) of the TEM images also support the present inventors' cellular gDNA-AuNP interaction hypothesis.

To assess the clinical utility of the assay, the present inventors next tested a cohort of 24 epigenomes isolated from different metastatic cancer types (e.g., ER+ breast, prostate and follicular lymphoma), and compared their adsorption profiles to epigenomes isolated from 24 matching normal tissues (see, Tables 1 to 4 for clinical information). The relative absorbance in FIG. 21D indicates that tumor samples favor AuNP adsorption as compared to DNA from healthy controls. Although the area under the ROC curve (0.761) is comparatively lower than that observed for electrochemistry, statistical diagnostic efficacy test at cut-off value % $i_r$=4 shows good accuracy (77.08%) with reasonable positive and negative predictive values (Table-FIG. 24D, PPV=80.95%, NPV=74.07%, see more details at Table 11). However, a larger sample cohort and optimization of experimental conditions might help in further increasing the sensitivity and specificity of this system.

Figure 25:
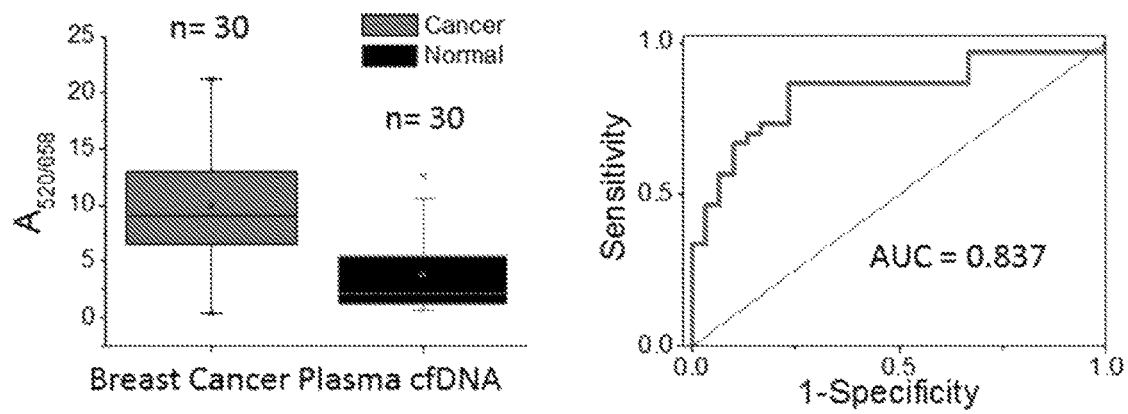
FIG. 25 is a graphical representation showing a box plot and an ROC curve. The box plot shows the mean relative absorbance values A520/658 of AuNP-cfDNA solution for cfDNA samples derived from the plasma of breast cancer patients or healthy donors. The ROC analysis is shown on the right. In the box and whisker plots, the middle lines of the boxes represent the median (50th percentile) and the terminal line of the boxes represents the 25th to 75th percentile. The whiskers represent the lowest and the highest value.
Figure 26:
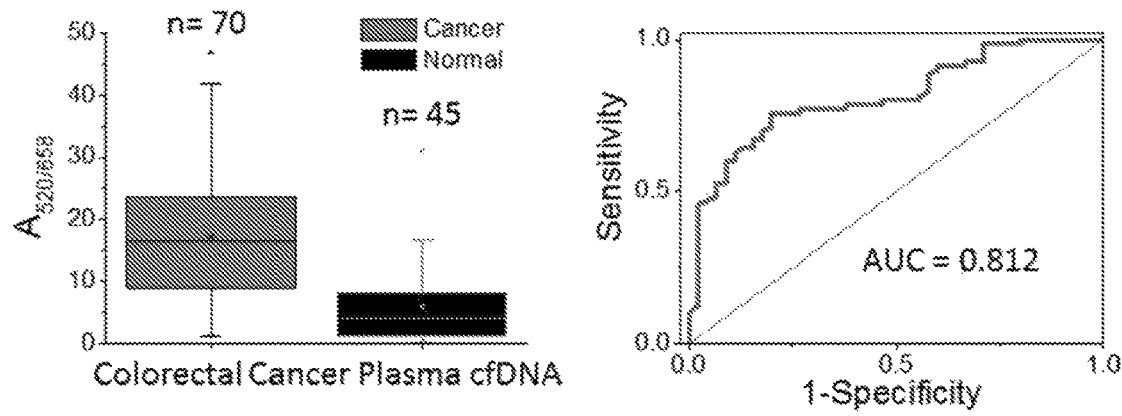
FIG. 26 is a graphical representation showing a box plot and an ROC curve. The box plot shows the mean relative absorbance values A520/658 of AuNP-cfDNA solution for cfDNA samples derived from the plasma of colorectal cancer patients or healthy donors. The ROC analysis is shown on the right. In the box and whisker plots, the middle lines of the boxes represent the median (50th percentile) and the terminal line of the boxes represents the 25th to 75th percentile. The whiskers represent the lowest and the highest value.
Figure 27:
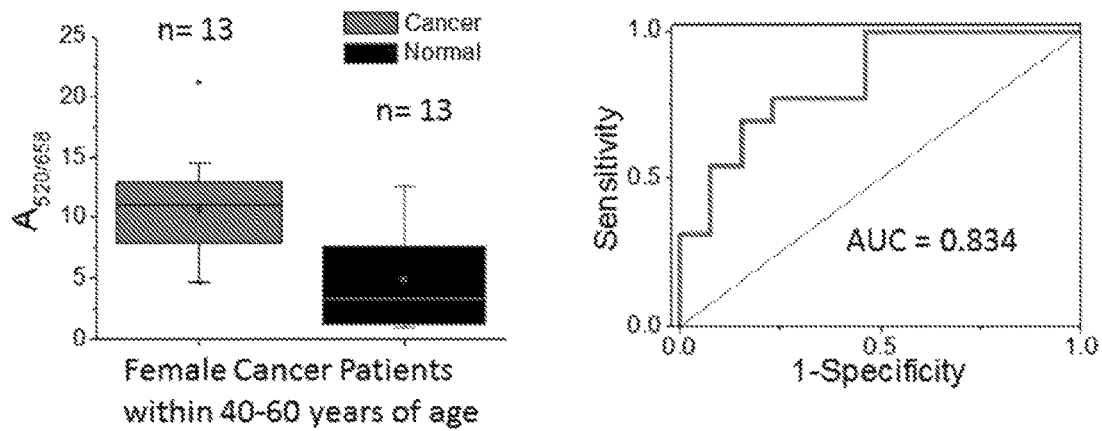
FIG. 27 is a graphical representation showing a box plot and an ROC curve. The box plot shows the mean relative absorbance values A520/658 of AuNP-cfDNA solution for cfDNA samples derived from the plasma of female cancer patients or healthy donors within 40-60 years of age. The ROC analysis is shown on the right. In the box and whisker plots, the middle lines of the boxes represent the median (50th percentile) and the terminal line of the boxes represents the 25th to 75th percentile. The whiskers represent the lowest and the highest value.

Finally, to test the applicability of naked eye system for non-invasive detection of cancer, the present inventors analyzed cfDNAs derived from plasma samples of 100 breast and colorectal cancer patients and 45 healthy individuals (see, Tables 7 to 9 for clinical information). Only 1 µg of cfDNA was required to stabilize the AuNP solution and prevent the salt-induced AuNP aggregation. As shown in the box plot in FIG. 21E, 75% of cancer samples provided a relative absorbance (A520i658) value higher than approximately 7 units; whereas, 75% of cfDNA derived from normal plasma showed significantly lower relative absorbance values. The P-values obtained from Student's t-test also confirmed the statistical significance of these data (see, Table 5). The area under the ROC curve (AUC=0.785), although slightly lower than that observed for electrochemistry, still shows good sensitivity and specificity. In this system, statistical diagnostic efficacy test at cut-off value % $i_r$=8.7 provides an accuracy of 73.10% with reasonable positive and negative predictive values (Table-FIG. 21E, PPV=88.61%, NPV=54.55%, see, more details In Table 12). Similar to the electrochemistry experiment, the separate study with only breast and colorectal samples also showed good sensitivity and specificity (see, FIGS. 25 and 26 for details). Furthermore, to eliminate any bias towards gender and age of the patients, an age and gender matched analysis was performed using the nanoparticle based approach. The present inventors compared 13 cfDNA samples from 40-60 years old breast cancer female patients with 13 samples of healthy individual within the same gender and age range. The box-plot presented in FIG. 27 shows that the adsorption values of patient samples are fairly different from the normal sample (Area under the ROC curve is 0.834). They also compared samples from 50 colorectal cancer patients with 19 samples from healthy individuals within the age range of 50-80 years. As shown in FIG. 28, cfDNA from colorectal cancer patients provided higher gold adsorption in comparison to the normal samples (Area under the ROC curve is 0.719). These data clearly outline that naked eye assay could potentially detect the presence of cancer in a rapid and cost-effective manner, thus paving the way for the development of new point-of-care cancer tests based on patient's epigenetic profile.

Discussion

Proposed Mechanism of Detecting Methylscape Biomarker

The work presented herein is based on the detection of a global methylation landscape in cancer which is referred to as "methylscape". The methylscape in cancer genome involves a change in global methylation levels and patterning in comparison to the methylscape in normal genome. Genomes from adult normal tissues tend to exhibit overall higher degrees of methylation, which are also quite evenly dispersed (uniform) throughout the genome. In contrast, this distribution changes during the course of cancer as DNA gradually loses methylation across the genome and exhibits more defined methylated areas where methylated sites are clustered within a short span (Suzuki, M. M. et al., 2008, supra). However, within this averaged trend, there is intrinsic heterogeneity in the DNA methylation patterns across cells within the tissue particularly in the context of cancer. Despite this heterogeneity, the changes in the cell's DNA methylation pattern and level during cancer progression are well documented in the literature as a key feature of cancer epigenetics (Smith, Z. D. et al., 2013, supra; Suzuki, M. M. et al., 2008, supra). It is this global change in the methylation pattern, and overall levels and distribution that the present invention is able to detect in a simplified way and the data presented herein provide the foundations for considering this phenomenon as a general biomarker for cancer.

The results presented herein show that the methylscape biomarker, which represent a unique footprint for cancer genomes, modulate the self-assembly of methylated DNA in solution and during their adsorption towards gold surfaces. However, self-assembly of DNA appears to be a process with dynamic tension, where adsorption of DNA onto a surface is initially enhanced by the presence of methylcytosine until it reaches an adsorption maximum in low-to-moderately methylated epigenomes, but once a methylation maxima threshold is exceeded the self-assembly process makes epigenome-surface interactions unfavorable. Given this, the present inventors propose that due to the large tracts of uniformly methylated regions in normal DNA, large number of hydrophobic methyl groups in solution come into proximity with each other and collapse into self-contained nano- and micro-sized domains surrounded by hydrophilic unmethylated regions, whose surface would then have the same properties and adsorption affinity as a fully unmethylated DNA. The empirical data presented herein supports this theory, and explains why a 100% methylated and heavily methylated normal epigenome have similar surface adsorption properties as a completely unmethylated sample (FIGS. 8B and 11A). In the same line, the fact that cancer cells have large tracts of variably demethylated DNA (with a high degree of heterogeneity) with hypermethylated CpG islands are also in agreement with this hypothesis. Despite some degree of variable demethylation across the genome, the reduction in the overall methylation levels compared to normal genomes, would reduce overall hydrophobicity of the DNA colloid and the chances for DNA to collapse into the above-described self-contained nano- and micro-sized domains. This, in turn, would contribute to increase its overall solubility in aqueous solutions and the chances for hyper-methylated CpG islands to be more accessible and exposed for interacting with the gold surface. This model is supported by the empirical data presented in FIGS. 8E and 22, which show an increasing affinity of methylated DNA towards gold surfaces until the methylation maxima is reached. However, below the methylation maxima, the presence of methylscape biomarker (i.e., cluster methylation separated by typically large hypomethylated regions across the genome) which is uniquely featured in cancer epigenomes starts to dominate the adsorption process. As a result, the adsorption maximum (as shown in FIG. 8F) is dramatically increased in case of cancer epigenomes—a trend that was not observed for artificially methylated (MssI enzyme) derived epigenomes with similar global methylation content.

While the interaction of methyl groups and methylcytosines with gold surfaces has previously been considered (Fojt, L. et al., 2009, *Bioelectrochemistry* 75:89-94; Camafeita, L. et al., 1995, *Journal of Raman Spectroscopy* 26:149-154; and Lee, S. et al., 2011, *The Journal of Physical Chemistry C* 115:12501-12507), the mechanism which drives their increased adsorption affinity towards gold is still unknown. Based on the data presented here, the present inventors propose that the electron donating properties of the methyl group might enhance the adsorption of methylated cytosines towards gold (and for that matter, other substrates to which hydrophobic moieties, particularly clustered hydrophobic moieties, bind under aqueous conditions) via an electron-donating mechanism, as methyl groups can donate electrons and increase the n electron density of the cytosine ring (Acosta-Silva, C. et al., 2010, *The Journal of Physical Chemistry B* 114:10217-10227; Hihath, J. et al., 2012, *Journal of Physics: Condensed Matter* 24:164204). Moreover, since the cytosine-base can interact with the gold through the pyrimidine ring in a planar manner (i.e., it aligns parallel to the surface) (Piana, S. et al., 2006, *The Journal of Physical Chemistry B* 110; 23467-23471), the increased n electron density in the ring may increase the chance of metal-cytosine n back-bonding—that is, bonding between the vacant d orbital of the metal and the n electron of cytosine. This metal-cytosine back-bonding could possibly increase the intrinsic affinity of methylcytosines towards gold compared to the unmethylated cytosine. Thus, the cluster methylation, which is uniquely over-represented in cancer genomes, could offer an ideal configuration for adsorption due to numerous methylcytosines in close proximity. This proximity could synergistically deliver a stronger force for holding the cellular gDNA onto the planar gold surface proving higher adsorption. Furthermore, hypermethylated CpG rich regions featuring CG-repetitions (Doluca, O. et al., 2013, *Chemical reviews* 113:3044-3083; Peck, L. J. et al., 1983, *Proceedings of the National Academy of Sciences* 80:6206-6210), could also enhance DNA gold-adsorption through these sites because they often experience B→Z transitions when become methylated (Rich, A. et al., 2003, *Nature Reviews Genetics* 4:566-572; Behe, M. et al., 1981, *Proceedings of the National Academy of Sciences* 78:1619-1623; Fujii, S. et al., 1982, *Nucleic Acids Res* 10:7879-7892; Klysik, J. et al., 1983, *Journal of molecular biology* 168:51-71). Since Z-DNA is not as tightly wrapped as the B-DNA (Doluca, O. et al., 2013, *Chemical reviews* 113:3044-3083), especially in the B-Z junction, DNA bases within this region could display more favourable orientation for gold-interaction.

The data for cfDNA analysis shows that the sensitivity for cfDNA is significantly improved in comparison to the tissue derived genomic DNA. Although the reason for the sensitivity improvement is unclear, the present inventors consider that this is associated to their relative size, in average of 165 bp. While this length is in principle sufficient for cancer-derived cfDNA to accommodate a highly methylated CpG island, fragments with the pattern commonly seen in normal samples, where methylated sites are very dispersed (on average 1 methylated CpG every 150 bp) (Suzuki, M. M. et al., 2008, supra) would essentially behave as non-methylated. This may possibly reduce the chances for DNA from normal cells to interfere with the interaction of cancer-derived cfDNA with gold, hence increasing the threshold gap to distinguish between them. In addition to this, it has been suggested that the fragmentation pattern of cfDNA varies as a function of tissue of origin (Sun, K. et al., 2015, *Proceedings of the National Academy of Sciences* 112: E5503-E5512; Snyder, M. W. et al., 2016, *Cell* 164:57-68; Guo, S. et al., 2017, *Nature genetics* 49:635), and that cancer-derived DNA also tends to be shorter (Underhill, H. R. et al., 2016, *PLoS genetics* 12:e1006162; Jiang, P. et al., 2015, *Proceedings of the National Academy of Sciences* 112:E1317-E1325). The presence of these smaller fragments, also featuring methylated clusters, may kinetically favour their adsorption compared to larger unmethylated or scarcely methylated cfDNA fragments from normal cells. This would also contribute to increase the adsorption gap difference between normal and cancer-derived cfDNAs significantly, so that a much lower DNA concentration is sufficient to distinguish them.

Summary

The results presented herein provide fundamental insight about the consequences of epigenetic reprogramming in the physical state of DNA polymer in solution and when it adsorbs onto hydrophobic moiety-binding substrates including metal surfaces such as gold. The TEM analysis disclosed herein suggests that methylation can impact the self-assembly of genomic DNA in solution—i.e., the larger the number of methylcytosines in the genome, the greater the chances will be for DNA to form aggregates in aqueous solution. Although TEM can potentially introduce artifacts during sample drying, the corresponding adsorption trend of DNA on gold surface observed by AFM and electrochemistry supports the present inventors' self-assembly hypothesis of cellular gDNA in solution. AFM and electrochemistry data suggest that the surface adsorption of cellular gDNA is potentially modulated by methylation dependent self-assembly of cellular gDNA in solution—i.e., the more the solvation is compromised, the lower the chances will be for DNA to properly interact with the plain gold surface. However, the adsorption of DNA towards gold is also found to be controlled by higher affinity of methylcytosines towards gold and their patterning across the genome. In particular, the unique enrichment of clustered methylation in cancer DNA at CpG rich regions of the genome exhibited significantly enhanced adsorption towards gold surface than the normal DNA. This significant difference in the solution and surface based physicochemical properties between cancer and normal DNA has enabled the present inventors to easily detect the proposed methylscape biomarker in a single step based on a novel interfacial biosensing strategy (i.e., it only requires direct adsorption of DNA onto the bare gold surface) using electrochemistry and a colloidal gold system. The ability of methylcytosines to enhance the interaction of DNA with colloidal gold particles is a notable discovery. Previous studies have shown that the stiffer ds-DNA has very low adsorption capability in gold nanoparticle systems, in contrast to more uncoiled ss-DNA (Koo, K. M. et al., 2015, supra). These are the first data known to the inventors, demonstrating that methylated ds-DNA can significantly adsorb onto gold nanoparticles due to the higher affinity of methyl-cytosine.

The most remarkable features of their interfacial-based strategy are that they can effectively identify the methylscape biomarker from cancer genomes without extensive sample preparation (e.g., bisulfite or enzyme treatment and PCR amplification) and sensor surface modification—a laborious process for most bio-sensing techniques. Moreover, the present strategy showed large potential for cancer diagnosis as evidenced by the ROC graphs (e.g., AUC=0.909 for tissue-derived DNA detection with electrochemistry) for cellular gDNAs extracted from cancer and normal tissues representing various organs (i.e., breast, prostate and lymph node). The present approach also enabled non-invasive cancer detection (i.e., a blood test) in 10 min from plasma derived cfDNA samples with excellent specificity (e.g., AUC=0.887 for cfDNA detection with electrochemistry) and sensitivity (100 fg/µL). Given that cfDNA has a short half-life in the blood; its detection is in fact more advantageous than other common blood tests based on detection of protein biomarkers. This is because cfDNA reflects well the present status of the original tumour rather than the past—a common drawback of most protein biomarkers that might last on the blood up to several weeks (Yong, E. 2014, *Nature* 511:524). The present inventors consider that this remarkably simple approach (i.e., methylscape) with the excellent sensitivity and specificity would potentially be a better alternative to the current techniques for cancer detection.

Materials and Methods

Materials

All the cancer cell lines were purchased from ATCC (USA) and cultured in the laboratory following the standard Protocol. The culture materials such as growth medium (RPMI 1640), fetal bovine serum (FBS) and antibiotics were purchased from Gibco, Life technologies. Human Mammalian Epithelial Cell (HMEC) line DNA was purchased from Science Cell. Aza treated Jurkat demethylated DNA was purchased from New England Biolabs. Breast cancer patient tissue samples were obtained from UK Forever Clinical Trial, UK. Prostate cancer patient tissue samples were collected from Aquesta Pathology, Brisbane, Australia. Lymphoma cancer patient tissue samples were collected from Princess Alexandria Hospital, Brisbane, Australia. Breast cancer plasma samples were collected from UK Forever Clinical Trial, UK. Colorectal cancer patient plasma sample were obtained from Hunter Medical Research Institute, The University of Newcastle, Australia. The relevant ethical approval was obtained from Bellberry Limited, Australia for all tissue and plasma patient samples analysis presented in this study.

DNA Samples Preparation

The genomic DNAs were extracted using standard-well known protocols (i.e., phenol-chloroform extraction followed by isopropanol/ethanol purification) and the purity of the DNA was confirmed by measuring A260/280 absorbance ratio. Briefly, the cells were suspended in lysis buffer to lyse and release the nucleic acids and proteins into the solution. To remove the protein and RNA in the solution a digestion step was performed using proteinase and RNase enzymes respectively. The digested proteins and RNA were removed by phenol chloroform solvent extraction and the DNA was purified by isopropanol/ethanol precipitation. Short DNA fragments were prepared by amplifying a bisulfite treated 140 bp region of EN1 gene using deoxycytidine triphosphate (dCTP) for unmethylated and methyl dCTP for methylated DNA. Whole Genomic Amplified (WGA) DNA samples were prepared by amplifying 50 ng of BT474 breast cancer cell derived DNA using a REPLI-g whole genome amplification kit (QIAGEN Pty. Ltd., Venlo, Netherlands) as per manufacturer's instruction. Jurkat 100% methylated and azacytidine treated Jurkat cellular gDNA were purchased from New England Biolabs. Enzymatically methylated cellular gDNAs are obtained using the M.SssI CpG methyltransferase enzyme (New England Biolabs), which was allowed to insert methyl groups onto CpG sites of unmethylated whole genome amplified (WGA) DNA in the presence of SAM donor, according to manufacturer instructions. Reaction was performed for periods of 2 min, 5 min, 10 min, 15 min, 30 min or 60 min and then stopped by thermal inactivation of the enzyme at 65 degrees. A negative control is obtained by performed reaction with previously inactivated enzyme (0 min reaction). DNA methylation levels are confirmed by restriction enzymatic digestion using methylation sensitive HpaII restriction enzyme (New England Biolabs). DNAs from tissues were extracted by following standard procedure. Briefly, formalin fixed paraffin embedded (FFPE) or PAXgene fixed paraffin embedded (PFPE) tissues were first treated with xylene to remove the paraffin. After washing with ethanol, the tissues were vacuum dried followed by complete overnight digestion with Proteinase K. The DNAs were then extracted by either using QIAGEN kit or following standard Phenol-Chloroform extraction procedure. The cfDNAs were extracted from plasma by using standard protocol. Briefly, 1 mL plasma was mixed with 100 µl of 250 mM EDTA and 750 mM NaCl solution followed by the addition of 100 µL of 100 g/L sodium dodecyl sulfate. To digest the protein in plasma, 20 µL of Proteinase K was then added to the mixture. The plasma solution was incubated at 56° C. for 2 hrs and 6M NaCl was used to precipitate the protein. Finally, the supernatant was taken for phenyl chloroform extraction and isopropanol precipitation of cfDNA. Since the clinical tumor samples used in the above experiment were extracted from paraffin embedded formalin fixed (FFPE) tissues or PAXgene tissue blocks, which is a process that may cause a certain degree of DNA degradation that may not be present in cellular gDNA from healthy individuals, we investigated the size fragmentation profile of a subset of cancerous epigenomes using the Agilent 2100 Bioanalyzer (High Sensitivity DNA chip) and these DNAs were found quite integrate and scarcely fragmented (See Supplementary FIG. 58b). To further test the effect of DNA degradation on their adsorption behavior, genomic BT474 DNA was sonicated for one minute and measured the adsorption level of the degraded BT474 DNA. As shown in Supplementary FIG. S8a, the degradation has little effect on the DNA adsorption towards gold surface.

Global DNA Methylation Analysis

Global methylation analysis of BT474 DNA was performed by using Imprint® Methylated DNA Quantification kit from Sigma Aldrich as per manufacturer instructions. Briefly, desired amount of DNA was diluted in 30 µl DNA Binding Solution and added to each well of the plate. The DNA Binding Solution alone was used as a blank. The wells were covered and the samples were incubated at 37° C. for 60 minutes. After incubation, 150 µL of Block Solution was directly added to each well and incubated again for 30 minutes. All the solution from each well was then removed and the wells were washed three times with 150 µL of 1× Wash Buffer. Methylation specific capture antibody was then diluted in 50 µL wash buffer, added to each well and incubated for 60 minutes. After that the capture antibody solution was removed from each well and the wells were washed four times with 150 µL wash buffer. Subsequently, the diluted Detection Antibody was added to each well and incubated, removed and washed. After that 100 µL of Developing Solution was added to each well and the wells were incubated at room temperature away from light for 1-10 minutes. When the solution turned blue, 50 µL of stop solution was added to each well and the solutions were turned yellow. The absorbance of the solutions in each well was then measured at 450 nm by using a plate reader. The global methylation level of all DNAs is calculated using following equation.

$$\text{Global Methylation level} = [(A450\ \text{Sample} - A450\ \text{Blank})/(A450\ \text{Methylated Control DNA} - A450\ \text{Blank})] \times 100 \quad (1)$$

Electrochemical Detection

All electrochemical experiments were carried out using a CH1040C potentiostat (CH Instruments) with a three-electrode system consisting of a gold working electrode (2 mm in diameter), Pt counter electrode, and Ag/AgCl reference electrode (all electrodes are from CH Instruments, USA). Differential pulse voltammetric (DPV) experiments were conducted in 10 mM PBS solution containing 2.5 mM [K3Fe(CN)6] and 2.5 mM [K4Fe(CN)6] electrolyte solution. DPV signals were obtained with a potential step of 5 mV, pulse amplitude of 50 mV, pulse width of 50 ms, and pulse period of 100 ms. For DNA methylation detection, the gold electrodes were initially cleaned by polishing with Alumina polishing powder (CH Instruments) followed by ultra-sonication with acetone and deionized water for 5 minutes and then dried under the flow of nitrogen. DPV signals of clean electrodes were measured in electrolyte solution to get the baseline current. Purified cellular gDNA (5 µL of 10 ng/µL concentration in SSC 5× buffer at neutral pH) was then adsorbed onto gold electrodes for 10 mins. Subsequently, the adsorption competence was measured by Differential Pulse voltammetry (DPV) in presence of the [Fe(CN)6]3−/4− redox system. Upon DNA adsorption, the coulombic repulsion between negatively-charged ferrocyanide ions in the buffer and negatively-charged DNA phosphate groups on the electrode surface partially hinder the diffusion of ferrocyanide ions to the electrode surface. This generates a Faradaic current signal, which is proportionally lower than the bare electrode signals as increasing numbers of DNA molecules become adsorbed onto the surface 25-27 (i.e., the greater the DNA adsorption is, the larger the relative current signal difference, % ir, with respect to the original baseline. The relative adsorption currents (i.e., % ir, % difference of the DPV signal generated for DNA sample (isample) with respect to the baseline current (ibaseline)) due to the adsorption of DNA samples were then measured by using equation 2.

$$\text{Adsorption current } (\%\ ir) = [(i\text{baseline} - i\text{sample})/i\text{baseline}] \times 100 \quad (2)$$

Detection by AuNP System

Experiments are performed using 8.5 µL of 10 nm Tannic-capped AuNPs (Sigma), which were mixed with 1 µL of DNA samples (i.e. genomic DNA at 50 ng/µL concentration or cfDNA at 1 pg/µl concentration). Aggregation was achieved by addition of 1.5 µL of SSC 5×. Absorbance ratio at 520/658 was measured using Nanodrop to quantify the shift of surface plasmon band due to the adsorption of DNA and aggregation of AuNPs.

TEM Measurements

Experiments were performed using a Jeol 1010 or Hitachi HT 7700 transmission electron microscope (TEM) at 100 kV. Equal amounts of normal and cancerous DNA were spotted and dried onto 400 mesh square carbon grids coated with formvar (Proscitech) and then stained with ammonium molybdate (1%, pH 7) for imaging purposes.

Atomic Force Microscopy

DNA Samples (10 ng/µL in SSC 5× buffer) were adsorbed on ultra-flat gold surface for 20 min and then AFM Experiments are performed with Cypher AFM system (Asylum Research) on air tapping-mode with a 30 nm radius sharp silicon tip.

Example 6

DNA Desorption/Elution from the Gold Surface

To investigate the desorption of DNA from the gold surface, the present inventors used mercaptohexanol (MCH) which has higher affinity towards gold in comparison to DNA. Thus it was assumed that the DNA would be desorbed from the gold surface if MCH is adsorbed in a gold electrode which has DNA previously adsorbed onto it. As shown in the gel image presented in FIG. 29, the BT474 Breast Cancer cell DNA (gel image band 1, 2, 3 and 4) and Normal Breast Tissue DNA (gel image band 5, 6, 7 and 8) were amplified by PCR amplification when desorbed DNA solution was added to the PCR mixture. In contrast, the solution with no desorbed DNA (gel image band 9) and no MCH (gel image band 10) showed no amplification. Moreover, the present inventors have performed PCR positive and negative controls to show that this method was not biased in amplifying the desired product. As shown in the gel image, the control experiments involving i) Normal Breast Tissue DNA without adsorption/desorption (gel image band 11) ii) BT474 Breast Cancer cell DNA without adsorption/desorption (gel image band 12 and 13) iii) PCR negative control without DNA (gel image band 14). These data clearly suggest that the present method can specifically desorb the DNA from the surface without any bias.

Method

Five microliters of designated concentration of DNA was adsorbed onto the gold electrode for 10 min. The unadsorbed DNA was then removed by washing the electrode with 1× PBS for 3 times and the electrodes were dried with gentle nitrogen flow. 5 μl of designated concentration of MCH was added the electrode to desorb the DNA from the surface and incubated for 1 hour. After that, MCH solution with desorbed DNA was taken off from the surface and used for PCR amplification to amplify a 200 base pair region of the human genome. The following primer set is used for the amplification.

```
                          (SEQ ID NO: 1)
Forward Primer    TGCCTGGGGCACCCGGCTCTT (SEQ ID NO: 2)
Reverse Primer    TGGGGACGTCTGCCCGCCCTCT
```

Example 7

DNA Adsorption at Different Solution Conditions

Figure 30:
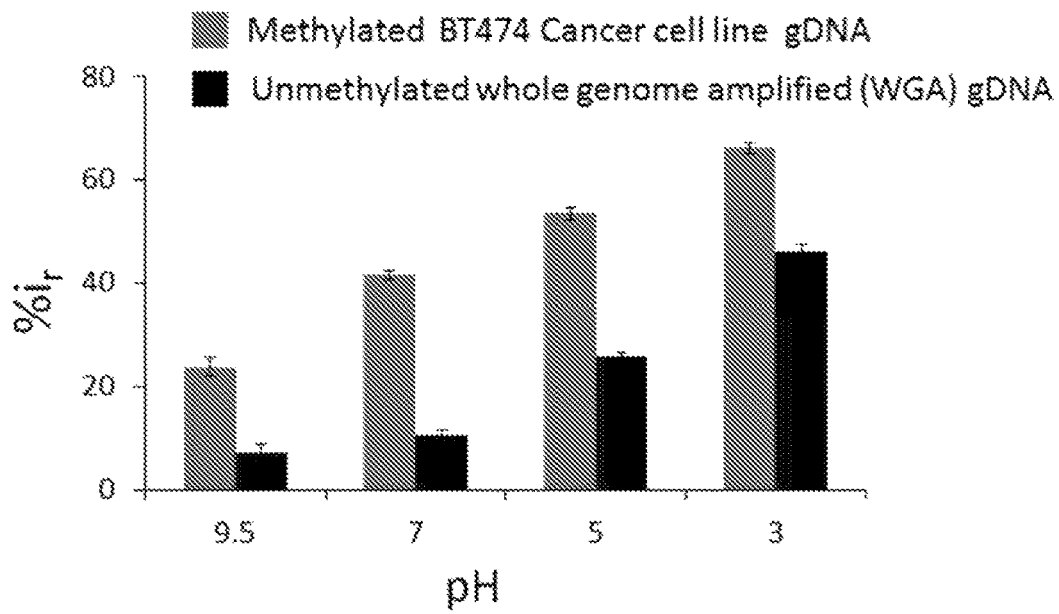
FIG. 30 is a graphical representation showing that the adsorption of genomic DNA increases with increasing pH.

To test the adsorption of DNA at different solution conditions, DNA solutions were prepared at different pH (9.5, 7, 5 and 3) and adsorbed onto gold electrodes. As shown in FIG. 30, the adsorption of both the methylated and DNA increased with increasing pH. It is believed that this is due to the protonation of DNA which minimized the charge effect. However, pH 7 provided the maximum differences between the relative DPV current for methylated BT474 and unmethylated WGA DNA and therefore this condition was used for experiments disclosed herein.

Method

DPV signals of clean electrodes were measured by using $[Fe(CN)_6]^{3-/4-}$ redox system to provide the baseline current. Purified cellular gDNA (5 μL of 10 ng/μL concentration) in SSC 5× buffer at different pH solution conditions (9.5, 7, 5 and 3) was adsorbed onto the gold electrodes for 10 mins. Subsequently, the adsorption competence was measured by Differential Pulse voltammetry (DPV) in presence of the $[Fe(CN)_6]^{3-/4-}$ redox system.

Example 8

Methylation Dependent Gold Adsorption Behavior of Extracellular Vesicular DNA Enables Liquid Biopsy Test for Cancer Extracellular vesicles (EV) play a major role in intercellular communication by transmitting cellular materials (e.g., protein, RNA) among distant cells. Recent evidence suggests that they could also contribute to carrying DNA which could inform on the mutational status of parent tumor genomic DNA. Thus, the fundamental analysis of EV-associated DNA (evDNA) may open a better understanding of tumor metastasis and provide new pathways for non-invasive detection and monitoring of cancer. To address these challenges, the isolation of pure evDNA from body fluids free of cfDNA contamination is important. This example discloses an improved evDNA isolation protocol free from cfDNA contamination for evaluating the methylation dependent physicochemical properties of evDNA and for developing an evDNA-based liquid biopsy test. Using a highly sensitive multiplex microelectrode device, the present inventors demonstrate that serum-evDNA derived from cancer patients shows different solution and surface based properties than normal evDNA due to their different methylation landscape (i.e., methylscape). This device allows simultaneous analysis of multiple samples in a single platform from as low as 500 pg/μL of evDNA.

Figure 31:
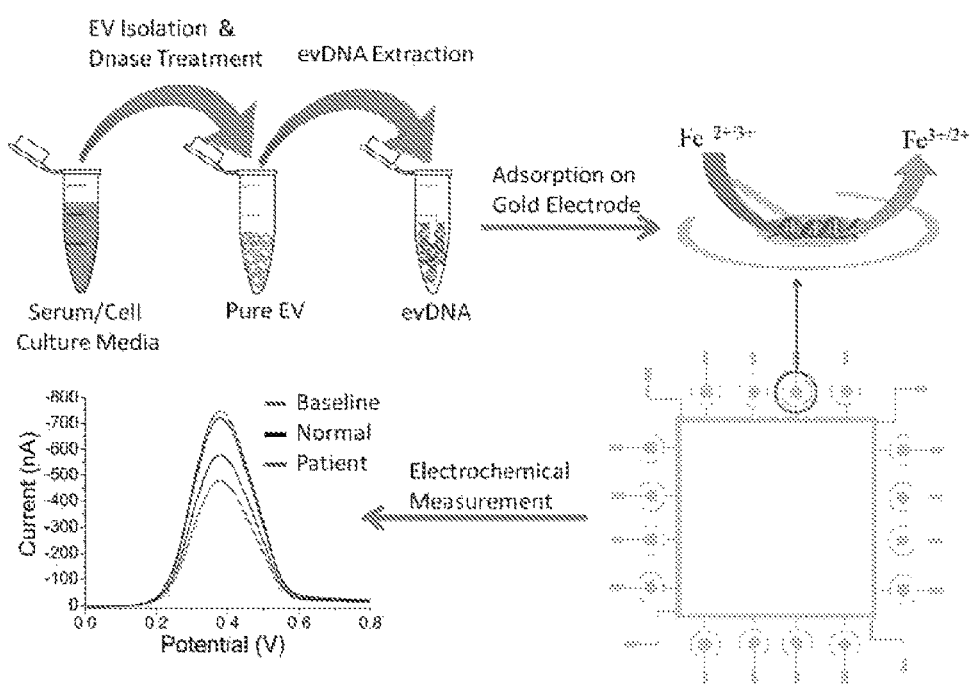
FIG. 31 is a schematic representation showing a methodological approach for the isolation and adsorption profiling of evDNA on microchip using differential pulse voltammetry (DPV) in the presence of the $[Fe(CN)_6]^{3-/4-}$ redox probe. The DPV graph shows the signal for empty electrode baselines (blue), normal evDNA (black) and cancer evDNA (red).
Figure 32:
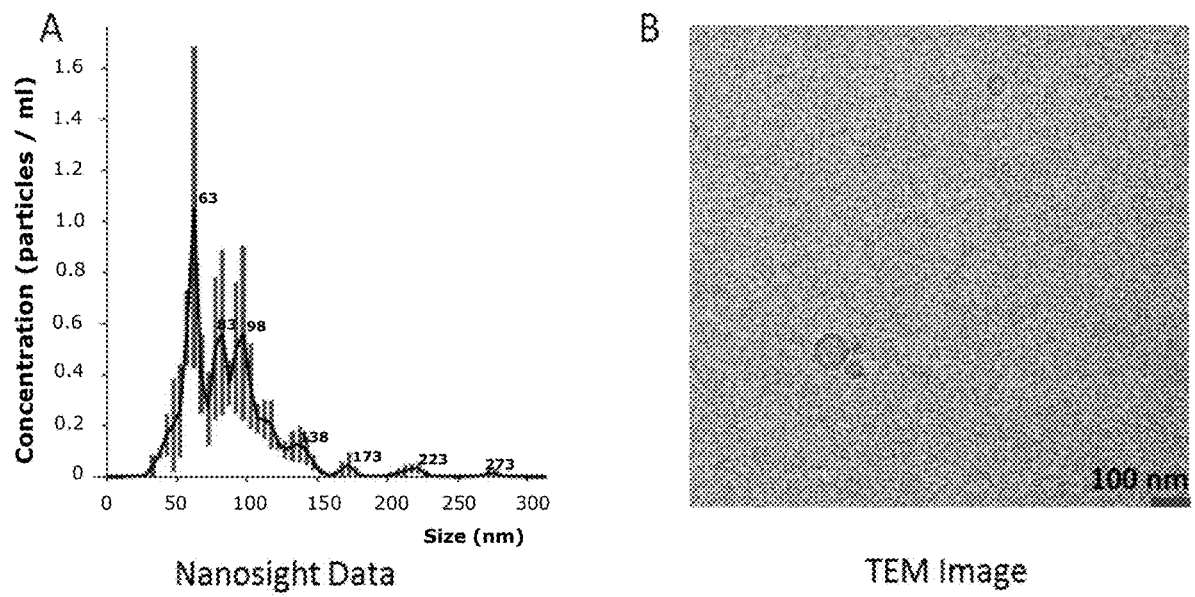
FIG. 32 is a graphical and photographic representation showing characterization of isolated EV from BT474 cell culture media. A) Nanosight data showing the size of EV ranging from approximately 30 nm-100 nm. B) TEM image showing the EV with lipid bilayer.
Figure 33:
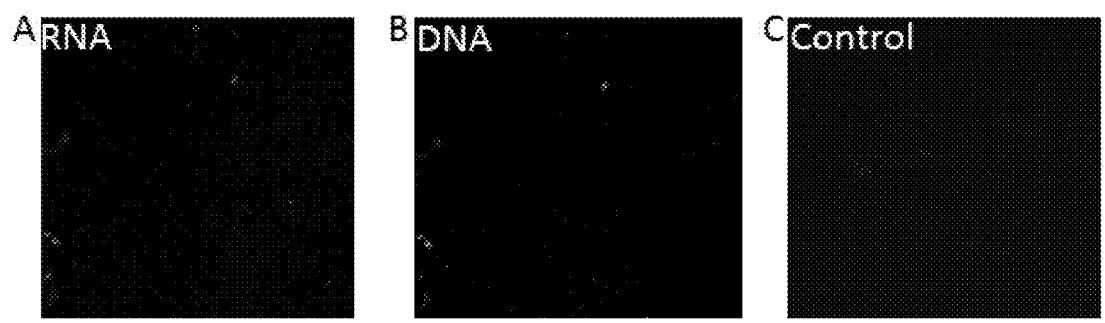
FIG. 33 is a fluorescence image of EV showing the presence of A) RNA and B) DNA in EV along with the C) control experiment with the dye without any EV.

FIG. 31 represents the methodological approach for the assay. In a first experiment, EV from BT474 cell culture media were isolated and characterized using Nanosight and transmission electron microscope (TEM). Nanosight data shows the size distribution of EV ranging from 30-250 nm and the TEM image shows the lipid bilayer membrane of EV (FIG. 32). The present inventors then sought to obtain information about the evDNA by staining the EV using Exo-Red, a nucleic acid sensitive fluorescence dye, which fluoresces red when it interacts with RNA and green when it interacts with DNA. Thus, isolated EVs were stained using Exo-Red dye and checked under the fluorescence microscope. As shown in FIG. 33, the red color indicates the presence of RNA in the isolated vesicles and the presence of green color at the same spot indicates the possibility of DNA associated with EV. The image for control experiments (i.e., dye in buffer without EV) showed no color which confirms that the fluorescent color was only derived from the EV associated nucleic acids. Although these data indicate the presence of DNA in EV, it remains unclear if this comprises contaminated cfDNA or EV encapsulated DNA.

Figure 34:
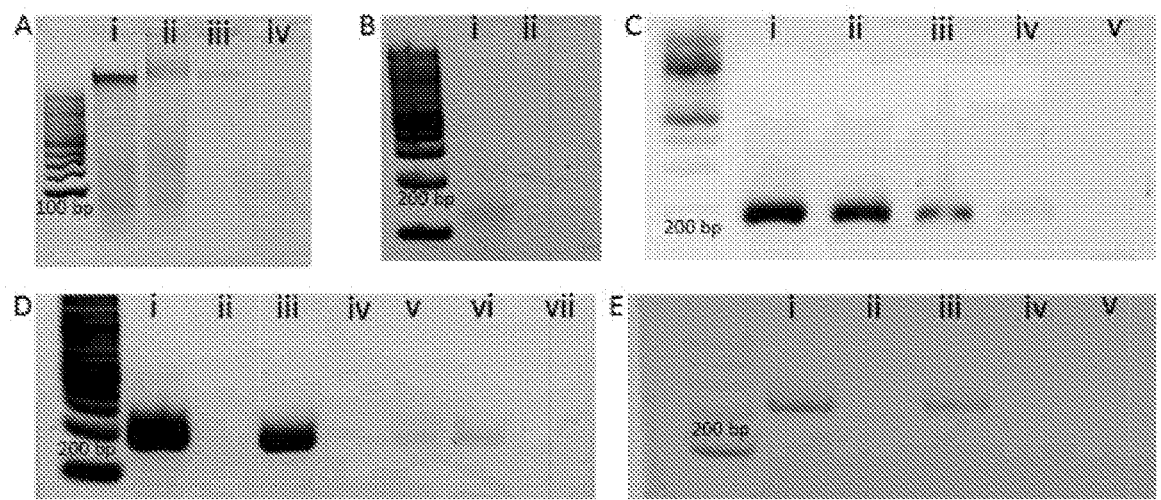
FIG. 34 is a photographic representation showing optimization of EV DNA purification using liposome model system and the adsorption profile towards the gold surface. (A) gel electrophoresis picture showing the band for i) BT474 cellular gDNA with no enzyme ii) BT474 cellular gDNA with Liposome without enzyme iii) BT474 cellular gDNA with liposome with enzyme and iv) BT474 cellular gDNA with enzyme without liposome. (B) gel electrophoresis picture showing the band for i) fragmented BT474 cellular gDNA with liposome without enzyme and ii) fragmented BT474 cellular gDNA with liposome with enzyme. (C) gel electrophoresis image showing the band after PCR amplification of the different concentration (i) 20 ng/μL, (ii) 5 ng/μL, (iii) 1.25 ng/μL, (iv) 0.3 ng/μL and (v) 10 ng/μL) of fragmented BT474 DNA with liposome solution. (D) gel electrophoresis image showing the bands for i) PCR positive control i.e. BT474 fragmented DNA and PCR mix, ii) PCR Negative Control i.e. No DNA and PCR mix iii) positive control, i.e. BT474 fragmented DNA with liposome without enzyme iv) negative control, i.e. no DNA with liposome with the enzyme and different concentration of liposome solution v) 1/200, vi) 1/500, and vii) 1/1000 with BT474 fragmented DNA with enzyme. (E) gel electrophoresis image showing the band for i) BT474 fragmented DNA and PCR mix ii) No DNA and PCR mix and iii) BT474 fragmented DNA with EVs without enzyme iv) no DNA with EVs and enzyme v) BT474 fragmented DNA with EVs with the enzyme.

To digest all the contaminating cfDNA before the EV isolation, the present inventors developed a model system using liposomes which are synthetic vesicles with one or more phospholipid bilayers, which resemble EV in terms of membrane composition and vesicle size (Lane et al., 2015., *Scientific reports* 5: 7639; Akbarzadeh et al., 2013. *Nanoscale research letters* 8: 102). A known concentration of DNA was spiked into a known concentration of liposome solution and DNase I enzyme was used to completely digest the spiked DNA present in the liposome solution following the manufacturer's instruction. As shown in the gel image shown in FIG. 34A(iv), 100 ng/μL of BT474 cell derived DNA was completely digested by DNase I enzyme. However, the same amount of DNA could not be digested completely in the presence of $1\times10^{13}$ particles/mL of liposomes (FIG. 34A(iii)). This indicates that the liposome reduced the enzyme activity and protected the DNA from digestion. Since cellular gDNA is a long polymer, it was hypothesized that the cellular gDNA possibly wrapped around the liposomes and prevented the digestion mechanism. However, the type of DNA that is likely to contaminate EVs is cell free DNA (cfDNA) rather than cellular gDNA, which typically has an average size of 200 bp. Accordingly, to mimic the cell free DNA and to facilitate the digestion, BT474 cell derived cellular gDNA was fragmented up to 200 bp by sonication and then spiked in liposome solution. The results presented in FIG. 34B(ii) show that with the addition of fragmented DNA (fgDNA), there is no visible band on the gel after digestion, indicating an enhancement of DNA digestion in the presence of liposome. However, the present inventors considered that it was a possibility that gel electrophoresis does not have sufficient sensitivity to visualize trace amounts of undigested fgDNA. To address this point, they decided to run a polymerase chain reaction (PCR) which targeted a repetitive region that is distributed across the whole genome, so the existence of trace amounts of DNA can be amplified and detected; if no DNA exists after digestion, there will be no amplicon detected on the gel. As shown in FIG. 34C, it is evident from the band for different concentration of amplified DNA that even after addition of low amounts of fgDNA (see, FIG. 34C(iv), 0.3 ng/µL) in liposome solution; the digestion enzyme could not eliminate the DNA. As such, it appeared that the liposomes even provided protection for fragmented DNA and prevented them from complete digestion.

Based on these results, the present inventors investigated whether decreasing the concentration of liposomes in the digestion reaction could facilitate better DNase enzyme access to the fgDNA and ensure the full digestion. Consequently, DNase digestion was performed on a series of samples containing different liposome dilutions from the liposome stock ($1\times10^{13}$ particles/mL) including 1 in 200, 1 in 500, and 1 in 1000 µL diluted liposomes. The results presented in FIG. 34D demonstrate that for the 1 in 1000 µL diluted liposomes (FIG. 34D(vii)), the PCR reaction did not amplify any detectable fragmented DNA, indicating that the full digestion of DNA was achieved under these conditions. The corresponding band for each control PCR experiments including i) DNA+PCR master solution (PCR positive control) ii) No DNA+PCR master solution (PCR negative control) iii) DNA+Liposome+PCR master solution (i.e. Positive control) iv) No DNA+Liposome+PCR master solution, confirms the specificity of the experiments and the absence of any contamination during PCR. This liposome concentration (1/1000 dilution) corresponds to approximately $1\times10^{10}$ particles/mL was therefore selected for future experiments in EVs.

To evaluate the performance of the model system in EV samples, the present inventors diluted the original stock of BT474 EVs equal to the optimized concentration of liposome ($1\times10^{10}$ particles/mL) and performed digestion of 1 ng/µL of spiked-in fgDNA followed by PCR amplification as previously performed for the liposome model system. The absence of any band after the PCR as evident in FIG. 2E (v), suggests that the spiked DNA was fully digested by the enzyme. This outcome indicates that cfDNA from EVs can be completely digested using DNase I enzyme in optimized conditions where the EVs are partially diluted.

Figure 35:
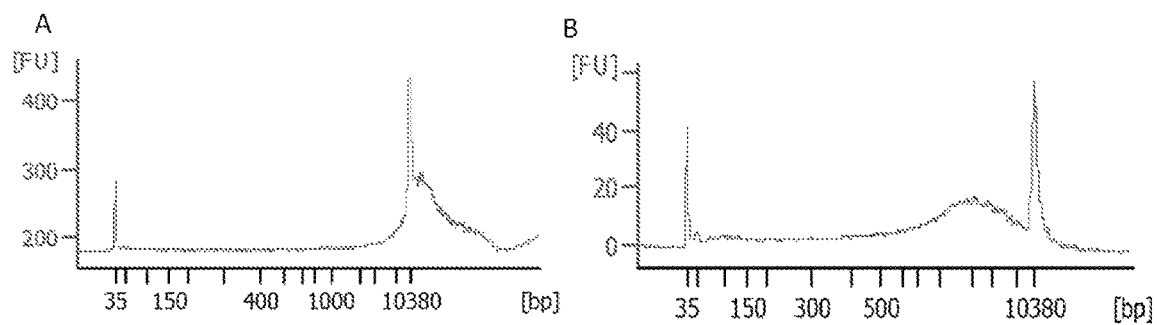
FIG. 35 is a graphical representation depicting Agilent Bio-analyzer data showing the size of BT474 breast cancer cell derived A) cellular gDNA and B) evDNA.

After successful digestion of extravesicular DNA, EV encapsulated DNA was extracted from isolated EV samples. Briefly, EVs were lysed using lysis buffer and evDNA was extracted using standard phenol-chloroform extraction procedures. The purity of the DNA was confirmed by measuring 260/280 absorbance ratio using a Nanodrop spectrophotometer and the concentration was measured by Qubit Fluorimeter. The average length of the DNA in base pairs was also measured by using Agilent Bio-analyzer. As shown in FIG. 35, the average size of evDNA is significantly different from the average size of cellular gDNA and cfDNA. While the cellular gDNA was very high molecular weight with an average size above 10 kb, the evDNA size was found 1 to 4 kb long (FIG. 35). Moreover, the cfDNA average size is known to be only 50-200 bp. These data support previous reports suggesting evDNA is fundamentally different in nature. Thus, the inventors postulated that evDNA may exhibit different methylation dependent physicochemical properties in comparison to the cellular gDNA and cfDNA.

To investigate the methylation dependent surface adsorption properties of evDNA, cell derived evDNA was adsorbed onto gold macro-electrodes for 10 min and their adsorption competence was measured using differential pulse voltammetry (DPV) in presence of $[Fe(CN)_6]^{3-/4-}$ redox probe. This system can reliably quantify the adsorption competence of biomolecules (e.g. DNA, RNA, protein) adsorbed onto the gold surface (Ahmed et al., 2017. *Biosensors and Bioelectronics* 91: 8-14; Koo et al., 2014. *Analyst* 139: 6178-6184; Sina et al., 2014. *Chem Commun* 50: 13153-13156; and Koo et al., 2016. *Anal Chem* 88: 6781-6788)

Figure 36:
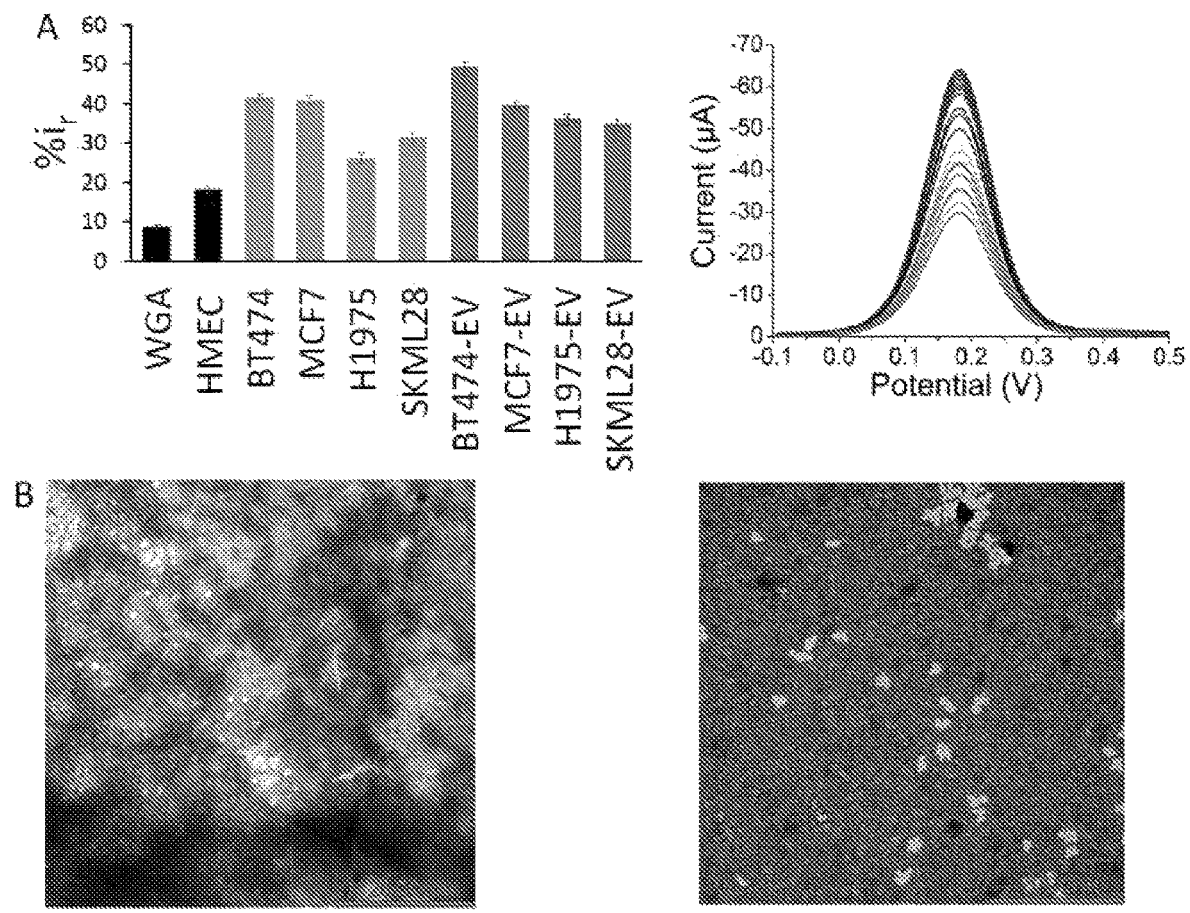
FIG. 36 is a graphical and photographic representation showing surface and solution based properties of cellular gDNA, and evDNA. (A) Bar graph showing the relative current mean value representing adsorption of 10 ng/μL of DNA from normal cellular gDNA (black), cancer cellular gDNA (orange) and cancer evDNA (red) derived from different cell lines. Right Panel: Corresponding DPV signals. Each data point represents the average of three separate trials, and error bars represent the standard deviation of measurements (% RSD=<5% for n=3). (B) TEM image of evDNA derived from the serum of a healthy individual (left) and a breast cancer patient (right).

As shown in FIG. 36A, only 5 µL of 10 ng/µL evDNA provided significant current reduction compared to the baseline indicating high adsorption of DNA towards the gold electrode. The present inventors also compared the adsorption of different cancer cell lines derived evDNA and cellular gDNA (Breast: BT474, MCF7; Lung: H1975; Melanoma: SKMEL28) with normal Human Mammalian Epithelial cell (HMEC) DNA and fully unmethylated WGA (whole genome amplified) DNA in which methylation marks were completely removed by whole genome amplification (see methods below for details). As can be seen in FIG. 36A, the relative DPV current for cancer cell derived evDNA (i.e. % $i_r$ for BT474 evDNA=49.5±1.03, MCF7 evDNA=39.47±0.97, H1975 evDNA=36.18±1.24, and SKMEL28 evDNA=34.59±1.67) is similar to cellular gDNA (i.e. % $i_r$ for BT474=41.58±0.87, MCF7=40.79±1.09, H1975=26.15±1.48, and SKMEL28=31.27±1.61), but significantly higher than the normal HMEC and unmethylated WGA DNA (i.e. % $i_r$ for HMEC=18.18±0.89, WGA=8.75±0.26). These data indicate that the similar and high adsorption of evDNA and cellular gDNA towards gold electrode is likely due to the presence of similar methylation profile in cancer evDNA and cellular gDNA. Moreover, evDNAs and cellular gDNAs were extracted from the same cell lines which further indicates the possibility of carrying the similar cancer specific methylation profile. In Examples 1 to 6, it was demonstrated that the cancer methylscape (cluster methylation with hypomethylated tail) can significantly increase the gold adsorption of cellular gDNA in comparison to the unmethylated or heavily methylated normal DNA. Thus, the present inventors hypothesize that cancer evDNA likely carries a similar methylscape like cellular gDNA which increases their adsorption towards the gold surface. To further confirm the methylation profile, methylation analysis of evDNA was performed and the data in Table 13 shows that evDNA derived from BT474 breast cancer and SKMEL28 melanoma cell line has a similar hypomethylation level to BT474 and melanoma cellular gDNA (Methylation level for BT474 evDNA=26.75%, MCF7 evDNA=43.59%, SKMEL28 evDNA=37.84% vs BT474 cellular gDNA=43.15%, MCF7 cellular gDNA=33.56 and SKMEL28 cellular gDNA=45.23%).

To investigate the solution-based properties of evDNA, cancer and normal evDNA was extracted from the serum of a cancer patient and a healthy individual. As shown in the TEM image presented in FIG. 36B, normal evDNA derived from serum of a healthy individual tended to aggregate in solution wherein, evDNA derived from the serum of a breast cancer patient provided dispersion in solution. These data are clearly consistent with the observation presented in Examples 1 to 5, in which the levels and distribution of methylation can significantly influence the solution properties of cellular gDNA. More specifically, normal cellular gDNA was found to be aggregated in solution due to the high level of overall methylation across the genome wherein, epigenetically reprogrammed cancer cellular gDNA was found to be uniformly dispersed in solution due to the overall hypomethylation across the genome and high level of cluster methylation in regulatory regions. This was attributed to the hydrophobicity of the methyl group, which was responsible for the large aggregates in normal DNA solution due to their large methylation level across the genome. However, in the case of cancer DNA, overall hypomethylation decreased the hydrophobicity and prevented aggregation in solution and cluster methylation increased the adsorption of cancer DNA towards gold. Since patient serum derived cancer evDNA showed significantly different solution based properties than normal evDNA, based on the cellular gDNA study described in Examples 1 to 5, it was assumed that the surface based properties of cancer and normal evDNA would also be different.

Figure 37:
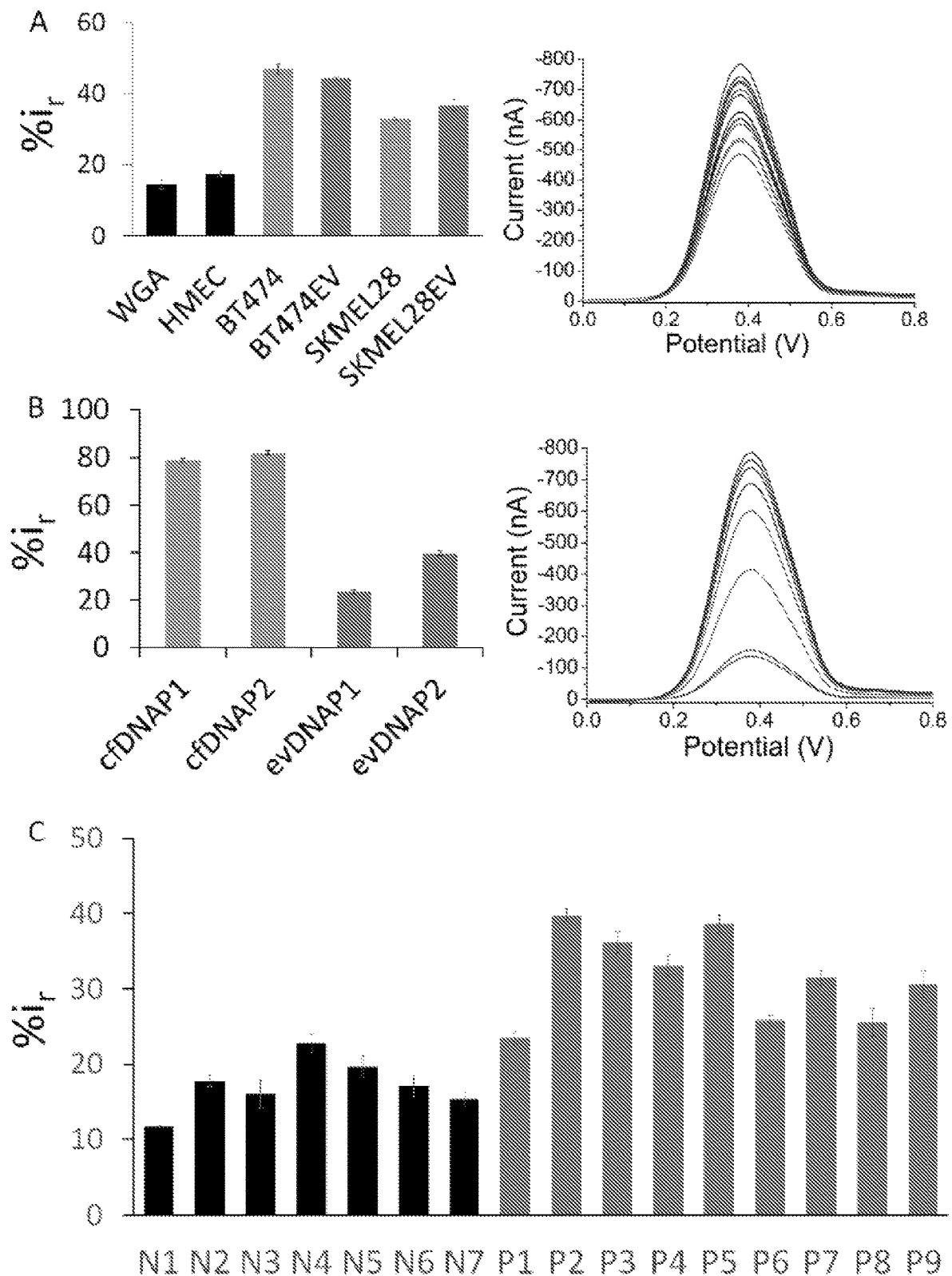
FIG. 37 is a graphical representation depicting microchip multiplex analysis for differential adsorption of genomic DNA, cfDNA, and evDNAs as a function of their cancer and normal origin. (A) Bar graph showing the relative current mean value representing adsorption of 10 ng/μL of normal cellular gDNA (Black), cancer cellular gDNA (orange), and cancer evDNA (red). Right Panel: Corresponding DPV signal. (B) Bar graph showing the signal for cfDNA (orange) and evDNA (red) derived from the same patient serum. Right Panel: Corresponding DPV signal. (C) Bar graph showing the relative current mean values derived from normal (black) and patient serum. Each data point represents the average of three separate trials, and error bars represent the standard deviation of measurements (% RSD=<5% for n=3).

To test the surface adsorption profile of patient serum derived evDNA, the present inventors first isolated evDNA from the serum of 5 breast cancer patients, 4 melanoma cancer patients and 7 healthy individuals (See Table 14 for clinical information) using the optimized model isolation procedure described above. However, the concentration of isolated evDNA from patient serum was very low which limited the ability to compare their adsorption profile using regular macroelectrodes. Accordingly, a microdevice was designed comprising an array of 16 microelectrodes (See Methods below for detail on the fabrication process) which enabled the detection of samples with low concentration and at the same time provided multiplexing capability. The diameter of these microelectrodes is considerably smaller (i.e., 250 μm) than the conventional macroelectrodes (e.g., diameter=3 mm). As reported in previous studies, these microelectrodes can significantly enhance the detection sensitivity due to the lower surface area of the electrodes and higher signal to noise ratio (Gasparac et al., 2004. *Journal of the American Chemical Society* 126: 12270-12271; Soleymani et al., 2009. *Angewandte Chemie International Edition* 48: 8457-8460). To test the sensitivity of the device, adsorption profiling of cell line derived cellular gDNA and evDNA was performed using the microchip and as shown in FIG. 37A, only 500 μg/μL of cellular gDNA and evDNA from different cancer and normal cell lines provided significant adsorption providing higher relative DPV current (i.e. % $i_r$) which is similar to the results obtained in case of macroelectrodes.

To further test whether evDNA is different from the cfDNA, evDNA and cfDNA were both isolated from the same patient serum samples and their adsorption profiling was performed using the microchip. As shown in the FIG. 37B, 500 pg/μL of evDNA provided significantly lower current than the same concentration of cfDNA (% $i_r$ for evDNAP1=23.51±0.93, evDNAP2=39.72±1.12 vs cfDNAP1=78.83±1.03 and cfDNAP2=82.01±0.84). These data are consistent with the results presented in Examples 1 to 5, in which cfDNA was determined to have higher adsorption in comparison to the cellular gDNA, probably due to their shorter length. These data also suggest that the evDNA is a different entity with its own characteristic methylation and adsorption profile. Finally, to evaluate the potential of evDNA as a biomarker for noninvasive cancer detection, experiments were performed with the isolated evDNA derived from the serum of breast and melanoma cancer patient and healthy individuals using the multiplex microchip. The data presented in FIG. 37C show that the relative DPV currents (i.e. % $i_r$) for the adsorption of patient serum derived evDNA range from 20-40% whereas the relative DPV currents for the normal serum derived evDNA are below 20%. These data suggest that the patient serum derived evDNA likely carry a similar methylscape pattern as overserved in the study presented herein for cellular gDNA and potentially enables liquid biopsy test for cancer. It is also believed that the multiplexing capability, high sensitivity and specificity in identifying cancer and normal evDNA makes this device suitable for clinical application.

Conclusion

This study established a high-quality method for isolating evDNA of high purity, which effectively minimizes the possibility of cfDNA contamination. From the characterization of evDNA, it was found that the size of evDNA is different from cfDNA and cellular gDNA. The affinity behavior of evDNA towards gold surface supports this observation and reveals that the adsorption behavior of evDNA is similar to cellular gDNA and completely different from the cfDNA. The overall findings based on their solution and surface based properties suggest that evDNA likely carry a similar methylation pattern to parent cell DNA and enable a liquid biopsy test for cancer. The highly sensitive micro-device with the ability to identify cancer and normal evDNA provides an inexpensive, simple, and non-invasive multiplex platform that underpins development of point of care cancer diagnostics.

Methods for Example 8

Cell Culture and Isolation of Extracellular Vesicles (EV)

BT-474 Breast cancer cell line was maintained in microvesicle depleted serum free Media 171 (Gibco, UK) supplemented with Mammary Epithelial supplement (Gibco, UK), 1% Penicillin/streptomycin and grown in 5% $CO_2$ at 37° C. The conditioned medium from $10^6$ cells was collected after 60 h and centrifuged at 2000×g for 30 min to eliminate cell contamination (e.g., cells and debris). EV were isolated using Total Exosome isolation reagent (Life Technologies) as per manufacturer's instructions. Briefly, the supernatant was transferred to a new tube and the isolation reagent was added to the tube in the ratio 2:1. The samples were incubated overnight at 4° C. followed by filtration using 0.22 μm filter and centrifugation at 10000×g for 1 h to obtain exosome pellets. Exosome pellets were then resuspended in 100 μL PBS (10 mM, pH 7.0) and stored at −20° C. for further use.

Cryo-Transmission Electron Microscopy (Cryo-TEM) and Nanosight Analysis

For cryo-TEM, 4 μL of exosome preparations were directly adsorbed onto lacey carbon grids (Quantifoil, Germany) and plunged into liquid ethane, using an FEI Vitrobot Mark 3 (FEI Company, The Netherlands). Grids were blotted at 100% humidity at 4° C. for about 3-4 s. Frozen/ vitrified samples were imaged using Tecnai T12 Transmission Electron Microscope (FEI Company) operating at an acceleration voltage of 120 kV. Images were taken at 30,000× magnification, (approximate dose of 13.6 electrons/A2), using an FEI Eagle 4k CCD (FEI Company), and Serial EM image acquisition software. Nanosight analysis were performed by using EVs Isolation (from Serum)

Invitrogen Total Exosome Isolation Kit was used to extract EVs from serum samples according to manufacturer's instructions. Firstly, after thawing, the serum samples were centrifuged at 2000 rcf for 30 minutes to remove debris and cells. Then the supernatant containing EV were transferred is to a new 1.5 mL Eppendorf and 0.2 volumes of the Total Exosome Isolation reagent was added, mixed with vortex and then incubate din ice for 30 minutes. After incubation, the samples were centrifuged at 10000 rcf for 10 minutes, and the EVs pallets were obtained. Supernatant solutions were removed and the isolated EV were resuspended in 1×PBS and stored at −20° C. for further use.

External DNA Digestion

Optimized digestion reaction protocol of cfDNA by DNase I (RNase-free) is: 80 µL of exosome (1×1010 particles/mL), 110 µL of 1× DNase I reaction buffer, and 10 µL of DNase I enzyme. Add 110 µL of 1× DNase I reaction buffer (10 mM Tris-HCl, 2.5 mM $MgCl_2$, 0.5 mM CaCl2, pH 7.6® 25° C.) to 80 µL of diluted liposomes/exosomes (1×1010 particle/mL). Add 10 µL DNase I enzyme (Biolab.Inc.M0303S) and incubate reaction at 37° C. for 20 minutes. Add 10 µL of 0.5 M EDTA, and heat at 75° C. for 10 minutes, and the exosome samples are further analyzed by NanoSight® LM10 (Nanosight Ltd., Minton Park, Amesbury, UK).

DNA Extraction (from EVs)

After digesting external cfDNA, EV-DNA was extracted by the DNeasy Blood & Tissue Kit (Cat. No. 69506, QIAGEN, Germany) according to the instructions. Firstly, transfer exosome to 2 mL Eppendorf and add 1×PBS until 200 µL. Add 20 µL of proteinase K and 200 µL of buffer AL Blood and tissue DNeasy Kit), vortex and incubate at 56° C. for 10 minutes. Add an equal volume (same as sample) of phenol: chloroform (pH 8.0, AMRESCO. 0833.) and vortex thoroughly until the two phases are mixed. Add small amount of silicone grease (ACC Silicones Ltd, SGM494.), and centrifuge the sample at 5000 rcf for 10 minutes. After two phases are separated, carefully transfer the aqueous (top) phase without disturbing the bottom layer (protein), which will be discarded. Take a known volume of DNA to be precipitated. Add 0.1 volume of 3 M sodium acetate (pH5.2), 1 volume of 100% isopropanol and 2 µL of glycogen. Centrifuge at 13000 rcf for 15 min at 4° C. Discard the majority of isopropanol. Add 1 mL of cold 70% ethanol and gently invert, then put tube on ice. When DNA pallet is visible, remove the ethanol by pipetting and heating carefully without disturbing pellet. Add suitable volume of ultrapure water (Depend on the size of pellet) to dissolve DNA pellet fully.

DNA Concentration Quantification

DNA concentrations are all quantified by Qubit high sensitive double strand DNA (HS dsDNA) Kit with sensitivity can be achieve to 100 pg/µL of ds DNA. Each reaction contains 2 µL of sample and 198 µL of HS dsDNA dye and HS dsDNA reaction buffer mixture in proportion 1:200.

Electrochemistry

All electrochemical experiments were carried out using a CH1040C potentiostat (CH Instruments) with a three electrode system consisting of a gold working electrode (2 mm in diameter), Pt counter electrode, and Ag/AgCl reference electrode (all electrodes are from CH Instruments, USA). Differential pulse voltammetric (DPV) experiments were conducted in 10 mM PBS solution containing 2.5 mM $[K_3Fe(CN)_6]$ and 2.5 mM $[K_4Fe(CN)_6]$ electrolyte solution. DPV signals were obtained with a potential step of 5 mV, pulse amplitude of 50 mV, pulse width of 50 ms, and pulse period of 100 ms. For DNA methylation detection, the gold electrodes were initially cleaned by polishing with Alumina polishing powder (CH Instruments) followed by ultrasonication with deionized water for 1 minutes and then dried under the flow of nitrogen. DPV signals of clean electrodes were measured in electrolyte solution to get the baseline current. The tested samples (5 µL, 10 ng/µL diluted by SSC 5× buffer) were then incubated on the electrode for 10 min with 350 rpm shaking speed. The electrodes were then washed with 1 mL of 1×PBS. The relative DPV currents (i.e., % ir, percent difference of the DPV signals generated for DNA sample (isample) with respect to the baseline current (ibaseline) due to the adsorption of DNA samples were then measured by using equation 1.

$$\text{Relative DPV signals } (\% \ i_r) = [(i_{baseline} - i_{sample})/i_{baseline}] \times 100 \quad (3)$$

Polymerase Chain Reaction (PCR)

The PCR was performed to confirm whether EV samples still contain external DNA. PCR was performed in 20 µL reaction solution, containing 0.4 µL of exosome samples, 1 µM of each primer (forward primer: 5'-ACCTGTGTTCAT-TCACATGAGG-3' (SEQ ID NO:3), reverse primer: 5'-AGAGCTTGTTCTGGCCGTTT-3' (SEQ ID NO:4)), 9.34 µL of water and 4 µL of 5× Green go Taq® Flexi buffer (Promega, Madison, USA), 1 µL of CES 5×, 4 µL of 25 mM $MgCl_2$, 0.2 µL of 10 mM dNTP and 0.06 µL of 5 U/µL Hot Start Taq. Amplification was carried out under following conditions: 95° C. for 7 min, 35 cycles of 94° C. for 20 s, 57° C. for 30 s, 72° C. for 30 s, 72° C. for 7 min, and 10° C. for 10 min. Then, the amplified samples were analyzed through electrophoresis, using 2% agarose gel (Sigma Ltd.) and running in 1×TAE buffer under 200 V for 20 min.

Example 9

Methylscape Biosensing Using Electroconductive Materials Other than Gold

To investigate the efficacy of Au—Ag alloy for cancer methylscape biosensing, the present inventors used the colorimetric assay (described above) to analyze various epigenomes extracted from, Unmethylated WGA (Au—Ag WGA), Hypomethylated cancer BT474 (Au—Ag BT474) and 100% CpG methylated Jurkat DNA (Au—Ag CM). 50 ng of purified DNA was incubated with AuAg nanoparticles for 5 min, followed by the addition of salt (SSC 5×) to induce aggregation (see, Methods for details).

Figure 38:
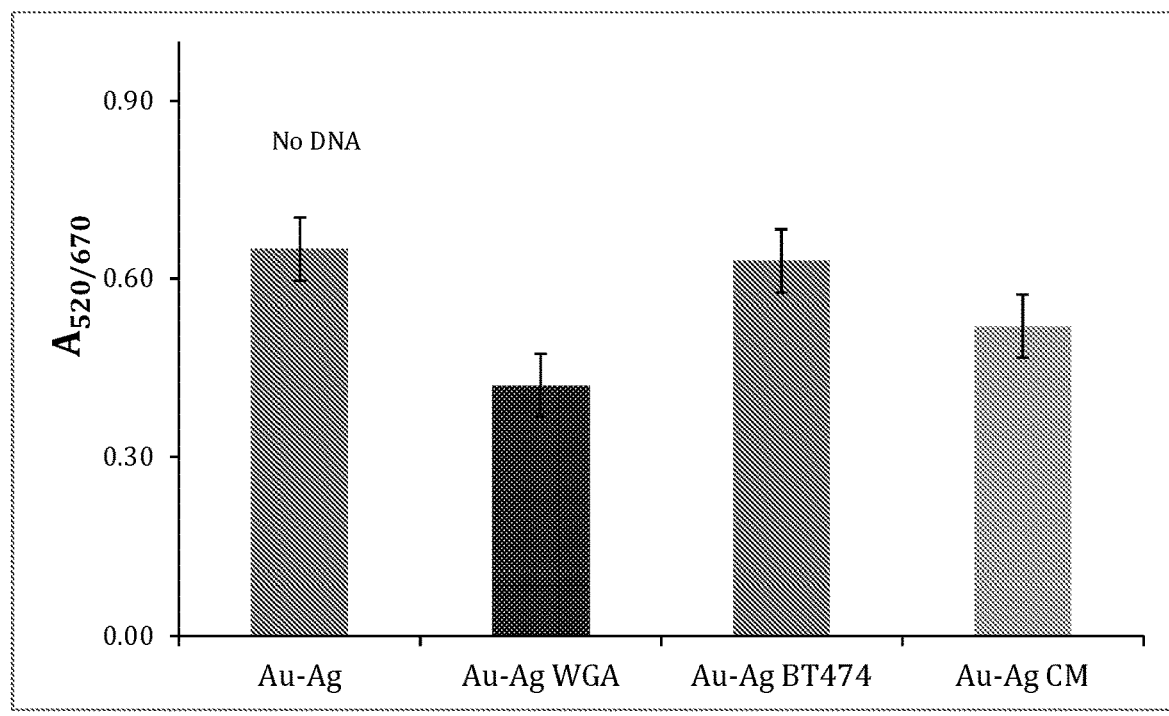
FIG. 38 is a graphical representation showing differential affinity/adsorption of cellular genomic DNAs as a function of gDNA methylation type using gold-silver alloy nanoparticles. Bars represent the mean relative absorbance values A520/658 of gold-silver alloy (Au—Ag) NP for unmethylated (WGA), hypomethylated cancer BT474 or 100% CpG methylated Jurkat cellular gDNA.

FIG. 38 represents the difference in absorbance ratios of bare gold-silver alloy (Au—Ag NP), Unmethylated WGA, Hypomethylated cancer BT474 and 100% CpG methylated Jurkat DNA. The absorbance for bare Silver-gold alloy particles (FIG. 38—blue bar, no DNA) were used as the control. Unmethylated WGA DNA had less affinity to the surface of Au—Ag nanoparticles caused the particles to readily aggregate on addition of salt causing a change in colour from blue to colourless and therefore provided less absorbance ratio. On the other hand, since hypomethylated BT474 samples, had a higher affinity to surface of the nanoparticles, the particles did not aggregate and the colour remains blue. The ratio of absorbance at 670 and 520 nm ($A_{670}/A_{520}$) was 0.63 for BT474, whereas the absorbance ratio for WGA was 0.53 and for 100% CpG methylated DNA, AU-Ag NP were also aggregated upon salt addition due to the less adsorption towards the NP and provided less absorption value (i.e., 0.52).

Figure 39:
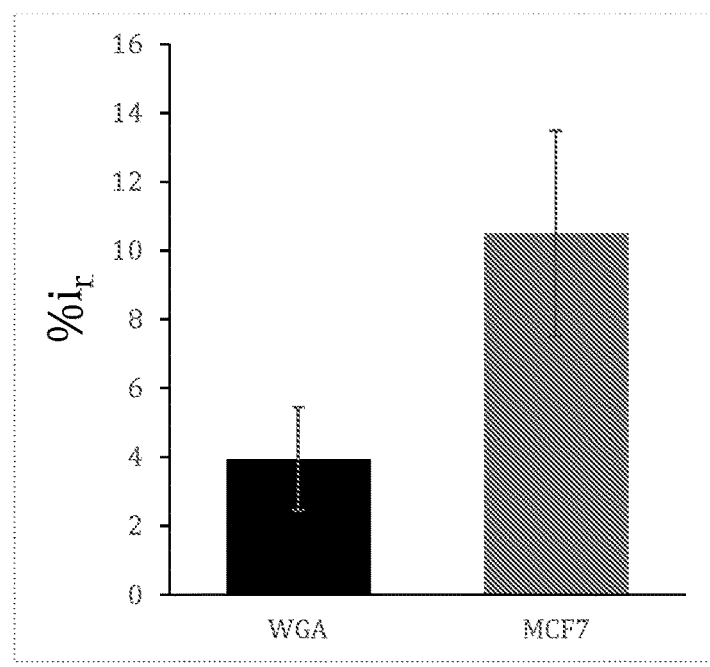
FIG. 39 is a graphical representation showing differential affinity/adsorption of cellular genomic DNAs as a function of gDNA methylation type using a graphene electrode. Bars represent the relative current value for unmethylated WGA or hypomethylated cancer BT474 based on their adsorption towards graphene electrode.

To investigate the efficacy of graphene, the present inventors used an electrochemical DPV assay to analyze unmethylated WGA (Au—Ag WGA) and hypomethylated cancer BT474 (Au—Ag BT474) DNA. 50 ng of purified DNA in 5×SSC was incubated on a graphene electrode for 10 min. FIG. 39 represents the relative current value for unmethylated WGA, hypomethylated cancer BT474 based on their adsorption towards graphene electrode. Unmethylated WGA DNA showed less affinity towards graphene electrode probably because of having no methylation and BT474 cancer DNA showed higher adsorption due to the presence of cancer methylscape methylation.

Example 10

Electrochemical Desorption of Genomic DNA from Gold Electrodes

To investigate the electrochemical desorption of DNA from the gold surface and subsequent utilization of this DNA for downstream molecular assays the present inventors prepared hypomethylated cancer BT474 DNA. Five microliters of designated concentration of DNA was adsorbed onto the gold electrode for 10 min. The unadsorbed DNA was then removed by washing the electrode with 1×PBS for 3 times. The gold electrode was then subjected to −1.2 volts in 1 mL of PBS for 4 minutes. After that, PBS solution along with desorbed DNA was taken off from the surface and stored for PCR amplification. FIG. 40C shows a representative example of the difference in current at baseline (red) after adsorption (black) and after desorption (blue). FIG. 40 B shows the reproducibility of this approach across 8 electrodes with the baseline current for the bare gold electrodes (blue bar, No DNA), current after adsorbing BT474 cancer DNA onto the gold electrodes (orange bar) and the current after desorbing the same DNA from the gold electrodes (grey bar).

Figure 41:
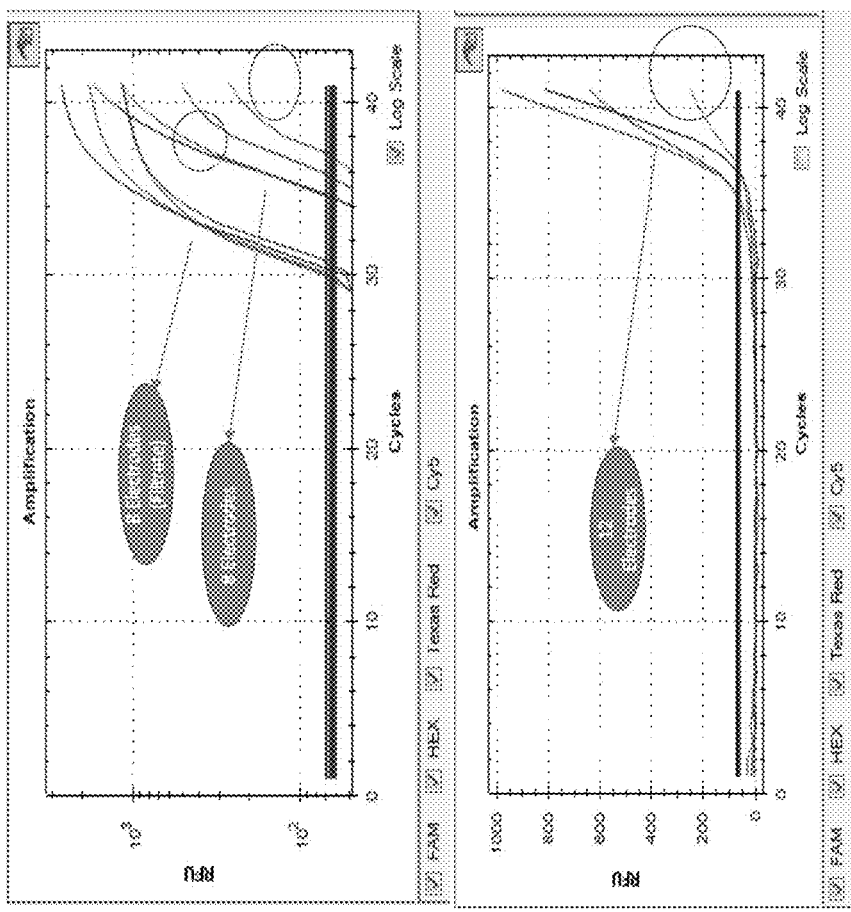
FIG. 41 is a tabular and graphical representation showing qPCR amplification of gDNA following electrochemical desorption. The graph represents the qPCR data of DNA after adsorbing from a different number of electrodes. Four target regions were amplified after desorption which indicates the successful desorption of DNA from the electrode using an electric potential. The first row in the table represents the data after desorption from 8 electrodes. Desorbed DNA containing solution was then directly used for qPCR. The second row represents the qPCR data after concentrating the desorbed DNA using a filter which results in a better CT value (the lower the CT value, the better the result). The last low represents a repeat experiment using 12 electrodes without filtration.

The desorbed DNA was subjected to quantitative PCR (qPCR). FIG. 41 represents the qPCR data of DNA after adsorbing from a different number of electrodes. 4 target regions were amplified after desorption which indicates the successful desorption of DNA from the electrode using an electric potential. The first row in the table represents the data after desorption from 8 electrodes. Desorbed DNA containing solution was then directly used for qPCR. The second row represents the qPCR data after concentrating the desorbed DNA using a microfuge filter column that results in a better CT value (the lower the CT value, the better the result). The last low represents a repeat experiment using 12 electrodes without filtration.

TABLE 1

P value obtained from the student's t- test for the analysis of paired normal and cancer DNA derived from tissue and plasma samples.

| | P value |
|---|---|
| Sample Tissue DNA-Electrochemistry (Methylscape) | |
| All Cancer tissue DNA vs All Normal tissue DNA | 0.0015 |
| Breast Cancer tissue DNA vs normal tissue DNA | 0.0001 |

TABLE 1-continued

P value obtained from the student's t- test for the analysis of paired normal and cancer DNA derived from tissue and plasma samples.

| | P value |
|---|---|
| Lymphoma tissue DNA vs normal tissue DNA | 0.2547 |
| Prostate cancer tissue DNA vs normal tissue DNA | 0.0012 |
| Sample Plasma DNA-Electrochemistry | |
| Breast and Colorectal Cancer Plasma DNA vs Normal Plasma DNA | 0.0001 |
| Sample Tissue and Plasma DNA- Nanoparticle (Nanomethylscape) | |
| All Cancer tissue DNA vs Normal tissue DNA | 0.0005 |
| Breast and Colorectal Cancer Plasma DNA vs Normal Plasma DNA | 0.0001 |

TABLE 2

Statistical Diagnostic Test evaluation for electrochemical analysis of tissue derived cellular gDNA. (Cut off % ir = 20, Cancer > 20 < normal).

| Statistic | Value for electrochemical cellular gDNA test |
|---|---|
| Sensitivity | 93.06% |
| Specificity | 80.65% |
| Disease Prevalence (DP) | 69.90% |
| Positive Predictive Value (PPV) | 91.78% |
| Negative Predictive Value(NPV) | 83.33% |
| Accuracy | 89.32% |

TABLE 3

Statistical Diagnostic Test evaluation for electrochemical analysis of plasma derived cfDNA. (Cut off % ir = 35.7, Cancer > 35.7 < normal).

| Statistic | Value for electrochemical cfDNA test |
|---|---|
| Sensitivity | 84.00% |
| Specificity | 82.22% |
| Disease Prevalence (DP) | 68.97% |
| Positive Predictive Value (PPV) | 91.30% |
| Negative Predictive Value(NPV) | 69.81% |
| Accuracy | 83.45% |

TABLE 4

Statistical Diagnostic Test evaluation for nanoparticle based analysis of of tissue derived cellular gDNA. (Cut off % ir = 35.7, Cancer > 35.7 < normal).

| Statistic | Value for colorimetric cellular gDNA test |
|---|---|
| Sensitivity | 70.83% |
| Specificity | 83.33% |
| Disease Prevalence (DP) | 50.00% |
| Positive Predictive Value (PPV) | 80.95% |
| Negative Predictive Value(NPV) | 74.07% |
| Accuracy | 77.08% |

TABLE 5

Statistical Diagnostic Test evaluation for nanoparticle based analysis of plasma derived cfDNA. (Cut off A520/658 = 8.7, Cancer > 8.7 < normal).

| Statistic | Value for colorimetric cfDNA test |
|---|---|
| Sensitivity | 70.00% |
| Specificity | 80.00% |
| Disease Prevalence (DP) | 68.97% |
| Positive Predictive Value (PPV) | 88.61% |
| Negative Predictive Value(NPV) | 54.55% |
| Accuracy | 73.10% |

TABLE 6

Clinical Information of Breast Cancer Patients (for tissue derived cellular gDNA samples)

| Sample Number | Gender | Age (Yrs) | Cancer Type | Cancer Stage | Global Methylation (%) | Mean Relative Adsorption (% $i_r$) |
|---|---|---|---|---|---|---|
| 1 | Female | 56 | ER+ Breast | Metastatic | 33.21 | 30.98 |
| 2 | Female | 76 | ER+ Breast | Metastatic | 41.46 | 39.69 |
| 3 | Female | 65 | ER+ Breast | Metastatic | 35.64 | 34.25 |
| 4 | Female | 71 | ER+ Breast | Metastatic | 39.25 | 33.66 |
| 5 | Female | 53 | ER+ Breast | Metastatic | 48.70 | 26.64 |
| 6 | Female | 44 | ER+ Breast | Metastatic | 45.32 | 32.02 |
| 7 | Female | N/A | ER+ Breast | Metastatic | 47.61 | 28.96 |
| 8 | Female | 63 | ER+ Breast | Metastatic | 34.28 | 32.69 |
| 9 | Female | 63 | ER+ Breast | Metastatic | 35.26 | 25.95 |
| 10 | Female | 59 | ER+ Breast | Metastatic | 46.14 | 35.97 |
| 11 | Female | 55 | ER+ Breast | Metastatic | 57.70 | 27.90 |
| 12 | Female | 85 | ER+ Breast | Metastatic | 48.93 | 32.03 |
| 13 | Female | 69 | ER+ Breast | Metastatic | 43.52 | 15.28 |
| 14 | Female | 66 | ER+ Breast | Metastatic | 34.61 | 25.95 |
| 15 | Female | 60 | ER+ Breast | Metastatic | Error reading | 32.11 |
| 16 | Female | 49 | ER+ Breast | Metastatic | 54.61 | 19.29 |
| 17 | Female | 66 | ER+ Breast | Metastatic | 43.68 | 27.42 |
| 18 | Female | 84 | ER+ Breast | Metastatic | 33.50 | 37.83 |
| 19 | Female | 60 | ER+ Breast | Metastatic | 39.20 | 26.10 |
| 20 | Female | 71 | ER+ Breast | Metastatic | 51.64 | 29.96 |
| 21 | Female | 64 | ER+ Breast | Metastatic | 53.61 | 22.81 |
| 22 | Female | 76 | ER+ Breast | Metastatic | 31.48 | 33.37 |
| 23 | Female | 66 | ER+ Breast | Metastatic | 56.82 | 22.11 |
| 24 | Female | 58 | ER+ Breast | Metastatic | 49.62 | 18.23 |
| 25 | Female | 64 | ER+ Breast | Metastatic | 36.59 | 30.42 |
| 26 | Female | 60 | ER+ Breast | Metastatic | 37.43 | 27.51 |
| 27 | Female | 46 | ER+ Breast | Metastatic | 42.90 | 25.92 |
| 28 | Female | 73 | ER+ Breast | Metastatic | 45.27 | 24.52 |
| 29 | Female | 52 | ER+ Breast | Metastatic | 40.20 | 23.62 |
| 30 | Female | 66 | ER+ Breast | Metastatic | No Sample left | 43.05 |
| 31 | Female | 53 | ER+ Breast | Metastatic | 37.63 | 31.28 |
| 32 | Female | 63 | ER+ Breast | Metastatic | 46.29 | 26.22 |
| 33 | Female | 66 | ER+ Breast | Metastatic | No Sample left | 30.70 |
| 34 | Female | 55 | ER+ Breast | Metastatic | 34.57 | 44.91 |
| 35 | Female | 57 | ER+ Breast | Metastatic | 62.80 | 25.66 |
| 36 | Female | N/A | ER+ Breast | Metastatic | No Sample left | 39.66 |
| 37 | Female | N/A | ER+ Breast | Metastatic | No Sample left | 32.38 |
| 38 | Female | N/A | ER+ Breast | Metastatic | No Sample left | 57.44 |
| 39 | Female | N/A | ER+ Breast | Metastatic | No Sample left | 34.05 |
| 40 | Female | N/A | ER+ Breast | Metastatic | No Sample left | 44.28 |
| 41 | Female | N/A | ER+ Breast | Metastatic | No Sample left | 47.56 |
| 42 | Female | N/A | ER+ Breast | Metastatic | No Sample left | 21.84 |
| 43 | Female | N/A | ER+ Breast | Metastatic | No Sample left | 24.21 |
| 44 | Female | N/A | ER+ Breast | Metastatic | 28.23 | 32.02 |
| 45 | Female | N/A | ER+ Breast | Metastatic | No Sample left | 28.96 |
| 46 | Female | N/A | ER+ Breast | Metastatic | No Sample left | 26.48 |
| 47 | Female | N/A | ER+ Breast | Metastatic | No Sample left | 26.51 |
| 48 | Female | N/A | ER+ Breast | Metastatic | No Sample left | 40.34 |
| 49 | Female | N/A | ER+ Breast | Metastatic | No Sample left | 21.50 |
| 50 | Female | N/A | ER+ Breast | Metastatic | 27.33 | 37.59 |
| 51 | Female | N/A | ER+ Breast | Metastatic | No Sample left | 32.16 |
| 52 | Female | N/A | ER+ Breast | Metastatic | No Sample left | 25.73 |
| 53 | Female | N/A | ER+ Breast | Metastatic | No Sample left | 40.63 |
| 54 | Female | N/A | ER+ Breast | Metastatic | No Sample left | 30.28 |

*N/A = Not Available

TABLE 7

Clinical Information of Lymphoma Patients
(for tissue derived cellular gDNA samples).

| 55 | Female | 78 | Lymphoma | Metastatic | 45.77 | 9.57 |
| 56 | Female | 65 | Lymphoma | Metastatic | 43.89 | 30.25 |
| 57 | Female | 75 | Lymphoma | Metastatic | 47.22 | 8.58 |
| 58 | Male | 72 | Lymphoma | Metastatic | 59.40 | 27.92 |
| 59 | Female | 71 | Lymphoma | Metastatic | 45.63 | 62.43 |
| 60 | Female | 81 | Lymphoma | Metastatic | 33.60 | 33.51 |
| 61 | Female | 40 | Lymphoma | Metastatic | 30.48 | 45.14 |
| 62 | Female | 73 | Lymphoma | Metastatic | 40.26 | 50.56 |
| 63 | Male | 49 | Lymphoma | Metastatic | 42.67 | 24.18 |
| 64 | Female | 73 | Lymphoma | Metastatic | 37.24 | 22.73 |

TABLE 8

Clinical Information of Prostate Cancer Patients
(for tissue derived cellular gDNA samples).

| 65 | Male | 60 | Prostate | Metastatic | 31.20 | 62.80 |
| 66 | Male | 67 | Prostate | Metastatic | 37.63 | 31.65 |
| 67 | Male | 58 | Prostate | Metastatic | 42.54 | 12.86 |
| 68 | Male | 77 | Prostate | Metastatic | 41.87 | 37.16 |
| 69 | Male | 60 | Prostate | Metastatic | 56.21 | 41.95 |
| 70 | Male | 79 | Prostate | Metastatic | 32.83 | 46.42 |
| 71 | Male | 68 | Prostate | Metastatic | 34.59 | 61.39 |
| 72 | Male | 65 | Prostate | Metastatic | 37.68 | 48.51 |

TABLE 9

Clinical Information of Healthy Individuals
(for tissue derived cellular gDNA samples).

| Sample Number | Gender | Age | Tissue Type | Global Methylation (%) | Mean Relative Adsorption (% $i_r$) |
|---|---|---|---|---|---|
| 1 | Female | 38 | Normal Breast | 74.29 | 17.96 |
| 2 | Female | 22 | Normal Breast | No Sample left | 12.66 |
| 3 | Female | 38 | Normal Breast | No Sample left | 5.47 |
| 4 | Female | 53 | Normal Breast | 63.51 | 16.60 |
| 5 | Female | 58 | Normal Breast | No Sample left | 10.09 |
| 6 | Female | 46 | Normal Breast | No Sample left | 11.14 |
| 7 | Female | 38 | Normal Breast | No Sample left | 17.68 |
| 8 | Female | 21 | Normal Breast | 56.74 | 27.50 |
| 9 | Female | 50 | Normal Breast | No Sample left | 19.38 |
| 10 | Female | 53 | Normal Breast | 60.91 | 17.15 |
| 11 | Female | 56 | Normal Breast | No Sample left | 16.70 |
| 12 | Female | 34 | Normal Breast | No Sample left | 21.99 |
| 13 | Female | N/A | Normal Breast | No Sample left | 11.65 |
| 14 | Female | N/A | Normal Breast | No Sample left | 7.98 |
| 15 | Female | N/A | Normal Breast | No Sample left | 10.71 |
| 16 | Female | N/A | Normal Breast | No Sample left | 11.28 |
| 17 | Female | N/A | Normal Breast | No Sample left | 7.87 |
| 18 | Female | N/A | Normal Breast | No Sample left | 10.89 |
| 19 | Female | N/A | Normal Breast | 60.59 | 10.95 |
| 20 | Female | 30 | Normal lymph node | 58.21 | 17.32 |
| 21 | Male | 56 | Normal lymph node | 61.24 | 15.10 |
| 22 | Male | 82 | Normal Prostate | 68.20 | 16.80 |
| 23 | Male | 72 | Normal Prostate | 51.43 | 35.72 |
| 24 | Male | 79 | Normal Prostate | 62.37 | 16.70 |
| 25 | Male | 44 | Normal Prostate | 55.81 | 26.48 |
| 26 | Male | 69 | Normal Prostate | 51.29 | 19.60 |
| 27 | Male | 91 | Normal Prostate | 49.23 | 17.08 |
| 28 | Male | 72 | Normal Prostate | 71.48 | 24.14 |
| 29 | Male | 59 | Normal Prostate | 42.65 | 13.68 |
| 30 | Male | 62 | Normal Prostate | 48.28 | 22.61 |
| 31 | Male | 76 | Normal Prostate | 57.60 | 15.43 |

TABLE 10

Clinical information of Breast cancer patient samples
(for cfDNA samples extracted from the plasma).

| Sample Number | Gender | Age | Cancer Type | Cancer Stage | Mean Relative Adsorption (% $i_r$) | Mean Relative Absorbance ($A_{520/658}$) |
|---|---|---|---|---|---|---|
| 1 | Female | 85 | ER+ Breast | Metastatic | 42.43 | 6.75 |
| 2 | Female | 76 | ER+ Breast | Metastatic | 41.67 | 5.85 |
| 3 | Female | 44 | ER+ Breast | Metastatic | 56.78 | 7.88 |
| 4 | Female | 66 | ER+ Breast | Metastatic | 16.23 | 1.27 |
| 5 | Female | 66 | ER+ Breast | Metastatic | 39.18 | 6.56 |
| 6 | Female | 58 | ER+ Breast | Metastatic | 38.56 | 11.50 |
| 7 | Female | 64 | ER+ Breast | Metastatic | 36.17 | 1.19 |
| 8 | Female | 59 | ER+ Breast | Metastatic | 35.77 | 4.61 |
| 9 | Female | 85 | ER+ Breast | Metastatic | 51.14 | 6.00 |
| 10 | Female | 76 | ER+ Breast | Metastatic | 60.49 | 5.63 |
| 11 | Female | 57 | ER+ Breast | Metastatic | 39.01 | 4.88 |
| 12 | Female | 66 | ER+ Breast | Metastatic | 8.69 | 1.13 |
| 13 | Female | 66 | ER+ Breast | Metastatic | 52.50 | 6.00 |
| 14 | Female | 58 | ER+ Breast | Metastatic | 42.16 | 4.88 |
| 15 | Female | 64 | ER+ Breast | Metastatic | 42.30 | 5.75 |
| 16 | Female | 59 | ER+ Breast | Metastatic | 48.60 | 10.05 |
| 17 | Female | 76 | ER+ Breast | Metastatic | 29.31 | 8.46 |
| 18 | Female | 60 | ER+ Breast | Metastatic | 34.67 | 11.00 |
| 19 | Female | 60 | ER+ Breast | Metastatic | 36.52 | 9.17 |
| 20 | Female | 85 | ER+ Breast | Metastatic | 30.58 | 9.75 |
| 21 | Female | 49 | ER+ Breast | Metastatic | 73.64 | 14.5 |
| 22 | Female | 63 | ER+ Breast | Metastatic | 37.94 | 10.83 |
| 23 | Female | 71 | ER+ Breast | Metastatic | 3.37 | 0.38 |
| 24 | Female | 71 | ER+ Breast | Metastatic | 77.14 | 15.83 |
| 25 | Female | 60 | ER+ Breast | Metastatic | 57.58 | 12.00 |

TABLE 10-continued

Clinical information of Breast cancer patient samples
(for cfDNA samples extracted from the plasma).

| Sample Number | Gender | Age | Cancer Type | Cancer Stage | Mean Relative Adsorption (% $i_r$) | Mean Relative Absorbance ($A_{520/658}$) |
|---|---|---|---|---|---|---|
| 26 | Female | 64 | ER+ Breast | Metastatic | 74.93 | 6.31 |
| 27 | Female | 58 | ER+ Breast | Metastatic | 78.26 | 13.00 |
| 28 | Female | 60 | ER+ Breast | Metastatic | 74.32 | 20.00 |
| 29 | Female | 46 | ER+ Breast | Metastatic | 61.13 | 13.00 |
| 30 | Female | 46 | ER+ Breast | Metastatic | 70.96 | 21.25 |

TABLE 11

Clinical information of Colorectal cancer patient samples
(for cfDNA samples extracted from the plasma).

| Sample Number | Gender | Age | Cancer Type | Cancer Stage | Mean Relative Adsortion (% $i_r$) | Mean Relative Absorbance ($A_{520/658}$) |
|---|---|---|---|---|---|---|
| 1 | F | 23* | Colorectal | Metastatic | 49.71 | 14.5 |
| 2 | M | 43 | Colorectal | Metastatic | 63.06 | 23.7 |
| 3 | M | 49 | Colorectal | Metastatic | 50.91 | 16.3 |
| 4 | M | 51 | Colorectal | Metastatic | 63.85 | 60 |
| 5 | M | 54 | Colorectal | Metastatic | 52.65 | 15 |
| 6 | F | 56 | Colorectal | Metastatic | 72.30 | 22.3 |
| 7 | M | 56 | Colorectal | Metastatic | 61.33 | 21 |
| 8 | F | 56 | Colorectal | Metastatic | 68.05 | 47 |
| 9 | F | 56 | Colorectal | Metastatic | 61.10 | 66 |
| 10 | M | 59 | Colorectal | Metastatic | 63.30 | 0.4 |
| 11 | M | 61 | Colorectal | Metastatic | 50.40 | 10.8 |
| 12 | M | 61 | Colorectal | Metastatic | 29.23 | 14.8 |
| 13 | M | 61 | Colorectal | Metastatic | 67.08 | 36 |
| 14 | F | 62 | Colorectal | Metastatic | 61.96 | 28.5 |
| 15 | F | 62 | Colorectal | Metastatic | 62.70 | 16.3 |
| 16 | F | 63 | Colorectal | Metastatic | 62.00 | 10.6 |
| 17 | F | 63 | Colorectal | Metastatic | 73.43 | 22 |
| 18 | M | 63 | Colorectal | Metastatic | 69.64 | 15.7 |
| 19 | M | 64 | Colorectal | Metastatic | 70.14 | 21.7 |
| 20 | M | 64 | Colorectal | Metastatic | 63.70 | 67 |
| 21 | M | 65 | Colorectal | Metastatic | 58.03 | 9 |
| 22 | M | 65 | Colorectal | Metastatic | 54.45 | 31 |
| 23 | F | 65 | Colorectal | Metastatic | 47.19 | 0.7 |
| 24 | M | 65 | Colorectal | Metastatic | 20.40 | 2 |
| 25 | F | 66 | Colorectal | Metastatic | 35.85 | 0.9 |
| 26 | M | 69 | Colorectal | Metastatic | 25.70 | 2.1 |
| 27 | M | 69 | Colorectal | Metastatic | 26.80 | 1.8 |
| 28 | F | 70 | Colorectal | Metastatic | 76.16 | 3 |
| 29 | F | 70 | Colorectal | Metastatic | 35.96 | 69 |
| 30 | F | 70 | Colorectal | Metastatic | 59.55 | 15.3 |
| 31 | M | 71 | Colorectal | Metastatic | 63.66 | 30 |
| 32 | F | 71 | Colorectal | Metastatic | 59.23 | 18 |
| 33 | M | 71 | Colorectal | Metastatic | 75.39 | 12.3 |
| 34 | M | 71 | Colorectal | Metastatic | 61.40 | 17 |
| 35 | F | 71 | Colorectal | Metastatic | 30.20 | 2.6 |
| 36 | F | 71 | Colorectal | Metastatic | 35.84 | 0.4 |
| 37 | M | 72 | Colorectal | Metastatic | 71.03 | 11.3 |
| 38 | M | 73 | Colorectal | Metastatic | 68.25 | 13.4 |
| 39 | M | 73 | Colorectal | Metastatic | 58.16 | 31 |
| 40 | M | 73 | Colorectal | Metastatic | 58.70 | 21 |
| 41 | F | 73 | Colorectal | Metastatic | 34.26 | 17.3 |
| 42 | F | 74 | Colorectal | Metastatic | 48.25 | 7.8 |
| 43 | M | 74 | Colorectal | Metastatic | 67.53 | 23.7 |
| 44 | F | 74 | Colorectal | Metastatic | 64.30 | 4.3 |
| 45 | M | 75 | Colorectal | Metastatic | 76.41 | 23 |
| 46 | M | 75 | Colorectal | Metastatic | 49.19 | 16.5 |
| 47 | F | 75 | Colorectal | Metastatic | 59.32 | 14.5 |
| 48 | M | 76 | Colorectal | Metastatic | 64.80 | 23.7 |
| 49 | M | 76 | Colorectal | Metastatic | 19.14 | 1.8 |
| 50 | M | 77 | Colorectal | Metastatic | 55.69 | 29 |
| 51 | M | 77 | Colorectal | Metastatic | 68.35 | 35.5 |
| 52 | M | 77 | Colorectal | Metastatic | 20.23 | 1.1 |
| 53 | M | 78 | Colorectal | Metastatic | 57.40 | 28 |
| 54 | M | 79 | Colorectal | Metastatic | 32.32 | 17.3 |
| 55 | F | 79 | Colorectal | Metastatic | 64.69 | 24.5 |

TABLE 11-continued

Clinical information of Colorectal cancer patient samples
(for cfDNA samples extracted from the plasma).

| Sample Number | Gender | Age | Cancer Type | Cancer Stage | Mean Relative Adsortion (% $i_r$) | Mean Relative Absorbance ($A_{520/658}$) |
|---|---|---|---|---|---|---|
| 56 | F | 79 | Colorectal | Metastatic | 53.00 | 18.7 |
| 57 | F | 79 | Colorectal | Metastatic | 76.00 | 3.3 |
| 58 | F | 80 | Colorectal | Metastatic | 55.59 | 9.5 |
| 59 | M | 80 | Colorectal | Metastatic | 60.01 | 21.7 |
| 60 | F | 81 | Colorectal | Metastatic | 45.62 | 11.6 |
| 61 | F | 81 | Colorectal | Metastatic | 63.19 | 29 |
| 62 | M | 81 | Colorectal | Metastatic | 60.21 | 16.3 |
| 63 | F | 83 | Colorectal | Metastatic | 63.36 | 2.3 |
| 64 | F | 84 | Colorectal | Metastatic | 60.91 | 9.3 |
| 65 | F | 85 | Colorectal | Metastatic | 60.02 | 15.8 |
| 66 | F | 85 | Colorectal | Metastatic | 60.05 | 23 |
| 67 | M | 88 | Colorectal | Metastatic | 61.01 | 6.7 |
| 68 | F | 89 | Colorectal | Metastatic | 22.31 | 1.1 |
| 69 | F | 92 | Colorectal | Metastatic | 65.56 | 16.7 |
| 70 | M | 92 | Colorectal | Metastatic | 68.27 | 22.7 |

*It is very unlikely to develop colorectal cancer at the age of 23. However, the present inventors assume this patient may have a heritable predisposition.

TABLE 12

Normal cfDNA samples extracted from the plasma of healthy individuals.

| Sample Number | Gender | Age | Sample Type | Cancer Stage | Mean Relative Adsorption (% ir) | Mean Relative Absorbance (A520/658) |
|---|---|---|---|---|---|---|
| 1 | F | 54 | Normal | NA | 3.98 | 1.02 |
| 2 | F | 31 | Normal | NA | 9.30 | 1.22 |
| 3 | F | 57 | Normal | NA | 33.31 | 7.53 |
| 4 | F | 18 | Normal | NA | 27.89 | 5.50 |
| 5 | F | 27 | Normal | NA | 17.95 | 7.15 |
| 6 | F | 54 | Normal | NA | 18.01 | 5.05 |
| 7 | F | 21 | Normal | NA | 18.53 | 2.14 |
| 8 | F | 23 | Normal | NA | 29.98 | 3.99 |
| 9 | F | 18 | Normal | NA | 5.60 | 0.96 |
| 10 | F | 43 | Normal | NA | 30.90 | 7.67 |
| 11 | F | 41 | Normal | NA | 16.93 | 2.13 |
| 12 | F | 25 | Normal | NA | 2.37 | 1.09 |
| 13 | F | 34 | Normal | NA | 0.97 | 1.15 |
| 14 | F | 47 | Normal | NA | 3.11 | 1.05 |
| 15 | F | 23 | Normal | NA | 4.22 | 0.86 |
| 16 | F | 41 | Normal | NA | 5.43 | 0.95 |
| 17 | F | 25 | Normal | NA | 22.76 | 4.03 |
| 18 | F | 46 | Normal | NA | 1.31 | 2.04 |
| 19 | F | 35 | Normal | NA | 28.17 | 5.08 |
| 20 | F | 49 | Normal | NA | 0.52 | 1.21 |
| 21 | F | 26 | Normal | NA | 21.3 | 2.27 |
| 22 | F | 46 | Normal | NA | 29.71 | 8.40 |
| 23 | F | 38 | Normal | NA | 35.34 | 4.00 |
| 24 | F | 48 | Normal | NA | 21.8 | 3.30 |
| 25 | F | 55 | Normal | NA | 43.83 | 10.60 |
| 26 | F | 60 | Normal | NA | 49.51 | 12.60 |
| 27 | F | N/A | Normal | NA | 22.4 | 7.00 |
| 28 | F | N/A | Normal | NA | 10.54 | 1.70 |
| 29 | F | N/A | Normal | NA | 0.59 | 2.08 |
| 30 | F | N/A | Normal | NA | 5.1 | 0.63 |
| 31 | F | 40 | Normal | NA | 56.2 | 8.40 |
| 32 | M | 56 | Normal | NA | 51.1 | 12.40 |
| 33 | M | 58 | Normal | NA | 18.31 | 2.40 |
| 34 | F | 59 | Normal | NA | 17.94 | 3.70 |
| 35 | M | 63 | Normal | NA | 10.37 | 0.30 |
| 36 | M | 63 | Normal | NA | 46.09 | 16.50 |
| 37 | M | 65 | Normal | NA | 33.26 | 11.50 |
| 38 | M | 65 | Normal | NA | 29.21 | 7.70 |
| 39 | M | 67 | Normal | NA | 25.81 | 16.20 |
| 40 | F | 70 | Normal | NA | 14.25 | 6.20 |
| 41 | M | 70 | Normal | NA | 58.24 | 0.70 |
| 42 | M | 75 | Normal | NA | 34.96 | 16.70 |
| 43 | M | 77 | Normal | NA | 56.84 | 31.00 |

TABLE 12-continued

Normal cfDNA samples extracted from the plasma of healthy individuals.

| Sample Number | Gender | Age | Sample Type | Cancer Stage | Mean Relative Adsorption (% i_r) | Mean Relative Absorbance (A520/658) |
|---|---|---|---|---|---|---|
| 44 | M | 77 | Normal | NA | 42.57 | 8.30 |
| 45 | M | 78 | Normal | NA | 35.65 | 12.70 |

*NA = Not Applicable

TABLE 13

Global Methylation Analysis of cell derived evDNAs and cellular gDNAs

| Cell Line | DNA Type | Cancer Type | Global Methylation (%) |
|---|---|---|---|
| BT474 | evDNA | Breast | 26.75 |
| MCF7 | evDNA | Breast | 43.49 |
| SKMEL28 | evDNA | Melanoma | 37.84 |
| BT474 | gDNA | Breast | 43.15 |
| MCF7 | gDNA | Breast | 33.56 |
| SKMEL28 | gDNA | Melanoma | 45.23 |

TABLE 14

Clinical Information of Cancer Patients.

| Sample Number | Gender | Age (Yrs) | Cancer Type | Cancer Stage | Mean Relative Adsorption (% i_r) |
|---|---|---|---|---|---|
| N1 | Female | 43 | N/A | N/A | 11.65 |
| N2 | Female | 41 | N/A | N/A | 17.76 |
| N3 | Female | 25 | N/A | N/A | 15.98 |
| N4 | Female | 25 | N/A | N/A | 22.78 |
| N5 | Female | 27 | N/A | N/A | 19.64 |
| N6 | Female | 21 | N/A | N/A | 17.02 |
| N7 | Female | 56 | N/A | N/A | 15.29 |
| P1 | Female | 66 | Breast | Metastatic | 23.52 |
| P2 | Female | 58 | Breast | Metastatic | 39.72 |
| P3 | Female | 64 | Breast | Metastatic | 36.19 |
| P4 | Female | 59 | Breast | Metastatic | 33.08 |
| P5 | Female | 76 | Breast | Metastatic | 38.58 |
| P6 | NA | NA | Melanoma | Metastatic | 25.80 |
| P7 | NA | NA | Melanoma | Metastatic | 31.43 |
| P8 | NA | NA | Melanoma | Metastatic | 25.54 |
| P9 | NA | NA | Melanoma | Metastatic | 30.60 |

*N/A = Not Applicable, NA = Not available

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included.

What is claimed is:

1. A method for detecting and measuring cancer DNA, the method comprising:
    exposing endogenous cancer DNA from a biological sample to a working electrode that comprises an electro-conductive material;
    applying a potential to the working electrode; and
    detecting an electrical signal from the working electrode that is indicative of adsorption of the endogenous cancer DNA to the electro-conductive material, wherein the electrical signal from the working electrode is different than another electrical signal generated from the working electrode when exposed to (1) one corresponding non-cancer DNA or (2) a total amount of endogenous cancer DNA from another biological sample that is different than a total amount of the endogenous cancer DNA from the biological sample.

2. The method of claim 1, wherein the electro-conductive material is selected from the group consisting of gold, platinum, palladium, silver, carbon, alloys thereof, and composites thereof.

3. The method of claim 1, wherein the electrical signal is selected from the group consisting of differential pulse voltammetry (DPV), cyclic voltammetry (CV), Linear Sweep Voltammetry (LSV), Square Wave Voltammetry (SWV), chronoamperometry, Electrochemical Impedance Spectroscopy (EIS), current, voltage, impedance, capacitance, charge, conductivity, resistance, and a combination thereof.

4. The method of claim 1, wherein the biological sample comprises a biological fluid.

5. The method of claim 4, wherein the biological fluid is selected from the group consisting of whole blood; lysed whole blood; serum; plasma; urine; sputum; sweat; follicular fluid; synovial fluid; amniotic fluid; a nasopharyngeal aspirate; a bronchial aspirate; semen; and cerebrospinal fluid.

6. The method of claim 1, wherein the endogenous cancer DNA is selected from the group consisting of cellular genomic DNA (cellular gDNA), cell-free DNA (cfDNA), circulating tumor DNA (ctDNA), and extracellular vesicular DNA (evDNA).

7. The method of claim 1, wherein the endogenous cancer DNA is derived from a subject that has been exposed to a treatment to treat a cancer.

8. The method of claim 7, further comprising comparing the electrical signal to a threshold.

9. The method of claim 8, wherein the threshold comprises a reference electrical signal that is indicative of a level of the cancer within the subject before the subject is exposed to the treatment.

* * * * *